United States Patent

(12) United States Patent
Kumar et al.

(10) Patent No.: US 12,343,378 B2
(45) Date of Patent: *Jul. 1, 2025

(54) COMPOSITIONS AND METHODS FOR TREATING PULMONARY HYPERTENSION

(71) Applicant: Acceleron Pharma Inc., Cambridge, MA (US)

(72) Inventors: Ravindra Kumar, Cambridge, MA (US); John Knopf, Cambridge, MA (US)

(73) Assignee: ACCELERON PHARMA INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/960,911

(22) Filed: Oct. 6, 2022

(65) Prior Publication Data

US 2023/0233648 A1 Jul. 27, 2023

Related U.S. Application Data

(63) Continuation of application No. 17/339,606, filed on Jun. 4, 2021, now Pat. No. 11,497,794, which is a continuation of application No. 17/002,542, filed on Aug. 25, 2020, now Pat. No. 11,065,303, which is a continuation of application No. 16/829,642, filed on Mar. 25, 2020, now Pat. No. 11,622,992, which is a continuation of application No. 15/945,565, filed on Apr. 4, 2018, now Pat. No. 10,695,405, which is a continuation of application No. 15/650,420, filed on Jul. 14, 2017, now Pat. No. 10,722,558.

(60) Provisional application No. 62/510,403, filed on May 24, 2017, provisional application No. 62/453,888, filed on Feb. 2, 2017, provisional application No. 62/362,955, filed on Jul. 15, 2016.

(51) Int. Cl.

| A61K 38/18 | (2006.01) |
| A61K 38/17 | (2006.01) |
| A61K 38/45 | (2006.01) |
| A61K 45/06 | (2006.01) |
| A61P 7/00 | (2006.01) |
| A61P 11/00 | (2006.01) |
| C07K 14/71 | (2006.01) |

(52) U.S. Cl.
CPC ........ *A61K 38/1875* (2013.01); *A61K 38/179* (2013.01); *A61K 38/1796* (2013.01); *A61K 38/45* (2013.01); *A61K 45/06* (2013.01); *A61P 7/00* (2018.01); *A61P 11/00* (2018.01); *C07K 14/71* (2013.01); *C07K 2319/30* (2013.01)

(58) Field of Classification Search
None
See application file for complete search history.

(56) References Cited

U.S. PATENT DOCUMENTS

| 5,288,931 A | 2/1994 | Chang et al. |
| 7,112,660 B1 | 9/2006 | Domingues et al. |
| 8,895,016 B2 | 11/2014 | Sherman et al. |
| 9,145,433 B2 | 9/2015 | Bhamidipati et al. |
| 10,695,405 B2 | 6/2020 | Kumar et al. |
| 10,722,558 B2 | 7/2020 | Kumar et al. |
| 10,946,067 B2 | 3/2021 | Kumar et al. |
| 10,973,880 B2 | 4/2021 | Kumar et al. |
| 11,065,303 B2 | 7/2021 | Kumar et al. |
| 11,219,666 B2 | 1/2022 | Kumar et al. |
| 11,622,992 B2 * | 4/2023 | Kumar ................ C07K 14/71 424/134.1 |
| 2003/0045474 A1 | 3/2003 | Sailer et al. |
| 2003/0144203 A1 | 7/2003 | Bowen |
| 2005/0239719 A1 | 10/2005 | Zeldis |
| 2007/0056050 A1 | 3/2007 | Clokie et al. |
| 2007/0248609 A1 | 10/2007 | De Kretser et al. |
| 2009/0017019 A1 | 1/2009 | Shields et al. |
| 2009/0142333 A1 | 6/2009 | Knopf et al. |
| 2010/0015144 A1 | 1/2010 | Sherman et al. |
| 2010/0056505 A1 | 3/2010 | Lee et al. |
| 2011/0224236 A1 | 9/2011 | Rothblatt |

(Continued)

FOREIGN PATENT DOCUMENTS

| AU | 2012244215 A1 | 11/2012 |
| CN | 103920139 A | 7/2014 |

(Continued)

OTHER PUBLICATIONS

Alaoui-Ismaili, M. and Falb, D., "Design of second generation therapeutic recombinant bone morphogenetic proteins," Cytokine & Growth Factor Reviews, vol. 20(5-6): 501-507 (2009).

Attie et al., "A phase I study of ACE-536, a regulator of erythroid differentiation, in healthy volunteers," American Journal of Hematology, vol. 89(7): 766-770 (2014).

Bernier et al., "Pharmacological chaperone action on G-protein-coupled receptors," Current Opinions in Pharmacology, vol. 4(5): 528-533 (2004).

(Continued)

*Primary Examiner* — Elizabeth C. Kemmerer
(74) *Attorney, Agent, or Firm* — White & Case LLP

(57) ABSTRACT

In some aspects, the disclosure relates to GDF/BMP antagonists and methods of using GDF3/BMP antagonists to treat, prevent, or reduce the progression rate and/or severity of pulmonary hypertension (PH), particularly treating, preventing or reducing the progression rate and/or severity of one or more PH-associated complications. The disclosure also provides methods of using a GDF/BMP antagonist to treat, prevent, or reduce the progression rate and/or severity of a variety of conditions including, but not limited to, pulmonary vascular remodeling, pulmonary fibrosis, and right ventricular hypertrophy. The disclosure further provides methods of using a GDF/BMP antagonist to reduce right ventricular systolic pressure in a subject in need thereof.

61 Claims, 31 Drawing Sheets

Specification includes a Sequence Listing.

(56) References Cited

U.S. PATENT DOCUMENTS

| | | |
|---|---|---|
| 2014/0045844 A1 | 2/2014 | Schafer et al. |
| 2014/0154743 A1 | 6/2014 | Levy et al. |
| 2014/0271459 A1 | 9/2014 | Dutzar et al. |
| 2014/0303068 A1 | 10/2014 | O'Hehir et al. |
| 2015/0266950 A1 | 9/2015 | Sung et al. |
| 2015/0283209 A1 | 10/2015 | Sung et al. |
| 2015/0306150 A1 | 10/2015 | Zhang et al. |
| 2015/0361163 A1 | 12/2015 | Kumar et al. |
| 2016/0039922 A1 | 2/2016 | Attie |
| 2016/0287664 A1 | 10/2016 | Yu et al. |
| 2016/0347814 A1 | 12/2016 | Levine et al. |
| 2017/0202918 A1 | 7/2017 | Yung et al. |
| 2018/0008672 A1 | 1/2018 | Chalothorn et al. |
| 2018/0125928 A1 | 5/2018 | Attie |
| 2018/0327477 A1 | 11/2018 | Kumar et al. |

FOREIGN PATENT DOCUMENTS

| | | |
|---|---|---|
| CN | 107709357 A | 2/2018 |
| EP | 2594280 A1 | 5/2013 |
| KR | 20150115961 A | 10/2015 |
| WO | WO-94/11502 A2 | 5/1994 |
| WO | WO-2005/084699 A1 | 9/2005 |
| WO | WO-2006/012627 A2 | 2/2006 |
| WO | WO-2007/062188 A2 | 5/2007 |
| WO | WO-2008/073351 A2 | 6/2008 |
| WO | WO-2008/073928 A1 | 6/2008 |
| WO | WO-2008/076437 A2 | 6/2008 |
| WO | WO-2008/094708 A2 | 8/2008 |
| WO | WO-2008/097541 A2 | 8/2008 |
| WO | WO-2009/134428 A2 | 11/2009 |
| WO | WO-2010/019261 A1 | 2/2010 |
| WO | WO-2010/062640 A1 | 6/2010 |
| WO | WO-2010/083034 A1 | 7/2010 |
| WO | WO-2010/114860 A1 | 10/2010 |
| WO | WO-2011/056497 A1 | 5/2011 |
| WO | WO-2011/115922 A1 | 9/2011 |
| WO | WO-2012/051559 A2 | 4/2012 |
| WO | WO-2014/071158 A1 | 5/2014 |
| WO | WO-2014/160336 A1 | 10/2014 |
| WO | WO-2015/017576 A1 | 2/2015 |
| WO | WO-2015/161220 A1 | 10/2015 |
| WO | WO-2015/192111 A1 | 12/2015 |
| WO | WO-2016/164089 A2 | 10/2016 |
| WO | WO-2016/164497 A1 | 10/2016 |
| WO | WO-2016/164501 A1 | 10/2016 |
| WO | WO-2016/171948 A1 | 10/2016 |
| WO | WO-2016/183280 A1 | 11/2016 |
| WO | WO-2017/015622 A2 | 1/2017 |

OTHER PUBLICATIONS

Bhattacharya et al., "Impact of genetic variation on three dimensional structure and function of proteins," PLoS One, vol. 12(3): e0171355.

BIOSIS Accession No. 2015:276893 & Piga, A. et al., 'ACE-536 Increases Hemoglobin and Decreases Transfusion Burden and Serum Ferritin in Adults with Beta-Thalassemia: Preliminary Results from a Phase 2 Study', Blood, vol. 124(21): p. 53 (2014).

Cappellini et al., "A Phase 2a, Open-Label, Dose-Finding Study to Determine the Safety and Tolerability of Sotatercept (ACE-011) in Adults with Beta (β)-Thalassemia: Interim Results," Blood, vol. 122(21): 3448 (2013).

Carrancio et al., "An activin receptor IIA ligand trap promotes erythropoiesis resulting in a rapid induction of red blood cells and haemoglobin," British Journal of Haematology, vol. 165:870-882 (2014).

Castonguay et al., "Soluble endoglin specifically binds bone morphongenetic proteins 9 and 10 via its orphan domain, inhibits blood vessel formation, and suppress tumor growth," The Journal of Biological Chemistry, vol. 286(34): 30034-30046 (2011).

"Efficacy versus Potency", https://step1.medbullets.com/pharmacology/; 107007/efficacy-vs-patency, accessed Jan. 2, 2019.

Fenton, et al., "Rheostat positions: A new classification of protein positions relevant to pharmacogenomics", Medicinal Chemistry Research 29: 1133-1146 (2020).

Fox et al., "Pulmonary arterial hypertension: classification, diagnosis and contemporary management," Postgrad Medicine J, vol. 82:717-722 (2006).

Guazzi et al., "Pulmonary Hypertension Due to Left Heart Disease," Circulation, vol. 126(8):975-990 (2012).

Guo et al., "Protein tolerance to random amino acid change," Proceedings of the National Academy of Sciences, vol. 101(25): 9205-9210 (2004).

Hill et al., "Postoperative Pulmonary Hypertension: Etiology and Treatment of a Dangerous Complication," Respiratory Care, vol. 54(7): 958-968 (2009).

Humbert, M., "Update in Pulmonary Hypertension 2008," American Journal of Respiratory Critical Care Medicine, vol. 179: 650-656 (2009).

Kohno et al., "Binding Characteristics of Tumor Necrosis Factor Receptor-FC Fusion Proteins vs Anti-Tumor Necrosis Factor mAbs," J. Investigative Dermatology, vol. 12(1): 5-8 (2007).

Lis et al., "Tumor necrosis factor inhibitors—state of knowledge," Arch Med Sci. vol. 10(6): 1175-1185 (2014).

Long et al., "Selective enhancement of endothelial BMPR-II with BMP9 reverses pulmonary arterial hypertension," Nature Medicine, vol. 21(7): 777-785 (2015).

Montani et al., "Pulmonary arterial hypertension," Orphanet Journal of Rare Diseases, vol. 8(1): p. 97: 1-28 (2013).

Pietra, et al., "Pathologic Assessment of Vasculopathies in Pulmonary Hypertension," Journal of the American College of Cardiology, vol. 43(12) Suppl S: 25S-32S (2004).

Project Information No. 5R01HL074352-07 "BMPR2 and the Pathogenesis of Pulmonary Hypertension", NIH RePorter—NIH Research Portfolio Online Reporting Tool Expenditures and Results (Feb. 20, 2020) 2 pages.

National Organization for Rare Disorders, "Pulmonary Arterial Hypertension", The website downloaded Nov. 2, 2020 from https://rarediseases.org/rare-disease/pulmonary-arterial-hypertensin/; 13 pages (2020).

Rose-Jones et al., "Pulmonary Hypertension: Types and Treatments," Current Cardiology Reviews, vol. 11:73-79 (2015).

Rubin, L.J., "Diagnosis and Management of Pulmonary Arterial Hypertension: ACCP Evidence-Based Clinical Practice Guidelines," Chest, vol. 126(1): 7S-10S (2004).

Simonneau et al., "Updated Clinical Classification of Pulmonary Hypertension," Journal of the American College of Cardiology, vol. 54(1) Suppl S: S43-S54 (2009).

Sotatercept (https://www.genome.jp/dbget-bin/www_bget?dr:D09670; accessed Feb. 1, 2022).

Spiess et al., "Alternative molecular formats and therapeutic applications for bispecific antibodies," Molecular Immunology, vol. 67: 95-106 (2015).

Tokuriki et al., "Stability effects of mutations and protein evolvability," Current Opinions in Structural Biology, vol. 19(5): 596-604 (2009).

Ulloa-Aguirre et al., "Pharmacologic rescue of conformationally-defective proteins: implications for the treatment of human disease," Traffic, vol. 5(11): 821-837 (2004).

Yndestad et al., Elevated levels of activin A in clinical and experimental pulmonary hypertension, J. Applied Physiology, vol. 106(4): 1356-1364 (2009).

Yung et al., "ACTRIIA-Fc rebalances activin/GDF versus BMP signaling in pulmonary hypertension," Science Translational Medicine, vol. 12(543): 5660 (2020).

Issued U.S. Pat. No. 10,722,558 (U.S. Appl. No. 15/650,420).
Issued U.S. Pat. No. 10,695,405 (U.S. Appl. No. 15/945,565).
Issued U.S. Pat. No. 11,622,992 U.S. Appl. No. 16/829,642.
Issued U.S. Pat. No. 10,973,880 (U.S. Appl. No. 17/002,288.
Issued U.S. Pat. No. 11,219,666 (U.S. Appl. No. 17/002,292).
Issued U.S. Pat. No. 11,065,303 (U.S. Appl. No. 17/002,542).
Issued U.S. Pat. No. 10,946,067 (U.S. Appl. No. 17/002,553).
Abandoned U.S. Appl. No. 17/155,559.
Issued U.S. Patent No. 11,318, 188 (U.S. Appl. No. 17/339,593).
Issued U.S. Pat. No. 11,497,794, (U.S. Appl. No. 17/339,606).

(56) References Cited

OTHER PUBLICATIONS

Issued U.S. Pat. No. 7,709,605 (U.S. Appl. No. 11/190,202).
Issued U.S. Pat. No. 8,252,900 (U.S. Appl. No. 12/751,868).
Issued U.S. Pat. No. 9,138,459 (U.S. Appl. No. 13/588,468).
Abandoned U.S. Appl. No. 14/836,684.
Abandoned U.S. Appl. No. 16/222,562.
Issued U.S. Pat. No. 7,612,041 (U.S. Appl. No. 11/603,485).
Issued U.S. Pat. No. 7,951,771 (U.S. Appl. No. 12/284,864).
Issued U.S. Pat. No. 8,067,360 (U.S. Appl. No. 12/284,862).
Issued U.S. Pat. No. 8,629,109 (U.S. Appl. No. 13/176,718).
Issued U.S. Pat. No. 9,163,075 (U.S. Appl. No. 14/027,542).
Issued U.S. Pat. No. 10,071,135 (U.S. Appl. No. 14/849,313).
Issued U.S. Pat. No. 11,129,873 (U.S. Appl. No. 16/054,107).
Pending U.S. Appl. No. 17/410,175.
Pending U.S. Appl. No. 18/443,985.
Abandoned U.S. Appl. No. 12/459,202.
Abandoned U.S. Appl. No. 15/005,762.
Abandoned U.S. Appl. No. 16/821,593 (Pub No. 2021/0038689).
Issued U.S. Pat. No. 8,895,016 (U.S. Appl. No. 12/459,188).
Issued U.S. Pat. No. 10,093,707 (U.S. Appl. No. 14/549,263).
Abandoned U.S. Appl. No. 16/121,338.
Abandoned U.S. Appl. No. 17/132,155.
Abandoned U.S. Appl. No. 17/395,372.
Issued U.S. Pat. No. 7,988,973 (U.S. Appl. No. 12/002,872).
Abandoned U.S. Appl. No. 12/286,381.
Issued U.S. Pat. No. 8,007,809 (U.S. Appl. No. 12/286,333).
Abandoned U.S. Appl. No. 13/189,353.
Abandoned U.S. Appl. No. 16/240,276.
Abandoned U.S. Appl. No. 17/132,024.
Abandoned U.S. Appl. No. 17/395,365.
Issued U.S. Pat. No. 10,227,393 (U.S. Appl. No. 15/092,609).
Issued U.S. Pat. No. 10,906,958 (U.S. Appl. No. 16/251,325).
Abandoned U.S. Appl. No. 16/951,192.
Pending U.S. Appl. No. 18/236,082.
Pending U.S. Appl. No. 17/666,705.
Issued U.S. Pat. No. 10,934,532 (U.S. Appl. No. 15/726,255).
Allowed U.S. Appl. No. 17/134,703.
Myllarniemi et al., "Upregulation of activin-B and follistatin in pulmonary fibrosis—a translational study using human biopsies and a specific inhibior in mouse fibrosis models," BMC Pulmonary Medicine, vol. 14(170): (14 pages) (2014).
Montani, David et al., "Pulmonary arterial hypertension", Orphanet Journal of Rare Diseases, vol. 8:97, 1-58 (2013).
Kenny, Jane R. et al., "Therapeutic Protein Drug-Drug Interactions: Navigating the Knowledge Gaps-Highlights from the 2012 AAPS NBC Roundtable and IQ Consortium/FDA Workshop", The AAPS Journal, vol. 15(4): 933-940 (2013).
Oba et al., "Pulmonary hypertension associated with left ventricular disease," Medical Progress, vol. 255(1):89-93 (2015).
Rath et al., "Fc-fusion proteins and FcRn: structural insights for longer-lasting and more effective therapeutics," Critical Reviews in Biotechnology, vol. 35(2): 235-254 (2015).
Sugimura et al., "Pulmonary hypertension associated with left ventricular disease," Angiology Frontier, vol. 14(2): 117-122 (2015).
Tyagi et al., "Chemical modification and chemical cross-linking for protein/enzyme stabilization", Biochemistry (Mosc)P. vol. 63(3): 334-344 (1998).

* cited by examiner

```
ActRIIa   ILGRSETQEC  LFFNANWEKD  RTNQTGVEPC  YGDKDKRRHC  PATWKNISGS
ActRIIb   GRGEAETREC  IYYNANWELE  RTNQSGLERC  EGEQDKRLHC  YASWRNSSGT

IEIVKQGCWL  DDINCYDRTD  CVEKKDSPEV  YFCCCEGNMC  NEKFSYPPEM
          IELVKKGCWL  DDFNCYDRQE  CVATEENPQV  YFCCCEGNFC  NERFTHLPEA

EVTQPTSNPV  TPKPP
          GGPEVTYEPP  PTAPT
```

FIGURE 1

|         | 10         | 20         | 30         | 40         | 50         |
|---------|------------|------------|------------|------------|------------|
| human   | ILGRSETQEC | LFFNANWERD | RTNQTGVEPC | YGDKDKRRHC | FATWKNISGS |
| sheep   | ILGRSETQEC | IFFNANWERD | RTNRTGVESC | YGDKDKRRHC | FATWKNISGS |
| mole    | ILGRSETQEC | LFFNANWERD | RTNQTGVEPC | YGDKDKRRHC | FATWKNISGS |
| mouse   | ILGRSETQEC | LFFNANWERD | RTNQTGVEPC | YGDKDKRRHC | FATWKNISGS |
| chicken | ILGRSETQEC | IYYNANWEKD | KTNRSGIEPC | YGDKDKRRHC | FATWKNISGS |
| cow     | ILGRSETQEC | IFFNANWERD | RTNRTGVESC | YGDKDKRRHC | FATWKNISGS |
| owl     | ILGRSETQEC | IYYNANWEKD | KTNRSGIEPC | YGDKDKRRHC | FATWKNISGS |
| bat     | ILGRSETQEC | IFYNANWERD | KTNRTGVELC | YGDKDKRRHC | FATWKNISGS |

|         | 60         | 70         | 80         | 90         | 100        |
|---------|------------|------------|------------|------------|------------|
| human   | IEIVKQGCWL | DDINCYDRTD | CVEKKDSPEV | YFCCCEGNMC | NEKFSYFPEM |
| sheep   | IEIVKQGCWL | DDINCYDRTD | CIEKKDSPEV | YFCCCEGNMC | NERFSYFPEM |
| mole    | IEIVKQGCWL | DDINCYDRTD | CIEKKDSPEV | YFCCCEGNMC | NEKFSYFPEM |
| mouse   | IEIVKQGCWL | DDINCYDRTD | CIEKKDSPEV | YFCCCEGNMC | NERFSYFPEM |
| chicken | IEIVKQGCWL | DDINCYDRND | CIEKKDSPEV | YFCCCEGNMC | NERFYFPEM  |
| cow     | IEIVKQGCWL | DDINCYDRTD | CIEKKDSPEV | FFCCCEGNMC | NERFSYFPEM |
| owl     | IEIVKQGCWL | DDINCYDRND | CIEKKDSPEV | YFCCCEGNMC | NERFYFPEM  |
| bat     | IEIVKQGCWL | DDINCYDRTD | CIEKKDSPEV | YFCCCEGNMC | NERFSYFPEM |

|         | 110        |        |
|---------|------------|--------|
| human   | EVTQPTSNPV | TPKPP  |
| sheep   | EVTQPTSNPV | TPKPP  |
| mole    | EVTQPTSNPV | TPKPP  |
| mouse   | EVTQPTSNPV | TPKAP  |
| chicken | EVTQPTSNPV | TPKPP  |
| cow     | EVTQPTSNPV | TPKPP  |
| owl     | EVTQPTSNPV | TPKPP  |
| bat     | EVTQPTSNPV | TPKPP  |

FIGURE 3

```
IgG1  --------THTCPPCPAPELLGGPSVFLFPPKPKDTLMISRTPEVTCVVVDVSHEDPEVKF  53
IgG4  ---ESKYGPPCPSCPAPEFLGGPSVFLFPPKPKDTLMISRTPEVTCVVVDVSQEDPEVQF  57
IgG2  --------VECPPCPAPPVAG-PSVFLFPPKPKDTLMISRTPEVTCVVVDVSHEDPEVQF  51
IgG3  EPKSCDTPPPCPRCPAPELLGGPSVFLFPPKPKDTLMISRTPEVTCVVVDVSHEDPEVQF  60
          ** ****  . * *****************************:*****:*

IgG1  NWYVDGVEVHNAKTKPREEQYNSTYRVVSVLTVLHQDWLNGKEYKCKVSNKALPAPIEKT  113
IgG4  NWYVDGVEVHNAKTKPREEQFNSTYRVVSVLTVLHQDWLNGKEYKCKVSNKGLPSSIEKT  117
IgG2  NWYVDGVEVHNAKTKPREEQFNSTFRVVSVLTVVHQDWLNGKEYKCKVSNKGLPAPIEKT  111
IgG3  KWYVDGVEVHNAKTKPREEQYNSTFRVVSVLTVLHQDWLNGKEYKCKVSNKALPAPIEKT  120
      :*****************:***:********:*****************.**:.****

IgG1  ISKAKGQPREPQVYTLPPSREEMTKNQVSLTCLVKGFYPSDIAVEWESNGQPENNYKTTP  173
IgG4  ISKAKGQPREPQVYTLPPSQEEMTKNQVSLTCLVKGFYPSDIAVEWESNGQPENNYKTTP  177
IgG2  ISKTKGQPREPQVYTLPPSREEMTKNQVSLTCLVKGFYPSDIAVEWESNGQPENNYKTTP  171
IgG3  ISKTKGQPREPQVYTLPPSREEMTKNQVSLTCLVKGFYPSDIAVEWESSGQPENNYNTTP  180
      ***:**************:*************************.******:***

IgG1  PVLDSDGSFFLYSKLTVDKSRWQQGNVFSCSVMHEALHNHYTQKSLSLSPGK  225
IgG4  PVLDSDGSFFLYSRLTVDKSRWQEGNVFSCSVMHEALHNHYTQKSLSLSLGK  229
IgG2  PMLDSDGSFFLYSKLTVDKSRWQQGNVFSCSVMHEALHNHYTQKSLSLSPGK  223
IgG3  PMLDSDGSFFLYSKLTVDKSRWQQGNIFSCSVMHEALHNRFTQKSLSLSPGK  232
      *:***********:********:***:***********::*******  **
```

FIGURE 4

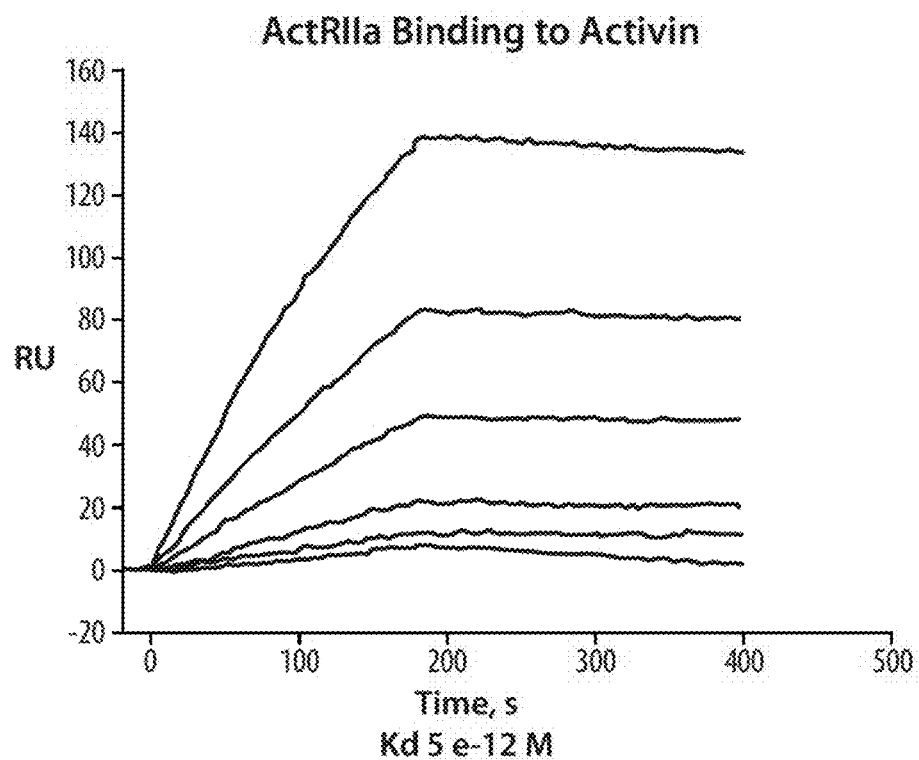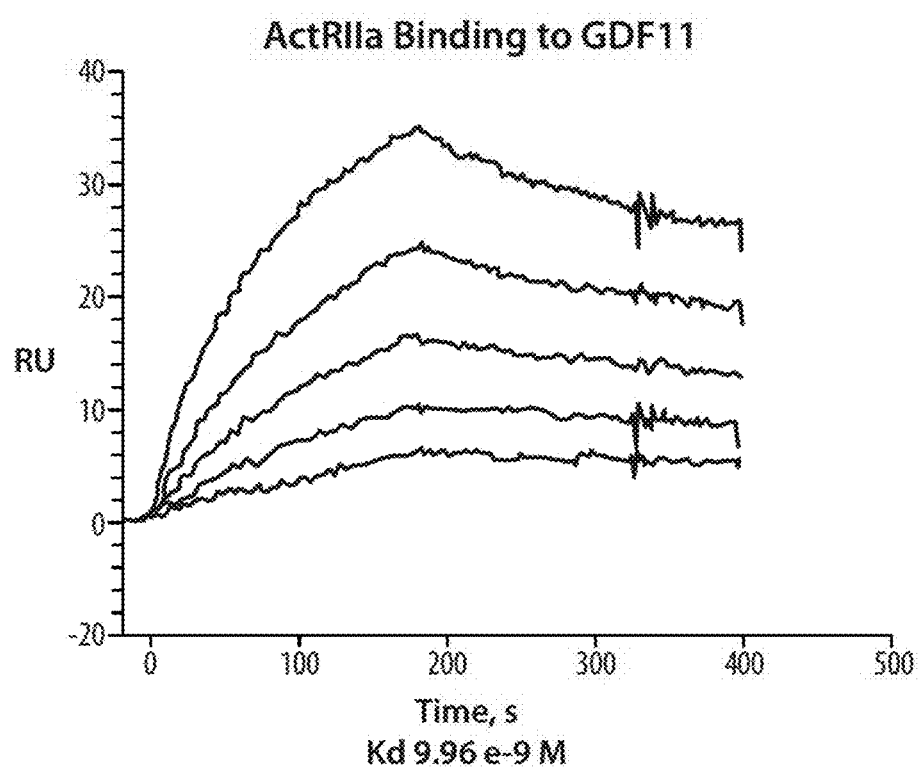
FIGURE 6

```
  1  MDAMKRGLCC VLLLCGAVFV SPGAAETREC IYYNANWELE RTNQSGLERC
 51  EGEQDKRLHC YASWRNSSGT IELVKKGCWL DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 69)
```

FIGURE 7

```
                                                                            A   E   T   R   E   C   I   Y   Y
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N   A   N   W   E   L   E   R   T   N   Q   S   G   L   E   R   C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E   G   E   Q   D   K   R   L   H   C   Y   A   S   W   R   N   S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S   G   T   I   E   L   V   K   K   G   C   W   L   D   D   F
201  CTCTGGCACC ATCGAGCTCG TGAAGAAGGG CTGCTGGCTA GATGACTTCA
     GAGACCGTGG TAGCTCGAGC ACTTCTTCCC GACGACCGAT CTACTGAAGT

N   C   Y   D   R   Q   E   C   V   A   T   E   E   N   P   Q   V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y   F   C   C   C   E   G   N   F   C   N   E   R   F   T   H   L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P   E   A   G   G   P   E   V   T   Y   E   P   P   P   T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
     CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
     TTTCGGTTTC CCGTCGGGGC TCTTGGTGTC CACATGTGGG ACGGGGGTAG
```

FIGURE 8A

```
801   CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA (SEQ ID NO: 70)
      GTCTTCTCGG AGAGGGACAG GGGCCCATTT ACT (SEQ ID NO: 71)
```

FIGURE 8B

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

A  E  T     R  E  C     I  Y  Y
 51  AGTCTTCGTT TCGCCCGGCG CCGCCGAAAC CCGCGAATGT ATTTATTACA
     TCAGAAGCAA AGCGGGCCGC GGCGGCTTTG GGCGCTTACA TAAATAATGT

N  A  N  W     E  L  E     R  T  N     Q  S  G     L  E  R  C
101  ATGCTAATTG GAACTCGAA CGGACGAACC AATCCGGGCT CGAACGGTGT
     TACGATTAAC CCTTGAGCTT GCCTGCTTGG TTAGGCCCGA GCTTGCCACA

E  G  E     Q  D  K  R     L  H  C     Y  A  S     W  R  N  S
151  GAGGGGGAAC AGGATAAACG CCTCCATTGC TATGCGTCGT GGAGGAACTC
     CTCCCCCTTG TCCTATTTGC GGAGGTAACG ATACGCAGCA CCTCCTTGAG

S  G  T     I  E  L     V  K  K  G     C  W  L     D  D  F
201  CTCCGGGACG ATTGAACTGG TCAAGAAAGG GTGCTGGCTG GACGATTTCA
     GAGGCCCTGC TAACTTGACC AGTTCTTTCC CACGACCGAC CTGCTAAAGT

N  C  Y  D     R  Q  E     C  V  A     T  E  E  N     P  Q  V
251  ATTGTTATGA CCGCCAGGAA TGTGTCGCGA CCGAAGAGAA TCCGCAGGTC
     TAACAATACT GGCGGTCCTT ACACAGCGCT GGCTTCTCTT AGGCGTCCAG

Y  F  C     C  C  E  G     N  F  C     N  E  R     F  T  H  L
301  TATTTCTGTT GTTGCGAGGG GAATTTCTGT AATGAACGGT TTACCCACCT
     ATAAAGACAA CAACGCTCCC CTTAAAGACA TTACTTGCCA AATGGGTGGA

P  E  A     G  G  P     E  V  T  Y     E  P  P     P  T
351  CCCCGAAGCC GGCGGGCCCG AGGTGACCTA TGAACCCCCG CCCACCGGTG
     GGGGCTTCGG CCGCCCGGGC TCCACTGGAT ACTTGGGGC GGGTGGCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
     CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
     TTTCGGTTTC CCGTCGGGGC TCTTGGTGTC CACATGTGGG ACGGGGGTAG
```

FIGURE 9A

```
 801 CCGGGAGGAG ATGACCAAGA ACCAGGTCAG CCTGACCTGC CTGGTCAAAG
     GGCCCTCCTC TACTGGTTCT TGGTCCAGTC GGACTGGACG GACCAGTTTC

851 GCTTCTATCC CAGCGACATC GCCGTGGAGT GGGAGAGCAA TGGGCAGCCG
     CGAAGATAGG GTCGCTGTAG CGGCACCTCA CCCTCTCGTT ACCCGTCGGC

901 GAGAACAACT ACAAGACCAC GCCTCCCGTG CTGGACTCCG ACGGCTCCTT
     CTCTTGTTGA TGTTCTGGTG CGGAGGGCAC GACCTGAGGC TGCCGAGGAA

951 CTTCCTCTAT AGCAAGCTCA CCGTGGACAA GAGCAGGTGG CAGCAGGGGA
     GAAGGAGATA TCGTTCGAGT GGCACCTGTT CTCGTCCACC GTCGTCCCCT

1001 ACGTCTTCTC ATGCTCCGTG ATGCATGAGG CTCTGCACAA CCACTACACG
     TGCAGAAGAG TACGAGGCAC TACGTACTCC GAGACGTGTT GGTGATGTGC

1051 CAGAAGAGCC TCTCCCTGTC CCCGGGTAAA TGA (SEQ ID NO: 72)
     GTCTTCTCGG AGAGGGACAG GGGCCCATTT ACT (SEQ ID NO: 73)
```

FIGURE 9B

1     MDAMKRGLCC VLLLCGAVFV SPGASGRGEA ETRECIYYNA NWELERTNQS

51    GLERCEGEQD KRLHCYASWR NSSGTIELVK KGCWDDDFNC YDRQECVATE

101   ENPQVYFCCC EGNFCNERFT HLPEAGGPEV TYEPPPTAPT GGGTHTCPPC

151   PAPELLGGPS VFLFPPKPKD TLMISRTPEV TCVVVDVSHE DPEVKFNWYV

201   DGVEVHNAKT KPREEQYNST YRVVSVLTVL HQDWLNGKEY KCKVSNKALP

251   APIEKTISKA KGQPREPQVY TLPPSREEMT KNQVSLTCLV KGFYPSDIAV

301   EWESNGQPEN NYKTTPPVLD SDGSFFLYSK LTVDKSRWQQ GNVFSCSVMH

351   EALHNHYTQK SLSLSPGK (SEQ ID NO: 74)

FIGURE 10

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

51  AGTCTTCGTT TCGCCCGGCG CCTCTGGGCG TGGGGAGGCT GAGACACGGG
     TCAGAAGCAA AGCGGGCCGC GGAGACCCGC ACCCCTCCGA CTCTGTGCCC

101  AGTGCATCTA CTACAACGCC AACTGGGAGC TGGAGCGCAC CAACCAGAGC
     TCACGTAGAT GATGTTGCGG TTGACCCTCG ACCTCGCGTG GTTGGTCTCG

151  GGCCTGGAGC GCTGCGAAGG CGAGCAGGAC AAGCGGCTGC ACTGCTACGC
     CCGGACCTCG CGACGCTTCC GCTCGTCCTG TTCGCCGACG TGACGATGCG

201  CTCCTGGCGC AACAGCTCTG GCACCATCGA GCTCGTGAAG AAGGGCTGCT
     GAGGACCGCG TTGTCGAGAC CGTGGTAGCT CGAGCACTTC TTCCCGACGA

251  GGGATGATGA CTTCAACTGC TACGATAGGC AGGAGTGTGT GGCCACTGAG
     CCCTACTACT GAAGTTGACG ATGCTATCCG TCCTCACACA CCGGTGACTC

301  GAGAACCCCC AGGTGTACTT CTGCTGCTGT GAAGGCAACT TCTGCAACGA
     CTCTTGGGGG TCCACATGAA GACGACGACA CTTCCGTTGA AGACGTTGCT

351  GCGCTTCACT CATTTGCCAG AGGCTGGGGG CCCGGAAGTC ACGTACGAGC
     CGCGAAGTGA GTAAACGGTC TCCGACCCCC GGGCCTTCAG TGCATGCTCG

401  CACCCCCGAC AGCCCCCACC GGTGGTGGAA CTCACACATG CCCACCGTGC
     GTGGGGGCTG TCGGGGGTGG CCACCACCTT GAGTGTGTAC GGGTGGCACG

451  CCAGCACCTG AACTCCTGGG GGGACCGTCA GTCTTCCTCT TCCCCCCAAA
     GGTCGTGGAC TTGAGGACCC CCCTGGCAGT CAGAAGGAGA AGGGGGGTTT

501  ACCCAAGGAC ACCCTCATGA TCTCCCGGAC CCCTGAGGTC ACATGCGTGG
     TGGGTTCCTG TGGGAGTACT AGAGGGCCTG GGGACTCCAG TGTACGCACC

551  TGGTGGACGT GAGCCACCAA GACCCTGAGG TCAAGTTCAA CTGGTACGTG
     ACCACCTGCA CTCGGTGCTT CTGGGACTCC AGTTCAAGTT GACCATGCAC

601  GACGGCGTGG AGGTGCATAA TGCCAAGACA AAGCCGCGGG AGGAGCAGTA
     CTGCCGCACC TCCACGTATT ACGGTTCTGT TTCGGCGCCC TCCTCGTCAT

651  CAACAGCACG TACCGTGTGG TCAGCGTCCT CACCGTCCTG CACCAGGACT
     GTTGTCGTGC ATGGCACACC AGTCGCAGGA GTGGCAGGAC GTGGTCCTGA

701  GGCTGAATGG CAAGGAGTAC AAGTGCAAGG TCTCCAACAA AGCCCTCCCA
     CCGACTTACC GTTCCTCATG TTCACGTTCC AGAGGTTGTT TCGGGAGGGT

751  GCCCCCATCG AGAAAACCAT CTCCAAAGCC AAAGGGCAGC CCCGAGAACC
     CGGGGGTAGC TCTTTTGGTA GAGGTTTCGG TTTCCCGTCG GGGCTCTTGG
```

FIGURE 11A

```
801  ACAGGTGTAC ACCCTGCCCC CATCCCGGGA GGAGATGACC AAGAACCAGG
     TGTCCACATG TGGGACGGGG GTAGGGCCCT CCTCTACTGG TTCTTGGTCC

851  TCAGCCTGAC CTGCCTGGTC AAAGGCTTCT ATCCCAGCGA CATCGCCGTG
     AGTCGGACTG GACGGACCAG TTTCCGAAGA TAGGGTCGCT GTAGCGGCAC

901  GAGTGGGAGA GCAATGGGCA GCCGGAGAAC AACTACAAGA CCACGCCTCC
     CTCACCCTCT CGTTACCCGT CGGCCTCTTG TTGATGTTCT GGTGCGGAGG

951  CGTGCTGGAC TCCGACGGCT CCTTCTTCCT CTATAGCAAG CTCACCGTGG
     GCACGACCTG AGGCTGCCGA GGAAGAAGGA GATATCGTTC GAGTGGCACC

1001 ACAAGAGCAG GTGGCAGCAG GGAACGTCT TCTCATGCTC CGTGATGCAT
     TGTTCTCGTC CACCGTCGTC CCCTTGCAGA AGAGTACGAG GCACTACGTA

1051 GAGGCTCTGC ACAACCACTA CACGCAGAAG AGCCTCTCCC TGTCCCCGGG
     CTCCGAGACG TGTTGGTGAT GTGCGTCTTC TCGGAGAGGG ACAGGGGCCC

1051 TAAATGA (SEQ ID NO: 75)
     ATTTACT (SEQ ID NO: 76)
```

FIGURE 11B

```
1    MDAMKRGLCC VLLLCGAVFV SPGAAETREC IYYNANWELE RTNQSGLERC
51   EGEQDKRLHC YASWRNSSGT IELVKKGCWD DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 77)
```

FIGURE 12

1    ETRECIYYNA NWELERTNQS GLERCEGEQD KRLHCYASWR NSSGTIELVK

51   KGCWDDDFNC YDRQECVATE ENPQVYFCCC EGNFCNERFT HLPEAGGPEV

101  TYEPPPTGGG THTCPPCPAP ELLGGPSVFL FPPKPKDTLM ISRTPRVTCV

151  VVDVSHEDPE VKFNWYVDGV EVHNAKTKPR EEQYNSTYRV VSVLTVLHQD

201  WLNGKEYKCK VSNKALPAPI EKTISKAKGQ PREPQVYTLP PSREEMTKNQ

251  VSLTCLVKGF YPSDIAVEWE SNGQPENNYK TTPPVLDSDG SFFLYSKLTV

301  DKSRWQQGNV FSCSVMHEAL HNHYTQKSLS LSPGK (SEQ ID NO: 78)

FIGURE 13

```
1    ETRECIYYNA NWELERTNQS GLERCEGEQD KRLHCYASWR NSSGTIELVK

51   KGCWDDDFNC    YDRQECVATE    ENPQVYFCCC    EGNFCNERFT

101  HLPEAGGPEV TYEPPPT  (SEQ ID NO: 79)
```

FIGURE 14

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

E   T   R   E   C   I   Y   Y
 51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N   A   N   W   E   L   E   R   T   N   Q   S   G   L   E   R   C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E   G   E   Q   D   K   R   L   H   C   Y   A   S   W   R   N   S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S   G   T   I   E   L   V   K   K   G   C   W   D   D   F
201  CTCTGGCACC ATCGAGCTCG TGAAGAAGGG CTGCTGGGAC GATGACTTCA
     GAGACCGTGG TAGCTCGAGC ACTTCTTCCC GACGACCCTG CTACTGAAGT

N   C   Y   D   R   Q   E   C   V   A   T   E   E   N   P   Q   V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y   F   C   C   E   G   N   F   C   N   E   R   F   T   H   L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P   E   A   G   G   P   E   V   T   Y   E   P   P   P   T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC CTGCACCTGC CGCACCTCCA CGTATTACGG
```

FIGURE 15A

```
601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
     CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
     TTTCGGTTTC CCGTCGGGGC TCTTGGTGTC CACATGTGGG ACGGGGGTAG

801  CCGGGAGGAG ATGACCAAGA ACCAGGTCAG CCTGACCTGC CTGGTCAAAG
     GGCCCTCCTC TACTGGTTCT TGGTCCAGTC GGACTGGACG GACCAGTTTC

851  GCTTCTATCC CAGCGACATC GCCGTGGAGT GGGAGAGCAA TGGGCAGCCG
     CGAAGATAGG GTCGCTGTAG CGGCACCTCA CCCTCTCGTT ACCCGTCGGC

901  GAGAACAACT ACAAGACCAC GCCTCCCGTG CTGGACTCCG ACGGCTCCTT
     CTCTTGTTGA TGTTCTGGTG CGGAGGGCAC GACCTGAGGC TGCCGAGGAA

951  CTTCCTCTAT AGCAAGCTCA CCGTGGACAA GAGCAGGTGG CAGCAGGGGA
     GAAGGAGATA TCGTTCGAGT GGCACCTGTT CTCGTCCACC GTCGTCCCCT

1001 ACGTCTTCTC ATGCTCCGTG ATGCATGAGG CTCTGCACAA CCACTACACG
     TGCAGAAGAG TACGAGGCAC TACGTACTCC GAGACGTGTT GGTGATGTGC

1051 CAGAAGAGCC TCTCCCTGTC CCCGGGTAAA TGA (SEQ ID NO: 80)
     GTCTTCTCGG AGAGGGACAG GGGCCCATTT ACT (SEQ ID NO: 81)
```

FIGURE 15B

```
                                        E   T   R   E   C   I   Y   Y
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

51  AGTCTTCGTT TCGCCCGGCG CCGCCGAAAC CCGCGAATGT ATTTATTACA
     TCAGAAGCAA AGCGGGCCGC GGCGGCTTTG GGCGCTTACA TAAATAATGT

N  A  N  W  E  L  E  R  T  N  Q  S  G  L  E  R  C
101  ATGCTAATTG GAACTCGAA CGGACGAACC AATCCGGGCT CGAACGGTGT
     TACGATTAAC CCTTGAGCTT GCCTGCTTGG TTAGGCCCGA GCTTGCCACA

E  G  E  Q  D  K  R  L  H  C  Y  A  S  W  R  N  S
151  GAGGGGGAAC AGGATAAACG CCTCCATTGC TATGCGTCGT GGAGGAACTC
     CTCCCCCTTG TCCTATTTGC GGAGGTAACG ATACGCAGCA CCTCCTTGAG

S  G  T  I  E  L  V  K  K  G  C  W  D  D  F
201  CTCCGGGACG ATTGAACTGG TCAAGAAAGG GTGCTGGGAC GACGATTTCA
     GAGGCCCTGC TAACTTGACC AGTTCTTTCC CACGACCCTG CTGCTAAAGT

N  C  Y  D  R  Q  E  C  V  A  T  E  N  P  Q  V
251  ATTGTTATGA CCGCCAGGAA TGTGTCGCGA CCGAAGAGAA TCCGCAGGTC
     TAACAATACT GGCGGTCCTT ACACAGCGCT GGCTTCTCTT AGGCGTCCAG

Y  F  C  C  E  G  N  F  C  N  E  R  F  T  H  L
301  TATTTCTGTT GTTGCGAGGG GAATTTCTGT AATGAACGGT TTACCCACCT
     ATAAAGACAA CAACGCTCCC CTTAAAGACA TTACTTGCCA AATGGGTGGA

P  E  A  G  G  P  E  V  T  Y  E  P  P  P  T
351  CCCCGAAGCC GGCGGGCCCG AGGTGACCTA TGAACCCCCG CCCACCGGTG
     GGGGCTTCGG CCGCCCGGGC TCCACTGGAT ACTTGGGGGC GGGTGGCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA
```

FIGURE 16A

```
701   GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG

801   CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA (SEQ ID NO: 82)
      GTCTTCTCGG AGAGGACAG GGGCCCATTT ACT (SEQ ID NO: 83)
```

FIGURE 16B

GAAAC CCGCGAATGT ATTTATTACA ATGCTAATTG GGAACTCGAA CGGACGAACC

AATCCGGCT CGAACGGTGT GAGGGGGAAC AGGATAAACG CCTCCATTGC TATGCGTCGT

GGAGGAACTC CTCCGGGACG ATTGAACTGG TCAAGAAAGG GTGCTGGAC GACGATTTCA

ATTGTTATGA CCGCCAGGAA TGTGTCGCGA CCGAAGAGAA TCCGCAGGTC TATTTCTGTT

GTTGCGAGGG GAATTTCTGT AATGAACGGT TTACCCACCT CCCCGAAGCC GGCGGGCCCG

AGGTGACCTA TGAACCCCCG CCCACC  (SEQ ID NO: 84)

FIGURE 17

```
                  .        .        10        .         .        20        .         .        30        .         .        40        .         .        50
Human     : SGPRGVQALLCACTSCLQANYTCETDGACMVSIFNLDGMEHHVRTCIPKV
Mole      : SGPRGIQALLCACTSCLQANLTCETDGACMVSIFNLDGLEHHVRTCIPKV
Hedgehog  : SGPRGIQALLCACTSCLQANYTCETDGACMVSIFNLDGMEHHVRTCIPKV
Chicken   : -APGGARALTCLCSDCKQANSTCETDGACMVSIFNLDGVKHHVRTCIPEA
Mouse     : AGPRGIQALLCACTSCLQANYTCETDGACMVSIFNLDGVEHHVRTCIPKV
Pig       : SGPRGIQALLCACTSCLQANYTCETDGACMVSIFNLDGMEHHVRTCIPKV
Ras       : SGPRGIQALLCACTSCLQTNYTCETDGACMVSIFNLDGMEHHVRTCIPKV .        .        60        .         .        70        .         .        80        .         .        90        .         .       100
Human     : ELVPAGKPFYCLSSEDLRNTHCCYTDYCNRIDLRVPSGHLKEPEHPSMWG
Mole      : ELVPAGKPFYCLSSEDLRNTHCCYTDFCNKIDLRVPSGHVKEPERPSVWG
Hedgehog  : ELVPAGKPFYCLSSEDLRNTHCCYTDFCNKIDLRVPSGHPKESEQASMWG
Chicken   : KLIPAGKPFYCLSSEDLRNTHCCYSDFCNKIDLMVPSGHPKDNEPASSWG
Mouse     : ELVPAGKPFYCLSSEDLRNTHCCYIDFCNKIDLRVPSGHLKEPAHPSMWG
Pig       : ELVPAGKPFYCLSSEDLRNTHCCYTDFCNKIDLRVPSGHLKEPEHPSMWG
Ras       : ELVPAGKPFYCLSSEDLRNTHCCYIDFCNKIDLRVPSGHLKEPEHPSMWG Human     : PVE
Mole      : PVE
Hedgehog  : PVE
Chicken   : PVE
Mouse     : PVE
Pig       : PVE
Ras       : PVE
```

FIGURE 18

COMPOSITIONS AND METHODS FOR TREATING PULMONARY HYPERTENSION

CROSS-REFERENCE TO RELATED APPLICATIONS

This application is a continuation of U.S. application Ser. No. 17/339,606, filed Jun. 4, 2021 (now U.S. Pat. No. 11,497,794), which is a continuation of U.S. application Ser. No. 17/002,542, filed Aug. 25, 2020 (now U.S. Pat. No. 11,065,303), which is a continuation of U.S. application Ser. No. 16/829,642, filed Mar. 25, 2020 (now pending), which is a continuation of U.S. application Ser. No. 15/945,565, filed Apr. 4, 2018 (now U.S. Pat. No. 10,695,405), which is a continuation of U.S. application Ser. No. 15/650,420, filed Jul. 14, 2017 (now U.S. Pat. No. 10,722,558), which claims the benefit of priority to U.S. provisional application Ser. No. 62/362,955, filed on Jul. 15, 2016; 62/453,888, filed on Feb. 2, 2017; and 62/510,403, filed on May 24, 2017. The specifications of each of the foregoing applications are hereby incorporated by reference in their entirety.

SEQUENCE LISTING

The instant application contains a Sequence Listing which has been submitted electronically in XML format and is hereby incorporated by reference in its entirety. Said XML copy, created on Feb. 9, 2023, is named 1848179-114-111.XML and is 182,881 bytes in size.

BACKGROUND OF THE INVENTION

Pulmonary hypertension (PH) is a disease characterized by high blood pressure in lung vasculature, including pulmonary arteries, pulmonary veins, and pulmonary capillaries. In general, PH is defined as a mean pulmonary arterial (PA) pressure 25 mm Hg at rest or 30 mm Hg with exercise [Hill et al., Respiratory Care 54(7):958-68 (2009)]. The main PH symptom is difficulty in breathing or shortness of breath, and other symptoms include fatigue, dizziness, fainting, peripheral edema (swelling in foot, legs or ankles), bluish lips and skin, chest pain, angina pectoris, lightheadedness during exercise, non-productive cough, racing pulse and palpitations. PH can be a severe disease causing heart failure, which is one of the most common causes of death in people who have pulmonary hypertension. Postoperative pulmonary hypertension may complicate many types of surgeries or procedures, and present a challenge associated with a high mortality.

PH may be grouped based on different manifestations of the disease sharing similarities in pathophysiologic mechanisms, clinical presentation, and therapeutic approaches [Simonneau et al., JACC 54(1):S44-54 (2009)]. Clinical classification of PH was first proposed in 1973, and a recent updated clinical classification was endorsed by the World Health Organization (WHO) in 2008. According to the updated PH clinical classification, there are five main groups of PH: pulmonary arterial hypertension (PAH), characterized by a PA wedge pressure ≤15 mm Hg; PH owing to a left heart disease (also known as pulmonary venous hypertension or congestive heart failure), characterized by a PA wedge pressure >15 mm Hg; PH owing to lung diseases and/or hypoxia; chronic thromboemboli PH; and PH with unclear or multifactorial etiologies [Simonneau et al., JACC 54(1):S44-54 (2009); Hill et al., Respiratory Care 54(7): 958-68 (2009)]. PAH is further classified into idiopathic PAH (IPAH), a sporadic disease in which there is neither a family history of PAH nor an identified risk factor; heritable PAH; PAH induced by drugs and toxins; PAH associated with connective tissue diseases, HIV infection, portal hypertension, congenital heart diseases, schistosomiasis, and chronic hemolytic anemia; and persistent PH of newborns [Simonneau et al., JACC 54(1):S44-54 (2009)]. Diagnosis of various types of PH requires a series of tests.

In general, PH treatment depends on the cause or classification of the PH. Where PH is caused by a known medicine or medical condition, it is known as a secondary PH, and its treatment is usually directed at the underlying disease. Treatment of pulmonary venous hypertension generally involves optimizing left ventricular function by administering diuretics, beta blockers, and ACE inhibitors, or repairing or replacing a mitral valve or aortic valve. PAH therapies include pulmonary vasodilators, digoxin, diuretics, anticoagulants, and oxygen therapy. Pulmonary vasodilators target different pathways, including prostacyclin pathway (e.g., prostacyclins, including intravenous epoprostenol, subcutaneous or intravenous treprostinil, and inhaled iloprost), nitric oxide pathway (e.g., phosphodiesterase-5 inhibitors, including sildenafil and tadalafil), and endotheline-1 pathway (e.g., endothelin receptor antagonists, including oral bosentan and oral ambrisentan) [Humbert, M. Am. J. Respir. Crit. Care Med. 179:650-6 (2009); Hill et al., Respiratory Care 54(7): 958-68 (2009)]. However, current therapies provide no cure for PH, and they do not directly treat the underling vascular remodeling and muscularization of blood vessels observed in many PH patients.

Thus, there is a high, unmet need for effective therapies for treating pulmonary hypertension. Accordingly, it is an object of the present disclosure to provide methods for treating, preventing, or reducing the progression rate and/or severity of PH, particular treating, preventing or reducing the progression rate and/or severity of one or more PH-associated complications.

SUMMARY OF THE INVENTION

In part, the data presented herein demonstrates that GDF/BMP antagonists (inhibitors) can be used to treat pulmonary hypertension. For example, it was shown that a soluble ActRIIA polypeptide and an ALK4:ActRIIB heterodimer can be used, individually, to reduce blood pressure, cardiac hypertrophy, and lung weight in a monocrotaline-induced pulmonary arterial hypertension (PAH) model. Similar positive effects were observed for the ActRIIA polypeptide in the Sugen hypoxia PAH model. Histological analysis further revealed that the ActRIIA polypeptide had surprising and significant effects on decreasing vascular remodeling and muscularization of blood vessels in both the monocrotaline-induced and Sugen hypoxia models of PAH. Moreover, both the ActRIIA polypeptide and ALK4:ActRIIB heterodimer surprisingly had a greater effect on ameliorating various complications of PAH compared to sildenafil, which is a drug approved for the treatment of PAH. Thus, the disclosure establishes that antagonists of the ActRII (ActRIIA and ActRIIB) signaling pathways may be used to reduce the severity of pulmonary hypertension. While soluble ActRIIa polypeptides and ALK4:ActRIIB heteromultimers may affect pulmonary hypertension through a mechanism other than ActRIIA/B ligand antagonisms, the disclosure nonetheless demonstrates that desirable therapeutic agents may be selected on the basis of ActRII signaling antagonist activity. Therefore, in some embodiments, the disclosure provides methods for using various ActRII signaling antagonists for treating hypertension, particularly pulmonary hypertension, including, for example, antagonists that inhibit one or more ActRIIA/B ligands [e.g., activin (activin A, activin B, activin AB, activin C, activin AC, activin BC, activin E, activin AE, and/or activin BE), GDF8, GDF11, GDF3, BMP6, BMP15, and BMP10]; antagonists that inhibit of one or more type I and/or type II receptors (e.g., ActRIIA, ActRIIB, ALK4, ALK7, and ALK5); and antagonists that inhibit one or more downstream signaling components (e.g., Smad proteins such as Smads 2 and 3). As used herein, such signaling antagonists are collectively referred to as "GDF/BMP antagonists" or "GDF/BMP inhibitors". Accordingly, the disclosure provides, in part, GDF/BMP antagonist compositions and methods for treating pulmonary hypertension (e.g., PAH), particularly treating one or more complications of pulmonary hypertension (e.g., elevated blood pressure, cardiac hypertrophy, vascular remodeling, and muscularization of vessels). GDF/BMP antagonists to be used in accordance with the methods and uses of the disclosure include, for example, ligand traps (e.g., soluble ActRIIA polypeptides, ActRIIB polypeptides, ALK4:ActRIIB heterodimers, follistatin polypeptides, and FLRG polypeptides), antibody antagonists, small molecule antagonists, and nucleotide antagonists. Optionally, GDF/BMP antagonists may be used in combination with one or more supportive therapies and/or additional active agents for treating pulmonary hypertension.

In certain aspects, the disclosure relates to methods of treating pulmonary arterial hypertension comprising administering to a patient in need thereof an effective amount of an ActRIIA polypeptide. In some embodiments, the ActRIIA polypeptide comprises an amino acid sequence that is at least 70% (e.g., at least 70%, 75%, 80%, 85%, 86%, 87%, 88%, 89%, 90%, 91%, 92%, 93%, 94%, 95%, 96%, 97%, 98%, 99%, or 100%) identical to an amino acid sequence that begins at any one of amino acids 21, 22, 23, 24, 25, 26, 27, 28, 29, or 30 of SEQ ID NO: 9 and ends at any one of amino acids 110, 111, 112, 113, 114, 115, 116, 117, 118, 119, 120, 121, 122, 123, 124, 125, 126, 127, 128, 129, 130, 131, 132, 133, 134, or 135 of SEQ ID NO: 9. In some embodiments, the ActRIIA polypeptide comprises an amino acid sequence that is at least 70% (e.g., at least 70%, 75%, 80%, 85%, 86%, 87%, 88%, 89%, 90%, 91%, 92%, 93%, 94%, 95%, 96%, 97%, 98%, 99%, or 100%) identical to the amino acid sequence of SEQ ID NO: 10. In some embodiments, the ActRIIA polypeptide comprises an amino acid sequence that is at least 70% (e.g., at least 70%, 75%, 80%, 85%, 86%, 87%, 88%, 89%, 90%, 91%, 92%, 93%, 94%, 95%, 96%, 97%, 98%, 99%, or 100%) identical to the amino acid sequence of SEQ ID NO: 11. In some embodiments, the ActRIIA polypeptide is a fusion protein comprising an ActRIIA domain and one or more polypeptide domains heterologous to ActRIIA. In some embodiments, the ActRIIA polypeptide is a fusion protein comprising an Fc domain of an immunoglobulin. In some embodiments, the Fc domain of the immunoglobulin is an Fc domain of an IgG1 immunoglobulin. In some embodiments, the ActRIIA fusion protein further comprises a linker domain positioned between the ActRIIA polypeptide domain and the one or more heterologous domains (e.g., an Fc immunoglobulin domain). In some embodiments, the linker domain is selected from the group consisting of: TGGG (SEQ ID NO: 23), TGGGG (SEQ ID NO: 21), SGGGG (SEQ ID NO: 22), GGGGS (SEQ ID NO: 25), GGG (SEQ ID NO: 19), GGGG (SEQ ID NO: 20), and SGGG (SEQ ID NO: 24). In some embodiments, the ActRIIA polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 32. In some embodiments, the ActRIIA polypeptide comprises the amino acid sequence of SEQ ID NO: 32. In some embodiments, the ActRIIA polypeptide consists of the amino acid sequence of SEQ ID NO: 32. In some embodiments, the ActRIIA polypeptide is part of a homodimer protein complex. In some embodiments, the ActRIIA polypeptide is glycosylated. In some embodiments, the ActRIIA polypeptide has a glycosylation pattern obtainable by expression in a Chinese hamster ovary cell. In some embodiments, administration of the ActRIIA polypeptide decreases pulmonary arterial pressure in the patient. In some embodiments, administration of the ActRIIA polypeptide decreases pulmonary arterial pressure in the patient by at least 10% (e.g., 10%, 15%, 20%, 25%, 30%, 35%, 40%, 45%, 50%, 55%, 60%, 65%, 70%, 75%, or at least 80%). In some embodiments, administration of the ActRIIA polypeptide decreases ventricle hypertrophy in the patient. In some embodiments, administration of the ActRIIA polypeptide decreases ventricle hypertrophy in the patient by at least 10% (e.g., 10%, 15%, 20%, 25%, 30%, 35%, 40%, 45%, 50%, 55%, 60%, 65%, 70%, 75%, or at least 80%). In some embodiments, administration of the ActRIIA polypeptide decreases smooth muscle hypertrophy in the patient. In some embodiments, administration of the ActRIIA polypeptide decreases smooth muscle hypertrophy in the patient by at least 10% (e.g., 10%, 15%, 20%, 25%, 30%, 35%, 40%, 45%, 50%, 55%, 60%, 65%, 70%, 75%, or at least 80%). In some embodiments, administration of the ActRIIA polypeptide decreases pulmonary arteriole muscularity in the patient. In some embodiments, administration of the ActRIIA polypeptide decreases pulmonary arteriole muscularity in the patient by at least 10% (e.g., 10%, 15%, 20%, 25%, 30%, 35%, 40%, 45%, 50%, 55%, 60%, 65%, 70%, 75%, or at least 80%). In some embodiments, administration of the ActRIIA polypeptide decreases pulmonary vascular resistance in the patient. In some embodiments, administration of the ActRIIA polypeptide decreases pulmonary vascular resistance in the patient by at least 10% (e.g., 10%, 15%, 20%, 25%, 30%, 35%, 40%, 45%, 50%, 55%, 60%, 65%, 70%, 75%, or at least 80%). In some embodiments, administration of the ActRIIA polypeptide decreases pulmonary vascular resistance in the patient by at least 25-30%. In some embodiments, the patient has pulmonary arterial hypertension and has Functional Class II or Class III pulmonary hypertension in accordance with the World Health Organization's functional classification system for pulmonary hypertension. In some embodiments, the patient has pulmonary arterial hypertension that is classified as one or more subtypes selected from the group consisting of: idiopathic or heritable pulmonary arterial hypertension, drug- and/or toxin-induced pulmonary hypertension, pulmonary hypertension associated with connective tissue disease, and pulmonary hypertension associated with congenital systemic-to-pulmonary shunts at least 1 year following shunt repair. In some embodiments, the patient has been treated with one or more vasodilators. In some embodiments, the patient has been treated with one or more agents selected from the group consisting of: phosphodiesterase type 5 inhibitors, soluble guanylate cyclase stimulators, prostacyclin receptor agonist, and endothelin receptor antagonists. In some embodiments, the one or more agents is selected from the group consisting of: bosentan, sildenafil, beraprost, macitentan, selexipag, epoprostenol, treprostinil, iloprost, ambrisentan, and tadalafil. In some embodiments, the method further comprises administration of one or more vasodilators. In some embodiments, the method further comprises administration of one or more agents selected from the group consisting of: phosphodiesterase type 5 inhibitors, soluble guanylate cyclase stimulators, prostacyclin receptor agonist, and endothelin receptor antagonists. In some embodiments, the one or more agents is selected from the group consisting of: bosentan, sildenafil, beraprost, macitentan, selexipag, epoprostenol, treprostinil, iloprost, ambrisentan, and tadalafil. In some embodiments, the patient has a 6-minute walk distance from 150 to 400 meters. In some embodiments, the method increases the patient's 6-minute walk distance by at least 10 meters (e.g., at least 10, 20, 30, 40, 50, 60, 70, 80, 90, 100, 125, 150, 175, 200, 250, 300, or more than 400 meters). In some embodiments, the patient has a hemoglobin level from >8 and <15 g/dl. In some embodiments, the method delays clinical worsening of pulmonary arterial hypertension. In some embodiments, the method delays clinical worsening of pulmonary hypertension in accordance with the World Health Organization's functional classification system for pulmonary hypertension. In some embodiments, the method reduces the risk of hospitalization for one or more complications associated with pulmonary arterial hypertension. In some embodiments, the ActRIIA polypeptides binds to one or more ligands selected from the group consisting of: activin A, activin B, GDF11, GDF8, BMP10, and BMP6.

In some embodiments, the present disclosure relates to methods of treating pulmonary hypertension comprising administering to a patient in need thereof an effective amount of a GDF/BMP antagonist, or combination of GDF/BMP antagonists. In certain aspects, the disclosure relates to methods of preventing pulmonary hypertension comprising administering to a patient in need thereof an effective amount of a GDF/BMP antagonist, or combination of GDF/BMP antagonists. In certain aspects, the disclosure relates to methods of reducing the progression rate of pulmonary hypertension comprising administering to a patient in need thereof an effective amount of a GDF/BMP antagonist, or combination of GDF/BMP antagonists. In some embodiments, the disclosure provides for a method of treating an interstitial lung disease, comprising administering to a patient in need thereof an effective amount of a GDF/BMP antagonist, wherein the GDF/BMP antagonist inhibits one or more of activin, GDF8, GDF11, GDF3, BMP6, BMP15, BMP10, ActRIIA, ActRIIB, ALK4, ALK5, and ALK7. In some embodiments, the disclosure provides for a method of treating, preventing, or reducing the progression rate and/or severity of one or more complications of an interstitial lung disease, comprising administering to a patient in need thereof an effective amount of a GDF/BMP antagonist, wherein the GDF/BMP antagonist inhibits one or more of activin, GDF8, GDF11, GDF3, BMP6, BMP15, BMP10, ActRIIA, ActRIIB, ALK4, ALK5, and ALK7. In some embodiments, the interstitial lung disease is idiopathic pulmonary fibrosis. In certain aspects, the disclosure relates to methods of reducing the severity of pulmonary hypertension comprising administering to a patient in need thereof an effective amount of a GDF/BMP antagonist, or combination of GDF/BMP antagonists. In certain aspects, the disclosure relates to methods of treating one or more complications (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) of pulmonary hypertension comprising administering to a patient in need thereof an effective amount of a GDF/BMP antagonist, or combination of GDF/BMP antagonists. In certain aspects, the disclosure relates to methods of preventing one or more complication of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount a GDF/BMP antagonist, or combination of GDF/BMP antagonists. In certain aspects, the disclosure relates to methods of reducing the progression rate of one or more complication of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount a GDF/BMP antagonist, or combination of GDF/BMP antagonists. In certain aspects, the disclosure relates to methods of reducing the severity of one or more complication of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount of a GDF/BMP antagonist, or combination of GDF/BMP antagonists. In certain preferred embodiments, methods described herein relate to a patient having pulmonary arterial hypertension. In some embodiments, methods described herein relate to a patient having a resting pulmonary arterial pressure (PAP) of at least 25 mm Hg (e.g., at least 25, 30, 35, 40, 45, or 50 mm Hg). In some embodiments, the methods described herein reduce PAP in a patient having pulmonary hypertension. For example, the method may reduce PAP by at least 3 mmHg (e.g., at least 3, 5, 7, 10, 12, 15, 20, or 25 mm Hg) in a patient having pulmonary hypertension. In some embodiments, the methods described herein reduce pulmonary vascular resistance in a patient having pulmonary hypertension. In some embodiments, the methods described herein increase pulmonary capillary wedge pressure in a patient having pulmonary hypertension. In some embodiments, the methods described herein increase left ventricular end-diastolic pressure in a patient having pulmonary hypertension. In some embodiments, the methods described herein increase (improves) exercise capacity (ability, tolerance) in a patient having pulmonary hypertension. For example, the method may increase 6-minute walk distance in a patient having pulmonary hypertension, optionally increasing 6-minute walk distance by at least 10 meters (e.g., at least 10, 20, 30, 40, 50, 60, 70, 80, 90, 100 or more meters). In addition, the method may reduce the patient's Borg dyspnea index (BDI), which optionally may be assessed after a 6-minute walk test. In some embodiments, the method reduces the patient's Borg dyspnea index (BDI) by at least 0.5 index points (e.g., at least 0.5, 1, 1.5, 2, 2.5, 3, 3.5, 4, 4.5, 5, 5.5, 6, 6.5, 7, 7.5, 8, 8.5, 9, 9.5, or 10 index points). In some embodiments, the methods described herein relate to a patient having Class I, Class II, Class III, or Class IV pulmonary hypertension as recognized by the World Health Organization. In some embodiments, the methods described herein relate to delaying clinical progression (worsening) of pulmonary hypertension (e.g., progression as measured by the World Health Organization standard). In some embodiments, the method prevents or delays pulmonary hypertension Class progression (e.g., prevents or delays progression from Class I to Class II, Class II to Class III, or Class III to Class IV pulmonary hypertension as recognized by the World Health Organization). In some embodiments, the method promotes or increases pulmonary hypertension Class regression (e.g., promotes or increases regression from Class IV to Class III, Class III to Class II, or Class II to Class I pulmonary hypertension as recognized by the World Health Organization). In some embodiments, the patient is further administered one or more supportive therapies or active agents for treating pulmonary hypertension in addition to the one or more GDF/BMP antagonist. For example, the patient also may be administered one or more supportive therapies or active agents selected from the group consisting of: prostacyclin and derivatives thereof (e.g., epoprostenol, treprostinil, and iloprost); prostacyclin receptor agonists (e.g., selexipag); endothelin receptor antagonists (e.g., thelin, ambrisentan, macitentan, and bosentan); calcium channel blockers (e.g., amlodipine, diltiazem, and nifedipine; anticoagulants (e.g., warfarin); diuretics; oxygen therapy; atrial septostomy; pulmonary thromboendarterectomy; phosphodiesterase type 5 inhibitors (e.g., sildenafil and tadalafil); activators of soluble guanylate cyclase (e.g., cinaciguat and riociguat); ASK-1 inhibitors (e.g., CIIA; SCH79797; GS-4997; MSC2032964A; 3H-naphtho[1,2,3-de]quiniline-2,7-diones, NQDI-1; 2-thioxo-thiazolidines, 5-bromo-3-(4-oxo-2-thioxo-thiazolidine-5-ylidene)-1,3-dihydro-indol-2-one); NF-κB antagonists (e.g., dh404, CDDO-epoxide; 2.2-difluoropropionamide; C28 imidazole (CDDO-Im); 2-cyano-3,12-dioxoolean-1,9-dien-28-oic acid (CDDO); 3-Acetyloleanolic Acid; 3-Triflouroacetyloleanolic Acid; 28-Methyl-3-acetyloleanane; 28-Methyl trifluoroacetyloleanane; 28-Methyloxyoleanolic Acid; SZC014; SCZ015; SZC017; PEGylated derivatives of oleanolic acid; 3-O-(beta-D-glucopyranosyl) oleanolic acid; 3-O-[beta-D-glucopyranosyl-(1→3)-beta-D-glucopyranosyl] oleanolic acid; 3-O-[beta-D-glucopyranosyl-(1→2)-beta-D-glucopyranosyl] oleanolic acid; 3-O-[beta-D-glucopyranosyl-(1→3)-beta-D-glucopyranosyl] oleanolic acid 28-O-beta-D-glucopyranosyl ester; 3-O-[beta-D-glucopyranosyl-(1→2)-beta-D-glucopyranosyl] oleanolic acid 28-O-beta-D-glucopyranosyl ester; 3-O-[a-L-rhamnopyranosyl-(1→3)-beta-D-glucuronopyranosyl] oleanolic acid; 3-O-[alpha-L-rhamnopyranosyl-(1→3)-beta-D-glucuronopyranosyl] oleanolic acid 28-O-beta-D-glucopyranosyl ester; 28-O-β-D-glucopyranosyl-oleanolic acid; 3-O-β-D-glucopyranosyl (1→3)-3-D-glucopyranosiduronic acid (CS1); oleanolic acid 3-O-β-D-glucopyranosyl (1→3)-β-D-glucopyranosiduronic acid (CS2); methyl 3,11-dioxoolean-12-en-28-olate (DIOXOL); ZCVI$_4$-2; Benzyl 3-dehydr-oxy-1,2,5-oxadiazolo[3',4':2,3]oleanolate) lung and/or heart transplantation. In some embodiment, the patient may also be administered a BMP9 polypeptide. In some embodiments the BMP9 polypeptide is a mature BMP9 polypeptide. In some embodiments, the BMP9 polypeptide comprises a BMP9 prodomain polypeptide. In some embodiments, the BMP9 polypeptide is administered in a pharmaceutical preparation, which optionally may comprise a BMP9 prodomain polypeptide. In such BMP9 pharmaceutical preparations comprising a BMP9 prodomain polypeptide, the BMP9 polypeptide may be noncovalently associated with the BMP9 prodomain polypeptide. In some embodiments, BMP9 pharmaceutical preparations are substantially free, or does not comprise, of BMP9 prodomain polypeptide. In some embodiments, the patient may also be administered oleanolic acid or a derivative thereof.

In certain aspects, a GDF/BMP antagonist, or combination of antagonists, to be used in accordance with methods and uses described herein is an agent that inhibits at least GDF11 (e.g., a GDF11 antagonist). Effects on GDF11 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least GDF11. Ligand binding activity may be determined, for example, using a binding affinity assay including those described herein. In some embodiments, a GDF/BMP antagonist, or combination of antagonists, of the disclosure binds to at least GDF11 with a $K_D$ of at least $1\times10^{-7}$M (e.g., at least $1\times10^{-8}$ M, at least $1\times10^{-9}$M, at least $1\times10^{-10}$ M, at least $1\times10^{-11}$ M, or at least $1\times10^{-12}$M). As described herein, various GDF/BMP antagonists that inhibit GDF11 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits GDF11 may further inhibit one or more of: activin (e.g., activin A, activin B, activin AB, activin C, activin AC, activin BC, activin E, activin AE, and/or activin BE), GDF8, GDF3, BMP6, BMP15, BMP10, ActRIIA, ActRIIB, ALK4, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least GDF8 (e.g., a GDF8 antagonist). Effects on GDF8 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least GDF8. Ligand binding activity may be determined, for example, using a binding affinity assay including those described herein. In some embodiments, a GDF/BMP antagonist, or combination of antagonists, of the disclosure binds to at least GDF8 with a $K_D$ of at least $1\times10^{-7}$M (e.g., at least $1\times10^{-8}$M, at least $1\times10^{-9}$M, at least $1\times10^{-10}$ M, at least $1\times10^{-11}$ M, or at least $1\times10^{-12}$M). As described herein, various GDF/BMP antagonists that inhibit GDF8 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits GDF8 may further inhibit one or more of: activin (e.g., activin A, activin B, activin AB, activin C, activin AC, activin BC, activin E, activin AE, and/or activin BE), GDF11, GDF3, BMP6, BMP15, BMP10, ActRIIA, ActRIIB, ALK4, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least GDF3 (e.g., a GDF3 antagonist). Effects on GDF3 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least GDF3. Ligand binding activity may be determined, for example, using a binding affinity assay including those described herein. In some embodiments, a GDF/BMP antagonist, or combination of antagonists, of the disclosure binds to at least GDF3 with a $K_D$ of at least $1\times10^{-7}$M (e.g., at least $1\times10^{-8}$M, at least $1\times10^{-9}$ M, at least $1\times10^{-10}$ M, at least $1\times10^{-11}$ M, or at least $1\times10^{-12}$ M). As described herein, various GDF/BMP antagonists that inhibit GDF3 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits GDF3 may further inhibit one or more of: activin (e.g., activin A, activin B, activin AB, activin C, activin AC, activin BC, activin E, activin AE, and/or activin BE), GDF8, GDF11, BMP6, BMP15, BMP10, ActRIIA, ActRIIB, ALK4, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least BMP6 (e.g., a BMP6 antagonist). Effects on BMP6 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least BMP6. Ligand binding activity may be determined, for example, using a binding affinity assay including those described herein. In some embodiments, a GDF/BMP antagonist, or combination of antagonists, of the disclosure binds to at least BMP6 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various GDF/BMP antagonists that inhibit BMP6 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits BMP6 may further inhibit one or more of: activin (e.g., activin A, activin B, activin AB, activin C, activin AC, activin BC, activin E, activin AE, and/or activin BE), GDF8, GDF3, GDF11, BMP15, BMP10, ActRIIA, ActRIIB, ALK4, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least BMP15 (e.g., a BMP15 antagonist). Effects on BMP15 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least BMP15. Ligand binding activity may be determined, for example, using a binding affinity assay including those described herein. In some embodiments, a GDF/BMP antagonist, or combination of antagonists, of the disclosure binds to at least BMP15 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various GDF/BMP antagonists that inhibit BMP15 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits BMP15 may further inhibit one or more of: activin (e.g., activin A, activin B, activin AB, activin C, activin AC, activin BC, activin E, activin AE, and/or activin BE), GDF8, GDF3, GDF11, BMP6, BMP10, ActRIIA, ActRIIB, ALK4, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least BMP10 (e.g., a BMP10 antagonist). Effects on BMP10 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least BMP10. Ligand binding activity may be determined, for example, using a binding affinity assay including those described herein. In some embodiments, a GDF/BMP antagonist, or combination of antagonists, of the disclosure binds to at least BMP10 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various GDF/BMP antagonists that inhibit BMP10 can be used in accordance with the methods and uses described herein including, for example, ligand traps (e.g., ActRII polypeptides, GDF Traps, follistatin polypeptides, and FLRG polypeptides, and ALK4:ActRIIB heteromultimers FLRG polypeptides), antibodies, small molecules, nucleotide sequences, and combinations thereof. In certain embodiments, a GDF/BMP antagonist, or combination of antagonists, that inhibits BMP10 may further inhibit one or more of: activin (e.g., activin A, activin B, activin AB, activin C, activin AC, activin BC, activin E, activin AE, and/or activin BE), GDF8, GDF3, GDF11, BMP6, BMP15, ActRIIA, ActRIIB, ALK4, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least activin (e.g., activin A, activin B, activin AB, activin C, activin AC, activin BC, activin E, activin AE, and/or activin BE) (e.g., an activin antagonist). Effects on activin inhibition may be determined, for example, using a cell-based assay including those described herein (e.g., a Smad signaling reporter assay). Therefore, in some embodiments, a GDF/BMP antagonist, or combination of antagonists, of the disclosure may bind to at least activin. Ligand binding activity may be determined, for example, using a binding affinity assay including those described herein. In some embodiments, a GDF/BMP antagonist, or combination of antagonists, of the disclosure binds to at least activin with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various GDF/BMP antagonists that inhibit activin can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits activin may further inhibit one or more of: BMP15 GDF8, GDF3, GDF11, BMP6, BMP10, ActRIIA, ActRIIB, ALK4, ALK5, ALK7, and one or more Smads (e.g., Smads 2 and 3). In certain preferred embodiments, a GDF/BMP antagonist, or combination of antagonists, to be used in accordance with methods and uses described herein is an agent that inhibits at least activin B. In some embodiments, a GDF/BMP antagonist, or combination of antagonists, to be used in accordance with methods and uses described herein does not substantially bind to activin A (e.g., binds to activin A with a $K_D$ higher than $1\times10^{-7}$ M or has relatively modest binding, e.g., about $1\times10^{-8}$M or about $1\times10^{-9}$ M) and/or inhibit activin A activity. In certain preferred embodiments, a GDF/BMP antagonist, or combination of antagonists, to be used in accordance with methods and uses described herein is an agent that inhibits at least activin B but does not substantially bind to activin A (e.g., binds to activin A with a $K_D$ higher than $1\times10^{-7}$ M or has relatively modest binding, e.g., about $1\times10^{-8}$ M or about $1\times10^{-9}$M) and/or inhibit activin A activity.

In certain aspects, a GDF/BMP antagonist, or combination of antagonists, to be used in accordance with methods and uses described herein is an agent that inhibits at least ActRII (e.g., ActRIIA and/or ActRIIB) (e.g., an ActRII antagonist). Effects on ActRII inhibition may be determined, for example, using a cell-based assay including those described herein (e.g., a Smad signaling reporter assay). Therefore, in some embodiments, a GDF/BMP antagonist, or combination of antagonists, of the disclosure may bind to at least ActRII. Ligand binding activity may be determined, for example, using a binding affinity assay including those described herein. In some embodiments, a GDF/BMP antagonist, or combination of antagonists, of the disclosure binds to at least ActRII with a $K_D$ of at least $1\times10^{-7}$ M (e.g., at least $1\times10^{-8}$M, at least $1\times10^{-9}$M, at least $1\times10^{-10}$ M, at least $1\times10^{-11}$M, or at least $1\times10^{-12}$ M). As described herein, various GDF/BMP antagonists that inhibit ActRII can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits ActRII may further inhibit one or more of: activin (e.g., activin A, activin B, activin AB, activin C, activin AC, activin BC, activin E, activin AE, and/or activin BE), GDF8, GDF3, GDF11, BMP6, BMP15, BMP10, ALK4, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least ALK4 (e.g., an ALK4 antagonist). Effects on ALK4 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least ALK4. Ligand binding activity may be determined, for example, using a binding affinity assay including those described herein. In some embodiments, a GDF/BMP antagonist, or combination of antagonists, of the disclosure binds to at least ALK4 with a $K_D$ of at least $1\times10^{-7}$M (e.g., at least $1\times10^{-8}$M, at least $1\times10^{-9}$M, at least $1\times10^{-10}$ M, at least $1\times10^{-11}$ M, or at least $1\times10^{-12}$M). As described herein, various GDF/BMP antagonists that inhibit ALK4 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits ALK4 may further inhibit one or more of: activin (e.g., activin A, activin B, activin AB, activin C, activin AC, activin BC, activin E, activin AE, and/or activin BE), GDF8, GDF3, GDF11, BMP6, BMP15, BMP10, ActRIIA, ActRIIB, ALK5, ALK7, and one or more Smads (e.g., Smads 2 and 3).

In certain aspects, a GDF/BMP antagonist, or combination of antagonists, to be used in accordance with methods and uses described herein is an agent that inhibits at least ALK5 (e.g., an ALK5 antagonist). Effects on ALK5 inhibition may be determined, for example, using a cell-based assay including those described herein (e.g., a Smad signaling reporter assay). Therefore, in some embodiments, a GDF/BMP antagonists, or combination of antagonist, of the disclosure may bind to at least ALK5. Ligand binding activity may be determined, for example, using a binding affinity assay including those described herein. In some embodiments, a GDF/BMP antagonist, or combination of antagonists, of the disclosure binds to at least ALK5 with a $K_D$ of at least $1\times10^{-7}$M (e.g., at least $1\times10^{-8}$M, at least $1\times10^{-9}$M, at least $1\times10^{-10}$ M, at least $1\times10^{-11}$ M, or at least $1\times10^{-12}$M). As described herein, various GDF/BMP antagonists that inhibit ALK5 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits ALK5 may further inhibit one or more of: activin (e.g., activin A, activin B, activin AB, activin C, activin AC, activin BC, activin E, activin AE, and/or activin BE), GDF8, GDF3, GDF11, BMP6, BMP15, BMP10, ActRIIA, ActRIIB, ALK7, ALK4, and one or more Smads (e.g., Smads 2 and 3)

In certain aspects, a GDF/BMP antagonist, or combination of antagonists, to be used in accordance with methods and uses described herein is an agent that inhibits at least ALK7 (e.g., an ALK7 antagonist). Effects on ALK7 inhibition may be determined, for example, using a cell-based assay including those described herein (e.g., a Smad signaling reporter assay). Therefore, in some embodiments, a GDF/BMP antagonist, or combination of antagonists, of the disclosure may bind to at least ALK7. Ligand binding activity may be determined, for example, using a binding affinity assay including those described herein. In some embodiments, a GDF/BMP antagonist, or combination of antagonists, of the disclosure binds to at least ALK7 with a $K_D$ of at least $1\times10^{-7}$ M (e.g., at least $1\times10^{-8}$M, at least $1\times10^{-9}$M, at least $1\times10^{-10}$ M, at least $1\times10^{-11}$ M, or at least $1\times10^{-12}$ M). As described herein, various GDF/BMP antagonists that inhibit ALK7 can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits ALK7 may further inhibit one or more of: activin (e.g., activin A, activin B, activin AB, activin C, activin AC, activin BC, activin E, activin AE, and/or activin BE), GDF8, GDF3, GDF11, BMP6, BMP15, BMP10, ActRIIA, ActRIIB, ALK5, ALK4, and one or more Smads (e.g., Smads 2 and 3).

In certain aspects, a GDF/BMP antagonist, or combination of antagonists, to be used in accordance with methods and uses described herein is an agent that inhibits at least one or more Smad proteins (e.g., Smads 2 and 3). Effects on Smad inhibition may be determined, for example, using a cell-based assay including those described herein (e.g., a Smad signaling reporter assay). Therefore, in some embodiments, a GDF/BMP antagonist, or combination of antagonists, of the disclosure may bind to at least one or more one or more Smad proteins (e.g., Smads 2 and 3). Ligand binding activity may be determined, for example, using a binding affinity assay including those described herein. In some embodiments, a GDF/BMP antagonist, or combination of antagonists, of the disclosure binds to at least one or more Smad proteins (e.g., Smads 2 and 3) with a $K_D$ of at least $1\times10^{-7}$ M (e.g., at least $1\times10^{-8}$ M, at least $1\times10^{-9}$M, at least $1\times10^{-10}$ M, at least $1\times10^{-11}$M, or at least $1\times10^{-12}$ M). As described herein, various GDF/BMP antagonists that inhibit one or more Smad proteins (e.g., Smads 2 and 3) can be used in accordance with the methods and uses described herein including, for example, ligand traps (e.g., ActRII polypeptides, GDF Traps, follistatin polypeptides, FLRG polypeptides, and ALK4:ActRIIB heteromultimers), antibodies, small molecules, nucleotide sequences, and combinations thereof. In certain embodiments, a GDF/BMP antagonist, or combination of antagonists, that inhibits one or more Smad proteins (e.g., Smads 2 and 3) may further inhibit one or more of: activin (e.g., activin A, activin B, activin AB, activin C, activin AC, activin BC, activin E, activin AE, and/or activin BE), GDF8, GDF3, GDF11, BMP6, BMP15, BMP10, ActRIIA, ActRIIB, ALK5, and ALK4.

In certain aspects, a GDF/BMP antagonist to be used in accordance with methods and uses described herein is an ActRII polypeptide. The term "ActRII polypeptide" collectively refers to naturally occurring ActRIIA and ActRIIB polypeptides as well as truncations and variants thereof such as those described herein (e.g., GDF trap polypeptides). Preferably ActRII polypeptides comprise, consist essentially of, or consist of a ligand-binding domain of an ActRII polypeptide or modified (variant) form thereof. For example, in some embodiments, an ActRIIA polypeptide comprises, consists essentially of, or consists of an ActRIIA ligand-binding domain of an ActRIIA polypeptide, for example, a portion of the ActRIIA extracellular domain. Similarly, an ActRIIB polypeptide may comprise, consist essentially of, or consist of an ActRIIB ligand-binding domain of an ActRIIB polypeptide, for example, a portion of the ActRIIB extracellular domain. Preferably, ActRII polypeptides to be used in accordance with the methods described herein are soluble polypeptides.

In certain aspects, the disclosure relates compositions comprising an ActRIIA polypeptide and uses thereof. For example, in some embodiments, an ActRIIA polypeptide of the disclosure comprises an amino acid sequence that is at least 70%, 75%, 80%, 85%, 90%, 91%, 92%, 93%, 94%, 95%, 96%, 97%, 98%, 99%, or 100% identical to the sequence of amino acids 30-110 of SEQ ID NO: 9. In some embodiments, an ActRIIA polypeptides of the discloses comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to any one of amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134, or 135) of SEQ ID NO: 9. In other embodiments, an ActRIIA polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 9. In other embodiments, an ActRIIA polypeptide may comprise of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 10. In even other embodiments, an ActRIIA polypeptide may comprise of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 11. In still other embodiments, an ActRIIA polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 32. In still even other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 36. In still even other embodiments, an ActRIIA polypeptide may comprise, consist essentially of, or consist of an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 39.

In other aspects, the disclosure relates compositions comprising an ActRIIB polypeptide and uses thereof. For example, in some embodiments, an ActRIIB polypeptide of the disclosure comprises an amino acid sequence that is at least 70%, 75%, 80%, 85%, 90%, 91%, 92%, 93%, 94%, 95%, 96%, 97%, 98%, 99%, or 100% identical to the sequence of amino acids 29-109 of SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the sequence of amino acids 29-109 of SEQ ID NO: 1, wherein the ActRIIB polypeptide comprises an acidic amino acid [naturally occurring (E or D) or artificial acidic amino acid] at position 79 with respect to SEQ ID NO: 1. In other embodiments, qan ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the sequence of amino acids 25-131 of SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the sequence of amino acids 25-131 of SEQ ID NO: 1, wherein the ActRIIB polypeptide comprises an acidic amino acid at position 79 with respect to SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to a sequence starting at a residue corresponding to any one of amino acids 20, 21, 22, 23, 24, 25, 26, 27, 28, or 29 of SEQ ID NO: 1 and ending at a residue corresponding to any one of amino acids 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to a sequence starting at a residue corresponding to any one of amino acids 20, 21, 22, 23, 24, 25, 26, 27, 28, or 29 of SEQ ID NO: 1 and ending at a residue corresponding to any one of amino acids 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1, wherein the ActRIIB polypeptide comprises an acidic amino acid at position 79 with respect to SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 1. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 1, wherein the ActRIIB polypeptide comprises an acidic amino acid at position 79 with respect to SEQ ID NO: 1. In even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 2. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 2, wherein the ActRIIB polypeptide comprises an acidic amino acid at position 79 with respect to SEQ ID NO: 1. In still other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 3. In other, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 3, wherein the ActRIIB polypeptide comprises an acidic amino acid at position 79 with respect to SEQ ID NO: 1. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 4. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 4, wherein the ActRIIB polypeptide comprises an acidic amino acid at position 79 with respect to SEQ ID NO: 4. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 5. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 5, wherein the ActRIIB polypeptide comprises an acidic amino acid at position 79 with respect to SEQ ID NO: 5. In other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 6. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 6, wherein the ActRIIB polypeptide comprises an acidic amino acid at position 79 with respect to SEQ ID NO: 6. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 40. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 42. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 45. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 46. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 46, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 47. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 47, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 48. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 48, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 69. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 74. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 74, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 77. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 77, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 78. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 78, wherein the ActRIIB polypeptide comprises an acidic amino acid at position 79 with respect to SEQ ID NO: 1. In still even other embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 79. In some embodiments, an ActRIIB polypeptide may comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NO: 79, wherein the ActRIIB polypeptide comprises an acidic amino acid at position 79 with respect to SEQ ID NO: 1. In certain embodiments, ActRIIB polypeptides to be used in accordance with the methods and uses described herein do not comprise an acidic amino acid at the position corresponding to L79 of SEQ ID NO: 1.

As described herein, ActRII polypeptides, ALK4 polypeptides and variants thereof (GDF traps) may be homomultimers, for example, homodimer, homotrimers, homotetramers, homopentamers, and higher order homomultimer complexes. In certain preferred embodiments, ActRII polypeptides and variants thereof are homodimers. In certain embodiments, ActRII polypeptide dimers described herein comprise an first ActRII polypeptide covalently, or non-covalently, associated with an second ActRII polypeptide wherein the first polypeptide comprises an ActRII domain and an amino acid sequence of a first member (or second member) of an interaction pair (e.g., a constant domain of an immunoglobulin) and the second polypeptide comprises an ActRII polypeptide and an amino acid sequence of a second member (or first member) of the interaction pair.

In certain aspects, a GDF/BMP antagonist to be used in accordance with methods and uses described herein is an ALK4:ActRIIB heteromultimer. As described herein, it has been discovered that an ALK4:ActRIIB heterodimer protein complex has a different ligand-binding profile/selectivity compared to corresponding ActRIIB and ALK4 homodimers. In particular, ALK4:ActRIIB heterodimer displays enhanced binding to activin B compared to either homodimer, retains strong binding to activin A, GDF8, and GDF11 as observed with ActRIIB homodimer, and exhibits substantially reduced binding to BMP9, BMP10, and GDF3. In particular, BMP9 displays low to no observable affinity for ALK4:ActRIIB heterodimer, whereas this ligand binds strongly to ActRIIB homodimer. Like ActRIIB homodimer, ALK4:ActRIIB heterodimer retains intermediate-level binding to BMP6. See FIG. 19. These results therefore demonstrate that ALK4:ActRIIB heterodimers are a more selective antagonists (inhibitors) of activin A, activin B, GDF8, and GDF11 compared to ActRIIB homodimers. Accordingly, an ALK4:ActRIIB heterodimer will be more useful than an ActRIIB homodimer in certain applications where such selective antagonism is advantageous. Examples include therapeutic applications where it is desirable to retain antagonism of one or more of activin (e.g., activin A, activin B, activin AB, activin AC), GDF8, and GDF11 but minimize antagonism of one or more of BMP9, BMP10, and GDF3. Moreover, an ALK4:ActRIIB heterodimer has been shown treat PAH in patient. While not wishing to be bound to a particular mechanisms of action, it is expected that ALK4:ActRIIB heteromultimers, as well as variants thereof, that bind to at least one or more of activin (e.g., activin A, activin B, activin AB, and activin AC), GDF8, and/or GDF11 will be useful agents for promoting beneficial effects in PAH patients.

Therefore, the present disclosure provides heteromultimer complexes (heteromultimers) comprising at least one ALK4 polypeptide and at least one ActRIIB polypeptide (ALK4:ActRIIB heteromultimers) as well as uses thereof. Preferably, ALK4 polypeptides comprise a ligand-binding domain of an ALK4 receptor, for example, a portion of the ALK4 extracellular domain. Similarly, ActRIIB polypeptides generally comprise a ligand-binding domain of an ActRIIB receptor, for example, a portion of the ActRIIB extracellular domain. Preferably, such ALK4 and ActRIIB polypeptides, as well as resultant heteromultimers thereof, are soluble.

In certain aspects, an ALK4:ActRIIB heteromultimer comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NO: 100. In other embodiments, ALK4:ActRIIB heteromultimers comprises an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 101. In other embodiments, ALK4:ActRIIB heteromultimers comprises an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 105. In other embodiments, ALK4:ActRIIB heteromultimers comprises an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 122. In other embodiments, ALK4:ActRIIB heteromultimers comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 124. In other embodiments, ALK4:ActRIIB heteromultimers comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 116. In still other embodiments, ALK4:ActRIIB heteromultimers comprises an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 117. In other embodiments, ALK4:ActRIIB heteromultimers comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 111. In still other embodiments, ALK4:ActRIIB heteromultimers comprises an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 113.

In certain aspects, an ALK4:ActRIIB heteromultimer comprises an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 29-109 of SEQ ID NO: 1. In other embodiments, ALK4:ActRIIB heteromultimers comprises an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 2. In other embodiments, ALK4:ActRIIB heteromultimers comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 3. In other embodiments, ALK4:ActRIIB heteromultimers comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 5. In other embodiments, ALK4:ActRIIB heteromultimers comprises an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 6. In other embodiments, ALK4:ActRIIB heteromultimers comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 118. In still even other embodiments, ALK4:ActRIIB heteromultimers comprises an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 120 In other embodiments, ALK4:ActRIIB heteromultimers comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 114. In other embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 115. In other embodiments, ALK4:ActRIIB heteromultimers comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 108. In other embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 110. In certain preferred embodiments, ALK4:ActRIIB heteromultimers do not comprise an ActRIIB polypeptide comprising an acidic amino acid (e.g., an E or D) at the position corresponding to L79 of SEQ ID NO: 1.

As described herein, ALK4:ActRIIB heteromultimer structures include, for example, heterodimers, heterotrimers, heterotetramers, heteropentamers, and higher order heteromultimer complexes. See, e.g., FIGS. 21-23. In certain preferred embodiments, ALK4:ActRIIB heteromultimers are heterodimers. In certain aspects, ALK4 and/or ActRIIB polypeptides may be fusion proteins.

In certain aspects, ActRII polypeptides, ALK4 polypeptides, including variants thereof (e.g., GDF traps), may be fusion proteins. For example, in some embodiments, an ActRII (or ALK4) polypeptide may be a fusion protein comprising an ActRII (or ALK4) polypeptide domain and one or more heterologous (non-ActRII) polypeptide domains. In some embodiments, an ActRII (or ALK4) polypeptide may be a fusion protein that has, as one domain, an amino acid sequence derived from an ActRII (or ALK4) polypeptide (e.g., a ligand-binding domain of an ActRII (or ALK4) receptor or a variant thereof) and one or more heterologous domains that provide a desirable property, such as improved pharmacokinetics, easier purification, targeting to particular tissues, etc. For example, a domain of a fusion protein may enhance one or more of in vivo stability, in vivo half-life, uptake/administration, tissue localization or distribution, formation of protein complexes, multimerization of the fusion protein, and/or purification. Optionally, an ActRII (or ALK4) polypeptide domain of a fusion protein is connected directly (fused) to one or more heterologous polypeptide domains or an intervening sequence, such as a linker, may be positioned between the amino acid sequence of the ActRII (or ALK4) polypeptide and the amino acid sequence of the one or more heterologous domains. In certain embodiments, an ActRII (or ALK4) fusion protein comprises a relatively unstructured linker positioned between the heterologous domain and the ActRII (or ALK4) domain. This unstructured linker may correspond to the roughly 15 amino acid unstructured region at the C-terminal end of the extracellular domain of ActRII (or ALK4), or it may be an artificial sequence of between 3 and 15, 20, 30, 50 or more amino acids that are relatively free of secondary structure. A linker may be rich in glycine and/or proline residues and may, for example, contain repeating sequences of threonine/serine and glycines. Examples of linkers include, but are not limited to, the sequences TGGG (SEQ ID NO: 23), SGGG (SEQ ID NO: 24), TGGGG (SEQ ID NO: 21), SGGGG (SEQ ID NO: 22), GGGGS (SEQ ID NO: 25), GGGG (SEQ ID NO: 20), and GGG (SEQ ID NO: 19). In some embodiments, ActRII (or ALK4) fusion proteins may comprise a constant domain of an immunoglobulin, including, for example, the Fc portion of an immunoglobulin. For example, an amino acid sequence that is derived from an Fc domain of an IgG (IgG1, IgG2, IgG3, or IgG4), IgA (IgA1 or IgA2), IgE, or IgM immunoglobulin. For example, an Fc portion of an immunoglobulin domain may comprise, consist essentially of, or consist of an amino acid sequence that is at least 70%, 75%, 80%, 85%, 90%, 91%, 92%, 93%, 94%, 95%, 96%, 97%, 98%, 99% or 100% identical to any one of SEQ ID NOs: 14-18. Such immunoglobulin domains may comprise one or more amino acid modifications (e.g., deletions, additions, and/or substitutions) that confer an altered Fc activity, e.g., decrease of one or more Fc effector functions. In some embodiment, an ActRII (or ALK4) fusion protein comprises an amino acid sequence as set forth in the formula A-B-C. For example, the B portion is an N- and C-terminally truncated ActRII (or ALK4) polypeptide, e.g., as described herein. The A and C portions may be independently zero, one, or more than one amino acids, and both A and C portions are heterologous to B. The A and/or C portions may be attached to the B portion via a linker sequence. In certain embodiments, an ActRII (or ALK4) fusion protein comprises a leader sequence. The leader sequence may be a native ActRII (or ALK4) leader sequence or a heterologous leader sequence. In certain embodiments, the leader sequence is a tissue plasminogen activator (TPA) leader sequence (e.g., SEQ ID NO: 34).

An ActRII polypeptide or ALK4 polypeptide, including variants thereof, may comprise a purification subsequence, such as an epitope tag, a FLAG tag, a polyhistidine sequence, and a GST fusion. Optionally, an ActRII polypeptide or ALK4 polypeptide comprises one or more modified amino acid residues selected from: a glycosylated amino acid, a PEGylated amino acid, a farnesylated amino acid, an acetylated amino acid, a biotinylated amino acid, and/or an amino acid conjugated to a lipid moiety. ActRII polypeptides and ALK4 polypeptides may comprise at least one N-linked sugar, and may include two, three or more N-linked sugars. Such polypeptides may also comprise O-linked sugars. In general, it is preferable that ActRII and ALK4 polypeptides be expressed in a mammalian cell line that mediates suitably natural glycosylation of the polypeptide so as to diminish the likelihood of an unfavorable immune response in a patient. ActRII and ALK4 polypeptides may be produced in a variety of cell lines that glycosylate the protein in a manner that is suitable for patient use, including engineered insect or yeast cells, and mammalian cells such as COS cells, CHO cells, HEK cells and NSO cells. In some embodiments, an ActRII or ALK4 polypeptide is glycosylated and has a glycosylation pattern obtainable from a Chinese hamster ovary cell line. In some embodiments, ActRII or ALK4 polypeptides of the disclosure exhibit a serum half-life of at least 4, 6, 12, 24, 36, 48, or 72 hours in a mammal (e.g., a mouse or a human). Optionally, ActRII or ALK4 polypeptides may exhibit a serum half-life of at least 6, 8, 10, 12, 14, 20, 25, or 30 days in a mammal (e.g., a mouse or a human).

In certain aspects, the disclosure provides pharmaceutical preparations comprising one or more GDF/BMP antagonists of the present disclosure and a pharmaceutically acceptable carrier. A pharmaceutical preparation may also comprise one or more additional active agents such as a compound that is used to treat pulmonary hypertension, particularly treating or preventing one or more complications of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) including, for example, vasodilators such as prostacyclin, epoprostenol, and sildenafil; endothelin receptor antagonists such as bosentan; calcium channel blockers such as amlodipine, diltiazem, and nifedipine; anticoagulants such as warfarin; diuretics; BMP9 polypeptides; BMP10 polypeptides; bardoxolone methyl; and oleanolic acid. In general pharmaceutical preparation will preferably be pyrogen-free (meaning pyrogen free to the extent required by regulations governing the quality of products for therapeutic use).

In certain instances, when administering an GDF/BMP antagonist, or combination of antagonists, of the disclosure to disorders or conditions described herein, it may be desirable to monitor the effects on red blood cells during administration of the GDF/BMP antagonist, or to determine or adjust the dosing of the GDF/BMP antagonist, in order to reduce undesired effects on red blood cells. For example, increases in red blood cell levels, hemoglobin levels, or hematocrit levels may cause undesirable increases in blood pressure.

In certain aspects, a GDF/BMP antagonist to be used in accordance with methods and uses of the disclosure is an antibody, or combination of antibodies. In some embodiments, the antibody binds to at least ActRII (ActRIIA and/or ActRIIB) In certain embodiments, an antibody that binds to ActRII inhibits ActRII signaling, optionally as measured in a cell-based assay such as those described herein. In certain embodiments, an antibody that binds to ActRII inhibits one or more GDF/BMP ligands, type I receptors, or co-receptors from binding to ActRII. In certain embodiments an antibody that binds to ActRII inhibits one or more GDF/BMP ligands from binding to ActRII selected from the group consisting of: activin (e.g., activin A, activin B, activin C, activin AB, activin AC, activin BC, activin E, activin AE, and activin BE), GDF8, GDF11, BMP6, BMP15, BMP10, and GDF3. In some embodiments, the antibody binds to at least ALK4. In certain embodiments, an antibody that binds to ALK4 inhibits ALK4 signaling, optionally as measured in a cell-based assay such as those described herein. In certain embodiments, an antibody that binds to ALK4 inhibits one or more GDF/BMP ligands, type II receptors, or co-receptors from binding to ALK4. In certain embodiments an antibody that binds to ALK4 inhibits one or more GDF/BMP ligands from binding to ALK4 selected from the group consisting of: activin (e.g., activin A, activin B, activin C, activin AB, activin AC, activin BC, activin E, activin AE, and activin BE), GDF8, GDF11, BMP6, BMP15, BMP10, and GDF3. In some embodiments, the antibody binds to at least ALK5. In certain embodiments, an antibody that binds to ALK5 inhibits ALK5 signaling, optionally as measured in a cell-based assay such as those described herein. In certain embodiments, an antibody that binds to ALK5 inhibits one or more GDF/BMP ligands, type II receptors, or co-receptors from binding to ALK5. In certain embodiments an antibody that binds to ALK5 inhibits one or more GDF/BMP ligands from binding to ALK5 selected from the group consisting of: activin (e.g., activin A, activin B, activin C, activin AB, activin AC, activin BC, activin E, activin AE, and activin BE), GDF8, GDF11, BMP6, BMP15, BMP10, and GDF3. In some embodiments, the antibody binds to at least ALK7. In certain embodiments, an antibody that binds to ALK7 inhibits ALK7 signaling, optionally as measured in a cell-based assay such as those described herein. In certain embodiments, an antibody that binds to ALK7 inhibits one or more GDF/BMP ligands, type II receptors, or co-receptors from binding to ALK7. In certain embodiments an antibody that binds to ALK7 inhibits one or more GDF/BMP ligands from binding to ALK7 selected from the group consisting of: activin (e.g., activin A, activin B, activin C, activin AB, activin AC, activin BC, activin E, activin AE, and activin BE), GDF8, GDF11, BMP6, BMP15, BMP10, and GDF3. In some embodiments, the antibody binds to at least GDF11. In certain embodiments, an antibody that binds to GDF11 inhibits ActRII signaling, optionally as measured in a cell-based assay such as those described herein. In certain embodiments, an antibody that binds to GDF11 inhibits GDF11-ActRII binding and/or GDF11-ALK binding (e.g., GDF11-ALK4, GDF11-ALK5, and/or GDF11-ALK7 binding). In some embodiments, the antibody binds to at least GDF8. In certain embodiments, an antibody that binds to GDF8 inhibits ActRII signaling, optionally as measured in a cell-based assay such as those described herein. In certain embodiments, an antibody that binds to GDF8 inhibits GDF8-ActRII binding and/or GDF8-ALK binding (e.g., GDF8-ALK4, GDF8-ALK5, and/or GDF8-ALK7 binding). In some embodiments, the antibody binds to at least BMP6. In certain embodiments, an antibody that binds to BMP6 inhibits ActRII signaling, optionally as measured in a cell-based assay such as those described herein. In certain embodiments, an antibody that binds to BMP6 inhibits BMP6-ActRII binding and/or BMP6-ALK binding (e.g., BMP6-ALK4, BMP6-ALK5, and/or BMP6-ALK7 binding). In some embodiments, the antibody binds to at least BMP15. In certain embodiments, an antibody that binds to BMP15 inhibits ActRII signaling, optionally as measured in a cell-based assay such as those described herein. In certain embodiments, an antibody that binds to BMP15 inhibits BMP15-ActRII binding and/or BMP15-ALK binding (e.g., BMP15-ALK4, BMP15-ALK5, and/or BMP15-ALK7 binding). In some embodiments, the antibody binds to at least GDF3. In certain embodiments, an antibody that binds to GDF3 inhibits ActRII signaling, optionally as measured in a cell-based assay such as those described herein. In certain embodiments, an antibody that binds to GDF3 inhibits GDF3-ActRII binding and/or GDF3-ALK binding (e.g., GDF3-ALK4, GDF3-ALK5, and/or GDF3-ALK7 binding). In some embodiments, the antibody binds to at least BMP10. In certain embodiments, an antibody that binds to BMP10 inhibits ActRII signaling, optionally as measured in a cell-based assay such as those described herein. In certain embodiments, an antibody that binds to BMP10 inhibits BMP10-ActRII binding and/or BMP10-ALK binding (e.g., BMP10-ALK4, BMP10-ALK5, and/or BMP10-ALK7 binding). In some embodiments, the antibody binds to activin (e.g. activin A, activin B, activin C, activin AB, activin AC, activin BC, activin E, activin AE, and activin BE). In certain embodiments, an antibody that binds to activin (e.g. activin A, activin B, activin C, activin AB, activin AC, activin BC, activin E, activin AE, and activin BE) inhibits ActRII signaling, optionally as measured in a cell-based assay such as those described herein. In certain embodiments, an antibody that binds to activin (e.g. activin A, activin B, activin C, activin AB, activin AC, activin BC, activin E, activin AE, and activin BE) inhibits activin-ActRII binding and/or activin-ALK binding (e.g., activin-ALK4, activin-ALK5, and/or activin-ALK7 binding). In some embodiments, the antibody binds to activin B. In certain embodiments, an antibody that binds to activin B inhibits ActRII signaling, optionally as measured in a cell-based assay such as those described herein. In certain embodiments, an antibody that binds to activin B inhibits activin B-ActRII binding and/or activin B-ALK binding (e.g., activin B-ALK4, activin B-ALK5, and/or activin B-ALK7 binding). In some embodiments, the antibody is a multispecific antibody, or combination of multispecific antibodies that binds to one or more of ActRIIB, ActRIIA, ALK4, ALK5, ALK7, GDF11, GDF8, activin, BMP6, GDF3, BMP10, and BMP15. In certain aspects the multispecific antibody, or a combination of multispecific antibodies, inhibits signaling in a cell-based assay of one or more of: ActRIIB, GDF11, GDF8, activin, BMP6, GDF3, BMP10 and BMP15. In some embodiments, antibody is a chimeric antibody, a humanized antibody, or a human antibody. In some embodiments, the antibody is a single-chain antibody, an F(ab')$_2$ fragment, a single-chain diabody, a tandem single-chain Fv fragment, a tandem single-chain diabody, a or a fusion protein comprising a single-chain diabody and at least a portion of an immunoglobulin heavy-chain constant region.

In certain aspects, the GDF/BMP antagonist is a small molecule inhibitor or combination of small molecule inhibitors. In some embodiments, the small molecule inhibitor is an inhibitor of at least ActRII (e.g., ActRIIA and/or ActRIIB) In some embodiments, the small molecule inhibitor is an inhibitor of at least ALK4. In some embodiments, the small molecule inhibitor is an inhibitor of at least ALK5. In some embodiments, the small molecule inhibitor is an inhibitor of at least ALK7. In some embodiments, the small molecule inhibitor is an inhibitor of at least GDF11. In some embodiments, the small molecule inhibitor is an inhibitor of at least GDF8. In some embodiments, the small molecule inhibitor is an inhibitor of at least BMP6. In some embodiments, the small molecule inhibitor is an inhibitor of at least BMP15. In some embodiments, the small molecule inhibitor is an inhibitor of at least BMP10. In some embodiments, the small molecule inhibitor is an inhibitor of at least GDF3. In some embodiments, the small molecule inhibitor is an inhibitor of at least activin (e.g. activin A, activin B, activin C, activin AB, activin AC, activin BC, activin E, activin AE, and activin BE). In some embodiments, the small molecule inhibitor is an inhibitor of at least activin B. In some embodiments, the small molecule inhibitor is an inhibitor of at least one or more Smad proteins (e.g., Smads 2 and 3).

In certain aspects, the GDF/BMP antagonist is a nucleic acid inhibitor or combination of nucleic acid inhibitors. In some embodiments, the nucleic acid inhibitor is an inhibitor of at least ActRII (e.g., ActRIIA and/or ActRIIB) In some embodiments, the nucleic acid inhibitor is an inhibitor of at least ALK4. In some embodiments, the nucleic acid inhibitor is an inhibitor of at least ALK5. In some embodiments, the nucleic acid inhibitor is an inhibitor of at least ALK7. In some embodiments, the nucleic acid inhibitor is an inhibitor of at least GDF11. In some embodiments, the nucleic acid inhibitor is an inhibitor of at least GDF8. In some embodiments, the nucleic acid inhibitor is an inhibitor of at least BMP6. In some embodiments, the nucleic acid inhibitor is an inhibitor of at least BMP15. In some embodiments, the nucleic acid inhibitor is an inhibitor of at least BMP10. In some embodiments, the nucleic acid inhibitor is an inhibitor of at least GDF3. In some embodiments, the nucleic acid inhibitor is an inhibitor of at least activin (e.g. activin A, activin B, activin C, activin AB, activin AC, activin BC, activin E, activin AE, and activin BE). In some embodiments, the nucleic acid inhibitor is an inhibitor of at least activin B. In some embodiments, the nucleic acid inhibitor is an inhibitor of at least one or more Smads (e.g., Smads 2 and 3).

In certain aspects, the GDF/BMP antagonist is a follistatin polypeptide. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 26. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 27. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 28. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 29. In some embodiments, the follistatin polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 30.

In certain aspects, the GDF/BMP antagonist is a FLRG polypeptide. In some embodiments, the FLRG polypeptide comprises an amino acid sequence that is at least 70%, 75% 80%, 85%, 90%, 91%, 92%, 93%, 94%, 95%, 96%, 97%, 98%, 99%, or 100% identical to the amino acid sequence of SEQ ID NO: 31.

BRIEF DESCRIPTION OF THE DRAWINGS

FIG. 1 shows an alignment of extracellular domains of human ActRIIB (SEQ ID NO: 2) and human ActRIIA (SEQ ID NO: 10) with the residues that are deduced herein, based on composite analysis of multiple ActRIIB and ActRIIA crystal structures, to directly contact ligand indicated with boxes.

FIG. 3 shows a multiple sequence alignment of various vertebrate ActRIIA proteins and human ActRIIA (SEQ ID NOs: 61-68).

FIG. 4 shows multiple sequence alignment of Fc domains from human IgG isotypes using Clustal 2.1. Hinge regions are indicated by dotted underline. Double underline indicates examples of positions engineered in IgG1 (SEQ ID NO: 133) Fc to promote asymmetric chain pairing and the corresponding positions with respect to other isotypes IgG2 (SEQ ID NO: 135), IgG3 (SEQ ID NO: 136) and IgG4 (SEQ ID NO: 134).

FIG. 6 shows the binding of ActRIIA-hFc to activin (top panel) and GDF-11 (bottom panel), as measured by Biacore™ assay.

FIG. 7 shows the full, unprocessed amino acid sequence for ActRIIB(25-131)-hFc (SEQ ID NO: 69). The TPA leader (residues 1-22) and double-truncated ActRIIB extracellular domain (residues 24-131, using numbering based on the native sequence in SEQ ID NO: 1) are each underlined. Highlighted is the glutamate revealed by sequencing to be the N-terminal amino acid of the mature fusion protein, which is at position 25 relative to SEQ ID NO: 1.

FIGS. 8A and 8B show a nucleotide sequence encoding ActRIIB(25-131)-hFc (the coding strand is shown at top, SEQ ID NO: 70, and the complement shown at bottom 3'-5', SEQ ID NO: 71). Sequences encoding the TPA leader (nucleotides 1-66) and ActRIIB extracellular domain (nucleotides 73-396) are underlined. The corresponding amino acid sequence for ActRIIB(25-131)) (SEQ ID NO: 138) is also shown.

FIGS. 9A and 9B show an alternative nucleotide sequence encoding ActRIIB(25-131)-hFc (the coding strand is shown at top, SEQ ID NO: 72, and the complement shown at bottom 3'-5', SEQ ID NO: 73). This sequence confers a greater level of protein expression in initial transformants, making cell line development a more rapid process. Sequences encoding the TPA leader (nucleotides 1-66) and ActRIIB extracellular domain (nucleotides 73-396) are underlined, and substitutions in the wild type nucleotide sequence of the ECD (see FIG. 8) are highlighted. The corresponding amino acid sequence for ActRIIB(25-131) (SEQ ID NO: 138) is also shown.

FIG. 10 shows the full amino acid sequence for the GDF trap ActRIIB(L79D 20-134)-hFc (SEQ ID NO: 74), including the TPA leader sequence (double underline), ActRIIB extracellular domain (residues 20-134 in SEQ ID NO: 1; single underline), and hFc domain. The aspartate substituted at position 79 in the native sequence is double underlined and highlighted, as is the glycine revealed by sequencing to be the N-terminal residue in the mature fusion protein.

FIGS. 11A and 11B shows a nucleotide sequence encoding ActRIIB(L79D 20-134)-hFc. SEQ ID NO: 75 corresponds to the sense strand, and SEQ ID NO: 76 corresponds to the antisense strand. The TPA leader (nucleotides 1-66) is double underlined, and the ActRIIB extracellular domain (nucleotides 76-420) is single underlined.

FIG. 12 shows the full amino acid sequence for the truncated GDF trap ActRIIB(L79D 25-131)-hFc (SEQ ID NO: 77), including the TPA leader (double underline), truncated ActRIIB extracellular domain (residues 25-131 in SEQ ID NO:1; single underline), and hFc domain. The aspartate substituted at position 79 in the native sequence is double underlined and highlighted, as is the glutamate revealed by sequencing to be the N-terminal residue in the mature fusion protein.

FIG. 13 shows the amino acid sequence for the truncated GDF trap ActRIIB(L79D 25-131)-hFc without a leader (SEQ ID NO: 78). The truncated ActRIIB extracellular domain (residues 25-131 in SEQ ID NO: 1) is underlined. The aspartate substituted at position 79 in the native sequence is double underlined and highlighted, as is the glutamate revealed by sequencing to be the N-terminal residue in the mature fusion protein.

FIG. 14 shows the amino acid sequence for the truncated GDF trap ActRIIB(L79D 25-131) without the leader, hFc domain, and linker (SEQ ID NO: 79). The aspartate substituted at position 79 in the native sequence is underlined and highlighted, as is the glutamate revealed by sequencing to be the N-terminal residue in the mature fusion protein.

FIGS. 15A and 15B shows a nucleotide sequence encoding ActRIIB(L79D 25-131)-hFc. SEQ ID NO: 80 corresponds to the sense strand, and SEQ ID NO: 81 corresponds to the antisense strand. The TPA leader (nucleotides 1-66) is double underlined, and the truncated ActRIIB extracellular domain (nucleotides 76-396) is single underlined. The amino acid sequence for the ActRIIB extracellular domain (SEQ ID NO: 79) is also shown.

FIGS. 16A and 16B shows an alternative nucleotide sequence encoding ActRIIB(L79D 25-131)-hFc. SEQ ID NO: 82 corresponds to the sense strand, and SEQ ID NO: 83 corresponds to the antisense strand. The TPA leader (nucleotides 1-66) is double underlined, the truncated ActRIIB extracellular domain (nucleotides 76-396) is underlined, and substitutions in the wild-type nucleotide sequence of the extracellular domain are double underlined and highlighted (compare with SEQ ID NO: 81, FIG. 15). The amino acid sequence for the ActRIIB extracellular domain (SEQ ID NO: 79) is also shown.

FIG. 17 shows nucleotides 76-396 (SEQ ID NO: 84) of the alternative nucleotide sequence shown in FIG. 16 (SEQ ID NO: 82). The same nucleotide substitutions indicated in FIG. 16 are also underlined and highlighted here. SEQ ID NO: 84 encodes only the truncated ActRIIB extracellular domain (corresponding to residues 25-131 in SEQ ID NO: 1) with a L79D substitution, e.g., ActRIIB (L79D 25-131).

FIG. 18 shows a multiple sequence alignment of various vertebrate ALK4 proteins and human ALK4 (SEQ ID NOs: 126-132).

FIG. 21A depicts a heterodimeric protein complex comprising one type I receptor fusion polypeptide and one type II receptor fusion polypeptide, which can be assembled covalently or noncovalently via a multimerization domain contained within each polypeptide chain. Two assembled multimerization domains constitute an interaction pair, which can be either guided or unguided. FIG. 21B depicts a heterotetrameric protein complex comprising two heterodimeric complexes as depicted in FIG. 21A. Complexes of higher order can be envisioned.

DETAILED DESCRIPTION OF THE INVENTION

1. Overview

Figure 2:
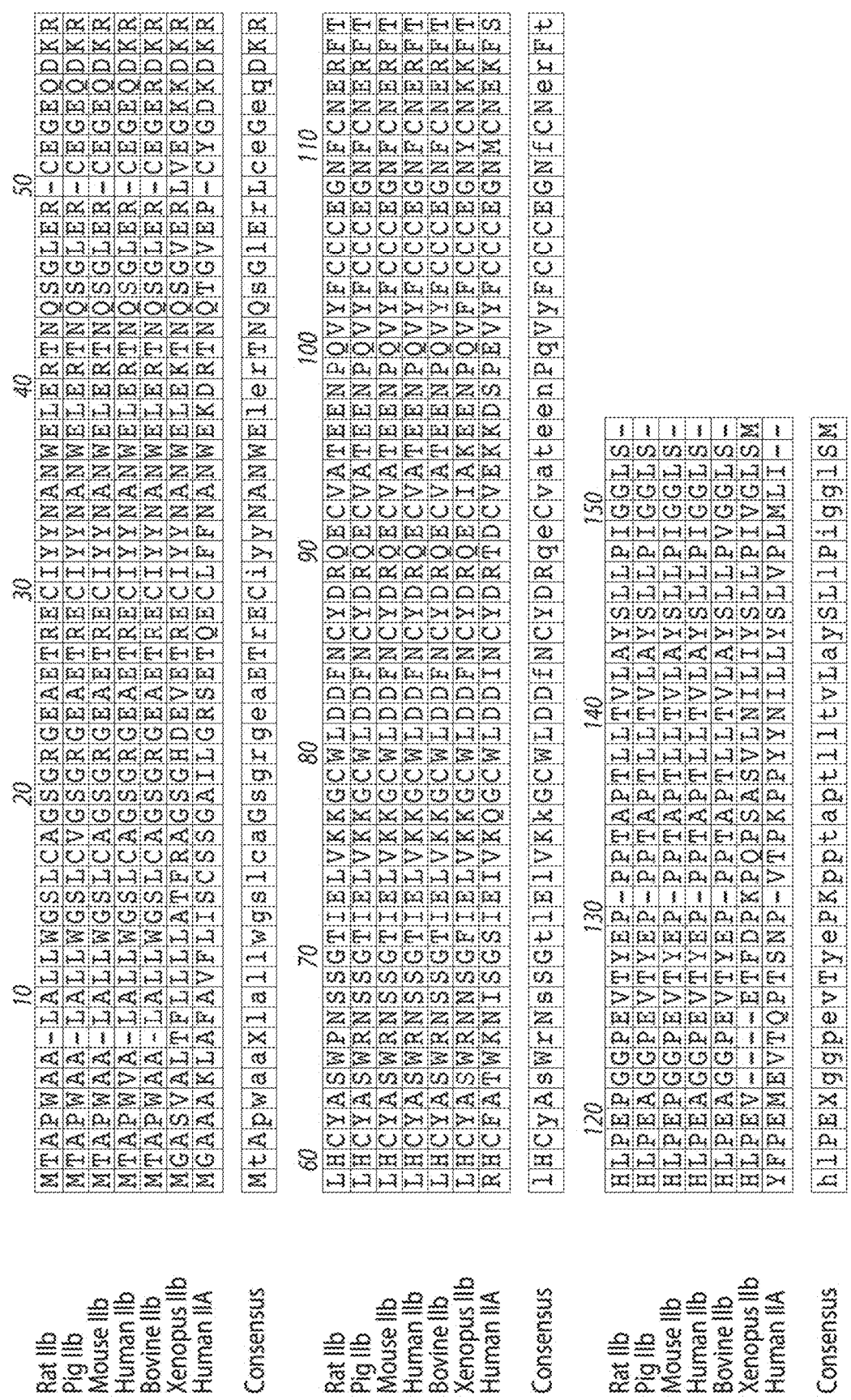
FIG. 2 shows a multiple sequence alignment of various vertebrate ActRIIB proteins (SEQ ID NOs: 53-58) and human ActRIIA (SEQ ID NO: 59) as well as a consensus ActRII sequence derived from the alignment (SEQ ID NO: 60).

The TGF-β superfamily is comprised of over 30 secreted factors including TGF-betas, activins, nodals, bone morphogenetic proteins (BMPs), growth and differentiation factors (GDFs), and anti-Mullerian hormone (AMR) [Weiss et al. (2013) Developmental Biology, 2(1): 47-63]. Members of the superfamily, which are found in both vertebrates and invertebrates, are ubiquitously expressed in diverse tissues and function during the earliest stages of development throughout the lifetime of an animal. Indeed, TGF-β superfamily proteins are key mediators of stem cell self-renewal, gastrulation, differentiation, organ morphogenesis, and adult tissue homeostasis. Consistent with this ubiquitous activity, aberrant TGF-beta superfamily signaling is associated with a wide range of human pathologies including, for example, autoimmune disease, cardiovascular disease, fibrotic disease, and cancer.

Ligands of the TGF-beta superfamily share the same dimeric structure in which the central 3½ turn helix of one monomer packs against the concave surface formed by the beta-strands of the other monomer. The majority of TGF-beta family members are further stabilized by an intermolecular disulfide bond. This disulfide bonds traverses through a ring formed by two other disulfide bonds generating what has been termed a 'cysteine knot' motif [Lin et al. (2006) Reproduction 132: 179-190; and Hinck et al. (2012) FEBS Letters 586: 1860-1870].

TGF-beta superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation [Massague (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGF-beta superfamily ligands. Type I and II receptors form a stable complex after ligand binding, resulting in phosphorylation of type I receptors by type II receptors.

The TGF-beta family can be divided into two phylogenetic branches based on the type I receptors they bind and the Smad proteins they activate. One is the more recently evolved branch, which includes, e.g., the TGF-betas, activins, GDF8, GDF9, GDF11, BMP3 and nodal, which signal through type I receptors that activate Smads 2 and 3 [Hinck (2012) FEBS Letters 586:1860-1870]. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8.

Activins are members of the TGF-beta superfamily and were initially discovered as regulators of secretion of follicle-stimulating hormone, but subsequently various reproductive and non-reproductive roles have been characterized. There are three principal activin forms (A, B, and AB) that are homo/heterodimers of two closely related β subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos [DePaolo et al. (1991) Proc Soc Ep Biol Med. 198:500-512; Dyson et al. (1997) Curr Biol. 7:81-84; and Woodruff (1998) Biochem Pharmacol. 55:953-963]. In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and $\alpha_2$-macroglobulin.

As described herein, agents that bind to "activin A" are agents that specifically bind to the $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the PA subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $R_B$ subunit of the complex). This principle applies also to agents that bind to and/or inhibit "activin B", "activin C", and "activin E". Agents disclosed herein that antagonize "activin AB" are agents that inhibit one or more activities as mediated by the $\beta_A$ subunit and one or more activities as mediated by the $R_B$ subunit.

The BMPs and GDFs together form a family of cysteine-knot cytokines sharing the characteristic fold of the TGF-beta superfamily [Rider et al. (2010) Biochem J., 429(1):1-12]. This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several specific BMP antagonist proteins that bind with high affinity to the cytokines. Curiously, a number of these antagonists resemble TGF-beta superfamily ligands.

Growth and differentiation factor-8 (GDF8) is also known as myostatin. GDF8 is a negative regulator of skeletal muscle mass and is highly expressed in developing and adult skeletal muscle. The GDF8 null mutation in transgenic mice is characterized by a marked hypertrophy and hyperplasia of skeletal muscle [McPherron et al. Nature (1997) 387:83-90]. Similar increases in skeletal muscle mass are evident in naturally occurring mutations of GDF8 in cattle and, strikingly, in humans [Ashmore et al. (1974) Growth, 38:501-507; Swatland and Kieffer, J. Anim. Sci. (1994) 38:752-757; McPherron and Lee, Proc. Natl. Acad. Sci. USA (1997) 94:12457-12461; Kambadur et al. Genome Res. (1997) 7:910-915; and Schuelke et al. (2004) N Engl J Med, 350:2682-8]. Studies have also shown that muscle wasting associated with HIV-infection in humans is accompanied by increases in GDF8 protein expression [Gonzalez-Cadavid et al., PNAS (1998) 95:14938-43]. In addition, GDF8 can modulate the production of muscle-specific enzymes (e.g., creatine kinase) and modulate myoblast cell proliferation [International Patent Application Publication No. WO 00/43781]. The GDF8 propeptide can noncovalently bind to the mature GDF8 domain dimer, inactivating its biological activity [Miyazono et al. (1988) J. Biol. Chem., 263: 6407-6415; Wakefield et al. (1988) J. Biol. Chem., 263; 7646-7654; and Brown et al. (1990) Growth Factors, 3: 35-43]. Other proteins which bind to GDF8 or structurally related proteins and inhibit their biological activity include follistatin, and potentially, follistatin-related proteins [Gamer et al. (1999) Dev. Biol., 208: 222-232].

GDF11, also known as BMP11, is a secreted protein that is expressed in the tail bud, limb bud, maxillary and mandibular arches, and dorsal root ganglia during mouse development [McPherron et al. (1999) Nat. Genet., 22: 260-264; and Nakashima et al. (1999) Mech. Dev., 80: 185-189]. GDF11 plays a unique role in patterning both mesodermal and neural tissues [Gamer et al. (1999) Dev Biol., 208:222-32]. GDF11 was shown to be a negative regulator of chondrogenesis and myogenesis in developing chick limb [Gamer et al. (2001) Dev Biol., 229:407-20]. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium [Wu et al. (2003) Neuron., 37:197-207]. Hence, GDF11 may have in vitro and in vivo applications in the treatment of diseases such as muscle diseases and neurodegenerative diseases (e.g., amyotrophic lateral sclerosis).

As demonstrated herein, a soluble ActRIIA polypeptide and ALK4:ActRIIB heterodimer, which both bind to various ActRIIA and ActRIIB-interacting ligands, is effective in decreasing blood pressure and cardiac hypertrophy in a PAH model. While not wishing to be bound to any particular mechanism, it is expected that the effects of these agents is caused primarily by an ActRIIA/B signaling antagonist effect. Regardless of the mechanism, it is apparent from the data presented herein that ActRIIA/B signaling antagonists (GDF/BMP antagonists) do decrease blood pressure, decrease cardiac hypertrophy, and have other positivity effects in treating pulmonary hypertension. It should be noted that blood pressure and hypertrophy are dynamic, with changes depending on a balance of factors that increase blood pressure and hypertrophy and factors that decrease blood pressure and hypertrophy. Blood pressure and cardiac hypertrophy can be decreased by increasing factors that reduce blood pressure and cardiac hypertrophy, decreasing factors that promote elevated blood pressure and cardiac hypertrophy, or both. The terms decreasing blood pressure or decreasing cardiac hypertrophy refer to the observable physical changes in blood pressure and cardiac tissue and are intended to be neutral as to the mechanism by which the changes occur.

The rat models for PAH that were used in the studies described herein are considered to be predicative of efficacy in humans, and therefore, this disclosure provides methods for using ActRIIA polypeptides, ALK4:ActRIIB heteromultimers, and other GDF/BMP antagonists to treat pulmonary hypertension (e.g., PAH), particularly treating, preventing, or reducing the severity or duration of one or more complications of pulmonary hypertension, in humans. As disclosed herein, the term GDF/BMP antagonists refers a variety of agents that may be used to antagonize ActRIIA/B signaling including, for example, antagonists that inhibit one or more ActRIIA/B ligands [e.g., activin (activin A, activin B, activin AB, activin C, activin AC, activin BC, activin E, activin AE, and/or activin BE), GDF8, GDF11, GDF3, BMP6, BMP15, BMP10]; antagonists that inhibit one or more type I and/or type II receptors (e.g., ActRIIA, ActRIIB, ALK4, ALK7, and ALK5); and antagonists that inhibit one or more downstream signaling components (e.g., Smad proteins such as Smads 2 and 3). GDF/BMP antagonists to be used in accordance with the methods and uses of the disclosure include a variety of forms, for example, ligand traps (e.g., soluble ActRIIA polypeptides, ActRIIB polypeptides, ALK4:ActRIIB heterodimers, follistatin polypeptides, and FLRG polypeptides), antibody antagonists (e.g., antibodies that inhibit one or more of activin, GDF8, GDF11, GDF3, BMP6, BMP15, BMP10, ActRIIA, ActRIIB, ALK4, ALK7, and ALK5), small molecule antagonists [e.g., small molecules that inhibit one or more of activin, GDF8, GDF11, GDF3, BMP6, BMP15, BMP10, ActRIIA, ActRIIB, ALK4, ALK7, ALK5, and one or more Smad proteins (e.g., Smads 2 and 3)], and nucleotide antagonists [e.g., nucleotide sequences that inhibit one or more of activin, GDF8, GDF11, GDF3, BMP6, BMP15, BMP10, ActRIIA, ActRIIB, ALK4, ALK7, ALK5, and one or more Smad proteins (e.g., Smads 2 and 3)].

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise.

The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. ActRII Polypeptides, ALK4 Polypeptides, ALK4:ActRIIB Heteromultimers, and Variants Thereof In certain aspects, the disclosure relates ActRII polypeptides and uses thereof (e.g., of treating, preventing, or reducing the progression rate and/or severity of pulmonary hypertension or one or more complications of pulmonary hypertension) and/or an interstitial lung disease (e.g., idiopathic pulmonary fibrosis). As used herein, the term "ActRII" refers to the family of type II activin receptors. This family includes activin receptor type IIA (ActRIIA) and activin receptor type IIB (ActRIIB).

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication Nos. WO 2006/012627, WO 2008/097541, WO 2010/151426, and WO 2011/020045, which are incorporated herein by reference in their entirety. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

```
                                            (SEQ ID NO: 1)
  1  MTAPWVALAL LWGSLCAGSG RGEAETRECI YYNANWELER
     TNQSGLERCE

51  GEQDKRLHCY ASWRNSSGTI ELVKKGCWLD DFNCYDRQEC
     VATEENPQVY
```

```
101  FCCCEGNFCN ERFTHLPEAG GPEVTYEPPP TAPTLLTVLA
     YSLLPIGGLS

151  LIVLLAFWMY RHRKPPYGHV DIHEDPGPPP PSPLVGLKPL
     QLLEIKARGR

201  FGCVWKAQLM NDFVAVKIFP LQDKQSWQSE REIFSTPGMK
     HENLLQFIAA

251  EKRGSNLEVE LWLITAFHDK GSLTDYLKGN IITWNELCHV
     AETMSRGLSY

301  LHEDVPWCRG EGHKPSIAHR DFKSKNVLLK SDLTAVLADF
     GLAVRFEPGK

351  PPGDTHGQVG TRRYMAPEVL EGAINFQRDA FLRIDMYAMG
     LVLWELVSRC

401  KAADGPVDEY MLPFEEEIGQ HPSLEELQEV VVHKKMRPTI
     KDHWLKHPGL

451  AQLCVTIEEC WDHDAEARLS AGCVEERVSL IRRSVNGTTS
     DCLVSLVTSV

501  TNVDLPPKES SI
```

The signal peptide is indicated with a single underline; the extracellular domain is indicated in bold font; and the potential, endogenous N-linked glycosylation sites are indicated with a double underline.

The processed (mature) extracellular ActRIIB polypeptide sequence is as follows:

```
                                            (SEQ ID NO: 2)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT.
```

In some embodiments, the protein may be produced with an "SGR . . . " sequence at the N-terminus. The C-terminal "tail" of the extracellular domain is indicated by a single underline. The sequence with the "tail" deleted (a Δ15 sequence) is as follows:

```
                                            (SEQ ID NO: 3)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA.
```

A form of ActRIIB with an alanine at position 64 of SEQ ID NO: 1 (A64) is also reported in the literature. See, e.g., Hilden et al. (1994) Blood, 83(8): 2163-2170. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

```
                                            (SEQ ID NO: 4)
  1  MTAPWVALAL LWGSLCAGSG RGEAETRECI YYNANWELER
     TNQSGLERCE

51  GEQDKRLHCY ASWANSSGTI ELVKKGCWLD DFNCYDRQEC
     VATEENPQVY
```

```
101 FCCCEGNFCN ERFTHLPEAG GPEVTYEPPP TAPTLLTVLA
    YSLLPIGGLS

151 LIVLLAFWMY RHRKPPYGHV DIHEDPGPPP PSPLVGLKPL
    QLLEIKARGR

201 FGCVWKAQLM NDFVAVKIFP LQDKQSWQSE REIFSTPGMK
    HENLLQFIAA

251 EKRGSNLEVE LWLITAFHDK GSLTDYLKGN IITWNELCHV
    AETMSRGLSY

301 LHEDVPWCRG EGHKPSIAHR DFKSKNVLLK SDLTAVLADF
    GLAVRFEPGK

351 PPGDTHGQVG TRRYMAPEVL EGAINFQRDA FLRIDMYAMG
    LVLWELVSRC

401 KAADGPVDEY MLPFEEEIGQ HPSLEELQEV VVHKKMRPTI
    KDHWLKHPGL

451 AQLCVTIEEC WDHDAEARLS AGCVEERVSL IRRSVNGTTS
    DCLVSLVTSV

501 TNVDLPPKES SI
```

The signal peptide is indicated by single underline and the extracellular domain is indicated by bold font.

The processed (mature) extracellular ActRIIB polypeptide sequence of the alternative A64 form is as follows:

(SEQ ID NO: 5)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA

GGPEVTYEPPPTAPT

In some embodiments, the protein may be produced with an "SGR . . . " sequence at the N-terminus. The C-terminal "tail" of the extracellular domain is indicated by single underline. The sequence with the "tail" deleted (a Δ15 sequence) is as follows:

(SEQ ID NO: 6)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA

A nucleic acid sequence encoding the human ActRIIB precursor protein is shown below (SEQ ID NO: 7), representing nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

```
                                                    (SEQ ID NO: 7)
   1 ATGACGGCGC CTGGGTGGC CCTCGCCCTC CTCTGGGGAT CGCTGTGCGC

51 CGGCTCTGGG CGTGGGGAGG CTGAGACACG GGAGTGCATC TACTACAACG

101 CCAACTGGGA GCTGGAGCGC ACCAACCAGA GCGGCCTGGA GCGCTGCGAA

151 GGCGAGCAGG ACAAGCGGCT GCACTGCTAC GCCTCCTGGC GCAACAGCTC

201 TGGCACCATC GAGCTCGTGA AGAAGGGCTG CTGGCTAGAT GACTTCAACT

251 GCTACGATAG GCAGGAGTGT GTGGCCACTG AGGAGAACCC CCAGGTGTAC

301 TTCTGCTGCT GTGAAGGCAA CTTCTGCAAC GAACGCTTCA CTCATTTGCC

351 AGAGGCTGGG GGCCCGGAAG TCACGTACGA GCCACCCCCG ACAGCCCCCA

401 CCCTGCTCAC GGTGCTGGCC TACTCACTGC TGCCCATCGG GGGCCTTTCC

451 CTCATCGTCC TGCTGGCCTT TTGGATGTAC CGGCATCGCA AGCCCCCCTA

501 CGGTCATGTG GACATCCATG AGGACCCTGG GCCTCCACCA CCATCCCCTC

551 TGGTGGGCCT GAAGCCACTG CAGCTGCTGG AGATCAAGGC TCGGGGGCGC

601 TTTGGCTGTG TCTGGAAGGC CCAGCTCATG AATGACTTTG TAGCTGTCAA

651 GATCTTCCCA CTCCAGGACA AGCAGTCGTG GCAGAGTGAA CGGGAGATCT

701 TCAGCACACC TGGCATGAAG CACGAGAACC TGCTACAGTT CATTGCTGCC

751 GAGAAGCGAG GCTCCAACCT CGAAGTAGAG CTGTGGCTCA TCACGGCCTT

801 CCATGACAAG GGCTCCCTCA CGGATTACCT CAAGGGGAAC ATCATCACAT

851 GGAACGAACT GTGTCATGTA GCAGAGACGA TGTCACGAGG CCTCTCATAC

901 CTGCATGAGG ATGTGCCCTG GTGCCGTGGC GAGGGCCACA AGCCGTCTAT

951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA
```

-continued

```
1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG

1351 GCCCAGCTTT GTGTGACCAT CGAGGAGTGC TGGGACCATG ATGCAGAGGC

1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC
```

A nucleic acid sequence encoding processed extracellular human ActRIIB polypeptide is as follows (SEQ ID NO: 8). The sequence as shown provides an arginine at position 64, and may be modified to provide an alanine instead.

```
                                              (SEQ ID NO: 8)
  1 GGGCGTGGGG AGGCTGAGAC ACGGGAGTGC ATCTACTACA
    ACGCCAACTG

51 GGAGCTGGAG CGCACCAACC AGAGCGGCCT GGAGCGCTGC
    GAAGGCGAGC

101 AGGACAAGCG GCTGCACTGC TACGCCTCCT GGCGCAACAG
    CTCTGGCACC

151 ATCGAGCTCG TGAAGAAGGG CTGCTGGCTA GATGACTTCA
    ACTGCTACGA

201 TAGGCAGGAG TGTGTGGCCA CTGAGGAGAA CCCCCAGGTG
    TACTTCTGCT

251 GCTGTGAAGG CAACTTCTGC AACGAACGCT TCACTCATTT
    GCCAGAGGCT

301 GGGGGCCCGG AAGTCACGTA CGAGCCACCC CCGACAGCCC
    CCACC
```

An alignment of the amino acid sequences of human ActRIIB extracellular domain and human ActRIIA extracellular domain are illustrated in FIG. 1. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

In addition, ActRIIB is well-conserved among vertebrates, with large stretches of the extracellular domain completely conserved. For example, FIG. 2 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant to substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences. Without meaning to be limiting, the following examples illustrate this approach to defining an active ActRIIB variant. L46 in the human extracellular domain (SEQ ID NO: 2) is a valine in Xenopus ActRIIB (SEQ ID NO: 58), and so this position may be altered, and optionally may be altered to another hydrophobic residue, such as V, I or F, or a non-polar residue such as A. E52 in the human extracellular domain is a K in Xenopus, indicating that this site may be tolerant of a wide variety of changes, including polar residues, such as E, D, K, R, H, S, T, P, G, Y and probably A. T93 in the human extracellular domain is a K in Xenopus, indicating that a wide structural variation is tolerated at this position, with polar residues favored, such as S, K, R, E, D, H, G, P, G and Y. F108 in the human extracellular domain is a Y in Xenopus, and therefore Y or other hydrophobic group, such as I, V or L should be tolerated. E111 in the human extracellular domain is K in Xenopus, indicating that charged residues will be tolerated at this position, including D, R, K and H, as well as Q and N. R112 in the human extracellular domain is K in Xenopus, indicating that basic residues are tolerated at this position, including R and H. A at position 119 in the human extracellular domain is relatively poorly conserved, and appears as P in rodents and V in Xenopus, thus essentially any amino acid should be tolerated at this position.

Moreover, ActRII proteins have been characterized in the art in terms of structural and functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRIIB variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIB, as demarcated by the outermost of these conserved cysteines, corresponds to positions 29-109 of SEQ ID NO: 1 (ActRIIB precursor). The structurally less-ordered amino acids flanking these cysteine-demarcated core sequences can be truncated by 1, 2, 3, 4, 5, 6, 7, 8, 9, 10, 11, 12, 13, 14, 15, 16, 17, 18, 19, 20, 21, 22, 23, 24, 25, 26, 27, or 28 residues at the N-terminus and/or 1, 2, 3, 4, 5, 6, 7, 8, 9, 10, 11, 12, 13, 14, 15, 16, 17, 18, 19, 20, 21, or 22 residues a the C-terminus without necessarily altering ligand binding. Exemplary ActRIIB extracellular domains for N-terminal and/or C-terminal truncation include SEQ ID NOs: 2, 3, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted.

Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO:1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding [U.S. Pat. No. 7,842,663]. This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S. Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) of SEQ ID NO: 1 and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) of SEQ ID NO: 1 and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, 133, or 134) or 129-134 (e.g., any one of positions 129, 130, 131, 132, 133, or 134) of SEQ ID NO: 1. Variants within these ranges are also contemplated, particularly those comprising, consisting essentially of, or consisting of an amino acid sequence that has at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, optionally zero, one or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) does not appear to decrease ligand binding in the R64 background [U.S. Pat. No. 7,842,663]. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 [U.S. Pat. No. 7,842,663]. Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

It has been previously demonstrated that the addition of a further N-linked glycosylation site (N-X-S/T) into the ActRIIB extracellular domain is well-tolerated (see, e.g., U.S. Pat. No. 7,842,663). Therefore, N-X-S/T sequences may be generally introduced at positions outside the ligand binding pocket defined in FIG. 1 in ActRIIB polypeptide of the present disclosure. Particularly suitable sites for the introduction of non-endogenous N-X-S/T sequences include amino acids 20-29, 20-24, 22-25, 109-134, 120-134 or 129-134 (with respect to SEQ ID NO: 1). N-X-S/T sequences may also be introduced into the linker between the ActRIIB sequence and an Fc domain or other fusion component as well as optionally into the fusion component itself. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E105N, R112N, G120N, E123N, P129N, A132N, R112S and R112T (with respect to SEQ ID NO: 1). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T (with respect to SEQ ID NO: 1) are contemplated. Likewise, in an A24N variant, an S26T alteration may be used. Accordingly, an ActRIIB polypeptide of the present disclosure may be a variant having one or more additional, non-endogenous N-linked glycosylation consensus sequences as described above.

In certain embodiments, the disclosure relates to GDF/BMP antagonists (inhibitors) that comprise a ActRIIB polypeptide, which includes fragments, functional variants, and modified forms thereof as well as uses thereof (e.g., treating or preventing PH or one or more PH-associated complication). Preferably, ActRIIB polypeptides are soluble (e.g., comprise an extracellular domain of ActRIIB) In some embodiments, ActRIIB polypeptides antagonize activity (e.g., Smad signaling) of one or more GDF/BMP ligands [e.g., GDF11, GDF8, activin (activin A, activin B, activin AB, activin C, activin E) BMP6, GDF3, BMP15, and BMP10]. Therefore, in some embodiments, ActRIIB polypeptides bind to one or more GDF/BMP ligands [e.g., GDF11, GDF8, activin (activin A, activin B, activin AB, activin C, activin E) BMP6, GDF3, BMP15, and BMP10]. In some embodiments, ActRIIB polypeptides of the disclosure comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at any one of amino acids 20, 21, 22, 23, 24, 25, 26, 27, 28, or 29) of SEQ ID NO: 1 and ending at a position corresponding to amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In some embodiments, ActRIIB polypeptides comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1. In some embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1, wherein the position corresponding to L79 of SEQ ID NO: 1 is an acidic amino acid (naturally occurring acidic amino acids D and E or an artificial acidic amino acid). In certain embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1. In certain embodiments, ActRIIB polypeptides of the disclosure comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1, wherein the position corresponding to L79 of SEQ ID NO: 1 is an acidic amino acid. In some embodiments, ActRIIB polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 40, 42, 45, 46, 47, 48, 69, 74, 77, 78, 79, 108, 110, 114, 115, 118, and 120. In some embodiments, ActRIIB polypeptide of disclosure comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 40, 42, 45, 46, 47, 48, 69, 74, 77, 78, 79, 108, 110, 114, 115, 118, and 120, wherein the position corresponding to L79 of SEQ ID NO: 1 is an acidic amino acid. In some embodiments, ActRIIB polypeptides of the disclosure comprise, consist, or consist essentially of, at least one ActRIIB polypeptide wherein the position corresponding to L79 of SEQ ID NO: 1 is not an acidic amino acid (i.e., is not naturally occurring acid amino acids D or E or an artificial acidic amino acid residue).

In certain embodiments, the present disclosure relates to ActRIIA polypeptides. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication Nos. WO 2006/012627 and WO 2007/062188, which are incorporated herein by reference in their entirety. Numbering of amino acids for all ActRIIA-related polypeptides described herein is based on the numbering of the human ActRIIA precursor protein sequence provided below (SEQ ID NO: 9), unless specifically designated otherwise.

The canonical human ActRIIA precursor protein sequence is as follows:

(SEQ ID NO: 9)
1   MGAAAKLAFA VFLISCSSGA ILGRSETQEC LFFNANWEKD
    RTNQTGVEPC

51  YGDKDKRRHC FATWKNISGS IEIVKQGCWL DDINCYDRTD
    CVEKEDSPEV

```
101  YFCCCEGNMC NEKFSYFPEM EVTQPTSNPV TPKPPYYNIL
     LYSLVPLMLI

151  AGIVICAFWV YRHHKMAYPP VLVPTQDPGP PPPSPLLGLK
     PLQLLEVKAR

201  GRFGCVWKAQ LLNEYVAVKI FPIQDKQSWQ NEYEVYSLPG
     MKHENILQFI

251  GAEKRGTSVD VDLWLITAFH EKGSLSDFLK ANVVSWNELC
     HIAETMARGL

301  AYLHEDIPGL KDGHKPAISH RDIKSKNVLL KNNLTACIAD
     FGLALKFEAG

351  KSAGDTHGQV GTRRYMAPEV LEGAINFQRD AFLRIDMYAM
     GLVLWELASR

401  CTAADGPVDE YMLPFEEEIG QHPSLEDMQE VVVHKKKRPV
     LRDYWQKHAG

451  MAMLCETIEE CWDHDAEARL SAGCVGERIT QMQRLTNIIT
     TEDIVTVVTM

501  VTNVDFPPKE SSL
```

The signal peptide is indicated by a single underline; the extracellular domain is indicated in bold font; and the potential, endogenous N-linked glycosylation sites are indicated by a double underline.

The processed (mature) extracellular human ActRIIA polypeptide sequence is as follows:

(SEQ ID NO: 10)

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP

The C-terminal "tail" of the extracellular domain is indicated by single underline. The sequence with the "tail" deleted (a Δ15 sequence) is as follows:

(SEQ ID NO: 11)

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

The nucleic acid sequence encoding human ActRIIA precursor protein is shown below (SEQ ID NO: 12), as follows nucleotides 159-1700 of Genbank Reference Sequence NM_001616.4. The signal sequence is underlined.

(SEQ ID NO: 12)

```
   1 ATGGGAGCTG CTGCAAAGTT GGCGTTTGCC GTCTTTCTTA TCTCCTGTTC
  51 TTCAGGTGCT ATACTTGGTA GATCAGAAAC TCAGGAGTGT CTTTTCTTTA
 101 ATGCTAATTG GGAAAAAGAC AGAACCAATC AAACTGGTGT TGAACCGTGT
 151 TATGGTGACA AAGATAAACG GCGGCATTGT TTTGCTACCT GGAAGAATAT
 201 TTCTGGTTCC ATTGAAATAG TGAAACAAGG TTGTTGGCTG GATGATATCA
 251 ACTGCTATGA CAGGACTGAT TGTGTAGAAA AAAAAGACAG CCCTGAAGTA
 301 TATTTTTGTT GCTGTGAGGG CAATATGTGT AATGAAAAGT TTTCTTATTT
 351 TCCGGAGATG GAAGTCACAC AGCCCACTTC AAATCCAGTT ACACCTAAGC
 401 CACCCTATTA CAACATCCTG CTCTATTCCT TGGTGCCACT TATGTTAATT
 451 GCGGGGATTG TCATTTGTGC ATTTTGGGTG TACAGGCATC ACAAGATGGC
 501 CTACCCTCCT GTACTTGTTC CAACTCAAGA CCCAGGACCA CCCCCACCTT
 551 CTCCATTACT AGGTTTGAAA CCACTGCAGT TATTAGAAGT GAAAGCAAGG
 601 GGAAGATTTG GTTGTGTCTG GAAAGCCCAG TTGCTTAACG AATATGTGGC
 651 TGTCAAAATA TTTCCAATAC AGGACAAACA GTCATGGCAA AATGAATACG
 701 AAGTCTACAG TTTGCCTGGA ATGAAGCATG AGAACATATT ACAGTTCATT
 751 GGTGCAGAAA AACGAGGCAC CAGTGTTGAT GTGGATCTTT GGCTGATCAC
 801 AGCATTTCAT GAAAAGGGTT CACTATCAGA CTTTCTTAAG GCTAATGTGG
 851 TCTCTTGGAA TGAACTGTGT CATATTGCAG AAACCATGGC TAGAGGATTG
 901 GCATATTTAC ATGAGGATAT ACCTGGCCTA AAAGATGGCC ACAAACCTGC
 951 CATATCTCAC AGGGACATCA AAAGTAAAAA TGTGCTGTTG AAAAACAACC
1001 TGACAGCTTG CATTGCTGAC TTTGGGTTGG CCTTAAAATT TGAGGCTGGC
1051 AAGTCTGCAG GCGATACCCA TGGACAGGTT GGTACCCGGA GGTACATGGC
1101 TCCAGAGGTA TTAGAGGGTG CTATAAACTT CCAAAGGGAT GCATTTTTGA
1151 GGATAGATAT GTATGCCATG GGATTAGTCC TATGGGAACT GGCTTCTCGC
```

```
1201  TGTACTGCTG  CAGATGGACC  TGTAGATGAA  TACATGTTGC  CATTTGAGGA

1251  GGAAATTGGC  CAGCATCCAT  CTCTTGAAGA  CATGCAGGAA  GTTGTTGTGC

1301  ATAAAAAAAA  GAGGCCTGTT  TTAAGAGATT  ATTGGCAGAA  ACATGCTGGA

1351  ATGGCAATGC  TCTGTGAAAC  CATTGAAGAA  TGTTGGGATC  ACGACGCAGA

1401  AGCCAGGTTA  TCAGCTGGAT  GTGTAGGTGA  AAGAATTACC  CAGATGCAGA

1451  GACTAACAAA  TATTATTACC  ACAGAGGACA  TTGTAACAGT  GGTCACAATG

1501  GTGACAAATG  TTGACTTTCC  TCCCAAAGAA  TCTAGTCTA
```

The nucleic acid sequence encoding processed soluble (extracellular) human ActRIIA polypeptide is as follows:

```
                                           (SEQ ID NO: 13)
  1  ATACTTGGTA  GATCAGAAAC  TCAGGAGTGT  CTTTTCTTTA
     ATGCTAATTG

51  GGAAAAAGAC  AGAACCAATC  AAACTGGTGT  TGAACCGTGT
     TATGGTGACA

101  AAGATAAACG  GCGGCATTGT  TTTGCTACCT  GGAAGAATAT
     TTCTGGTTCC

151  ATTGAAATAG  TGAAACAAGG  TTGTTGGCTG  GATGATATCA
     ACTGCTATGA

201  CAGGACTGAT  TGTGTAGAAA  AAAAAGACAG  CCCTGAAGTA
     TATTTTTGTT

251  GCTGTGAGGG  CAATATGTGT  AATGAAAAGT  TTTCTTATTT
     TCCGGAGATG

301  GAAGTCACAC  AGCCCACTTC  AAATCCAGTT  ACACCTAAGC
     CACCC
```

ActRIIA is well-conserved among vertebrates, with large stretches of the extracellular domain completely conserved. For example, FIG. 3 depicts a multi-sequence alignment of a human ActRIIA extracellular domain compared to various ActRIIA orthologs. Many of the ligands that bind to ActRIIA are also highly conserved. Accordingly, from these alignments, it is possible to predict key amino acid positions within the ligand-binding domain that are important for normal ActRIIA-ligand binding activities as well as to predict amino acid positions that are likely to be tolerant to substitution without significantly altering normal ActRIIA-ligand binding activities. Therefore, an active, human ActRIIA variant polypeptide useful in accordance with the presently disclosed methods may include one or more amino acids at corresponding positions from the sequence of another vertebrate ActRIIA, or may include a residue that is similar to that in the human or other vertebrate sequences.

Without meaning to be limiting, the following examples illustrate this approach to defining an active ActRIIA variant. As illustrated in FIG. 3, F13 in the human extracellular domain is Y in *Ovis aries* (SEQ ID NO: 62), *Gallus gallus* (SEQ ID NO: 65), *Bos Taurus* (SEQ ID NO: 66), *Tyto alba* (SEQ ID NO: 67), and *Myotis davidii* (SEQ ID NO: 68) ActRIIA, indicating that aromatic residues are tolerated at this position, including F, W, and Y. Q24 in the human extracellular domain is R in *Bos Taurus* ActRIIA, indicating that charged residues will be tolerated at this position, including D, R, K, H, and E. S95 in the human extracellular domain is F in *Gallus gallus* and *Tyto alba* ActRIIA, indicating that this site may be tolerant of a wide variety of changes, including polar residues, such as E, D, K, R, H, S, T, P, G, Y, and probably hydrophobic residue such as L, I, or F. E52 in the human extracellular domain is D in *Ovis aries* ActRIIA, indicating that acidic residues are tolerated at this position, including D and E. P29 in the human extracellular domain is relatively poorly conserved, appearing as S in *Ovis aries* ActRIIA and L in *Myotis davidii* ActRIIA, thus essentially any amino acid should be tolerated at this position.

Moreover, as discussed above, ActRII proteins have been characterized in the art in terms of structural/functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRII variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIA, as demarcated by the outermost of these conserved cysteines, corresponds to positions 30-110 of SEQ ID NO: 9 (ActRIIA precursor). Therefore, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, 28, or 29 residues at the N-terminus and by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRIIA extracellular domains truncations include SEQ ID NOs: 10 and 11.

Accordingly, a general formula for an active portion (e.g., ligand binding) of ActRIIA is a polypeptide that comprises, consists essentially of, or consists of amino acids 30-110 of SEQ ID NO: 9. Therefore ActRIIA polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to any one of amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134, or 135) of SEQ ID NO: 9. Other examples include constructs that begin at a position selected from 21-30 (e.g., beginning at any one of amino acids 21, 22, 23, 24, 25, 26, 27, 28, 29, or 30), 22-30 (e.g., beginning at any one of amino acids 22, 23, 24, 25, 26, 27, 28, 29, or 30), 23-30 (e.g., beginning at any one of amino acids 23, 24, 25, 26, 27, 28, 29, or 30), 24-30 (e.g., beginning at any one of amino acids 24, 25, 26, 27, 28, 29, or 30) of SEQ ID NO: 9, and end at a position selected from 111-135 (e.g., ending at any one of amino acids 111, 112, 113, 114, 115, 116, 117, 118, 119, 120, 121, 122, 123, 124, 125, 126, 127, 128, 129, 130, 131, 132, 133, 134 or 135), 112-135 (e.g., ending at any one of amino acids 112, 113, 114, 115, 116, 117, 118, 119, 120, 121, 122, 123, 124, 125, 126, 127, 128, 129, 130, 131, 132, 133, 134 or 135), 113-135 (e.g., ending at any one of amino acids 113, 114, 115, 116, 117, 118, 119, 120, 121, 122, 123, 124, 125, 126, 127, 128, 129, 130, 131, 132, 133, 134 or 135), 120-135 (e.g., ending at any one of amino acids 120, 121, 122, 123, 124, 125, 126, 127, 128, 129, 130, 131, 132, 133, 134 or 135), 130-135 (e.g., ending at any one of amino acids 130, 131, 132, 133, 134 or 135), 111-134 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 134), 111-133 (e.g., ending at any one of amino acids 110, 111, 112, 113, 114, 115, 116, 117, 118, 119, 120, 121, 122, 123, 124, 125, 126, 127, 128, 129, 130, 131, 132, or 133), 111-132 (e.g., ending at any one of amino acids 110, 111, 112, 113, 114, 115, 116, 117, 118, 119, 120, 121, 122, 123, 124, 125, 126, 127, 128, 129, 130, 131, or 132), or 111-131 (e.g., ending at any one of amino acids 110, 111, 112, 113, 114, 115, 116, 117, 118, 119, 120, 121, 122, 123, 124, 125, 126, 127, 128, 129, 130, or 131) of SEQ ID NO: 9. Variants within these ranges are also contemplated, particularly those comprising, consisting essentially of, or consisting of an amino acid sequence that has at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 9. Thus, in some embodiments, an ActRIIA polypeptide may comprise, consists essentially of, or consist of a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9. Optionally, ActRIIA polypeptides comprise a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 9, and comprising no more than 1, 2, 5, 10 or 15 conservative amino acid changes in the ligand-binding pocket.

In certain embodiments, the disclosure relates to GDF/BMP antagonists (inhibitors) that comprise an ActRIIA polypeptide, which includes fragments, functional variants, and modified forms thereof as well as uses thereof (e.g., increasing an immune response in a patient in need thereof and treating cancer). Preferably, ActRIIA polypeptides are soluble (e.g., an extracellular domain of ActRIIA). In some embodiments, ActRIIA polypeptides inhibit (e.g., Smad signaling) of one or more GDF/BMP ligands [e.g., GDF11, GDF8, activin (activin A, activin B, activin AB, activin C, activin E) BMP6, GDF3, BMP15, and/or BMP10]. In some embodiments, ActRIIA polypeptides bind to one or more GDF/BMP ligands [e.g., GDF11, GDF8, activin (activin A, activin B, activin AB, activin C, activin E) BMP6, GDF3, BMP15, and/or BMP10]. In some embodiments, ActRIIA polypeptide of the disclosure comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIA beginning at a residue corresponding to amino acids 21-30 (e.g., beginning at any one of amino acids 21, 22, 23, 24, 25, 26, 27, 28, 29, or 30) of SEQ ID NO: 9 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134 or 135) of SEQ ID NO: 9. In some embodiments, ActRIIA polypeptides comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 30-110 of SEQ ID NO: 9. In certain embodiments, ActRIIA polypeptides comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 21-135 of SEQ ID NO: 9. In some embodiments, ActRIIA polypeptides comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 9, 10, 11, 32, 36, and 39.

In certain aspects, the present disclosure relates to GDF trap polypeptides (also referred to as "GDF traps"). In some embodiments, GDF traps of the present disclosure are variant ActRII polypeptides (e.g., ActRIIA and ActRIIB polypeptides) that comprise one or more mutations (e.g., amino acid additions, deletions, substitutions, and combinations thereof) in the extracellular domain (also referred to as the ligand-binding domain) of an ActRII polypeptide (e.g., a "wild-type" or unmodified ActRII polypeptide) such that the variant ActRII polypeptide has one or more altered ligand-binding activities than the corresponding wild-type ActRII polypeptide. In preferred embodiments, GDF trap polypeptides of the present disclosure retain at least one similar activity as a corresponding wild-type ActRII polypeptide. For example, preferable GDF traps bind to and inhibit (e.g. antagonize) the function of GDF11 and/or GDF8. In some embodiments, GDF traps of the present disclosure further bind to and inhibit one or more of ligand of the GDF/BMP. Accordingly, the present disclosure provides GDF trap polypeptides that have an altered binding specificity for one or more ActRII ligands.

To illustrate, one or more mutations may be selected that increase the selectivity of the altered ligand-binding domain for GDF11 and/or GDF8 over one or more ActRII-binding ligands such as activins (activin A, activin B, activin AB, activin C, and/or activin E), particularly activin A. Optionally, the altered ligand-binding domain has a ratio of $K_d$ for activin binding to $K_d$ for GDF11 and/or GDF8 binding that is at least 2-, 5-, 10-, 20-, 50-, 100- or even 1000-fold greater relative to the ratio for the wild-type ligand-binding domain. Optionally, the altered ligand-binding domain has a ratio of $IC_{50}$ for inhibiting activin to $IC_{50}$ for inhibiting GDF11 and/or GDF8 that is at least 2-, 5-, 10-, 20-, 50-, 100- or even 1000-fold greater relative to the wild-type ligand-binding domain. Optionally, the altered ligand-binding domain inhibits GDF11 and/or GDF8 with an $IC_{50}$ at least 2-, 5-, 10-, 20-, 50-, 100- or even 1000-times less than the $IC_{50}$ for inhibiting activin.

Amino acid residues of the ActRIIB proteins (e.g., E39, K55, Y60, K74, W78, L79, D80, and F101 with respect to SEQ ID NO: 1) are in the ActRIIB ligand-binding pocket and help mediated binding to its ligands including, for example, activin A, GDF11, and GDF8. Thus the present disclosure provides GDF trap polypeptides comprising an altered-ligand binding domain (e.g., a GDF8/GDF11-binding domain) of an ActRIIB receptor which comprises one or more mutations at those amino acid residues.

As a specific example, the positively-charged amino acid residue Asp (D80) of the ligand-binding domain of ActRIIB can be mutated to a different amino acid residue to produce a GDF trap polypeptide that preferentially binds to GDF8, but not activin. Preferably, the D80 residue with respect to SEQ ID NO: 1 is changed to an amino acid residue selected from the group consisting of: an uncharged amino acid residue, a negative amino acid residue, and a hydrophobic amino acid residue. As a further specific example, the hydrophobic residue L79 of SEQ ID NO: 1 can be altered to confer altered activin-GDF11/GDF8 binding properties. For example, an L79P substitution reduces GDF11 binding to a greater extent than activin binding. In contrast, replacement of L79 with an acidic amino acid [an aspartic acid or glutamic acid; an L79D or an L79E substitution] greatly reduces activin A binding affinity while retaining GDF11 binding affinity. In exemplary embodiments, the methods described herein utilize a GDF trap polypeptide which is a variant ActRIIB polypeptide comprising an acidic amino acid (e.g., D or E) at the position corresponding to position 79 of SEQ ID NO: 1, optionally in combination with one or more additional amino acid substitutions, additions, or deletions.

In certain aspects, the disclosure relates ALK4 polypeptides and uses thereof. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity. Numbering of amino acids for all ALK4-related polypeptides described herein is based on the numbering of the human ALK4 precursor protein sequence below (SEQ ID NO: 100), unless specifically designated otherwise.

A human ALK4 precursor protein sequence (NCBI Ref Seq NP_004293) is as follows:

```
                                      (SEQ ID NO: 100)
  1 MAESAGASSF FPLVVLLLAG SGGSGPRGVQ ALLCACTSCL
    QANYTCETDG ACMVSIFNLD

61 GMEHHVRTCI PKVELVPAGK PFYCLSSEDL RNTHCCYTDY
    CNRIDLRVPS GHLKEPEHPS

121 MWGPVELVGI IAGPVFLLFL IIIIVFLVIN YHQRVYHNRQ
    RLDMEDPSCE MCLSKDKTLQ

181 DLVYDLSTSG SGSGLPLFVQ RTVARTIVLQ EIIGKGRFGE
    VWRGRWRGGD VAVKIFSSRE

241 ERSWFREAEI YQTVMLRHEN ILGFIAADNK DNGTWTQLWL
    VSDYHEHGSL FDYLNRYTVT
```

-continued
```
301 IEGMIKLALS AASGLAHLHM EIVGTQGKPG IAHRDLKSKN
    ILVKKNGMCA IADLGLAVRH

361 DAVTDTIDIA PNQRVGTKRY MAPEVLDETI NMKHFDSFKC
    ADIYALGLVY WEIARRCNSG

421 GVHEEYQLPY YDLVPSDPSI EEMRKVVCDQ KLRPNIPNWW
    QSYEALRVMG KMMRECWYAN

481 GAARLTALRI KKTLSQLSVQ EDVKI
```

The signal peptide is indicated by a single underline and the extracellular domain is indicated in bold font.

A processed extracellular human ALK4 polypeptide sequence is as follows:

```
                                      (SEQ ID NO: 101)
SGPRGVQALLCACTSCLQANYTCETDGACMVSIFNLDGMEHHVRTCIPKV

ELVPAGKPFYCLSSEDLRNTHCCYTDYCNRIDLRVPSGHLKEPEHPSMWG

PVE
```

A nucleic acid sequence encoding the ALK4 precursor protein is shown below (SEQ ID NO: 102), corresponding to nucleotides 78-1592 of Genbank Reference Sequence NM_004302.4. The signal sequence is underlined and the extracellular domain is indicated in bold font.

```
                                      (SEQ ID NO: 102)
ATGGCGGAGTCGGCCGGAGCCTCCTCCTTCTTCCCCCTTGTTGTCCTCC

TGCTCGCCGGCAGCGGCGGGTCCGGGCCCCGGGGGGTCCAGGCTCTGCT

GTGTGCGTGCACCAGCTGCCTCCAGGCCAACTACACGTGTGAGACAGAT

GGGGCCTGCATGGTTTCCATTTTCAATCTGGATGGGATGGAGCACCATG

TGCGCACCTGCATCCCCAAAGTGGAGCTGGTCCCTGCCGGGAAGCCCTT

CTACTGCCTGAGCTCGGAGGACCTGCGCAACACCCACTGCTGCTACACT

GACTACTGCAACAGGATCGACTTGAGGGTGCCCAGTGGTCACCTCAAGG

AGCCTGAGCACCCGTCCATGTGGGGCCCGGTGGAGCTGGTAGGCATCAT

CGCCGGCCCGGTGTTCCTCCTGTTCCTCATCATCATCATTGTTTTCCTT

GTCATTAACTATCATCAGCGTGTCTATCACAACCGCCAGAGACTGGACA

TGGAAGATCCCTCATGTGAGATGTGTCTCTCCAAAGACAAGACGCTCCA

GGATCTTGTCTACGATCTCTCCACCTCAGGGTCTGGCTCAGGGTTACCC

CTCTTTGTCCAGCGCACAGTGGCCCGAACCATCGTTTTACAAGAGATTA

TTGGCAAGGGTCGGTTTGGGGAAGTATGGCGGGCCGCTGGAGGGGTGG

TGATGTGGCTGTGAAAATATTCTCTTCTCGTGAAGAACGGTCTTGGTTC

AGGGAAGCAGAGATATACCAGACGGTCATGCTGCGCCATGAAAACATCC

TTGGATTTATTGCTGCTGACAATAAAGATAATGGCACCTGGACACAGCT

GTGGCTTGTTTCTGACTATCATGAGCACGGGTCCCTGTTTGATTATCTG

AACCGGTACACAGTGACAATTGAGGGGATGATTAAGCTGGCCTTGTCTG

CTGCTAGTGGGCTGGCACACCTGCACATGGAGATCGTGGGCACCCAAGG

GAAGCCTGGAATTGCTCATCGAGACTTAAAGTCAAAGAACATTCTGGTG

AAGAAAAATGGCATGTGTGCCATAGCAGACCTGGGCCTGGCTGTCCGTC

ATGATGCAGTCACTGACACCATTGACATTGCCCCGAATCAGAGGGTGGG
```

-continued
```
GACCAAACGATACATGGCCCCTGAAGTACTTGATGAAACCATTAATATG

AAACACTTTGACTCCTTTAAATGTGCTGATATTTATGCCCTCGGGCTTG

TATATTGGGAGATTGCTCGAAGATGCAATTCTGGAGGAGTCCATGAAGA

ATATCAGCTGCCATATTACGACTTAGTGCCCTCTGACCCTTCCATTGAG

GAAATGCGAAAGGTTGTATGTGATCAGAAGCTGCGTCCCAACATCCCA

ACTGGTGGCAGAGTTATGAGGCACTGCGGGTGATGGGGAAGATGATGCG

AGAGTGTTGGTATGCCAACGGCGCAGCCCGCCTGACGGCCCTGCGCATC

AAGAAGACCCTCTCCCAGCTCAGCGTGCAGGAAGACGTGAAGATC
```

A nucleic acid sequence encoding the extracellular ALK4 polypeptide is as follows:

```
(SEQ ID NO: 103)
TCCGGGCCCCGGGGGGTCCAGGCTCTGCTGTGTGCGTGCACCAGCTGCC

TCCAGGCCAACTACACGTGTGAGACAGATGGGGCCTGCATGGTTTCCAT

TTTCAATCTGGATGGGATGGAGCACCATGTGCGCACCTGCATCCCCAAA

GTGGAGCTGGTCCCTGCCGGGAAGCCCTTCTACTGCCTGAGCTCGGAGG

ACCTGCGCAACACCCACTGCTGCTACACTGACTACTGCAACAGGATCGA

CTTGAGGGTGCCCAGTGGTCACCTCAAGGAGCCTGAGCACCCGTCCATG

TGGGGCCCGGTGGAG
```

An alternative isoform of human ALK4 precursor protein sequence, isoform B (NCBI Ref Seq NP_064732.3), is as follows:

(SEQ ID NO: 104)
```
  1   MVSIFNLDGM EHHVRTCIPK VELVPAGKPF YCLSSEDLRN THCCYTDYCN RIDLRVPSGH
 61   LKEPEHPSMW GPVELVGIIA GPVFLLFLII IIVFLVINYH QRVYHNRQRL DMEDPSCEMC
121   LSKDKTLQDL VYDLSTSGSG SGLPLFVQRT VARTIVLQEI IGKGRFGEVW RGRWRGGDVA
181   VKIFSSREER SWFREAEIYQ TVMLRHENIL GFIAADNKDN GTWTQLWLVS DYHEHGSLFD
241   YLNRYTVTIE GMIKLALSAA SGLAHLHMEI VGTQGKPGIA HRDLKSKNIL VKKNGMCAIA
301   DLGLAVRHDA VTDTIDIAPN QRVGTKRYMA PEVLDETINM KHFDSFKCAD IYALGLVYWE
361   IARRCNSGGV HEEYQLPYYD LVPSDPSIEE MRKVVCDQKL RPNIPNWWQS YEALRVMGKM
421   MRECWYANGA ARLTALRIKK TLSQLSVQED VKI
```

The extracellular domain is indicated in bold font.
A processed extracellular ALK4 polypeptide sequence is as follows:

(SEQ ID NO: 105)
```
  1   MVSIFNLDGM EHHVRTCIPK VELVPAGKPF YCLSSEDLRN THCCYTDYCN RIDLRVPSGH
 61   LKEPEHPSMW GPVE
```

A nucleic acid sequence encoding the ALK4 precursor protein (isoform B) is shown below (SEQ ID NO: 106), corresponding to nucleotides 186-1547 of Genbank Reference Sequence NM_020327.3. The nucleotides encoding the extracellular domain are indicated in bold font.

(SEQ ID NO: 106)
```
  1   ATGGTTTCCA TTTTCAATCT GGATGGGATG GAGCACCATG TGCGCACCTG
 51   CATCCCCAAA GTGGAGCTGG TCCCTGCCGG GAAGCCCTTC TACTGCCTGA
101   GCTCGGAGGA CCTGCGCAAC ACCCACTGCT GCTACACTGA CTACTGCAAC
151   AGGATCGACT TGAGGGTGCC CAGTGGTCAC CTCAAGGAGC CTGAGCACCC
201   GTCCATGTGG GGCCCGGTGG AGCTGGTAGG CATCATCGCC GGCCCGGTGT
251   TCCTCCTGTT CCTCATCATC ATCATTGTTT TCCTTGTCAT TAACTATCAT
301   CAGCGTGTCT ATCACAACCG CCAGAGACTG GACATGGAAG ATCCCTCATG
351   TGAGATGTGT CTCTCCAAAG ACAAGACGCT CCAGGATCTT GTCTACGATC
401   TCTCCACCTC AGGGTCTGGC TCAGGGTTAC CCCTCTTTGT CCAGCGCACA
451   GTGGCCCGAA CCATCGTTTT ACAAGAGATT ATTGGCAAGG GTCGGTTTGG
501   GGAAGTATGG CGGGGCCGCT GGAGGGGTGG TGATGTGGCT GTGAAAATAT
```

```
                            -continued
551    TCTCTTCTCG TGAAGAACGG TCTTGGTTCA GGGAAGCAGA GATATACCAG

601    ACGGTCATGC TGCGCCATGA AAACATCCTT GGATTTATTG CTGCTGACAA

651    TAAAGATAAT GGCACCTGGA CACAGCTGTG GCTTGTTTCT GACTATCATG

701    AGCACGGGTC CCTGTTTGAT TATCTGAACC GGTACACAGT GACAATTGAG

751    GGGATGATTA AGCTGGCCTT GTCTGCTGCT AGTGGGCTGG CACACCTGCA

801    CATGGAGATC GTGGGCACCC AAGGGAAGCC TGGAATTGCT CATCGAGACT

851    TAAAGTCAAA GAACATTCTG GTGAAGAAAA ATGGCATGTG TGCCATAGCA

901    GACCTGGGCC TGGCTGTCCG TCATGATGCA GTCACTGACA CCATTGACAT

951    TGCCCCGAAT CAGAGGGTGG GGACCAAACG ATACATGGCC CCTGAAGTAC

1001   TTGATGAAAC CATTAATATG AAACACTTTG ACTCCTTTAA ATGTGCTGAT

1051   ATTTATGCCC TCGGGCTTGT ATATTGGGAG ATTGCTCGAA GATGCAATTC

1101   TGGAGGAGTC CATGAAGAAT ATCAGCTGCC ATATTACGAC TTAGTGCCCT

1151   CTGACCCTTC CATTGAGGAA ATGCGAAAGG TTGTATGTGA TCAGAAGCTG

1201   CGTCCCAACA TCCCCAACTG GTGGCAGAGT TATGAGGCAC TGCGGGTGAT

1251   GGGGAAGATG ATGCGAGAGT GTTGGTATGC CAACGGCGCA GCCCGCCTGA

1301   CGGCCCTGCG CATCAAGAAG ACCCTCTCCC AGCTCAGCGT GCAGGAAGAC

1351   GTGAAGATCT AA
```

A nucleic acid sequence encoding the extracellular ALK4 polypeptide (isoform B) is as follows:

```
                                                          (SEQ ID NO: 107)
1      ATGGTTTCCA TTTTCAATCT GGATGGGATG GAGCACCATG TGCGCACCTG

51     CATCCCCAAA GTGGAGCTGG TCCCTGCCGG GAAGCCCTTC TACTGCCTGA

101    GCTCGGAGGA CCTGCGCAAC ACCCACTGCT GCTACACTGA CTACTGCAAC

151    AGGATCGACT TGAGGGTGCC CAGTGGTCAC CTCAAGGAGC CTGAGCACCC

201    GTCCATGTGG GGCCCGGTGG AGCTGGTAGG
```

ALK4 is well-conserved among vertebrates, with large stretches of the extracellular domain completely conserved. For example, FIG. 18 depicts a multi-sequence alignment of a human ALK4 extracellular domain compared to various ALK4 orthologs. Many of the ligands that bind to ALK4 are also highly conserved. Accordingly, from these alignments, it is possible to predict key amino acid positions within the ligand-binding domain that are important for normal ALK4-ligand binding activities as well as to predict amino acid positions that are likely to be tolerant to substitution without significantly altering normal ALK4-ligand binding activities. Therefore, an active, human ALK4 variant polypeptide useful in accordance with the presently disclosed methods may include one or more amino acids at corresponding positions from the sequence of another vertebrate ALK4, or may include a residue that is similar to that in the human or other vertebrate sequences.

Without meaning to be limiting, the following examples illustrate this approach to defining an active ALK4 variant. As illustrated in FIG. 18, V6 in the human ALK4 extracellular domain (SEQ ID NO: 126) is isoleucine in *Mus muculus* ALK4 (SEQ ID NO: 130), and so the position may be altered, and optionally may be altered to another hydrophobic residue such as L, I, or F, or a non-polar residue such as A, as is observed in *Gallus gallus* ALK4 (SEQ ID NO: 129). E40 in the human extracellular domain is K in *Gallus gallus* ALK4, indicating that this site may be tolerant of a wide variety of changes, including polar residues, such as E, D, K, R, H, S, T, P, G, Y, and probably a non-polar residue such as A. S15 in the human extracellular domain is D in *Gallus gallus* ALK4, indicating that a wide structural variation is tolerated at this position, with polar residues favored, such as S, T, R, E, K, H, G, P, G and Y. E40 in the human extracellular domain is K in *Gallus gallus* ALK4, indicating that charged residues will be tolerated at this position, including D, R, K, H, as well as Q and N. R80 in the human extracellular domain is K in *Condylura cristata* ALK4 (SEQ ID NO: 127), indicating that basic residues are tolerated at this position, including R, K, and H. Y77 in the human extracellular domain is F in *Sus scrofa* ALK4 (SEQ ID NO: 131), indicating that aromatic residues are tolerated at this position, including F, W, and Y. P93 in the human extracellular domain is relatively poorly conserved, appearing as S in *Erinaceus europaeus* ALK4 (SEQ ID NO: 128) and N in *Gallus gallus* ALK4, thus essentially any amino acid should be tolerated at this position.

Moreover, ALK4 proteins have been characterized in the art in terms of structural and functional characteristics, particularly with respect to ligand binding [e.g., Harrison et al. (2003) J Biol Chem 278(23):21129-21135; Romano et al.

(2012) J Mol Model 18(8):3617-3625; and Calvanese et al. (2009) 15(3):175-183]. In addition to the teachings herein, these references provide amply guidance for how to generate ALK4 variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ALK4, as demarcated by the outermost of these conserved cysteines, corresponds to positions 34-101 of SEQ ID NO: 100 (ALK4 precursor). The structurally less-ordered amino acids flanking these cysteine-demarcated core sequences can be truncated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 residues at the N-terminus and/or by 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ALK4 extracellular domains for N-terminal and/or C-terminal truncation include SEQ ID NOs: 101 and 105.

Accordingly, a general formula for an active portion (e.g., a ligand-binding portion) of ALK4 comprises amino acids 34-101 with respect to SEQ ID NO: 100. Therefore ALK4 polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ALK4 beginning at a residue corresponding to any one of amino acids 24-34 (e.g., beginning at any one of amino acids 24, 25, 26, 27, 28, 29, 30, 31, 32, 33, or 34) of SEQ ID NO: 100 and ending at a position corresponding to any one amino acids 101-126 (e.g., ending at any one of amino acids 101, 102, 103, 104, 105, 106, 107, 108, 109, 110, 111, 112, 113, 114, 115, 116, 117, 118, 119, 120, 121, 122, 123, 124, 125, or 126) of SEQ ID NO: 100. Other examples include constructs that begin at a position from 24-34 (e.g., any one of positions 24, 25, 26, 27, 28, 29, 30, 31, 32, 33, or 34), 25-34 (e.g., any one of positions 25, 26, 27, 28, 29, 30, 31, 32, 33, or 34), or 26-34 (e.g., any one of positions 26, 27, 28, 29, 30, 31, 32, 33, or 34) of SEQ ID NO: 100 and end at a position from 101-126 (e.g., any one of positions 101, 102, 103, 104, 105, 106, 107, 108, 109, 110, 111, 112, 113, 114, 115, 116, 117, 118, 119, 120, 121, 122, 123, 124, 125, or 126), 102-126 (e.g., any one of positions 102, 103, 104, 105, 106, 107, 108, 109, 110, 111, 112, 113, 114, 115, 116, 117, 118, 119, 120, 121, 122, 123, 124, 125, or 126), 101-125 (e.g., any one of positions 101, 102, 103, 104, 105, 106, 107, 108, 109, 110, 111, 112, 113, 114, 115, 116, 117, 118, 119, 120, 121, 122, 123, 124, or 125), 101-124 (e.g., any one of positions 101, 102, 103, 104, 105, 106, 107, 108, 109, 110, 111, 112, 113, 114, 115, 116, 117, 118, 119, 120, 121, 122, 123, or 124), 101-121 (e.g., any one of positions 101, 102, 103, 104, 105, 106, 107, 108, 109, 110, 111, 112, 113, 114, 115, 116, 117, 118, 119, 120, or 121), 111-126 (e.g., any one of positions 111, 112, 113, 114, 115, 116, 117, 118, 119, 120, 121, 122, 123, 124, 125, or 126), 111-125 (e.g., any one of positions 111, 112, 113, 114, 115, 116, 117, 118, 119, 120, 121, 122, 123, 124, or 125), 111-124 (e.g., any one of positions 111, 112, 113, 114, 115, 116, 117, 118, 119, 120, 121, 122, 123, or 124), 121-126 (e.g., any one of positions 121, 122, 123, 124, 125, or 126), 121-125 (e.g., any one of positions 121, 122, 123, 124, or 125), 121-124 (e.g., any one of positions 121, 122, 123, or 124), or 124-126 (e.g., any one of positions 124, 125, or 126) of SEQ ID NO: 100. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 100.

The variations described herein may be combined in various ways. In some embodiments, ALK4 variants comprise no more than 1, 2, 5, 6, 7, 8, 9, 10 or 15 conservative amino acid changes in the ligand-binding pocket. Sites outside the binding pocket, at which variability may be particularly well tolerated, include the amino and carboxy termini of the extracellular domain (as noted above).

In certain embodiments, the disclosure relates to BMP/GDF antagonists that are heteromultimers comprising at least one ALK4 polypeptide, which includes fragments, functional variants, and modified forms thereof as well as uses thereof (e.g., treating, preventing, or reducing the severity of PAH or one or more complications of PAH). Preferably, ALK4 polypeptides are soluble (e.g., an extracellular domain of ALK4). In some embodiments, heteromultimers comprising an ALK4 polypeptide inhibit (e.g., Smad signaling) of one or more TGFβ superfamily ligands [e.g., GDF11, GDF8, activin (activin A, activin B, activin AB, activin C, activin E) BMP6, GDF3, BMP10, and/or BMP9]. In some embodiments, heteromultimers comprising an ALK4 polypeptide bind to one or more TGFβ superfamily ligands [e.g., GDF11, GDF8, activin (activin A, activin B, activin AB, activin C, activin E) BMP6, GDF3, BMP10, and/or BMP9]. In some embodiments, heteromultimers comprise at least one ALK4 polypeptide that is at least 70%, 75%, 80%, 85%, 86%, 87%, 88%, 89%, 90%, 91%, 92%, 93%, 94%, 95%, 97%, 98%, 99%, 100% identical to amino acids 34-101 with respect to SEQ ID NO: 100. In some embodiments, heteromultimers comprise at least one ALK4 polypeptide that is at least 70%, 75%, 80%, 85%, 86%, 87%, 88%, 89%, 90%, 91%, 92%, 93%, 94%, 95%, 97%, 98%, 99%, or 100% identical to the amino acid sequence of SEQ ID NO: 100, 101, 104, 105, 111, 113, 116, 117, 122, and 124. In some embodiments, heteromultimer comprise at least one ALK4 polypeptide that consist or consist essentially of at least one ALK4 polypeptide that is at least 70%, 75%, 80%, 85%, 86%, 87%, 88%, 89%, 90%, 91%, 92%, 93%, 94%, 95%, 97%, 98%, 99%, or 100% identical to the amino acid sequence of SEQ ID NO: 100, 101, 104, 105, 111, 113, 116, 117, 122, and 124.

Figure 21A:
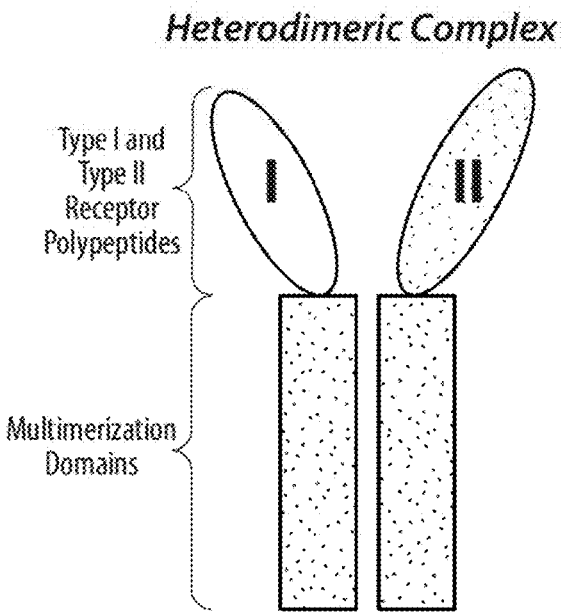
FIGS. 21A and 21B show two schematic examples of heteromeric protein complexes comprising type I receptor and type II receptor polypeptides.
Figure 21B:
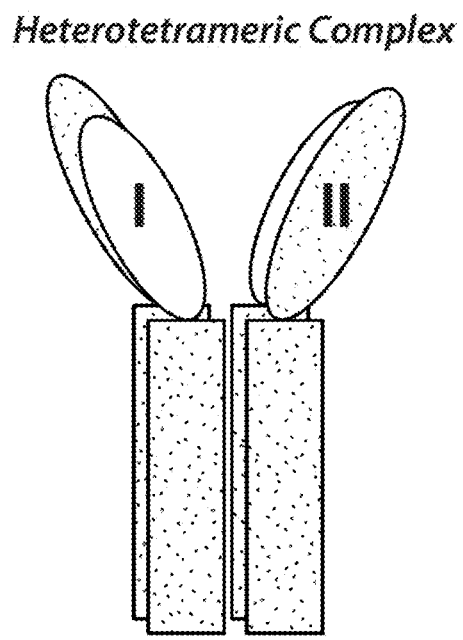
Figure 22:
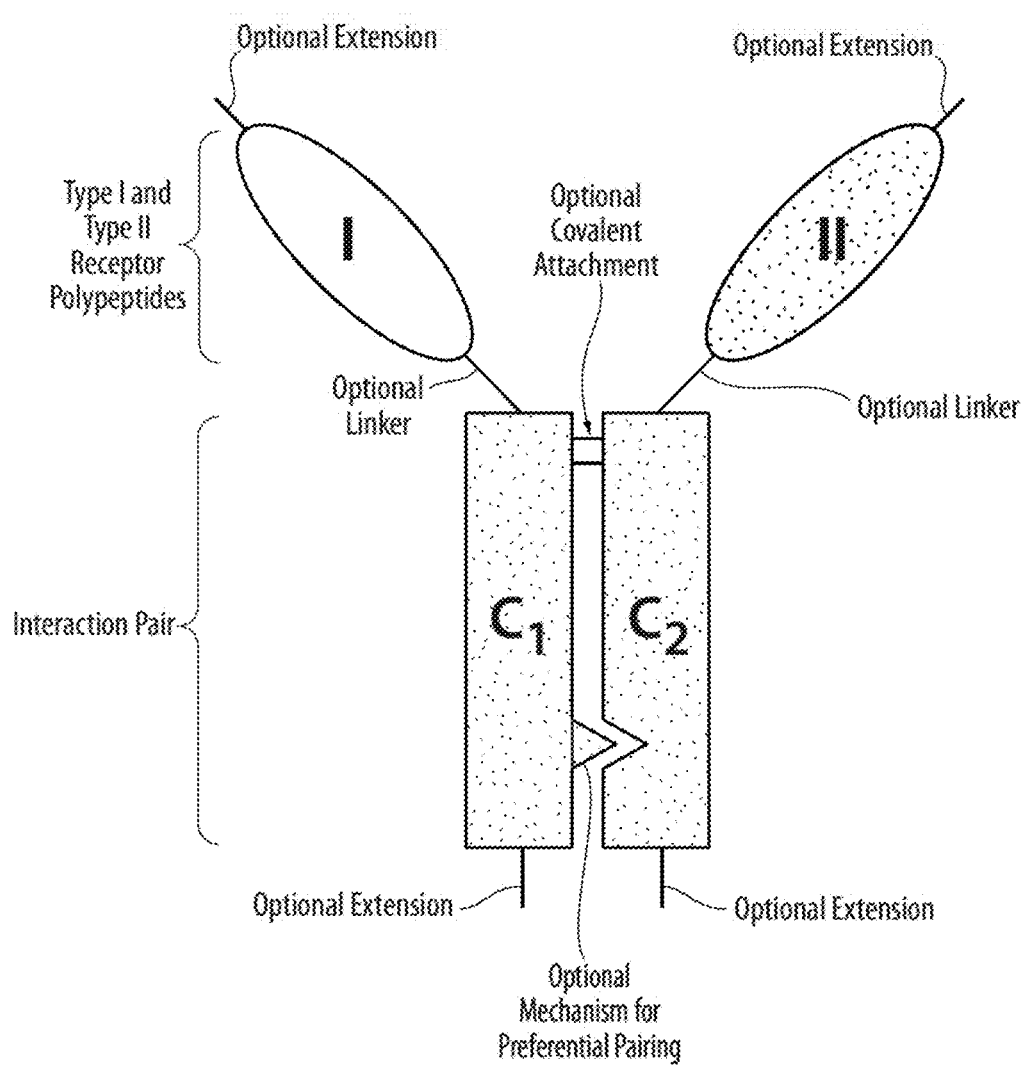
FIG. 22 show a schematic example of a heteromeric protein complex comprising a type I receptor polypeptide (indicated as "I") (e.g. a polypeptide that is at least 70%, 75%, 80%, 85%, 90%, 91%, 92%, 93%, 94%, 95%, 97%, 98%, 99% or 100% identical to an extracellular domain of an ALK4 protein from humans or other species such as those described herein) and a type II receptor polypeptide (indicated as "II") (e.g. a polypeptide that is at least 70%, 75%, 80%, 85%, 90%, 91%, 92%, 93%, 94%, 95%, 97%, 98%, 99% or 100% identical to an extracellular domain of an ActRIIB protein from humans or other species as such as those described herein). In the illustrated embodiments, the type I receptor polypeptide is part of a fusion polypeptide that comprises a first member of an interaction pair ("$C_1$"), and the type II receptor polypeptide is part of a fusion polypeptide that comprises a second member of an interaction pair ("$C_2$"). In each fusion polypeptide, a linker may be positioned between the type I or type II receptor polypeptide and the corresponding member of the interaction pair. The first and second members of the interaction pair may be a guided (asymmetric) pair, meaning that the members of the pair associate preferentially with each other rather than self-associate, or the interaction pair may be unguided, meaning that the members of the pair may associate with each other or self-associate without substantial preference and may have the same or different amino acid sequences. Traditional Fc fusion proteins and antibodies are examples of unguided interaction pairs, whereas a variety of engineered Fc domains have been designed as guided (asymmetric) interaction pairs [e.g., Spiess et al (2015) Molecular Immunology 67(2A): 95-106].
Figure 23A:
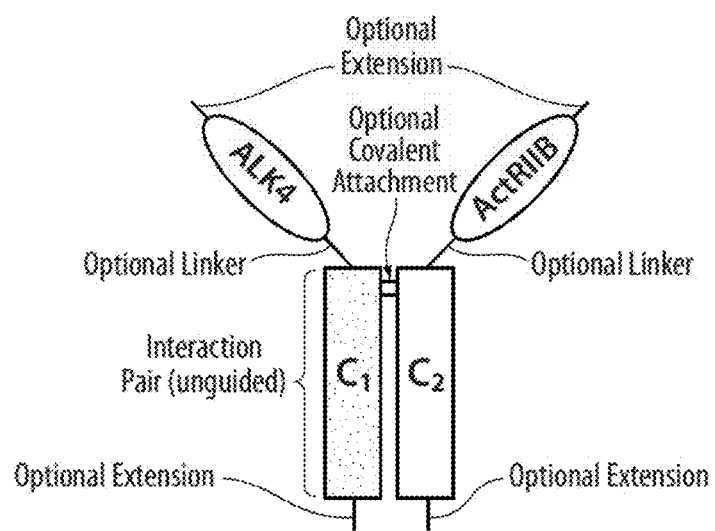
FIGS. 23A-23D show schematic examples of heteromeric protein complexes comprising an ALK4 polypeptide (e.g. a polypeptide that is at least 70%, 75%, 80%, 85%, 90%, 91%, 92%, 93%, 94%, 95%, 97%, 98%, 99% or 100% identical to an extracellular domain of an ALK4 protein from humans or other species such as those described herein) and an ActRIIB polypeptide (e.g. a polypeptide that is at least 70%, 75%, 80%, 85%, 90%, 91%, 92%, 93%, 94%, 95%, 97%, 98%, 99% or 100% identical to an extracellular domain of an ActRIIB protein from humans or other species such as those described herein). In the illustrated embodiments, the ALK4 polypeptide is part of a fusion polypeptide that comprises a first member of an interaction pair ("$C_1$"), and the ActRIIB polypeptide is part of a fusion polypeptide that comprises a second member of an interaction pair ("$C_2$"). Suitable interaction pairs included, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the ALK4 or ActRIIB polypeptide and the corresponding member of the interaction pair. The first and second members of the interaction pair may be unguided, meaning that the members of the pair may associate with each other or self-associate without substantial preference, and they may have the same or different amino acid sequences. See FIG. 23A. Alternatively, the interaction pair may be a guided (asymmetric) pair, meaning that the members of the pair associate preferentially with each other rather than self-associate. See FIG. 23B. Complexes of higher order can be envisioned. See FIGS. 23C and 23D.
Figure 23B:
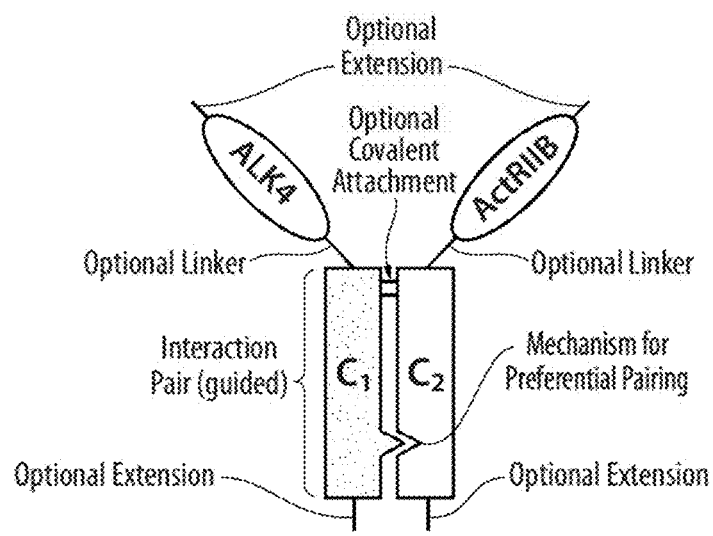
Figure 23C:
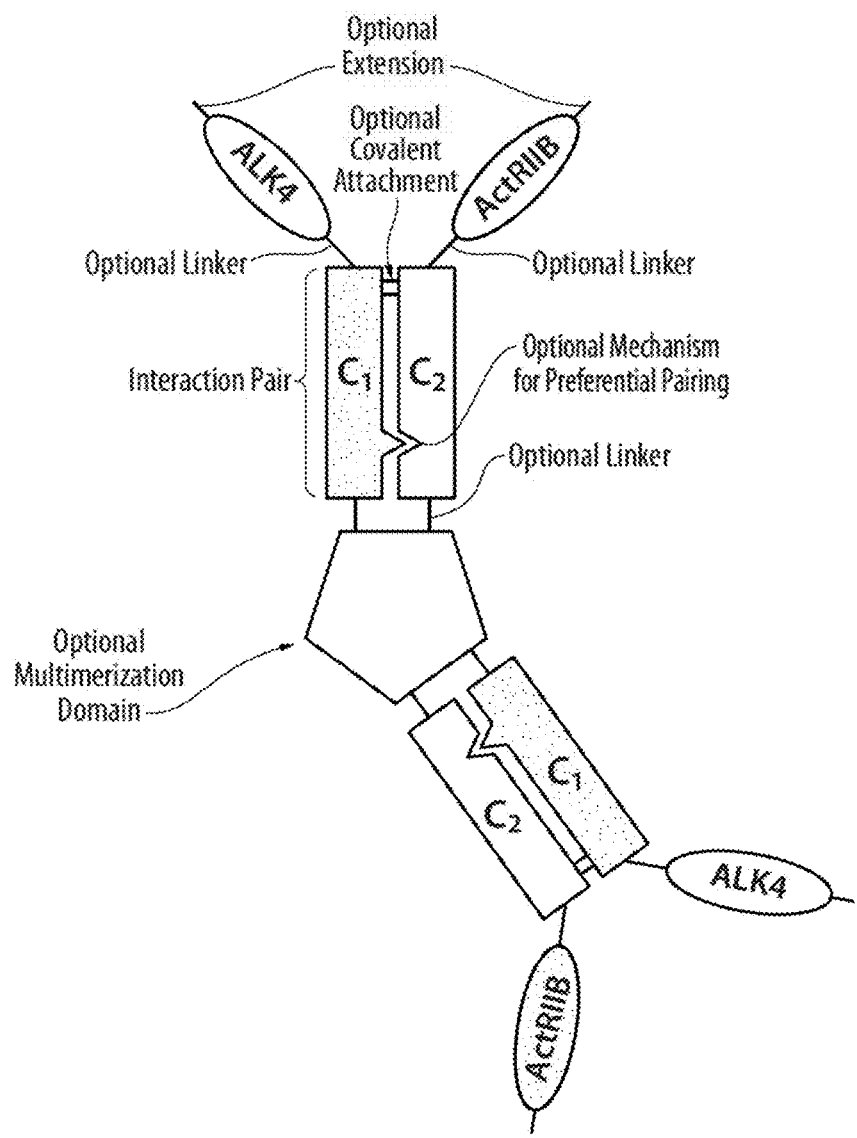
Figure 23D:
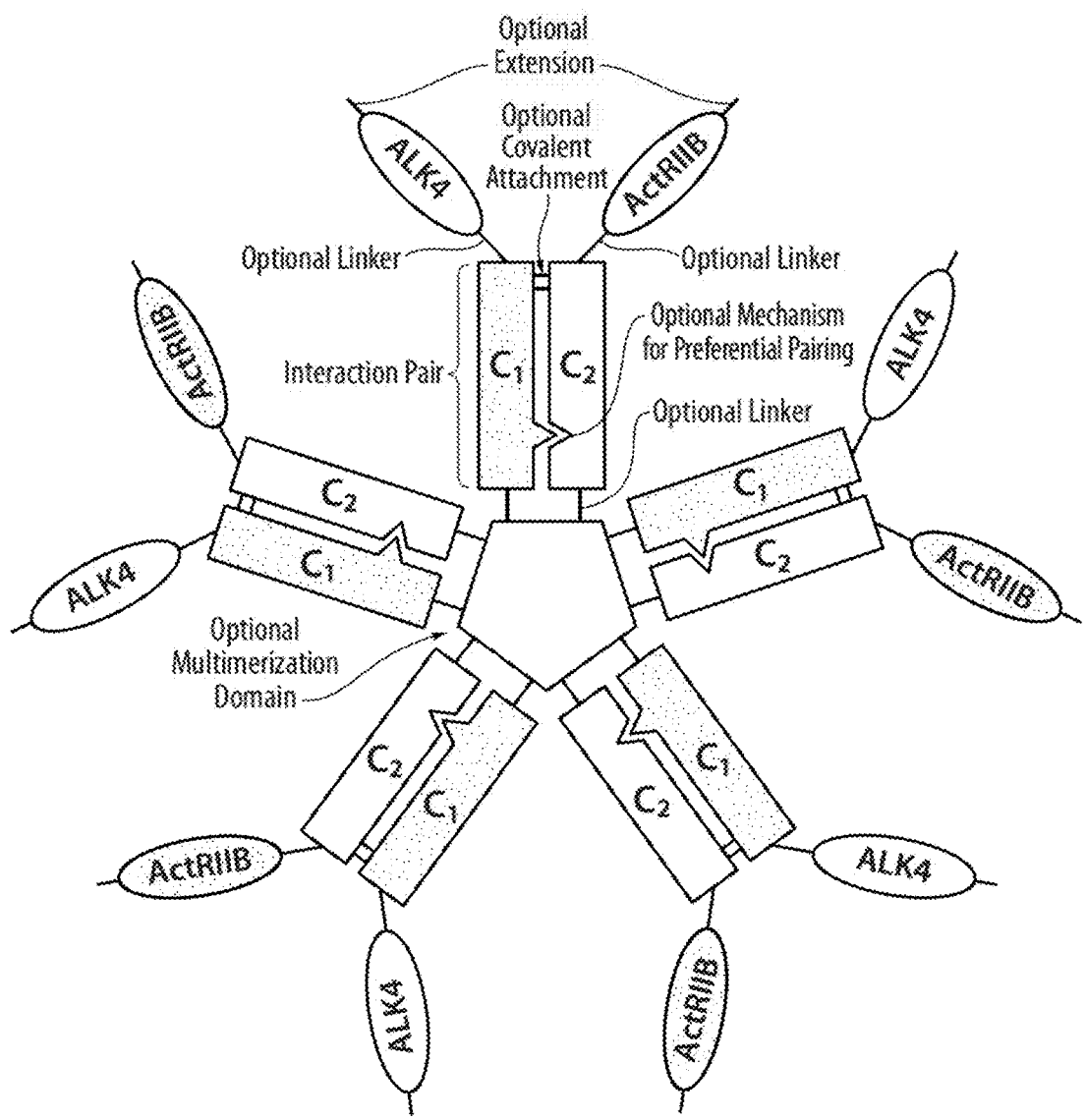

In certain aspects, the present disclosure relates to heteromultimer complexes comprising one or more ALK4 receptor polypeptides (e.g., SEQ ID Nos: 100, 101, 104, 105, 111, 113, 116, 117, 122, and 124 and variants thereof) and one or more ActRIIB receptor polypeptides (e.g., SEQ ID NOs: 1, 2, 3, 4, 5, 6, 58, 59, 60, 63, 64, 65, 66, 68, 69, 70, 71, 73, 77, 78, 108, 110, 114, 115, 118, and 120 and land variants thereof), which are generally referred to herein as "ALK4:ActRIIB heteromultimer complexes" or "ALK4:ActRIIB heteromultimers", including uses thereof (e.g., increasing an immune response in a patient in need thereof and treating cancer). Preferably, ALK4:ActRIIB heteromultimers are soluble [e.g., a heteromultimer complex comprises a soluble portion (domain) of an ALK4 receptor and a soluble portion (domain) of an ActRIIB receptor]. In general, the extracellular domains of ALK4 and ActRIIB correspond to soluble portion of these receptors. Therefore, in some embodiments, ALK4:ActRIIB heteromultimers comprise an extracellular domain of an ALK4 receptor and an extracellular domain of an ActRIIB receptor. In some embodiments, ALK4:ActRIIB heteromultimers inhibit (e.g., Smad signaling) of one or more TGFβ superfamily ligands [e.g., GDF11, GDF8, activin (activin A, activin B, activin AB, activin C, activin E) BMP6, GDF3, BMP10, and/or BMP9]. In some embodiments, ALK4:ActRIIB heteromultimers bind to one or more TGFβ superfamily ligands [e.g., GDF11, GDF8, activin (activin A, activin B, activin AB, activin C, activin E) BMP6, GDF3, BMP10, and/or BMP9]. In some embodiments, ALK4:ActRIIB heteromultimers comprise at least one ALK4 polypeptide that comprises, consists essentially of, or consists of a sequence that is at least 70%, 75%, 80%, 85%, 86%, 87%, 88%, 89%, 90%, 91%, 92%, 93%, 94% 95%, 97%, 98%, 99%, or 100% identical to the amino acid sequence of SEQ ID NO: 100, 101, 104, 105, 111, 113, 116, 117-122, and 124. In some embodiments, ALK4:ActRIIB heteromultimer complexes of the disclosure comprise at least one ALK4 polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to a portion of ALK4 beginning at a residue corresponding to any one of amino acids 24-34, 25-34, or 26-34 of SEQ ID NO: 100 and ending at a position from 101-126, 102-126, 101-125, 101-124, 101-121, 111-126, 111-125, 111-124, 121-126, 121-125, 121-124, or 124-126 of SEQ ID NO: 100. In some embodiments, ALK4:ActRIIB heteromultimers comprise at least one ALK4 polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to amino acids 34-101 with respect to SEQ ID NO: 100. In some embodiments, ALK4-ActRIIB heteromultimers comprise at least one ActRIIB polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to the amino acid sequence of any one of SEQ ID NOs: 1, 2, 3, 4, 5, 6, 58, 59, 60, 63, 64, 65, 66, 68, 69, 70, 71, 73, 77, 78, 108, 110, 114, 115, 118, and 120. In some embodiments, ALK4:ActRIIB heteromultimer complexes of the disclosure comprise at least one ActRIIB polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to a portion of ActRIIB beginning at a residue corresponding to any one of amino acids 20-29, 20-24, 21-24, 22-25, or 21-29 and end at a position from 109-134, 119-134, 119-133, 129-134, or 129-133 of SEQ ID NO: 1. In some embodiments, ALK4:ActRIIB heteromultimers comprise at least one ActRIIB polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to amino acids 29-109 of SEQ ID NO: 1. In some embodiments, ALK4:ActRIIB heteromultimers comprise at least one ActRIIB polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to amino acids 25-131 of SEQ ID NO: 1. In certain embodiments, ALK4: ActRIIB heteromultimer complexes of the disclosure comprise at least one ActRIIB polypeptide wherein the position corresponding to L79 of SEQ ID NO: 1 is not an acidic amino acid (i.e., not naturally occurring D or E amino acid residues or an artificial acidic amino acid residue). ALK4: ActRIIB heteromultimers of the disclosure include, e.g., heterodimers, heterotrimers, heterotetramers and further higher order oligomeric structures. See, e.g., FIGS. 21-23. In certain preferred embodiments, heteromultimer complexes of the disclosure are ALK4:ActRIIB heterodimers.

In some embodiments, the present disclosure contemplates making functional variants by modifying the structure of an ActRII and/or ALK4 polypeptide for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty.

In certain embodiments, the present disclosure contemplates specific mutations of an ActRII and/or ALK4 polypeptide so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, polypeptides of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of an ActRII and/or ALK4 polypeptide as well as truncation mutants. Pools of combinatorial mutants are especially useful for identifying functionally active (e.g., GDF/BMP ligand binding) ActRII sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, ActRII and/or ALK4 variants, and heteromultimers comprising the same, may be screened for ability to bind to one or more GDF/BMP ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin AB, activin AC, nodal, glial cell-derived neurotrophic factor (GDNF), neurturin, artemin, persephin, MIS, and Lefty), to prevent binding of a GDF/BMP ligand to an ActRII and/or ALK4 polypeptide, as well as heteromultimers thereof, and/or to interfere with signaling caused by an GDF/BMP ligand.

The activity of ActRII polypeptides, ALK4 polypeptides, and ALK4:ActRIIB heterodimers may also be tested in a cell-based or in vivo assay. For example, the effect of an ActRII polypeptide, ALK4 polypeptide, or ALK4:ActRIIB heterodimer on the expression of genes involved in PH pathogenesis assessed. This may, as needed, be performed in the presence of one or more recombinant ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty), and cells may be transfected so as to produce an ActRII polypeptide, ALK4 polypeptide, or ALK4:ActRIIB heterodimer, and optionally, an GDF/BMP ligand. Likewise, an ActRII polypeptide, ALK4 polypeptide, or ALK4:ActRIIB heterodimer may be administered to a mouse or other animal and effects on PH pathogenesis may be assessed using art-recognized methods. Similarly, the activity of an ActRII polypeptide, ALK4 polypeptide, or ALK4:ActRIIB heterodimer or variant thereof may be tested in blood cell precursor cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference ActRII polypeptide, ALK4 polypeptide, or ALK4:ActRIIB heterodimer. Such variants, when expressed from recombinant DNA constructs, can be used in gene therapy protocols. Likewise, mutagenesis can give rise to variants which have intracellular half-lives dramatically different than the corresponding unmodified ActRII polypeptide, ALK4 polypeptide, or ALK4:ActRIIB heterodimer. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter the half-life of the ActRII polypeptide, ALK4 polypeptide, or ALK4:ActRIIB heterodimer.

A combinatorial library may be produced by way of a degenerate library of genes encoding a library of polypeptides which each include at least a portion of potential ActRII polypeptide, ALK4 polypeptide, or ALK4:ActRIIB heterodimer sequences. For instance, a mixture of synthetic oligonucleotides can be enzymatically ligated into gene sequences such that the degenerate set of potential ActRII and/or or ALK4 encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art [Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; and Ike et al. (1983) Nucleic Acid Res. 11:477]. Such techniques have been employed in the directed evolution of other proteins [Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815].

Alternatively, other forms of mutagenesis can be utilized to generate a combinatorial library. For example, ActRII polypeptides, ALK4 polypeptides, and ALK4:ActRIIB heterodimers of the disclosure can be generated and isolated from a library by screening using, for example, alanine scanning mutagenesis [Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [Gustin et al. (1993) Virology 193:653-660; and Brown et al. (1992) Mol. Cell Biol. 12:2644-2652; McKnight et al. (1982) Science 232:316], by saturation mutagenesis [Meyers et al., (1986) Science 232:613]; by PCR mutagenesis [Leung et al. (1989) Method Cell Mol Biol 1:11-19]; or by random mutagenesis, including chemical mutagenesis [Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of ActRII polypeptides, ALK4 polypeptides, or ALK4:ActRIIB heterodimers.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRII polypeptides. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty) binding assays and/or ligand-mediated cell signaling assays.

As will be recognized by one of skill in the art, most of the described mutations, variants or modifications described herein may be made at the nucleic acid level or, in some cases, by post-translational modification or chemical synthesis. Such techniques are well known in the art and some of which are described herein. In part, the present disclosure identifies functionally active portions (fragments) and variants of ActRII polypeptides, ALK4 polypeptides, or ALK4:ActRIIB heterodimesr that can be used as guidance for generating and using other variant ActRII polypeptides within the scope of the inventions described herein.

In certain embodiments, functionally active fragments of ActRII polypeptides, ALK4 polypeptides, and ALK4:ActRIIB heterodimesr of the present disclosure can be obtained by screening polypeptides recombinantly produced from the corresponding fragment of the nucleic acid encoding an ActRII and/or ALK4 polypeptides. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRII and/or ALK4 receptors and/or one or more ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty).

In certain embodiments, ActRII polypeptide, ALK4 polypeptide, and/or ALK4:ActRIIB heterodimer of the present disclosure may further comprise post-translational modifications in addition to any that are naturally present in the ActRII polypeptide, ALK4 polypeptide, or ALK4:ActRIIB heterodimer. Such modifications include, but are not limited to, acetylation, carboxylation, glycosylation, phosphorylation, lipidation, and acylation. As a result, the ActRII polypeptide, ALK4 polypeptide, or ALK4:ActRIIB heterodimer may contain non-amino acid elements, such as polyethylene glycols, lipids, polysaccharide or monosaccharide, and phosphates. Effects of such non-amino acid elements on the functionality of a ligand trap polypeptide may be tested as described herein for other ActRII, AKL4, and ALK4:ActRIIB variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the ActRII polypeptides.

In certain aspects, ActRII and ALK4 polypeptides of the present disclosure include fusion proteins having at least a portion (domain) of an ActRII or ALK4 polypeptide and one or more heterologous portions (domains). Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress' system (Qiagen) useful with $(HIS_6)$ (SEQ ID NO: 137) fusion partners. As another example, a fusion domain may be selected so as to facilitate detection of the ActRII or ALK4 polypeptide. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or thrombin, which allows the relevant protease to partially digest the fusion proteins and thereby liberate the recombinant proteins therefrom. The liberated proteins can then be isolated from the fusion domain by subsequent chromatographic separation. Other types of fusion domains that may be selected include multimerizing (e.g., dimerizing, tetramerizing) domains and functional domains (that confer an additional biological function) including, for example constant domains from immunoglobulins (e.g., Fc domains).

In certain aspects, ActRII and ALK4 polypeptides of the present disclosure contain one or more modifications that are capable of "stabilizing" the polypeptides. By "stabilizing" is meant anything that increases the in vitro half-life, serum half-life, regardless of whether this is because of decreased destruction, decreased clearance by the kidney, or other pharmacokinetic effect of the agent. For example, such modifications enhance the shelf-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ActRII polypeptide (or ALK4 polypeptide) domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol. In certain preferred embodiments, an ActRII polypeptide (or ALK4 polypeptide) is fused with a heterologous domain that stabilizes the polypeptide (a "stabilizer" domain), preferably a heterologous domain that increases stability of the polypeptide in vivo. Fusions with a constant domain of an immunoglobulin (e.g., a Fc domain) are known to confer desirable pharmacokinetic properties on a wide range of proteins. Likewise, fusions to human serum albumin can confer desirable properties.

An example of a native amino acid sequence that may be used for the Fc portion of human IgG1 (G1Fc) is shown below (SEQ ID NO: 14). Dotted underline indicates the hinge region, and solid underline indicates positions with naturally occurring variants. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 14. Naturally occurring variants in G1Fc would include E134D and M136L according to the numbering system used in SEQ ID NO: 14 (see Uniprot P01857).

```
                                                              (SEQ ID NO: 14)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the WIC class I-related Fc-receptor (FcRN) relative to a wild-type IgG1 Fc domain.

An example of a native amino acid sequence that may be used for the Fc portion of human IgG2 (G2Fc) is shown below (SEQ ID NO: 15). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 15.

```
                                                              (SEQ ID NO: 15)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 16) contains a short hinge region consisting of a single 15-residue segment, whereas the second G3Fc sequence (SEQ ID NO: 17) contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 16 and 17.

```
                                                       (SEQ ID NO: 16)
  1 EPKSCDTPPP CPRCPAPELL GGPSVFLFPP KPKDTLMISR TPEVTCVVVD

51 VSHEDPEVQF KWYVDGVEVH NAKTKPREEQ YNSTFRVVSV LTVLHQDWLN

101 GKEYKCKVSN KALPAPIEKT ISKTKGQPRE PQVYTLPPSR EEMTKNQVSL

151 TCLVKGFYPS DIAVEWESSG QPENNYNTTP PMLDSDGSFF LYSKLTVDKS

201 RWQQGNIFSC SVMHEALHNR FTQKSLSLSP GK (SEQ ID NO: 17)
  1 ELKTPLGDTT HTCPRCPEPK SCDTPPCPR CPEPKSCDTP PPCPRCPEPK

51 SCDTPPPCPR CPAPELLGGP SVFLFPPKPK DTLMISRTPE VTCVVVDVSH

101 EDPEVQFKWY VDGVEVHNAK TKPREEQYNS TFRVVSVLTV LHQDWLNGKE

151 YKCKVSNKAL PAPIEKTISK TKGQPREPQV YTLPPSREEM TKNQVSLTCL

201 VKGEYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 16, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMNI may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 18). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 18.

```
                                                       (SEQ ID NO: 18)
  1 ESKYGPPCPS CPAPEFLGGP SVFLFPPKP DTLMISRTPE VTCVVVDVSQ

51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGEYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 14), and analogous mutations in G2Fc, G3Fc, and G4Fc can be derived from their alignment with G1Fc in FIG. 4. Due to unequal hinge lengths, analogous Fc positions based on isotype alignment (FIG. 4) possess different amino acid numbers in SEQ ID NOs: 14, 15, 16, 17, and 18. It can also be appreciated that a given amino acid position in an immunoglobulin sequence consisting of hinge, $C_H2$, and $C_H3$ regions (e.g., SEQ ID NOs: 14, 15, 16, 17, and 18) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 14), the human IgG1 heavy chain constant domain (Uniprot P01857), and the human IgG1 heavy chain is as follows.

| Correspondence of $C_H3$ Positions in Different Numbering Systems | | |
|---|---|---|
| G1Fc (Numbering begins at first threonine in hinge region) | IgG1 heavy chain constant domain (Numbering begins at $C_H1$) | IgG1 heavy chain (EU numbering scheme of Kabat et al., 1991*) |
| Y127 | Y232 | Y349 |
| S132 | S237 | S354 |
| E134 | E239 | E356 |
| T144 | T249 | T366 |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in Sequences of Proteins of Immunological Interest, 5th ed., Vol. 1, NIH, Bethesda, MD.

In certain aspects, the polypeptides disclosed herein may form protein complexes comprising at least one ALK4 polypeptide associated, covalently or non-covalently, with at least one ActRIIB polypeptide. Preferably, polypeptides disclosed herein form heterodimeric complexes, although higher order heteromultimeric complexes (heteromultimers) are also included such as, but not limited to, heterotrimers, heterotetramers, and further oligomeric structures (see, e.g., FIG. 21-23). In some embodiments, ALK4 and/or ActRIIB polypeptides comprise at least one multimerization domain. As disclosed herein, the term "multimerization domain" refers to an amino acid or sequence of amino acids that promote covalent or non-covalent interaction between at least a first polypeptide and at least a second polypeptide. Polypeptides disclosed herein may be joined covalently or non-covalently to a multimerization domain. Preferably, a multimerization domain promotes interaction between a first polypeptide (e.g., an ALK4 polypeptide) and a second polypeptide (e.g., an ActRIIB polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIG. 22).

Many methods known in the art can be used to generate ALK4:ActRIIB heteromultimers. For example, non-naturally occurring disulfide bonds may be constructed by replacing on a first polypeptide (e.g., an ALK4 polypeptide) a naturally occurring amino acid with a free thiol-containing residue, such as cysteine, such that the free thiol interacts with another free thiol-containing residue on a second polypeptide (e.g., an ActRIIB polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S.20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of an ALK4 polypeptide and the amino acid sequence of a first member of an interaction pair; and the second polypeptide comprises the amino acid sequence of an ActRIIB polypeptide and the amino acid sequence of a second member of an interaction pair. The interaction pair may be any two polypeptide sequences that interact to form a complex, particularly a heterodimeric complex although operative embodiments may also employ an interaction pair that can form a homodimeric complex. One member of the interaction pair may be fused to an ALK4 or ActRIIB polypeptide as described herein, including for example, a polypeptide sequence comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of any one of SEQ ID NOs: 2, 3, 5, 6, 101, and 103. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIG. 22). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion proteins comprising ALK4 or ActRIIB fused to a polypeptide comprising a constant domain of an immunoglobulin, such as a CH1, CH2, or CH3 domain derived from human IgG1, IgG2, IgG3, and/or IgG4 that has been modified to promote heteromultimer formation. A problem that arises in large-scale production of asymmetric immunoglobulin-based proteins from a single cell line is known as the "chain association issue". As confronted prominently in the production of bispecific antibodies, the chain association issue concerns the challenge of efficiently producing a desired multi-chain protein from among the multiple combinations that inherently result when different heavy chains and/or light chains are produced in a single cell line [Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multi-chain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing [Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605]. As described herein, these methods may be used to generate ALK4-Fc:ActRIIB-Fc heteromultimer complexes. See, e.g., FIG. 23.

ALK4:ActRIIB heteromultimers and method of making such heteromultimers have been previously disclosed. See, for example, WO 2016/164497, the entire teachings of which are incorporated by reference herein.

It is understood that different elements of the fusion proteins (e.g., immunoglobulin Fc fusion proteins) may be arranged in any manner that is consistent with desired functionality. For example, an ActRII polypeptide (or ALK4 polypeptide) domain may be placed C-terminal to a heterologous domain, or alternatively, a heterologous domain may be placed C-terminal to an ActRII polypeptide (or ALK4 polypeptide) domain. The ActRII polypeptide (or ALK4 polypeptide) domain and the heterologous domain need not be adjacent in a fusion protein, and additional domains or amino acid sequences may be included C- or N-terminal to either domain or between the domains.

For example, an ActRII (or ALK4) receptor fusion protein may comprise an amino acid sequence as set forth in the formula A-B-C. The B portion corresponds to an ActRII (or ALK4) polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 19), GGGG (SEQ ID NO: 20), TGGGG (SEQ ID NO: 21), SGGGG (SEQ ID NO: 22), TGGG (SEQ ID NO: 23), SGGG (SEQ ID NO: 24), or GGGGS (SEQ ID NO: 25) singlets, or repeats. In certain embodiments, an ActRII (or ALK4) fusion protein comprises an amino acid sequence as set forth in the formula A-B-C, wherein A is a leader (signal) sequence, B consists of an ActRII (or ALK4) polypeptide domain, and C is a polypeptide portion that enhances one or more of in vivo stability, in vivo half-life, uptake/administration, tissue localization or distribution, formation of protein complexes, and/or purification. In certain embodiments, an ActRII (or ALK4) fusion protein comprises an amino acid sequence as set forth in the formula A-B-C, wherein A is a TPA leader sequence, B consists of an ActRII (or ALK4) receptor polypeptide domain, and C is an immunoglobulin Fc domain. Preferred fusion proteins comprise the amino acid sequence set forth in any one of SEQ ID NOs: 32, 36, 39, 40, 42, 45, 46, 48, 69, 74, 77, 78, 108, 110, 111, 113, 114, 115, 116, 117, 118, 120, 122, and 124.

In preferred embodiments, ActRII polypeptides, ALK4 polypeptides, and ALK4:ActRIIB heteromultimers to be used in accordance with the methods described herein are isolated polypeptides. As used herein, an isolated protein or polypeptide is one which has been separated from a component of its natural environment. In some embodiments, a polypeptide of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of purity are well known in the art [see, e.g., Flatman et al., (2007) J. Chromatogr. B 848:79-87]. In some embodiments, ActRII polypeptides, ALK4 polypeptides, and ALK4:ActRIIB heteromultimers to be used in accordance with the methods described herein are recombinant polypeptides.

ActRII polypeptides, ALK4 polypeptides, and ALK4:ActRIIB heteromultimers of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the polypeptides of the disclosure, including fragments or variants thereof, may be recombinantly produced using various expression systems [e.g., *E. coli*, Chinese Hamster Ovary (CHO) cells, COS cells, baculovirus] as is well known in the art. In a further embodiment, the modified or unmodified polypeptides of the disclosure may be produced by digestion of recombinantly produced full-length ActRII polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites. Alternatively, such polypeptides may be produced from recombinantly generated full-length ActRII or ALK4 polypeptides using chemical cleavage (e.g., cyanogen bromide, hydroxylamine, etc.).

3. Nucleic Acids Encoding ActRII and ALK4 Polypeptides and Variants Thereof

In certain embodiments, the present disclosure provides isolated and/or recombinant nucleic acids encoding ActRII and/or ALK4 polypeptides (including fragments, functional variants, and fusion proteins thereof). For example, SEQ ID NO: 7 encodes a naturally occurring human ActRIIB precursor polypeptide (the R64 variant described above), while SEQ ID NO: 8 encodes the processed extracellular domain of ActRIIB (the R64 variant described above). The subject nucleic acids may be single-stranded or double-stranded. Such nucleic acids may be DNA or RNA molecules. These nucleic acids may be used, for example, in methods for making ActRII-based ligand trap polypeptides as described herein.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ActRII or ALK4 polypeptides of the disclosure are understood to include nucleic acids that are variants of any one of SEQ ID NOs: 7, 8, 12, 13, 37, 43, 49, 70, 71, 72, 73, 75, 76, 80, 81, 82, 83, 84, 102, 103, 106, 107, 109, 112, 119, 121, 123, and 135. Variant nucleotide sequences include sequences that differ by one or more nucleotide substitutions, additions, or deletions including allelic variants, and therefore, will include coding sequence that differ from the nucleotide sequence designated in any one of SEQ ID NOs: 7, 8, 12, 13, 37, 43, 49, 70, 71, 72, 73, 75, 76, 80, 81, 82, 83, 84, 102, 103, 106, 107, 109, 112, 119, 121, 123, and 135.

In certain embodiments, ActRII or ALK4 polypeptides of the disclosure are encoded by isolated and/or recombinant nucleic acid sequences that are at least 70%, 75%, 80%, 85%, 90%, 91%, 92%, 93%, 94% 95%, 96%, 97%, 98%, 99%, or 100% identical to any one of SEQ ID NOs: 7, 8, 12, 13, 37, 43, 49, 70, 71, 72, 73, 75, 76, 80, 81, 82, 83, 84, 102, 103, 106, 107, 109, 112, 119, 121, 123, and 135. One of ordinary skill in the art will appreciate that nucleic acid sequences that are at least 70%, 75%, 80%, 85%, 90%, 91%, 92%, 93%, 94% 95%, 96%, 97%, 98%, 99%, or 100% identical to the sequences complementary to SEQ ID NOs: 7, 8, 12, 13, 37, 43, 49, 70, 71, 72, 73, 75, 76, 80, 81, 82, 83, 84, 102, 103, 106, 107, 109, 112, 119, 121, 123, and 135, and variants thereof, are also within the scope of the present disclosure. In further embodiments, the nucleic acid sequences of the disclosure can be isolated, recombinant, and/or fused with a heterologous nucleotide sequence, or in a DNA library.

In other embodiments, nucleic acids of the present disclosure also include nucleotide sequences that hybridize under highly stringent conditions to the nucleotide sequence designated in SEQ ID NOs: 7, 8, 12, 13, 37, 43, 49, 70, 71, 72, 73, 75, 76, 80, 81, 82, 83, 84, 102, 103, 106, 107, 109, 112, 119, 121, 123, and 135, complement sequences of SEQ ID NOs: 7, 8, 12, 13, 37, 43, 49, 70, 71, 72, 73, 75, 76, 80, 81, 82, 83, 84, 102, 103, 106, 107, 109, 112, 119, 121, 123, and 135, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 37, 43, 49, 70, 71, 72, 73, 75, 76, 80, 81, 82, 83, 84, 102, 103, 106, 107, 109, 112, 119, 121, 123, and 135 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art and can be used in a variety of host cells. Typically, one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and can vary with the host cell used.

In certain aspects, the subject nucleic acid disclosed herein is provided in an expression vector comprising a nucleotide sequence encoding an ActRII and/or ALK4 polypeptide and operably linked to at least one regulatory sequence. Regulatory sequences are art-recognized and are selected to direct expression of the ActRII and/or ALK4 polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, CA (1990). For instance, any of a wide variety of expression control sequences that control the expression of a DNA sequence when operatively linked to it may be used in these vectors to express DNA sequences encoding an ActRII and/or ALK4 polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ActRII and/or ALK4 polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

In a preferred embodiment, a vector will be designed for production of the subject ActRII and/or ALK4 polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wisc.). As will be apparent, the subject gene constructs can be used to cause expression of the subject ActRII polypeptides in cells propagated in culture, e.g., to produce proteins, including fusion proteins or variant proteins, for purification.

This disclosure also pertains to a host cell transfected with a recombinant gene including a coding sequence for one or more of the subject ActRII and/or ALK4 polypeptides. The host cell may be any prokaryotic or eukaryotic cell. For example, an ActRII and/or ALK4 polypeptide of the disclosure may be expressed in bacterial cells such as E. coli, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ActRII and/or ALK4 polypeptides. For example, a host cell transfected with an expression vector encoding an ActRII and/or ALK4 polypeptide can be cultured under appropriate conditions to allow expression of the ActRII and/or ALK4 polypeptide to occur. The polypeptide may be secreted and isolated from a mixture of cells and medium containing the polypeptide. Alternatively, the ActRII and/or ALK4 polypeptide may be retained cytoplasmically or in a membrane fraction and the cells harvested, lysed and the protein isolated. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRII and/or ALK4 polypeptides, and affinity purification with an agent that binds to a domain fused to the ActRII polypeptide (e.g., a protein A column may be used to purify an ActRII-Fc and/or ALK4-Fc fusion proteins). In some embodiments, the ActRII and/or ALK4 polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ActRII and/or ALK4 protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ActRII and/or ALK4 polypeptide, can allow purification of the expressed fusion protein by affinity chromatography using a $Ni^{2+}$ metal resin. The purification leader sequence can then be subsequently removed by treatment with enterokinase to provide the purified ActRII and/or ALK4 polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. Antibody Antagonists

In certain aspects, a GDF/BMP antagonist to be used in accordance with the methods and uses disclosed herein is an antibody (GDF/BMP antagonist antibody), or combination of antibodies. A GDF/BMP antagonist antibody, or combination of antibodies, may bind to, for example, one or more ActRII ligands (e.g., activin, GDF8, GDF11, BMP6, BMP15, BMP10, and/or GDF3), ActRII receptor (ActRIIA and/or ActRIIB), type I receptor (ALK4, ALK5, and/or ALK7) and/or co-receptor. As described herein, GDF/BMP antagonist antibodies may be used, alone or in combination with one or more supportive therapies or active agents, to treat, prevent, or reduce the progression rate and/or severity of pulmonary hypertension (PH), particularly treating, preventing or reducing the progression rate and/or severity of one or more PH-associated complications.

In certain aspects, a GDF/BMP antagonist antibody, or combination of antibodies, is an antibody that inhibits at least activin (e.g., activin A, activin B, activin C, activin E, activin AB, activin AC, activin BC, activin AE, and/or activin BE). Therefore, in some embodiments, a GDF/BMP antagonist antibody, or combination of antibodies, binds to at least activin. As used herein, an activin antibody (or anti-activin antibody) generally refers to an antibody that binds to activin with sufficient affinity such that the antibody is useful as a diagnostic and/or therapeutic agent in targeting activin. In certain embodiments, the extent of binding of an activin antibody to an unrelated, non-activin protein is less than about 10%, 9%, 8%, 7%, 6%, 5%, 4%, 3%, 2%, or less than about 1% of the binding of the antibody to activin as measured, for example, by a radioimmunoassay (MA), Biacore, or other protein interaction or binding affinity assay. In certain embodiments, an activin antibody binds to an epitope of activin that is conserved among activin from different species. In certain preferred embodiments, an anti-activin antibody binds to human activin. In some embodiments, an activin antibody may inhibit activin from binding to a type I and/or type II receptor (e.g., ActRIIA, ActRIIB, ALK4, ALK5, and/or ALK7) and thus inhibit activin-mediated signaling (e.g., Smad signaling). In some embodiments, an activin antibody may inhibit activin from binding to an ActRII co-receptor and thus inhibit activin-mediated signaling (e.g., Smad signaling). It should be noted that activin A has similar sequence homology to activin B and therefore antibodies that bind to activin A, in some instances, may also bind to and/or inhibit activin B, which also applies to anti-activin B antibodies. In some embodiments, the disclosure relates to a multispecific antibody (e.g., bi-specific antibody), and uses thereof, that binds to activin and further binds to, for example, one or more additional GDF/BMP ligands [e.g., GDF11, GDF8, GDF3, BMP15, BMP10, and BMP6], one or more type I receptor and/or type II receptors (e.g., ActRIIA, ActRIIB, ALK4, ALK5, and/or ALK7), and/or one or more co-receptors. In some embodiments, a multispecific antibody that binds to activin does not bind or does not substantially bind to BMP9 (e.g., binds to BMP9 with a $K_D$ of greater than $1\times10^{-7}$ M or has relatively modest binding, e.g., about $1\times10^{-8}$M or about $1\times10^{-9}$M). In some embodiments, a multispecific antibody that binds to activin does not bind or does not substantially bind to activin A (e.g., binds to activin A with a $K_D$ of greater than $1\times10^{-7}$ M or has relatively modest binding, e.g., about $1\times10^{-8}$M or about $1\times10^{-9}$M). In some embodiments, the disclosure relates to combinations of antibodies, and uses thereof, wherein the combination of antibodies comprises an activin antibody and one or more additional antibodies that bind to, for example, one or more additional GDF/BMP superfamily ligands [e.g., GDF8, GDF11, GDF3, BMP6, and BMP15], one or more type I receptor and/or type II receptors (e.g., ActRIIA, ActRIIB, ALK4, ALK5, and/or ALK7), and/or one or more co-receptors. In some embodiments, a combination of antibodies that comprises an activin antibody does not comprise a BMP9 antibody. In some embodiments, a combination of antibodies that comprises an activin antibody does not comprise an activin A antibody.

In certain aspects, a GDF/BMP antagonist antibody, or combination of antibodies, is an antibody that inhibits at least activin B. Therefore, in some embodiments, a GDF/BMP antagonist antibody, or combination of antibodies, binds to at least activin B. As used herein, an activin B antibody (or anti-activin B antibody) generally refers to an antibody that binds to activin B with sufficient affinity such that the antibody is useful as a diagnostic and/or therapeutic agent in targeting activin B. In certain embodiments, the extent of binding of an activin B antibody to an unrelated, non-activin B protein is less than about 10%, 9%, 8%, 7%, 6%, 5%, 4%, 3%, 2%, or less than about 1% of the binding of the antibody to activin as measured, for example, by a radioimmunoassay (MA), Biacore, or other protein interaction or binding affinity assay. In certain embodiments, an activin B antibody binds to an epitope of activin B that is conserved among activin B from different species. In certain preferred embodiments, an anti-activin B antibody binds to human activin B. In some embodiments, an activin B antibody may inhibit activin B from binding to a type I and/or type II receptor (e.g., ActRIIA, ActRIIB, ALK4, ALK5, and/or ALK7) and thus inhibit activin B-mediated signaling (e.g., Smad signaling). In some embodiments, an activin B antibody may inhibit activin B from binding to a co-receptor and thus inhibit activin B-mediated signaling (e.g., Smad signaling). It should be noted that activin B has similar sequence homology to activin A and therefore antibodies that bind to activin B, in some instances, may also bind to and/or inhibit activin A. In some embodiments, the disclosure relates to a multispecific antibody (e.g., bi-specific antibody), and uses thereof, that binds to activin B and further binds to, for example, one or more additional GDF/BMP ligands [e.g., GDF11, GDF8, GDF3, BMP15, BMP10, and BMP6], one or more type I receptor and/or type II receptors (e.g., ActRIIA, ActRIIB, ALK4, ALK5, and/or ALK7), and/or one or more co-receptors. In some embodiments, a multispecific antibody that binds to activin B does not bind or does not substantially bind to BMP9 (e.g., binds to BMP9 with a $K_D$ of greater than $1\times10^{-7}$M or has relatively modest binding, e.g., about $1\times10^{-8}$M or about $1\times10^{-9}$ M). In some embodiments, a multispecific antibody that binds to activin B does not bind or does not substantially bind to activin A (e.g., binds to activin A with a $K_D$ of greater than $1\times10^{-7}$ M or has relatively modest binding, e.g., about $1\times10^{-8}$M or about $1\times10^{-9}$M). In some embodiments, the disclosure relates to combinations of antibodies, and uses thereof, wherein the combination of antibodies comprises an activin B antibody and one or more additional antibodies that bind to, for example, one or more additional GDF/BMP ligands [e.g., GDF8, GDF11, GDF3, BMP6, BMP10, and BMP15], one or more type I receptor and/or type II receptors (e.g., ActRIIA, ActRIIB, ALK4, ALK5, and/or ALK7), and/or one or more co-receptors. In some embodiments, a combination of antibodies that comprises an activin B antibody does not comprise a BMP9 antibody. In some embodiments, a combination of antibodies that comprises an activin B antibody does not comprise an activin A antibody.

In certain aspects, a GDF/BMP antagonist antibody, or combination of antibodies, is an antibody that inhibits at least GDF8. Therefore, in some embodiments, a GDF/BMP antagonist antibody, or combination of antibodies, binds to at least GDF8. As used herein, a GDF8 antibody (or anti-GDF8 antibody) generally refers to an antibody that binds to GDF8 with sufficient affinity such that the antibody is useful as a diagnostic and/or therapeutic agent in targeting GDF8. In certain embodiments, the extent of binding of a GDF8 antibody to an unrelated, non-GDF8 protein is less than about 10%, 9%, 8%, 7%, 6%, 5%, 4%, 3%, 2%, or less than about 1% of the binding of the antibody to GDF8 as measured, for example, by a radioimmunoassay (MA), Biacore, or other protein interaction or binding affinity assay. In certain embodiments, a GDF8 antibody binds to an epitope of GDF8 that is conserved among GDF8 from different species. In certain preferred embodiments, an anti-GDF8 antibody binds to human GDF8. In some embodiments, a GDF8 antibody may inhibit GDF8 from binding to a type I and/or type II receptor (e.g., ActRIIA, ActRIIB, ALK4, ALK5, and/or ALK7) and thus inhibit GDF8-mediated signaling (e.g., Smad signaling). In some embodiments, a GDF8 antibody may inhibit GDF8 from binding to a co-receptor and thus inhibit GDF8-mediated signaling (e.g., Smad signaling). It should be noted that GDF8 has high sequence homology to GDF11 and therefore antibodies that bind to GDF8, in some instances, may also bind to and/or inhibit GDF11. In some embodiments, the disclosure relates to a multispecific antibody (e.g., bi-specific antibody), and uses thereof, that binds to GDF8 and further binds to, for example, one or more additional GDF/BMP ligands [e.g., activin (e.g., activin A, activin B, activin C, activin E, activin AB, activin AC, activin BC, activin AE, activin BE), GDF11, GDF3, BMP15, BMP10, and BMP6], one or more type I receptor and/or type II receptors (e.g., ActRIIA, ActRIIB, ALK4, ALK5, and/or ALK7), and/or one or more co-receptors. In some embodiments, a multispecific antibody that binds to GDF8 does not bind or does not substantially bind to BMP9 (e.g., binds to BMP9 with a $K_D$ of greater than $1\times10^{-7}$ M or has relatively modest binding, e.g., about $1\times10^{-8}$ M or about $1\times10^{-9}$M). In some embodiments, a multispecific antibody that binds to GDF8 does not bind or does not substantially bind to activin A (e.g., binds to activin A with a $K_D$ of greater than $1\times10^{-7}$ M or has relatively modest binding, e.g., about $1\times10^{-8}$M or about $1\times10^{-9}$M). In some embodiments, the disclosure relates to combinations of antibodies, and uses thereof, wherein the combination of antibodies comprises a GDF8 antibody and one or more additional antibodies that bind to, for example, one or more additional GDF/BMP ligands [e.g., activin (e.g., activin A, activin B, activin C, activin E, activin AB, activin AC, activin BC, activin AE, activin BE), GDF11, GDF3, BMP6, BMP10, and BMP15], one or more type I receptor and/or type II receptors (e.g., ActRIIA, ActRIIB, ALK4, ALK5, and/or ALK7), and/or one or more co-receptors. In some embodiments, a combination of antibodies that comprises a GDF8 antibody does not comprise a BMP9 antibody. In some embodiments, a combination of antibodies that comprises a GDF8 antibody does not comprise an activin A antibody.

In certain aspects, a GDF/BMP antagonist antibody, or combination of antibodies, is an antibody that inhibits at least GDF11. Therefore, in some embodiments, a GDF/BMP antagonist antibody, or combination of antibodies, binds to at least GDF11. As used herein, a GDF11 antibody (or anti-GDF11 antibody) generally refers to an antibody that binds to GDF11 with sufficient affinity such that the antibody is useful as a diagnostic and/or therapeutic agent in targeting GDF11. In certain embodiments, the extent of binding of a GDF11 antibody to an unrelated, non-GDF11 protein is less than about 10%, 9%, 8%, 7%, 6%, 5%, 4%, 3%, 2%, or less than about 1% of the binding of the antibody to GDF11 as measured, for example, by a radioimmunoassay (MA), Biacore, or other protein interaction or binding affinity assay. In certain embodiments, a GDF11 antibody binds to an epitope of GDF11 that is conserved among GDF11 from different species. In certain preferred embodiments, an anti-GDF11 antibody binds to human GDF11. In some embodiments, a GDF11 antibody may inhibit GDF11 from binding to a type I and/or type II receptor (e.g., ActRIIA, ActRIIB, ALK4, ALK5, and/or ALK7) and thus inhibit GDF11-mediated signaling (e.g., Smad signaling). In some embodiments, a GDF11 antibody may inhibit GDF11 from binding to a co-receptor and thus inhibit GDF11-mediated signaling (e.g., Smad signaling). It should be noted that GDF11 has high sequence homology to GDF8 and therefore antibodies that bind to GDF11, in some instances, may also bind to and/or inhibit GDF8. In some embodiments, the disclosure relates to a multispecific antibody (e.g., bi-specific antibody), and uses thereof, that binds to GDF11 and further binds to, for example, one or more additional GDF/BMP ligands [e.g., activin (e.g., activin A, activin B, activin C, activin E, activin AB, activin AC, activin BC, activin AE, activin BE), GDF8, GDF3, BMP15, BMP10, and BMP6], one or more type I receptor and/or type II receptors (e.g., ActRIIA, ActRIIB, ALK4, ALK5, and/or ALK7), and/or one or more co-receptors. In some embodiments, a multispecific antibody that binds to GDF11 does not bind or does not substantially bind to BMP9 (e.g., binds to BMP9 with a $K_D$ of greater than $1\times10^{-7}$ M or has relatively modest binding, e.g., about $1\times10^{-8}$ M or about $1\times10^{-9}$ M). In some embodiments, a multispecific antibody that binds to GDF11 does not bind or does not substantially bind to activin A (e.g., binds to activin A with a $K_D$ of greater than $1\times10^{-7}$ M or has relatively modest binding, e.g., about $1\times10^{-8}$ M or about $1\times10^{-9}$ M). In some embodiments, the disclosure relates to combinations of antibodies, and uses thereof, wherein the combination of antibodies comprises a GDF11 antibody and one or more additional antibodies that bind to, for example, one or more additional GDF/BMP ligands [e.g., activin (e.g., activin A, activin B, activin C, activin E, activin AB, activin AC, activin BC, activin AE, activin BE), GDF8, GDF3, BMP6, BMP10, and BMP15], one or more type I receptor and/or type II receptors (e.g., ActRIIA, ActRIIB, ALK4, ALK5, and/or ALK7), and/or one or more co-receptors. In some embodiments, a combination of antibodies that comprises a GDF11 antibody does not comprise a BMP9 antibody. In some embodiments, a combination of antibodies that comprises a GDF11 antibody does not comprise an activin A antibody.

In certain aspects, a GDF/BMP antagonist antibody, or combination of antibodies, is an antibody that inhibits at least BMP6. Therefore, in some embodiments, a GDF/BMP antagonist antibody, or combination of antibodies, binds to at least BMP6. As used herein, a BMP6 antibody (or anti-BMP6 antibody) generally refers to an antibody that can bind to BMP6 with sufficient affinity such that the antibody is useful as a diagnostic and/or therapeutic agent in targeting BMP6. In certain embodiments, the extent of binding of a BMP6 antibody to an unrelated, non-BMP6 protein is less than about 10%, 9%, 8%, 7%, 6%, 5%, 4%, 3%, 2%, or less than about 1% of the binding of the antibody to BMP6 as measured, for example, by a radioimmunoassay (MA), Biacore, or other protein interaction or binding affinity assay. In certain embodiments, a BMP6 antibody binds to an epitope of BMP6 that is conserved among BMP6 from different species. In certain preferred embodiments, an anti-BMP6 antibody binds to human BMP6. In some embodiments, a BMP6 antibody may inhibit BMP6 from binding to a type I and/or type II receptor (e.g., ActRIIA, ActRIIB, ALK4, ALK5, and/or ALK7) and thus inhibit BMP6-mediated signaling (e.g., Smad signaling). In some embodiments, a BMP6 antibody may inhibit BMP6 from binding to a co-receptor and thus inhibit BMP6-mediated signaling (e.g., Smad signaling). In some embodiments, the disclosure relates to a multispecific antibody (e.g., bi-specific antibody), and uses thereof, that binds to BMP6 and further binds to, for example, one or more additional GDF/BMP ligands [e.g., activin (e.g., activin A, activin B, activin C, activin E, activin AB, activin AC, activin BC, activin AE, activin BE), GDF8, GDF3, BMP15, BMP10, and GDF11], one or more type I receptor and/or type II receptors (e.g., ActRIIA, ActRIIB, ALK4, ALK5, and/or ALK7), and/or one or more co-receptors. In some embodiments, a multispecific antibody that binds to BMP6 does not bind or does not substantially bind to BMP9 (e.g., binds to BMP9 with a $K_D$ of greater than $1\times10^{-7}$ M or has relatively modest binding, e.g., about $1\times10^{-8}$M or about $1\times10^{-9}$M). In some embodiments, a multispecific antibody that binds to BMP6 does not bind or does not substantially bind to activin A (e.g., binds to activin A with a $K_D$ of greater than $1\times10^{-7}$ M or has relatively modest binding, e.g., about $1\times10^{-8}$M or about $1\times10^{-9}$M). In some embodiments, the disclosure relates to combinations of antibodies, and uses thereof, wherein the combination of antibodies comprises a BMP6 antibody and one or more additional antibodies that bind to, for example, one or more additional GDF/BMP ligands [e.g., activin (e.g., activin A, activin B, activin C, activin E, activin AB, activin AC, activin BC, activin AE, activin BE), GDF8, GDF11, GDF3, BMP10, and BMP15], one or more type I receptor and/or type II receptors (e.g., ActRIIA, ActRIIB, ALK4, ALK5, and/or ALK7), and/or one or more co-receptors. In some embodiments, a combination of antibodies that comprises a BMP6 antibody does not comprise a BMP9 antibody. In some embodiments, a combination of antibodies that comprises a BMP6 antibody does not comprise an activin A antibody.

In certain aspects, a GDF/BMP antagonist antibody, or combination of antibodies, is an antibody that inhibits at least GDF3. Therefore, in some embodiments, a GDF/BMP antagonist antibody, or combination of antibodies, binds to at least GDF3. As used herein, a GDF3 antibody (or anti-GDF3antibody) generally refers to an antibody that can bind to GDF3 with sufficient affinity such that the antibody is useful as a diagnostic and/or therapeutic agent in targeting GDF3. In certain embodiments, the extent of binding of a GDF3 antibody to an unrelated, non-GDF3 protein is less than about 10%, 9%, 8%, 7%, 6%, 5%, 4%, 3%, 2%, or less than about 1% of the binding of the antibody to GDF3 as measured, for example, by a radioimmunoassay (MA), Biacore, or other protein interaction or binding affinity assay. In certain embodiments, a GDF3 antibody binds to an epitope of GDF3 that is conserved among GDF3 from different species. In certain preferred embodiments, an anti-GDF3 antibody binds to human GDF3. In some embodiments, a GDF3 antibody may inhibit GDF3 from binding to a type I and/or type II receptor (e.g., ActRIIA, ActRIIB, ALK4, ALK5, and/or ALK7) and thus inhibit GDF3-mediated signaling (e.g., Smad signaling). In some embodiments, a GDF3 antibody may inhibit GDF3 from binding to a co-receptor and thus inhibit GDF3-mediated signaling (e.g., Smad signaling). In some embodiments, the disclosure relates to a multispecific antibody (e.g., bi-specific antibody), and uses thereof, that binds to GDF3 and further binds to, for example, one or more additional GDF/BMP ligands [e.g., activin (e.g., activin A, activin B, activin C, activin E, activin AB, activin AC, activin BC, activin AE, activin BE), GDF8, BMP6, BMP15, BMP10, and GDF11], one or more type I receptor and/or type II receptors (e.g., ActRIIA, ActRIIB, ALK4, ALK5, and/or ALK7), and/or one or more co-receptors. In some embodiments, a multispecific antibody that binds to GDF3 does not bind or does not substantially bind to BMP9 (e.g., binds to BMP9 with a $K_D$ of greater than $1\times10^{-7}$M or has relatively modest binding, e.g., about $1\times10^{-8}$M or about $1\times10^{-9}$M). In some embodiments, a multispecific antibody that binds to GDF3 does not bind or does not substantially bind to activin A (e.g., binds to activin A with a $K_D$ of greater than $1\times10^{-7}$M or has relatively modest binding, e.g., about $1\times10^{-8}$M or about $1\times10^{-9}$M). In some embodiments, the disclosure relates to combinations of antibodies, and uses thereof, wherein the combination of antibodies comprises a GDF3 antibody and one or more additional antibodies that bind to, for example, one or more additional GDF/BMP ligands [e.g., activin (e.g., activin A, activin B, activin C, activin E, activin AB, activin AC, activin BC, activin AE, activin BE), GDF8, GDF11, BMP6, BMP10, and BMP15], one or more type I receptor and/or type II receptors (e.g., ActRIIA, ActRIIB, ALK4, ALK5, and/or ALK7), and/or one or more co-receptors. In some embodiments, a combination of antibodies that comprises a GDF3 antibody does not comprise a BMP9 antibody. In some embodiments, a combination of antibodies that comprises a GDF3 antibody does not comprise an activin A antibody.

In certain aspects, a GDF/BMP antagonist antibody, or combination of antibodies, is an antibody that inhibits at least BMP15. Therefore, in some embodiments, a GDF/BMP antagonist antibody, or combination of antibodies, binds to at least BMP15. As used herein, a BMP15 antibody (or anti-BMP15 antibody) generally refers to an antibody that can bind to BMP15 with sufficient affinity such that the antibody is useful as a diagnostic and/or therapeutic agent in targeting BMP15. In certain embodiments, the extent of binding of a BMP15 antibody to an unrelated, non-BMP15 protein is less than about 10%, 9%, 8%, 7%, 6%, 5%, 4%, 3%, 2%, or less than about 1% of the binding of the antibody to BMP15 as measured, for example, by a radioimmunoassay (MA), Biacore, or other protein interaction or binding affinity assay. In certain embodiments, a BMP15 antibody binds to an epitope of BMP15 that is conserved among BMP15 from different species. In certain preferred embodiments, an anti-BMP15 antibody binds to human BMP15. In some embodiments, a BMP15 antibody may inhibit BMP15 from binding to a type I and/or type II receptor (e.g., ActRIIA, ActRIIB, ALK4, ALK5, and/or ALK7) and thus inhibit BMP15-mediated signaling (e.g., Smad signaling). In some embodiments, a BMP15 antibody may inhibit BMP15 from binding to a co-receptor and thus inhibit BMP15-mediated signaling (e.g., Smad signaling). In some embodiments, the disclosure relates to a multispecific antibody (e.g., bi-specific antibody), and uses thereof, that binds to BMP15 and further binds to, for example, one or more additional GDF/BMP ligands [e.g., activin (e.g., activin A, activin B, activin C, activin E, activin AB, activin AC, activin BC, activin AE and activin BE), GDF8, GDF11, GDF3, BMP10, and BMP6], one or more type I receptor and/or type II receptors (e.g., ActRIIA, ActRIIB, ALK4, ALK5, and/or ALK7), and/or one or more co-receptors. In some embodiments, a multispecific antibody that binds to BMP15 does not bind or does not substantially bind to BMP9 (e.g., binds to BMP9 with a $K_D$ of greater than $1\times10^{-7}$ M or has relatively modest binding, e.g., about $1\times10^{-8}$M or about $1\times10^{-9}$M). In some embodiments, a multispecific antibody that binds to BMP15 does not bind or does not substantially bind to activin A (e.g., binds to activin A with a $K_D$ of greater than $1\times10^{-7}$ M or has relatively modest binding, e.g., about $1\times10^{-8}$M or about $1\times10^{-9}$M). In some embodiments, the disclosure relates to combinations of antibodies, and uses thereof, wherein the combination of antibodies comprises a BMP15 antibody and one or more additional antibodies that bind to, for example, one or more additional GDF/BMP ligands [e.g., activin (e.g., activin A, activin B, activin C, activin E, activin AB, activin AC, activin BC, activin AE and activin BE), GDF8, GDF3 BMP6, BMP10, and GDF11], one or more type I receptor and/or type II receptors (e.g., ActRIIA, ActRIIB, ALK4, ALK5, and/or ALK7), and/or one or more co-receptors. In some embodiments, a combination of antibodies that comprises a BMP15 antibody does not comprise a BMP9 antibody. In some embodiments, a combination of antibodies that comprises a BMP15 antibody does not comprise an activin A antibody.

In certain aspects, a GDF/BMP antagonist antibody, or combination of antibodies, is an antibody that inhibits at least BMP10. Therefore, in some embodiments, a GDF/BMP antagonist antibody, or combination of antibodies, binds to at least BMP10. As used herein, a BMP10 antibody (or anti-BMP10 antibody) generally refers to an antibody that can bind to BMP10 with sufficient affinity such that the antibody is useful as a diagnostic and/or therapeutic agent in targeting BMP10. In certain embodiments, the extent of binding of a BMP10 antibody to an unrelated, non-BMP10 protein is less than about 10%, 9%, 8%, 7%, 6%, 5%, 4%, 3%, 2%, or less than about 1% of the binding of the antibody to BMP10 as measured, for example, by a radioimmunoassay (RIA), Biacore, or other protein interaction or binding affinity assay. In certain embodiments, a BMP10 antibody binds to an epitope of BMP10 that is conserved among BMP10 from different species. In certain preferred embodiments, an anti-BMP10 antibody binds to human BMP10. In some embodiments, a BMP10 antibody may inhibit BMP10 from binding to a type I and/or type II receptor (e.g., ActRIIA, ActRIIB, ALK4, ALK5, and/or ALK7) and thus inhibit BMP10-mediated signaling (e.g., Smad signaling). In some embodiments, a BMP10 antibody may inhibit BMP10 from binding to a co-receptor and thus inhibit BMP10-mediated signaling (e.g., Smad signaling). In some embodiments, the disclosure relates to a multispecific antibody (e.g., bi-specific antibody), and uses thereof, that binds to BMP10 and further binds to, for example, one or more additional GDF/BMP ligands [e.g., activin (e.g., activin A, activin B, activin C, activin E, activin AB, activin AC, activin BC, activin AE and activin BE), GDF8, GDF11, GDF3, and BMP6], one or more type I receptor and/or type II receptors (e.g., ActRIIA, ActRIIB, ALK4, ALK5, and/or ALK7), and/or one or more co-receptors. In some embodiments, a multispecific antibody that binds to BMP10 does not bind or does not substantially bind to BMP9 (e.g., binds to BMP9 with a $K_D$ of greater than $1\times10^{-7}$ M or has relatively modest binding, e.g., about $1\times10^{-8}$M or about $1\times10^{-9}$M). In some embodiments, a multispecific antibody that binds to BMP10 does not bind or does not substantially bind to activin A (e.g., binds to activin A with a $K_D$ of greater than $1\times10^{-7}$ M or has relatively modest binding, e.g., about $1\times10^{-8}$M or about $1\times10^{-9}$M). In some embodiments, the disclosure relates to combinations of antibodies, and uses thereof, wherein the combination of antibodies comprises a BMP10 antibody and one or more additional antibodies that bind to, for example, one or more additional GDF/BMP ligands [e.g., activin (e.g., activin A, activin B, activin C, activin E, activin AB, activin AC, activin BC, activin AE and activin BE), GDF8, GDF3 BMP6, BMP10, and GDF11], one or more type I receptor and/or type II receptors (e.g., ActRIIA, ActRIIB, ALK4, ALK5, and/or ALK7), and/or one or more co-receptors. In some embodiments, a combination of antibodies that comprises a BMP10 antibody does not comprise a BMP9 antibody. In some embodiments, a combination of antibodies that comprises a BMP10 antibody does not comprise an activin A antibody.

In certain aspects, a GDF/BMP antagonist antibody, or combination of antibodies, is an antibody that inhibits at least ActRIIB Therefore, in some embodiments, a GDF/BMP antagonist antibody, or combination of antibodies, binds to at least ActRIIB As used herein, an ActRIIB antibody (anti-ActRIIB antibody) generally refers to an antibody that binds to ActRIIB with sufficient affinity such that the antibody is useful as a diagnostic and/or therapeutic agent in targeting ActRIIB In certain embodiments, the extent of binding of an anti-ActRIIB antibody to an unrelated, non-ActRIIB protein is less than about 10%, 9%, 8%, 7%, 6%, 5%, 4%, 3%, 2%, or less than about 1% of the binding of the antibody to ActRIIB as measured, for example, by a radioimmunoassay (RIA), Biacore, or other protein-protein interaction or binding affinity assay. In certain embodiments, an anti-ActRIIB antibody binds to an epitope of ActRIIB that is conserved among ActRIIB from different species. In certain preferred embodiments, an anti-ActRIIB antibody binds to human ActRIIB In some embodiments, an anti-ActRIIB antibody may inhibit one or more GDF/BMP ligands [e.g., GDF8, activin (e.g., activin A, activin B, activin C, activin E, activin AB, activin AC, activin BC, activin AE and activin BE) GDF11, BMP6, GDF3, BMP10, and BMP15] from binding to ActRIIB In some embodiments, an anti-ActRIIB antibody is a multispecific antibody (e.g., bi-specific antibody) that binds to ActRIIB and one or more GDF/BMP ligands [e.g., GDF11, GDF8, activin (e.g., activin A, activin B, activin C, activin E, activin AB, activin AC) GDF3, BMP6, and BMP10], type I receptor (e.g., ALK4, ALK5, and/or ALK7), co-receptor, and/or an additional type II receptor (e.g., ActRIIA). In some embodiments, the disclosure relates to combinations of antibodies, and uses thereof, wherein the combination of antibodies comprises an anti-ActRIIB antibody and one or more additional antibodies that bind to, for example, one or more GDF/BMP ligands [e.g., GDF11, GDF8, activin (e.g., activin A, activin B, activin C, activin E, activin AB, activin AC, activin BC, activin AE and activin BE) BMP6, GDF3, and BMP10], co-receptors, type I receptors (e.g., ALK4, ALK5, and/or ALK7), and/or additional type II receptors (e.g., ActRIIA). It should be noted that ActRIIB has sequence similarity to ActRIIA and therefore antibodies that bind to ActRIIB, in some instances, may also bind to and/or inhibit ActRIIA.

In certain aspects, a GDF/BMP antagonist antibody, or combination of antibodies, is an antibody that inhibits at least ActRIIA. Therefore, in some embodiments, a GDF/BMP antagonist antibody, or combination of antibodies, binds to at least ActRIIA. As used herein, an ActRIIA antibody (anti-ActRIIA antibody) generally refers to an antibody that binds to ActRIIA with sufficient affinity such that the antibody is useful as a diagnostic and/or therapeutic agent in targeting ActRIIA. In certain embodiments, the extent of binding of an anti-ActRIIA antibody to an unrelated, non-ActRIIA protein is less than about 10%, 9%, 8%, 7%, 6%, 5%, 4%, 3%, 2%, or less than about 1% of the binding of the antibody to ActRIIA as measured, for example, by a radioimmunoassay (MA), Biacore, or other protein-protein interaction or binding affinity assay. In certain embodiments, an anti-ActRIIA antibody binds to an epitope of ActRIIA that is conserved among ActRIIA from different species. In certain preferred embodiments, an anti-ActRIIA antibody binds to human ActRIIA. In some embodiments, an anti-ActRIIA antibody may inhibit one or more GDF/BMP ligands [e.g., GDF8, activin (e.g., activin A, activin B, activin C, activin E, activin AB, activin AC, activin BC, activin AE and activin BE) GDF11, BMP6, GDF3, BMP10, and BMP15] from binding to ActRIIA. In some embodiments, an anti-ActRIIA antibody is a multi-specific antibody (e.g., bi-specific antibody) that binds to ActRIIA and one or more GDF/BMP ligands [e.g., GDF11, GDF8, activin (e.g., activin A, activin B, activin C, activin E, activin AB, activin AC) GDF3, BMP6, and BMP10], type I receptor (e.g., ALK4, ALK5, and/or ALK7), co-receptor, and/or an additional type II receptor (e.g., ActRIIB) In some embodiments, the disclosure relates to combinations of antibodies, and uses thereof, wherein the combination of antibodies comprises an anti-ActRIIA antibody and one or more additional antibodies that bind to, for example, one or more GDF/BMP ligands [e.g., GDF11, GDF8, activin (e.g., activin A, activin B, activin C, activin E, activin AB, activin AC, activin BC, activin AE and activin BE) BMP6, and BMP10], co-receptors, type I receptors (e.g., ALK4, ALK5, and/or ALK7), and/or additional type II receptors (e.g., ActRIIB) It should be noted that ActRIIA has sequence similarity to ActRIIB and therefore antibodies that bind to ActRIIA, in some instances, may also bind to and/or inhibit ActRIIB In certain aspects, a GDF/BMP antagonist antibody, or combination of antibodies, is an antibody that inhibits at least ALK4. Therefore, in some embodiments, a GDF/BMP antagonist antibody, or combination of antibodies, binds to at least ALK4. As used herein, an ALK4 antibody (anti-ALK4 antibody) generally refers to an antibody that binds to ALK4 with sufficient affinity such that the antibody is useful as a diagnostic and/or therapeutic agent in targeting ALK4. In certain embodiments, the extent of binding of an anti-ALK4 antibody to an unrelated, non-ALK4 protein is less than about 10%, 9%, 8%, 7%, 6%, 5%, 4%, 3%, 2%, or less than about 1% of the binding of the antibody to ALK4 as measured, for example, by a radioimmunoassay (RIA), Biacore, or other protein-protein interaction or binding affinity assay. In certain embodiments, an anti-ALK4 antibody binds to an epitope of ALK4 that is conserved among ALK4 from different species. In certain preferred embodiments, an anti-ALK4 antibody binds to human ALK4. In some embodiments, an anti-ALK4 antibody may inhibit one or more GDF/BMP ligands [e.g., GDF8, activin (e.g., activin A, activin B, activin C, activin E, activin AB, activin AC, activin BC, activin AE and activin BE) GDF11, BMP6, GDF3, BMP10, and BMP15] from binding to ALK4. In some embodiments, an anti-ALK4 antibody is a multispecific antibody (e.g., bi-specific antibody) that binds to ALK4 and one or more GDF/BMP ligands [e.g., GDF11, GDF8, activin (e.g., activin A, activin B, activin C, activin E, activin AB, activin AC) GDF3, BMP6, and BMP10], type II receptor (e.g., ActRIIA and/or ActRIIB), co-receptor, and/or an additional type I receptor (e.g., ALK5 and/or ALK7). In some embodiments, the disclosure relates to combinations of antibodies, and uses thereof, wherein the combination of antibodies comprises an anti-ALK4 antibody and one or more additional antibodies that bind to, for example, one or more GDF/BMP ligands [e.g., GDF11, GDF8, activin (e.g., activin A, activin B, activin C, activin E, activin AB, activin AC, activin BC, activin AE and activin BE) BMP6, and BMP10], co-receptors, type II receptors (e.g., ActRIIA and/or ActRIIB), and/or additional type I receptors (e.g., ALK5 and/or ALK7).

In certain aspects, a GDF/BMP antagonist antibody, or combination of antibodies, is an antibody that inhibits at least ALK5. Therefore, in some embodiments, a GDF/BMP antagonist antibody, or combination of antibodies, binds to at least ALK5. As used herein, an ALK5 antibody (anti-ALK5 antibody) generally refers to an antibody that binds to ALK5 with sufficient affinity such that the antibody is useful as a diagnostic and/or therapeutic agent in targeting ALK5. In certain embodiments, the extent of binding of an anti-ALK5 antibody to an unrelated, non-ALK5 protein is less than about 10%, 9%, 8%, 7%, 6%, 5%, 4%, 3%, 2%, or less than about 1% of the binding of the antibody to ALK5 as measured, for example, by a radioimmunoassay (MA), Biacore, or other protein-protein interaction or binding affinity assay. In certain embodiments, an anti-ALK5 antibody binds to an epitope of ALK5 that is conserved among ALK5 from different species. In certain preferred embodiments, an anti-ALK5 antibody binds to human ALK5. In some embodiments, an anti-ALK5 antibody may inhibit one or more GDF/BMP ligands [e.g., GDF8, activin (e.g., activin A, activin B, activin C, activin E, activin AB, activin AC, activin BC, activin AE and activin BE) GDF11, BMP6, GDF3, BMP10, and BMP15] from binding to ALK5. In some embodiments, an anti-ALK5 antibody is a multispecific antibody (e.g., bi-specific antibody) that binds to ALK5 and one or more GDF/BMP ligands [e.g., GDF11, GDF8, activin (e.g., activin A, activin B, activin C, activin E, activin AB, activin AC) GDF3, BMP6, and BMP10], type II receptor (e.g., ActRIIA and/or ActRIIB), co-receptor, and/or an additional type I receptor (e.g., ALK4 and/or ALK7). In some embodiments, the disclosure relates to combinations of antibodies, and uses thereof, wherein the combination of antibodies comprises an anti-ALK5 antibody and one or more additional antibodies that bind to, for example, one or more GDF/BMP ligands [e.g., GDF11, GDF8, activin (e.g., activin A, activin B, activin C, activin E, activin AB, activin AC, activin BC, activin AE and activin BE) BMP6, and BMP10], co-receptors, type II receptors (e.g., ActRIIA and/or ActRIIB), and/or additional type I receptors (e.g., ALK4 and/or ALK7).

In certain aspects, a GDF/BMP antagonist antibody, or combination of antibodies, is an antibody that inhibits at least ALK7. Therefore, in some embodiments, a GDF/BMP antagonist antibody, or combination of antibodies, binds to at least ALK7. As used herein, an ALK7 antibody (anti-ALK7 antibody) generally refers to an antibody that binds to ALK7 with sufficient affinity such that the antibody is useful as a diagnostic and/or therapeutic agent in targeting ALK7. In certain embodiments, the extent of binding of an anti-ALK7 antibody to an unrelated, non-ALK7 protein is less than about 10%, 9%, 8%, 7%, 6%, 5%, 4%, 3%, 2%, or less than about 1% of the binding of the antibody to ALK7 as measured, for example, by a radioimmunoassay (MA), Biacore, or other protein-protein interaction or binding affinity assay. In certain embodiments, an anti-ALK7 antibody binds to an epitope of ALK7 that is conserved among ALK7 from different species. In certain preferred embodiments, an anti-ALK7 antibody binds to human ALK7. In some embodiments, an anti-ALK7 antibody may inhibit one or more GDF/BMP ligands [e.g., GDF8, activin (e.g., activin A, activin B, activin C, activin E, activin AB, activin AC, activin BC, activin AE and activin BE) GDF11, BMP6, GDF3, BMP10, and BMP15] from binding to ALK7. In some embodiments, an anti-ALK7 antibody is a multispecific antibody (e.g., bi-specific antibody) that binds to ALK7 and one or more GDF/BMP ligands [e.g., GDF11, GDF8, activin (e.g., activin A, activin B, activin C, activin E, activin AB, activin AC) GDF3, BMP6, and BMP10], type II receptor (e.g., ActRIIA and/or ActRIIB), co-receptor, and/or an additional type I receptor (e.g., ALK4 and/or ALK5). In some embodiments, the disclosure relates to combinations of antibodies, and uses thereof, wherein the combination of antibodies comprises an anti-ALK7 antibody and one or more additional antibodies that bind to, for example, one or more GDF/BMP ligands [e.g., GDF11, GDF8, activin (e.g., activin A, activin B, activin C, activin E, activin AB, activin AC, activin BC, activin AE and activin BE) BMP6, and BMP10], co-receptors, type II receptors (e.g., ActRIIA and/or ActRIIB), and/or additional type I receptors (e.g., ALK4 and/or ALK5).

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; diabodies; linear antibodies; single-chain antibody molecules (e.g., scFv); and multispecific antibodies formed from antibody fragments [see, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894; 5,587,458; and 5,869,046]. Diabodies are antibody fragments with two antigen-binding sites that may be bivalent or bispecific [see, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448]. Triabodies and tetrabodies are also described in Hudson et al. (2003) Nat. Med. 9:129-134. Single-domain antibodies are antibody fragments comprising all or a portion of the heavy-chain variable domain or all or a portion of the light-chain variable domain of an antibody. In certain embodiments, a single-domain antibody is a human single-domain antibody [see, e.g., U.S. Pat. No. 6,248,516]. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In certain preferred embodiments, the antibodies of the present disclosure are isolated antibodies. In certain preferred embodiments, the antibodies of the present disclosure are recombinant antibodies.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, $IgG_1$, $IgG_2$, $IgG_3$, $IgG_4$, $IgA_1$, and $IgA_2$. The heavy chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, Biacore, radiolabeled antigen-binding assay (RIA), and ELISA. In some embodiments, antibodies of the present disclosure bind to their target antigens (e.g. ActRIIB, ActRIIA, ALK4, ALK5, ALK7, activin, GDF11, GDF8, GDF3, BMP15, BMP10, and/or BMP6) with at least a $K_D$ of $1 \times 10^{-7}$ or stronger, $1 \times 10^{-8}$ or stronger, $1 \times 10^{-9}$ or stronger, $1 \times 10^{-10}$ or stronger, $1 \times 10^{-11}$ or stronger, $1 \times 10^{-12}$ or stronger, $1 \times 10^{-13}$ or stronger, or $1 \times 10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radio-labeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (BIAcore, Inc., Piscataway, N.J.) with immobilized antigen CM5 chips at about 10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NETS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ [see, e.g., Chen et al., (1999) J. Mol. Biol. 293:865-881]. If the on-rate exceeds, for example, $10^6$ $M^{-1}$ $s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophometer (Aviv Instruments) or a 8000-series SLM-AMINCO® spectrophotometer (ThermoSpectronic) with a stirred cuvette.

Antibody fragments can be made by various techniques, including but not limited to proteolytic digestion of an intact antibody as well as production by recombinant host cells (e.g., E. coli or phage), as described herein. The nucleic acid and amino acid sequences of human ActRIIA, ActRIIB, ALK4, ALK5, ALK7, activin (activin A, activin B, activin C, and activin E), GDF11, GDF8, BMP15, GDF3, BMP10, and BMP6, are known in the art. In addition, numerous methods for generating antibodies are well known in the art, some of which are described herein. Therefore antibody antagonists for use in accordance with this disclosure may be routinely made by the skilled person in the art based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337; 7,527,791; 6,982,321; and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling). Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light or heavy chain variable regions [see, e.g., Carter et al. (1992) Proc. Natl. Acad. Sci. USA, 89:4285; and Presta et al. (1993) J. Immunol., 151:2623]; human mature (somatically mutated) framework regions or human germline framework regions [see, e.g., Almagro and Fransson (2008) Front. Biosci. 13:1619-1633]; and framework regions derived from screening FR libraries [see, e.g., Baca et al., (1997) J. Biol. Chem. 272:10678-10684; and Rosok et al., (1996) J. Biol. Chem. 271:22611-22618].

In certain embodiments, an antibody provided herein is a human antibody. Human antibodies can be produced using various techniques known in the art. Human antibodies are described generally in van Dijk and van de Winkel (2008) Curr. Opin. Pharmacol. 5: 368-74 (2001) and Lonberg, Curr. Opin. Immunol. 20:450-459. For example, human antibodies may be prepared by administering an immunogen (e.g., a GDF11 polypeptide, an activin B polypeptide, an ActRIIA polypeptide, or an ActRIIB polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals see, for example, Lonberg (2005) Nat. Biotech. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91. Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are known in the art and described herein.

For example, antibodies of the present disclosure may be isolated by screening combinatorial libraries for antibodies with the desired activity or activities. A variety of methods are known in the art for generating phage display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., ActRIIA, ActRIIB, activin, GDF11, GDF8, BMP15, GDF3, or BMP6) without the requirement of constructing hybridomas. Alternatively, the naive repertoire can be cloned (e.g., from human) to provide a single source of antibodies to a wide range of non-self and also self-antigens without any immunization as described by Griffiths et al. (1993) EMBO J, 12: 725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) that have binding specificities for at least two different epitopes (e.g., two, three, four, five, or six or more) on one or more (e.g., two, three, four, five, six or more) antigens.

Techniques for making multispecific antibodies include, but are not limited to, recombinant co-expression of two immunoglobulin heavy-chain/light-chain pairs having different specificities [see, e.g., Milstein and Cuello (1983) Nature 305: 537; International patent publication no. WO 93/08829; and Traunecker et al. (1991) EMBO J. 10: 3655, and U.S. Pat. No. 5,731,168 ("knob-in-hole" engineering)]. Multispecific antibodies may also be made by engineering electrostatic steering effects for making antibody Fc-heterodimeric molecules (see, e.g., WO 2009/089004A1); cross-linking two or more antibodies or fragments [see, e.g., U.S. Pat. No. 4,676,980; and Brennan et al. (1985) Science, 229: 81]; using leucine zippers to produce bispecific antibodies [see, e.g., Kostelny et al. (1992) J. Immunol., 148 (5):1547-1553]; using "diabody" technology for making bispecific antibody fragments [see, e.g., Hollinger et al. (1993) Proc. Natl. Acad. Sci. USA, 90:6444-6448]; using single-chain Fv (sFv) dimers [see, e.g., Gruber et al. (1994) J. Immunol., 152:5368]; and preparing trispecific antibodies (see, e.g., Tutt et al. (1991) J. Immunol. 147: 60. Multispecific antibodies can be prepared as full-length antibodies or antibody fragments. Engineered antibodies with three or more functional antigen-binding sites, including "Octopus antibodies," are also included herein [see, e.g., US 2006/0025576A1].

In certain embodiments, an antibody disclosed herein is a monoclonal antibody. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from activin, anti-protein/anti-peptide antisera or monoclonal antibodies can be made by standard protocols [see, e.g., Antibodies: A Laboratory Manual ed. by Harlow and Lane (1988) Cold Spring Harbor Press: 1988]. A mammal, such as a mouse, hamster, or rabbit, can be immunized with an immunogenic form of the activin polypeptide, an antigenic fragment which is capable of eliciting an antibody response, or a fusion protein. Techniques for conferring immunogenicity on a protein or peptide include conjugation to carriers or other techniques well known in the art. An immunogenic portion of a activin polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of activin, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a activin polypeptide, and monoclonal antibodies isolated from a culture comprising such hybridoma cells.

In certain embodiments, one or more amino acid modifications may be introduced into the Fc region of an antibody provided herein thereby generating an Fc region variant. The Fc region variant may comprise a human Fc region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Natl. Acad. Sci. USA 83:7059-7063]; Hellstrom, I et al. (1985) Proc. Natl. Acad. Sci. USA 82:1499-1502; U.S. Pat. No. 5,821,337; Bruggemann, M. et al. (1987) J. Exp. Med. 166:1351-1361. Alternatively, non-radioactive assays methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Natl. Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g, Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Intl. Immunol. 18(12):1759-1769]. Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interactions between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Maryland), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into and/or substitutions of residues within the amino acid sequences of the antibody and/or binding polypeptide. Any combination of deletion, insertion, and substitution can be made to arrive at the final construct, provided that the final construct possesses the desired characteristics, e.g., target-binding (e.g., and activin such as activin E and/or activin C binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process [see, e.g., Chowdhury (2008) Methods Mol. Biol. 207:179-196 (2008)], and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of the antibody and/or the binding polypeptide that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody-antigen is affected. Further substitutions may be introduced at the amino acid locations demonstrating functional sensitivity to the initial substitutions. Alternatively, or additionally, a crystal structure of an antigen-antibody complex is determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional nonproteinaceous moieties that are known in the art and readily available. The moieties suitable for derivatization of the antibody and/or binding polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

5. Small Molecule Antagonists

In other aspects, a GDF/BMP antagonist to be used in accordance with the methods and uses described herein is a small molecule (GDF/BMP small molecule antagonist), or combination of small molecule antagonists. A GDF/BMP small molecule antagonist, or combination of small molecule antagonists, may inhibit, for example, one or more GDF/BMP ligands (e.g., activin, GDF11, GDF8, GDF3, BMP6, BMP10, and/or BMP15), a type I receptor (e.g., ALK4, ALK5, and/or ALK7), a type II receptor (e.g., ActRIIB and/or ActRIIA), a co-receptor, and/or one or more signaling factors (e.g. Smad proteins such as Smads 2 and 3). In some embodiments, a GDF/BMP small molecule antagonist, or combination of small molecule antagonists, inhibits signaling mediated by one or more GDF/BMP ligands, for example, as determined in a cell-based assay such as those described herein. As described herein, GDF/BMP small molecule antagonists may be used, alone or in combination with one or more supportive therapies or active agents, to treat, prevent, or reduce the progression rate and/or severity of pulmonary hypertension (PH), particularly treating, preventing or reducing the progression rate and/or severity of one or more PH-associated complications.

In some embodiments, a GDF/BMP small molecule antagonist, or combination of small molecule antagonists, inhibits at least GDF11, optionally further inhibiting one or more of GDF8, activin (e.g., activin A, activin B, activin C, activin E, activin AB, activin AC, activin BC, activin AE and/or activin BE), GDF3, BMP6, BMP10, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least GDF8, optionally further inhibiting one or more of GDF11, activin (e.g., activin A, activin B, activin C, activin E, activin AB, activin AC, activin BC, activin AE and/or activin BE), GDF3, BMP6, BMP10, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least activin (activin A, activin B, activin C, activin E, activin AB, activin AC, activin BC, activin AE and/or activin BE), optionally further inhibiting one or more of GDF8, GDF11, GDF3, BMP6, BMP10, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least activin B, optionally further inhibiting one or more of GDF8, GDF11, GDF3, BMP6, BMP10, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least BMP6, optionally further inhibiting one or more of GDF8, activin (e.g., activin A, activin B, activin C, activin E, activin AB, activin AC, activin BC, activin AE and/or activin BE), GDF3, GDF11, BMP10, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least BMP15, optionally further inhibiting one or more of GDF8, activin (e.g., activin A, activin B, activin C, activin E, activin AB, activin AC, activin BC, activin AE and/or activin BE), GDF3, BMP6, GDF11, BMP10, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least GDF3, optionally further inhibiting one or more of GDF8, activin (e.g., activin A, activin B, activin C, activin E, activin AB, activin AC, activin BC, activin AE and/or activin BE), BMP15, BMP6, GDF11, BMP10, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least BMP10, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least ActRIIA, optionally further inhibiting one or more of GDF8, activin (e.g., activin A, activin B, activin C, activin E, activin AB, activin AC, activin BC, activin AE and/or activin BE), BMP15, BMP6, GDF11, GDF3, BMP10, ActRIIB, ALK4, ALK5, ALK7, and one or more Smad proteins (e.g., Smads 2 and 3). In some embodiments, a GDF/BMP small molecule antagonist, or combination of small molecule antagonists, inhibits at least ActRIIB, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, BMP10, ALK4, ALK5, ALK7, and one or more Smad proteins (e.g., Smads 2 and 3). In some embodiments, a GDF/BMP small molecule antagonist, or combination of small molecule antagonists, inhibits at least ALK4, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, BMP10, ALK5, ALK7, and one or more Smad proteins (e.g., Smads 2 and 3). In some embodiments, a GDF/BMP small molecule antagonist, or combination of small molecule antagonists, inhibits at least ALK5, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, ALK4, BMP10, ALK7, and one or more Smad proteins (e.g., Smads 2 and 3). In some embodiments, a GDF/BMP small molecule antagonist, or combination of small molecule antagonists, inhibits at least ALK7, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, ALK4, ALK5, BMP10, and one or more Smad proteins (e.g., Smads 2 and 3). In some embodiments, a GDF/BMP small molecule antagonist, or combination of small molecule antagonists, as disclosed herein does not inhibit or does not substantially inhibit BMP9. In some embodiments, a GDF/BMP small molecule antagonist, or combination of small molecule antagonists, as disclosed herein does not inhibit or does not substantially inhibit activin A.

GDF/BMP small molecule antagonists can be direct or indirect inhibitors. For example, an indirect small molecule antagonist, or combination of small molecule antagonists, may inhibit the expression (e.g., transcription, translation, cellular secretion, or combinations thereof) of at least one or more GDF/BMP ligands [e.g., activin (e.g., activin A, activin B, activin C, activin E, activin AB, activin AC, activin B, activin BC, activin AE, or activin BE), GDF11, BMP15, BMP6, GDF3, BMP10, and/or GDF8], type I receptor (e.g., ALK4, ALK5, and/or ALK7), type II receptors (e.g., ActRIIA and/or ActRIIB), co-receptor, and/or one or more downstream signaling components (e.g., Smads). Alternatively, a direct small molecule antagonist, or combination of small molecule antagonists, may directly bind to and inhibit, for example, one or more one or more GDF/BMP ligands [e.g., activin (e.g., activin A, activin B, activin C, activin E, activin AB, activin AC, activin B, activin BC, activin AE, or activin BE), GDF11, BMP15, BMP6, GDF3, BMP10, and/or GDF8], type I receptor (e.g., ALK4, ALK5 and/or ALK7), type II receptors (e.g., ActRIIA and/or ActRIIB), co-receptor, and/or one or more downstream signaling components (e.g., Smads). Combinations of one or more indirect and one or more direct GDF/BMP small molecule antagonists may be used in accordance with the methods disclosed herein.

Binding small-molecule antagonists of the present disclosure may be identified and chemically synthesized using known methodology (see, e.g., PCT Publication Nos. WO 00/00823 and WO 00/39585). In general, small molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein. These small molecule antagonists may be identified without undue experimentation using well-known techniques. In this regard, it is noted that techniques for screening organic small-molecule libraries for molecules that are capable of binding to a polypeptide target are well known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazoli-

6. Polynucleotide Antagonists

In other aspects, a GDF/BMP antagonist to be used in accordance with the methods and uses disclosed herein is a polynucleotide (GDF/BMP polynucleotide antagonist), or combination of polynucleotides. A GDF/BMP polynucleotide antagonist, or combination of polynucleotide antagonists, may inhibit, for example, one or more GDF/BMP ligands (e.g., activin, GDF11, GDF8, GDF3, BMP6, BMP10, and/or BMP15), type I receptors (e.g., ALK4, ALK5, and/or ALK7), type II receptors (e.g., ActRIIA and/or ActRIIB), co-receptor, and/or downstream signaling component (e.g., Smads). In some embodiments, a GDF/BMP polynucleotide antagonist, or combination of polynucleotide antagonists, inhibits signaling mediated by one or more GDF/BMP ligands, for example, as determined in a cell-based assay such as those described herein. As described herein, GDF/BMP polynucleotide antagonists may be used, alone or in combination with one or more supportive therapies or active agents, to treat, prevent, or reduce the progression rate and/or severity of pulmonary hypertension (PH), particularly treating, preventing or reducing the progression rate and/or severity of one or more PH-associated complications In some embodiments, a GDF/BMP polynucleotide antagonist, or combination of polynucleotide antagonists, inhibits at least GDF11, optionally further inhibiting one or more of GDF8, activin (e.g., activin A, activin B, activin C, activin E, activin AB, activin AC, activin BC, activin AE and/or activin BE), GDF3, BMP6, BMP15, BMP10, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least GDF8, optionally further inhibiting one or more of GDF11, activin (e.g., activin A, activin B, activin C, activin E, activin AB, activin AC, activin BC, activin AE and/or activin BE), GDF3, BMP6, BMP15, BMP10, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least activin (activin A, activin B, activin C, activin E, activin AB, activin AC, activin BC, activin AE and/or activin BE), optionally further inhibiting one or more of GDF8, GDF11, GDF3, BMP6, BMP15, BMP10, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least activin B, optionally further inhibiting one or more of GDF8, GDF11, GDF3, BMP6, BMP15, BMP10, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least BMP6, optionally further inhibiting one or more of GDF8, activin (e.g., activin A, activin B, activin C, activin E, activin AB, activin AC, activin BC, activin AE and/or activin BE), GDF3, GDF11, BMP15, BMP10, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least BMP15, optionally further inhibiting one or more of GDF8, activin (e.g., activin A, activin B, activin C, activin E, activin AB, activin AC, activin BC, activin AE and/or activin BE), GDF3, BMP6, GDF11, BMP10, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least GDF3, optionally further inhibiting one or more of GDF8, activin (e.g., activin A, activin B, activin C, activin E, activin AB, activin AC, activin BC, activin AE and/or activin BE), BMP15, BMP6, GDF11, BMP10, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least BMP10, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least ActRIIA, optionally further inhibiting one or more of GDF8, activin (e.g., activin A, activin B, activin C, activin E, activin AB, activin AC, activin BC, activin AE and/or activin BE), BMP15, BMP6, GDF11, GDF3, BMP10, ActRIIB, ALK4, ALK5, ALK7, and one or more Smad proteins (e.g., Smads 2 and 3). In some embodiments, a GDF/BMP polynucleotide antagonist, or combination of polynucleotide antagonists, inhibits at least ActRIIB, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, BMP10, ALK4, ALK5, ALK7, and one or more Smad proteins (e.g., Smads 2 and 3). In some embodiments, a GDF/BMP polynucleotide antagonist, or combination of polynucleotide antagonists, inhibits at least ALK4, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, BMP10, ALK5, ALK7, and one or more Smad proteins (e.g., Smads 2 and 3). In some embodiments, a GDF/BMP polynucleotide antagonist, or combination of polynucleotide antagonists, inhibits at least ALK5, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, ALK4, BMP10, ALK7, and one or more Smad proteins (e.g., Smads 2 and 3). In some embodiments, a GDF/BMP polynucleotide antagonist, or combination of polynucleotide antagonists, inhibits at least ALK7, optionally further inhibiting one or more of GDF8, activin (e.g., activin A, activin B, activin C, activin E, activin AB, activin AC, activin BC, activin AE and/or activin BE), BMP15, BMP6, GDF11, GDF3, ActRIIA, ActRIIB, ALK4, ALK5, BMP10, and one or more Smad proteins (e.g., Smads 2 and 3). In some embodiments, a GDF/BMP polynucleotide antagonist, or combination of polynucleotide antagonists, as disclosed herein does not inhibit or does not substantially inhibit BMP9. In some embodiments, a GDF/BMP polynucleotide antagonist, or combination of polynucleotide antagonists, as disclosed herein does not inhibit or does not substantially inhibit activin A.

In some embodiments, the polynucleotide antagonists of the disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human GDF11, GDF8, activin (activin A, activin B, activin C, and activin E), BMP6, GDF3, ActRIIA, ActRIIB, BMP10, ALK4, ALK5, ALK7, BMP15, and Smad proteins are known in the art. In addition, many different methods of generating polynucleotide antagonists are well known in the art. Therefore polynucleotide antagonists for use in accordance with this disclosure may be routinely made by the skilled person in the art based on the knowledge in the art and teachings provided herein.

Antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple-helix formation is discussed in, for instance, Cooney et al. (1988) Science 241:456; and Dervan et al., (1991) Science 251:1300. The methods are based on binding of a polynucleotide to a complementary DNA or RNA. In some embodiments, the antisense nucleic acids comprise a single-stranded RNA or DNA sequence that is complementary to at least a portion of an RNA transcript of a gene disclosed herein. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-non-translated, non-coding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-, 3'- or coding region of an mRNA of the disclosure, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In one embodiment, the antisense nucleic acid of the present disclosure is produced intracellularly by transcription from an exogenous sequence. For example, a vector or a portion thereof is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 290:304-310], the promoter contained in the 3' long-terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA (RNAi) molecules that target the expression of one or more of: GDF11, GDF8, activin (activin A, activin B, activin C, and activin E), BMP6, GDF3, ActRIIA, ActRIIB, BMP10, ALK4, ALK5, ALK7, BMP15, and Smad proteins. RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to affect RNAi. Accordingly, such short-hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure, which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as *E. coli* RNase III (Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule. The generation and therapeutic use of aptamers are well established in the art (see, e.g., U.S. Pat. No. 5,475,096). Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096; 5,580,737; 5,567,588; 5,707,796; 5,763,177; 6,011,577; and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield nucleic acid ligands which bind with high affinity and specificity to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

7. Follistatin and FLRG Antagonists

In other aspects, a GDF/BMP antagonist is a follistatin or FLRG polypeptide. As described herein, follistatin and/or FLRG polypeptides may be used treat, prevent, or reduce the progression rate and/or severity of pulmonary hypertension (PH), particularly treating, preventing or reducing the progression rate and/or severity of one or more PH-associated complications.

The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. In certain preferred embodiments, follistatin polypeptides of the disclosure bind to and/or inhibit activin activity, particularly activin A. Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 28-30, the follistatin N-terminal domain ("FSND" SEQ ID NO: 28), FSD2 (SEQ ID NO: 30), and to a lesser extent FSD1 (SEQ ID NO: 29) represent exemplary domains within follistatin that are important for activin binding. In addition, methods for making and testing libraries of polypeptides are described above in the context of ActRII polypeptides, and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the mature follistatin polypeptide or shorter isoforms or other variants of the human follistatin precursor polypeptide (SEQ ID NO: 26) as described, for example, in WO2005/025601.

The human follistatin precursor polypeptide isoform FST344 is as follows:

```
                                 (SEQ ID NO: 26; NCBI Reference No. NP_037541.1)
  1  MVRARHQPGG LCLLLLLLCQ FMEDRSAQAG NCWLRQAKNG RCQVLYKTEL

51  SKEECCSTGR LSTSWTEEDV NDNTLFKWMI FNGGAPNCIP CKETCENVDC

101  GPGKKCRMNK KNKPRCVCAP DCSNITWKGP VCGLDGKTYR NECALLKARC

151  KEQPELEVQY QGRCKKTCRD VFCPGSSTCV VDQTNNAYCV TCNRICPEPA

201  SSEQYLCGND GVTYSSACHL RKATCLLGRS IGLAYEGKCI KAKSCEDIQC

251  TGGKKCLWDF KVGRGRCSLC DELCPDSKSD EPVCASDNAT YASECAMKEA

301  ACSSGVLLEV KHSGSCNSIS EDTEEEEEDE DQDYSFPISS ILEW
```

The signal peptide is underlined; also underlined above are the last 27 residues which represent the C-terminal extension distinguishing this follistatin isoform from the shorter follistatin isoform FST317 shown below.

The human follistatin precursor polypeptide isoform FST317 is as follows:

```
                    (SEQ ID NO: 27; NCBI Reference No. NP_006341.1)
  1  MVRARHQPGG LCLLLLLLCQ FMEDRSAQAG NCWLRQAKNG RCQVLYKTEL

51  SKEECCSTGR LSTSWTEEDV NDNTLFKWMI FNGGAPNCIP CKETCENVDC

101  GPGKKCRMNK KNKPRCVCAP DCSNITWKGP VCGLDGKTYR NECALLKARC

151  KEQPELEVQY QGRCKKTCRD VFCPGSSTCV VDQTNNAYCV TCNRICPEPA

201  SSEQYLCGND GVTYSSACHL RKATCLLGRS IGLAYEGKCI KAKSCEDIQC

251  TGGKKCLWDF KVGRGRCSLC DELCPDSKSD EPVCASDNAT YASECAMKEA

301  ACSSGVLLEV KHSGSCN
```

The signal peptide is underlined.

The follistatin N-terminal domain (FSND) sequence is as follows:

```
                                        (SEQ ID NO: 28; FSND)
GNCWLRQAKNGRCQVLYKTELSKEECCSTGRLSTSWTEEDVNDNTLF

KWMIFNGGAPNCIPCK
```

The FSD1 and FSD2 sequences are as follows:

```
                                        (SEQ ID NO: 29; FSD1)
ETCENVDCGPGKKCRMNKKNKPRCV (SEQ ID NO: 30; FSD2)
KTCRDVFCPGSSTCVVDQTNNAYCVT
```

In other aspects, an agent for use in accordance with the methods disclosed herein is a follistatin-like related gene (FLRG), also known as follistatin-related protein 3 (FSTL3).

The term "FLRG polypeptide" includes polypeptides comprising any naturally occurring polypeptide of FLRG as well as any variants thereof (including mutants, fragments, fusions, and peptidomimetic forms) that retain a useful activity. In certain preferred embodiments, FLRG polypeptides of the disclosure bind to and/or inhibit activin activity, particularly activin A. Variants of FLRG polypeptides that retain activin binding properties can be identified using routine methods to assay FLRG and activin interactions (see, e.g., U.S. Pat. No. 6,537,966). In addition, methods for making and testing libraries of polypeptides are described above in the context of ActRII polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG precursor (follistatin-related protein 3 precursor) polypeptide is as follows:

```
                    (SEQ ID NO: 31; NCBI Reference No. NP_005851.1)
  1  MRPGAPGPLW PLPWGALAWA VGFVSSMGSG NPAPGGVCWL QQGQEATCSL

51  VLQTDVTRAE CCASGNIDTA WSNLTHPGNK INLLGFLGLV HCLPCKDSCD

101  GVECGPGKAC RMLGGRPRCE CAPDCSGLPA RLQVCGSDGA TYRDECELRA

151  ARCRGHPDLS VMYRGRCRKS CEHVVCPRPQ SCVVDQTGSA HCVVCRAAPC

201  PVPSSPGQEL CGNNNVTYIS SCHMRQATCF LGRSIGVRHA GSCAGTPEEP

251  PGGESAEEEE NFV
```

The signal peptide is underlined.

In certain embodiments, functional variants or modified forms of the follistatin polypeptides and FLRG polypeptides include fusion proteins having at least a portion of the follistatin polypeptide or FLRG polypeptide and one or more fusion domains, such as, for example, domains that facilitate isolation, detection, stabilization or multimerization of the polypeptide. Suitable fusion domains are discussed in detail above with reference to the ActRII polypeptides. In some embodiment, an antagonist agent of the disclosure is a fusion protein comprising an activin-binding portion of a follistatin polypeptide fused to an Fc domain. In another embodiment, an antagonist agent of the disclosure is a fusion protein comprising an activin binding portion of an FLRG polypeptide fused to an Fc domain.

8. Screening Assays

In certain aspects, the present disclosure relates to the use of the subject GDF/BMP antagonists (e.g., ActRII polypeptides and variants thereof) to identify compounds (agents) which may be used to treat, prevent, or reduce the progression rate and/or severity of pulmonary hypertension (PH), particularly treating, preventing or reducing the progression rate and/or severity of one or more PH-associated complications.

There are numerous approaches to screening for therapeutic agents for treating PH by targeting signaling (e.g., Smad signaling) of one or more GDF/BMP ligands. In certain embodiments, high-throughput screening of compounds can be carried out to identify agents that perturb GDF/BMP ligands-mediated effects on a selected cell line. In certain embodiments, the assay is carried out to screen and identify compounds that specifically inhibit or reduce binding of an GDF/BMP ligand (e.g., activin A, activin B, activin AB, activin C, GDF3, BMP6, GDF8, GDF15, GDF11 or BMP10) to its binding partner, such as an a type II receptor (e.g., ActRIIA and/or ActRIIB) Alternatively, the assay can be used to identify compounds that enhance binding of a GDF/BMP ligand to its binding partner such as a type II receptor. In a further embodiment, the compounds can be identified by their ability to interact with a type II receptor.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a GDF/BMP ligand (e.g., activin A, activin B, activin AB, activin C, GDF8, GDF15, GDF11, GDF3, BMP6, or BMP10) to its binding partner, such as an a type II receptor (e.g., ActRIIA and/or ActRIIB).

Merely to illustrate, in an exemplary screening assay of the present disclosure, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added to a composition containing an ActRIIB ligand (e.g., GDF11). Detection and quantification of ActRIIB/ActRIIB-ligand complexes provides a means for determining the compound's efficacy at inhibiting (or potentiating) complex formation between the ActRIIB polypeptide and its binding protein. The efficacy of the compound can be assessed by generating dose-response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between GDF/BMP ligand and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIB polypeptide and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between a GDF/BMP ligand and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between a GDF/BMP ligand and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between a GDF/BMP ligand and its binding protein [see, e.g., Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with a GDF/BMP ligand. The interaction between the compound and the GDF/BMP ligand may be covalent or non-covalent. For example, such interaction can be identified at the protein level using in vitro biochemical methods, including photo-crosslinking, radio-labeled ligand binding, and affinity chromatography [see, e.g., Jakoby W B et al. (1974) Methods in Enzymology 46:1]. In certain cases, the compounds may be screened in a mechanism-based assay, such as an assay to detect compounds which bind to a GDF/BMP ligand. This may include a solid-phase or fluid-phase binding event. Alternatively, the gene encoding GDF/BMP ligand can be transfected with a reporter system (e.g., β-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

9. Therapeutic Uses

In part, the present disclosure relates to methods of treating pulmonary hypertension (e.g., pulmonary arterial hypertension) comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins). In some embodiments, the disclosure contemplates methods of treating one or more complications of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount of a GDF/BMP antagonist. In some embodiments, the disclosure contemplates methods of preventing one or more complications of pulmonary hypertension comprising administering to a patient in need thereof an effective amount of a GDF/BMP antagonist. In some embodiments, the disclosure contemplates methods of reducing the progression rate of pulmonary hypertension comprising administering to a patient in need thereof an effective amount of a GDF/BMP antagonist. In some embodiments, the disclosure contemplates methods of reducing the progression rate of one or more complications of pulmonary hypertension comprising administering to a patient in need thereof an effective amount of a GDF/BMP antagonist. In some embodiments, the disclosure contemplates methods of reducing the severity of pulmonary hypertension comprising administering to a patient in need thereof an effective amount of a GDF/BMP antagonist. In some embodiments, the disclosure contemplates methods of reducing the severity of one or more complications of pulmonary hypertension comprising administering to a patient in need thereof an effective amount of a GDF/BMP antagonist. Optionally, methods disclosed herein for treating, preventing, or reducing the progression rate and/or severity of pulmonary hypertension, particularly treating, preventing, or reducing the progression rate and/or severity of one or more complications of pulmonary hypertension, may further comprise administering to the patient one or more supportive therapies or additional active agents for treating pulmonary hypertension. For example, the patient also may be administered one or more supportive therapies or active agents selected from the group consisting of: prostacyclin and derivatives thereof (e.g., epoprostenol, treprostinil, and iloprost); prostacyclin receptor agonists (e.g., selexipag); endothelin receptor antagonists (e.g., thelin, ambrisentan, macitentan, and bosentan); calcium channel blockers (e.g., amlodipine, diltiazem, and nifedipine; anticoagulants (e.g., warfarin); diuretics; oxygen therapy; atrial septostomy; pulmonary thromboendarterectomy; phosphodiesterase type 5 inhibitors (e.g., sildenafil and tadalafil); activators of soluble guanylate cyclase (e.g., cinaciguat and riociguat); ASK-1 inhibitors (e.g., CIIA; SCH79797; GS-4997; MSC2032964A; 3H-naphtho[1,2,3-de]quiniline-2,7-diones, NQDI-1; 2-thioxo-thiazolidines, 5-bromo-3-(4-oxo-2-thioxo-thiazolidine-5-ylidene)-1,3-dihydro-indol-2-one); NF-κB antagonists (e.g., dh404, CDDO-epoxide; 2.2-difluoropropionamide; C28 imidazole (CDDO-Im); 2-cyano-3,12-dioxoolean-1,9-dien-28-oic acid (CDDO); 3-Acetyloleanolic Acid; 3-Triflouroacetyloleanolic Acid; 28-Methyl-3-acetyloleanane; 28-Methyl-3-trifluoroacetyloleanane; 28-Methyloxyoleanolic Acid; SZCO14; SCZ015; SZCO17; PEGylated derivatives of oleanolic acid; 3-O-(beta-D-glucopyranosyl) oleanolic acid; 3-O-[beta-D-glucopyranosyl-(1→3)-beta-D-glucopyranosyl] oleanolic acid; 3-O-[beta-D-glucopyranosyl-(1→2)-beta-D-glucopyranosyl] oleanolic acid; 3-O-[beta-D-glucopyranosyl-(1→3)-beta-D-glucopyranosyl] oleanolic acid 28-O-beta-D-glucopyranosyl ester; 3-O-[beta-D-glucopyranosyl-(1→2)-beta-D-glucopyranosyl] oleanolic acid 28-O-beta-D-glucopyranosyl ester; 3-O-[a-L-rhamnopyranosyl-(1→3)-beta-D-glucuronopyranosyl] oleanolic acid; 3-O-[alpha-L-rhamnopyranosyl-(1→3)-beta-D-glucuronopyranosyl] oleanolic acid 28-O-beta-D-glucopyranosyl ester; 28-O-β-D-glucopyranosyl-oleanolic acid; 3-O-β-D-glucopyranosyl (1→3)-β-D-glucopyranosiduronic acid (CS1); oleanolic acid 3-O-β-D-glucopyranosyl (1→3)-β-D-glucopyranosiduronic acid (CS2); methyl 3,11-dioxoolean-12-en-28-olate (DIOXOL); ZCVI$_4$-2; Benzyl 3-dehydr-oxy-1,2,5-oxadiazolo[3',4':2,3]oleanolate) lung and/or heart transplantation. In some embodiment, the patient may also be administered a BMP9 polypeptide. In some embodiments the BMP9 polypeptide is a mature BMP9 polypeptide. In some embodiments, the BMP9 polypeptide comprises a BMP9 prodomain polypeptide. In some embodiments, the BMP9 polypeptide is administered in a pharmaceutical preparation, which optionally may comprise a BMP9 prodomain polypeptide. In such BMP9 pharmaceutical preparations comprising a BMP9 prodomain polypeptide, the BMP9 polypeptide may be noncovalently associated with the BMP9 prodomain polypeptide. In some embodiments, BMP9 pharmaceutical preparations are substantially free, or does not comprise, of BMP9 prodomain polypeptide. BMP9 polypeptides (mature and pro-polypeptides), BMP9 prodomain polypeptides, pharmaceutical compositions comprising the same as well as method of generative such polypeptides and pharmaceutical compositions are described in, for example, WO 2013/152213, which is incorporated by reference herein in its entirety. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

In some embodiments, the present disclosure relates to methods of treating an interstitial lung disease (e.g., idiopathic pulmonary fibrosis) comprising administering to a patient in need thereof an effective amount of any of the GDF/BMP antagonists disclosed herein (e.g., an antagonist of one or more of activin, GDF8, GDF11, GDF3, BMP6, BMP15, BMP10, ActRIIA, ActRIIB, ALK4, ALK5, ALK7, and one or more Smad proteins). In some embodiments, the interstitial lung disease is pulmonary fibrosis. In some embodiments, the interstitial lung disease is caused by any one of the following: silicosis, asbestosis, berylliosis, hypersensitivity pneumonitis, drug use (e.g., antibiotics, chemotherapeutic drugs, antiarrhythmic agents, statins), systemic sclerosis, polymyositis, dermatomyositis, systemic lupus erythematosus, rheumatoid arthritis, an infection (e.g., atypical pneumonia, pneumocystis pneumonia, tuberculosis, *Chlamydia trachomatis*, and/or respiratory syncytial virus), lymphangitic carcinomatosis, cigarette smoking, or developmental disorders. In some embodiments, the interstitial lung disease is idiopathic (e.g., sarcoidosis, idiopathic pulmonary fibrosis, Hamman-Rich syndrome, and/or antisynthetase syndrome). In particular embodiments, the interstitial lung disease is idiopathic pulmonary fibrosis. In some embodiments, the treatment for idiopathic pulmonary fibrosis is administered in combination with an additional therapeutic agent. In some embodiments, the additional therapeutic agent is selected from the group consisting of: pirfenidone, N-acetylcysteine, prednisone, azathioprine, nintedanib, derivatives thereof and combinations thereof.

The term "treating" as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering a GDF/BMP antagonist in an effective amount. An effective amount of an agent refers to an amount effective, at dosages and for periods of time necessary, to achieve the desired therapeutic or prophylactic result. A therapeutically effective amount of an agent of the present disclosure may vary according to factors such as the disease state, age, sex, and weight of the individual, and the ability of the agent to elicit a desired response in the individual. A prophylactically effective amount refers to an amount effective, at dosages and for periods of time necessary, to achieve the desired prophylactic result.

The terms "subject," an "individual," or a "patient" are interchangeable throughout the specification and generally refer to mammals. Mammals include, but are not limited to, domesticated animals (e.g., cows, sheep, cats, dogs, and horses), primates (e.g., humans and non-human primates such as monkeys), rabbits, and rodents (e.g., mice and rats).

Pulmonary hypertension (PH) has been previously classified as primary (idiopathic) or secondary. Recently, the World Health Organization (WHO) has classified pulmonary hypertension into five groups: Group 1: pulmonary arterial hypertension (PAH); Group 2: pulmonary hypertension with left heart disease; Group 3: pulmonary hypertension with lung disease and/or hypoxemia; Group 4: pulmonary hypertension due to chronic thrombotic and/or embolic disease; and Group 5: miscellaneous conditions (e.g., sarcoidosis, histiocytosis X, lymphangiomatosis and compression of pulmonary vessels). See, for example, Rubin (2004) Chest 126:7-10.

In certain aspects, the disclosure relates to methods of treating, preventing, or reducing the progression rate and/or severity of pulmonary hypertension (e.g., treating, preventing, or reducing the progression rate and/or severity of one or more complications of pulmonary hypertension) comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins). In some embodiments, the method relates to pulmonary hypertension patients that have pulmonary arterial hypertension. In some embodiments, the method relates pulmonary hypertension patients that have pulmonary hypertension with left heart disease. In some embodiments, the method relates to pulmonary hypertension patients that have lung disease and/or hypoxemia. In some embodiments, the method relates to pulmonary hypertension patients that have chronic thrombotic and/or embolic disease. In some embodiments, the method relates to pulmonary hypertension patients that have sarcoidosis, histiocytosis X, or lymphangiomatosis and compression of pulmonary vessels.

Pulmonary arterial hypertension is a serious, progressive and life-threatening disease of the pulmonary vasculature, characterized by profound vasoconstriction and an abnormal proliferation of smooth muscle cells in the walls of the pulmonary arteries. Severe constriction of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in pulmonary vascular resistance (PVR) and sustained elevations in pulmonary artery pressure (PAP), which ultimately lead to right ventricular failure and death. Patients diagnosed with PAH have a poor prognosis and equally compromised quality of life, with a mean life expectancy of 2 to 5 years from the time of diagnosis if untreated.

A variety of factors contribute to the pathogenesis of pulmonary hypertension including proliferation of pulmonary cells which can contribute to vascular remodeling (i.e., hyperplasia). For example, pulmonary vascular remodeling occurs primarily by proliferation of arterial endothelial cells and smooth muscle cells of patients with pulmonary hypertension. Overexpression of various cytokines is believed to promote pulmonary hypertension. Further, it has been found that pulmonary hypertension may rise from the hyperproliferation of pulmonary arterial smooth cells and pulmonary endothelial cells. Still further, advanced PAH may be characterized by muscularization of distal pulmonary arterioles, concentric intimal thickening, and obstruction of the vascular lumen by proliferating endothelial cells. Pietra et al., J. Am. Coll. Cardiol., 43:255-325 (2004).

In certain aspects, the disclosure relates to methods of treating, preventing, or reducing the progression rate and/or severity of pulmonary hypertension (e.g., treating, preventing, or reducing the progression rate and/or severity of one or more complications of pulmonary hypertension) comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins), wherein the patient has resting pulmonary arterial pressure (PAP) of at least 25 mm Hg (e.g., 25, 30, 35, 40, 45, or 50 mm Hg). In some embodiments, the method relates to patients having a resting PAP of at least 25 mm Hg. In some embodiments, the method relates to patients having a resting PAP of at least 30 mm Hg. In some embodiments, the method relates to patients having a resting PAP of at least 35 mm Hg. In some embodiments, the method relates to patients having a resting PAP of at least 40 mm Hg. In some embodiments, the method relates to patients having a resting PAP of at least 45 mm Hg. In some embodiments, the method relates to patients having a resting PAP of at least 50 mm Hg.

In some embodiments, the disclosure relates to methods of adjusting one or more hemodynamic parameters in the PH patient toward a more normal level (e.g., normal as compared to healthy people of similar age and sex), comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins). In some embodiments, the method relates to reducing PAP. In some embodiments, the method relates to reducing the patient's PAP by at least 3 mmHg. In certain embodiments, the method relates to reducing the patient's PAP by at least 5 mmHg. In certain embodiments, the method relates to reducing the patient's PAP by at least 7 mmHg. In certain embodiments, the method relates to reducing the patient's PAP by at least 10 mmHg. In certain embodiments, the method relates to reducing the patient's PAP by at least 12 mmHg. In certain embodiments, the method relates to reducing the patient's PAP by at least 15 mmHg. In certain embodiments, the method relates to reducing the patient's PAP by at least 20 mmHg. In certain embodiments, the method relates to reducing the patient's PAP by at least 25 mmHg. In some embodiments, the method relates to reducing pulmonary vascular resistance (PVR). In some embodiments, the method relate to increasing pulmonary capillary wedge pressure (PCWP). In some embodiments, the method relate to increasing left ventricular end-diastolic pressure (LVEDP).

In certain aspects, the disclosure relates to methods of treating, preventing, or reducing the progression rate and/or severity of one or more complications of pulmonary hypertension comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins). In some embodiments, the method relates to treating, preventing, or reducing the progression rate and/or severity of cell proliferation in the pulmonary artery of a pulmonary hypertension patient. In some embodiments, the method relates to treating, preventing, or reducing the progression rate and/or severity of smooth muscle and/or endothelial cells proliferation in the pulmonary artery of a pulmonary hypertension patient. In some embodiments, the method relates to treating, preventing, or reducing the progression rate and/or severity of angiogenesis in the pulmonary artery of a pulmonary hypertension patient. In some embodiments, the method relates to increasing physical activity of a patient having pulmonary hypertension. In some embodiments, the method relates to treating, preventing, or reducing the progression rate and/or severity of dyspnea in a pulmonary hypertension patient. In some embodiments, the method relates to treating, preventing, or reducing the progression rate and/or severity of chest pain in a pulmonary hypertension patient. In some embodiments, the method relates to treating, preventing, or reducing the progression rate and/or severity of fatigue in a pulmonary hypertension patient. In some embodiments, the method relates to treating, preventing, or reducing the progression rate and/or severity of pulmonary fibrosis in a pulmonary hypertension patient. In some embodiments, the method relates to treating, preventing, or reducing the progression rate and/or severity of fibrosis in a pulmonary hypertension patient. In some embodiments, the method relates to treating, preventing, or reducing the progression rate and/or severity of pulmonary vascular remodeling in a pulmonary hypertension patient. In some embodiments, the method relates to treating, preventing, or reducing the progression rate and/or severity of right ventricular hypertrophy in a pulmonary hypertension patient.

In certain aspects, the disclosure relates to methods of increasing exercise capacity in a patient having pulmonary hypertension comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins). Any suitable measure of exercise capacity can be used. For example, exercise capacity in a 6-minute walk test (6MWT), which measures how far the subject can walk in 6 minutes, i.e., the 6-minute walk distance (6MWD), is frequently used to assess pulmonary hypertension severity and disease progression. The Borg dyspnea index (BDI) is a numerical scale for assessing perceived dyspnea (breathing discomfort). It measures the degree of breathlessness, for example, after completion of the 6MWT, where a BDI of 0 indicates no breathlessness and 10 indicates maximum breathlessness. In some embodiments, the method relates to increasing 6MWD by at least 10 meters in the patient having pulmonary hypertension. In some embodiments, the method relates to increasing 6MWD by at least 20 meters in the patient having pulmonary hypertension. In some embodiments, the method relates to increasing 6MWD by at least 30 meters in the patient having pulmonary hypertension. In some embodiments, the method relates to increasing 6MWD by at least 40 meters in the patient having pulmonary hypertension. In some embodiments, the method relates to increasing 6MWD by at least 50 meters in the patient having pulmonary hypertension. In some embodiments, the method relates to increasing 6MWD by at least 60 meters in the patient having pulmonary hypertension. In some embodiments, the method relates to increasing 6MWD by at least 70 meters in the patient having pulmonary hypertension. In some embodiments, the method relates to increasing 6MWD by at least 80 meters in the patient having pulmonary hypertension. In some embodiments, the method relates to increasing 6MWD by at least 90 meters in the patient having pulmonary hypertension. In some embodiments, the method relates to increasing 6MWD by at least 100 meters in the patient having pulmonary hypertension. In some embodiments, the method relate to lowering BDI by at least 0.5 index points in the patient having pulmonary hypertension. In some embodiments, the method relate to lowering BDI by at least 1 index points in the patient having pulmonary hypertension. In some embodiments, the method relate to lowering BDI by at least 1.5 index points in the patient having pulmonary hypertension. In some embodiments, the method relate to lowering BDI by at least 2 index points in the patient having pulmonary hypertension. In some embodiments, the method relate to lowering BDI by at least 2.5 index points in the patient having pulmonary hypertension. In some embodiments, the method relate to lowering BDI by at least 3 index points in the patient having pulmonary hypertension. In some embodiments, the method relate to lowering BDI by at least 3.5 index points in the patient having pulmonary hypertension. In some embodiments, the method relate to lowering BDI by at least 4 index points in the patient having pulmonary hypertension. In some embodiments, the method relate to lowering BDI by at least 4.5 index points in the patient having pulmonary hypertension. In some embodiments, the method relate to lowering BDI by at least 5 index points in the patient having pulmonary hypertension. In some embodiments, the method relate to lowering BDI by at least 5.5 index points in the patient having pulmonary hypertension. In some embodiments, the method relate to lowering BDI by at least 6 index points in the patient having pulmonary hypertension. In some embodiments, the method relate to lowering BDI by at least 6.5 index points in the patient having pulmonary hypertension. In some embodiments, the method relate to lowering BDI by at least 7 index points in the patient having pulmonary hypertension. In some embodiments, the method relate to lowering BDI by at least 7.5 index points in the patient having pulmonary hypertension. In some embodiments, the method relate to lowering BDI by at least 8 index points in the patient having pulmonary hypertension. In some embodiments, the method relate to lowering BDI by at least 8.5 index points in the patient having pulmonary hypertension. In some embodiments, the method relate to lowering BDI by at least 9 index points in the patient having pulmonary hypertension. In some embodiments, the method relate to lowering BDI by at least 9.5 index points in the patient having pulmonary hypertension. In some embodiments, the method relate to lowering BDI by at least 3 index points in the patient having pulmonary hypertension. In some embodiments, the method relate to lowering BDI by 10 index points in the patient having pulmonary hypertension.

Pulmonary hypertension at baseline can be mild, moderate or severe, as measured for example by World Health Organization (WHO) functional class, which is a measure of disease severity in patients with pulmonary hypertension. The WHO functional classification is an adaptation of the New York Heart Association (NYHA) system and is routinely used to qualitatively assess activity tolerance, for example in monitoring disease progression and response to treatment (Rubin (2004) Chest 126:7-10). Four functional classes are recognized in the WHO system: Class I: pulmonary hypertension without resulting limitation of physical activity; ordinary physical activity does not cause undue dyspnea or fatigue, chest pain or near syncope; Class II: pulmonary hypertension resulting in slight limitation of physical activity; patient comfortable at rest; ordinary physical activity causes undue dyspnea or fatigue, chest pain or near syncope; Class III: pulmonary hypertension resulting in marked limitation of physical activity; patient comfortable at rest; less than ordinary activity causes undue dyspnea or fatigue, chest pain or near syncope; Class IV: pulmonary hypertension resulting in inability to carry out any physical activity without symptoms; patient manifests signs of right-heart failure; dyspnea and/or fatigue may be present even at rest; discomfort is increased by any physical activity.

In certain aspects, the disclosure relates to methods of treating, preventing, or reducing the progression rate and/or severity of pulmonary hypertension (e.g., treating, preventing, or reducing the progression rate and/or severity of one or more complications of pulmonary hypertension) comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins), wherein the patient has Class I, Class II, Class III, or Class IV pulmonary hypertension as recognized by the WHO. In some embodiments, the method relates to a patient that has Class I pulmonary hypertension as recognized by the WHO. In some embodiments, the method relates to a patient that has Class II pulmonary hypertension as recognized by the WHO. In some embodiments, the method relates to preventing or delaying patient progression from Class I pulmonary hypertension to Class II pulmonary hypertension as recognized by the WHO. In some embodiments, the method relates to promoting or increasing patient regression from Class II pulmonary hypertension to Class I pulmonary hypertension as recognized by the WHO. In some embodiments, the method relates to a patient that has Class III pulmonary hypertension as recognized by the WHO. In some embodiments, the method relates to preventing or delaying patient progression from Class II pulmonary hypertension to Class III pulmonary hypertension as recognized by the WHO. In some embodiments, the method relates to promoting or increasing patient regression from Class III pulmonary hypertension to Class II pulmonary hypertension as recognized by the WHO. In some embodiments, the method relates to promoting or increasing patient regression from Class III pulmonary hypertension to Class I pulmonary hypertension as recognized by the WHO. In some embodiments, the method relates to a patient that has Class IV pulmonary hypertension as recognized by the WHO. In some embodiments, the method relates to preventing or delaying patient progression from Class III pulmonary hypertension to Class IV pulmonary hypertension as recognized by the WHO. In some embodiments, the method relates to promoting or increasing patient regression from Class IV pulmonary hypertension to Class III pulmonary hypertension as recognized by the WHO. In some embodiments, the method relates to promoting or increasing patient regression from Class IV pulmonary hypertension to Class II pulmonary hypertension as recognized by the WHO. In some embodiments, the method relates to promoting or increasing patient regression from Class IV pulmonary hypertension to Class I pulmonary hypertension as recognized by the WHO.

There is no known cure for pulmonary hypertension; current methods of treatment focus on prolonging patient lifespan and enhancing patient quality of life. Current methods of treatment of pulmonary hypertension include administration of: vasodilators such as prostacyclin, epoprostenol, and sildenafil; endothelin receptor antagonists such as bosentan; calcium channel blockers such as amlodipine, diltiazem, and nifedipine; anticoagulants such as warfarin; and diuretics. Treatment of pulmonary hypertension has also been carried out using oxygen therapy, atrial septostomy, pulmonary thromboendarterectomy, and lung and/or heart transplantation. Each of these methods, however, suffers from one or multiple drawbacks which may include lack of effectiveness, serious side effects, low patient compliance, and high cost. In certain aspects, the method relate to treating, preventing, or reducing the progression rate and/or severity of pulmonary hypertension (e.g., treating, preventing, or reducing the progression rate and/or severity of one or more complications of pulmonary hypertension) comprising administering to a patient in need thereof an effective amount of a GDF/BMP antagonist (e.g., an antagonist of one or more of activin, GDF8, GDF11, GDF3, BMP6, BMP15, BMP10, ActRIIA, ActRIIB, ALK4, ALK5, ALK7, and one or more Smad proteins) in combination (e.g., administered at the same time or different times, but generally in such a manner as to achieve overlapping pharmacological/physiological effects) with one or more additional active agents and/or supportive therapies for treating pulmonary hypertension (e.g., vasodilators such as prostacyclin, epoprostenol, and sildenafil; endothelin receptor antagonists such as bosentan; calcium channel blockers such as amlodipine, diltiazem, and nifedipine; anticoagulants such as warfarin; diuretics; oxygen therapy; atrial septostomy; pulmonary thromboendarterectomy: and lung and/or heart transplantation); BMP9 polypeptides; BMP10 polypeptides; bardoxolone methyl or a derivative thereof; oleanolic acid or derivative thereof.

In certain embodiments, the present disclosure provides methods for managing a patient that has been treated with, or is a candidate to be treated with, one or more one or more GDF/BMP antagonists of the disclosure (e.g., ligand traps such as ActRIIA polypeptides, ActRIIB polypeptides, and GDF Trap polypeptides) by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more GDF/BMP antagonists may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more GDF/BMP antagonists, then onset of administration of the one or more antagonists of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more antagonists of the disclosure may be delayed until the levels have returned to a normal or acceptable level.

In certain embodiments, if one or more hematologic parameters are outside the normal range or on the high side of normal in a patient who is a candidate to be treated with one or more GDF/BMP antagonists, then the onset of administration may not be delayed. However, the dosage amount or frequency of dosing of the one or more antagonists of the disclosure may be set at an amount that would reduce the risk of an unacceptable increase in the hematologic parameters arising upon administration of the one or more antagonists of the disclosure. Alternatively, a therapeutic regimen may be developed for the patient that combines one or more GDF/BMP antagonists with a therapeutic agent that addresses the undesirable level of the hematologic parameter. For example, if the patient has elevated blood pressure, then a therapeutic regimen may be designed involving administration of one or more GDF/BMP antagonist agents and a blood pressure lowering agent. For a patient having lower than desired iron stores, a therapeutic regimen may be developed involving one or more GDF/BMP antagonists of the disclosure and iron supplementation.

In one embodiment, baseline parameter(s) for one or more hematologic parameters may be established for a patient who is a candidate to be treated with one or more GDF/BMP antagonists of the disclosure and an appropriate dosing regimen established for that patient based on the baseline value(s). Alternatively, established baseline parameters based on a patient's medical history could be used to inform an appropriate antagonist dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more GDF/BMP antagonists of the disclosure may also be used as the relevant comparative values for monitoring any changes to the hematologic parameters during treatment with the one or more antagonists of the disclosure.

In certain embodiments, one or more hematologic parameters are measured in patients who are being treated with one or more GDF/BMP antagonists. The hematologic parameters may be used to monitor the patient during treatment and permit adjustment or termination of the dosing with the one or more antagonists of the disclosure or additional dosing with another therapeutic agent. For example, if administration of one or more GDF/BMP antagonists results in an increase in blood pressure, red blood cell level, or hemoglobin level, or a reduction in iron stores, then the dose of the one or more antagonists of the disclosure may be reduced in amount or frequency in order to decrease the effects of the one or more antagonists of the disclosure on the one or more hematologic parameters. If administration of one or more GDF/BMP antagonists results in a change in one or more hematologic parameters that is adverse to the patient, then the dosing of the one or more antagonists of the disclosure may be terminated either temporarily, until the hematologic parameter(s) return to an acceptable level, or permanently. Similarly, if one or more hematologic parameters are not brought within an acceptable range after reducing the dose or frequency of administration of the one or more antagonists of the disclosure, then the dosing may be terminated. As an alternative, or in addition to, reducing or terminating the dosing with the one or more antagonists of the disclosure, the patient may be dosed with an additional therapeutic agent that addresses the undesirable level in the hematologic parameter(s), such as, for example, a blood pressure lowering agent or an iron supplement. For example, if a patient being treated with one or more GDF/BMP antagonists has elevated blood pressure, then dosing with the one or more antagonists of the disclosure may continue at the same level and a blood-pressure-lowering agent is added to the treatment regimen, dosing with the one or more antagonist of the disclosure may be reduced (e.g., in amount and/or frequency) and a blood-pressure-lowering agent is added to the treatment regimen, or dosing with the one or more antagonist of the disclosure may be terminated and the patient may be treated with a blood-pressure-lowering agent.

10. Pharmaceutical Compositions

The therapeutic agents described herein (e.g., GDF/BMP antagonists) may be formulated into pharmaceutical compositions. Pharmaceutical compositions for use in accordance with the present disclosure may be formulated in conventional manner using one or more physiologically acceptable carriers or excipients. Such formulations will generally be substantially pyrogen-free, in compliance with most regulatory requirements.

In certain embodiments, the therapeutic methods of the disclosure include administering the composition systemically, or locally as an implant or device. When administered, the therapeutic composition for use in this disclosure is in a substantially pyrogen-free, or pyrogen-free, physiologically acceptable form. Therapeutically useful agents other than the GDF/BMP antagonists which may also optionally be included in the composition as described above, may be administered simultaneously or sequentially with the subject compounds in the methods disclosed herein.

Typically, protein therapeutic agents disclosed herein will be administered parentally, and particularly intravenously or subcutaneously. Pharmaceutical compositions suitable for parenteral administration may comprise one or more GDF/BMP antagonist in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more therapeutic compounds (e.g., GDF/BMP antagonists) to a target tissue site, providing a structure for the developing tissue and optimally capable of being resorbed into the body. For example, the matrix may provide slow release of the GDF/BMP antagonist. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the disclosure (e.g., GDF/BMP antagonists). The various factors include, but are not limited to, the patient's age, sex, and diet, the severity disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the present invention also provides gene therapy for the in vivo production of GDF/BMP antagonists. Such therapy would achieve its therapeutic effect by introduction of the GDF/BMP antagonist polynucleotide sequences into cells or tissues having the disorders as listed above. Delivery of GDF/BMP antagonist polynucleotide sequences can be achieved using a recombinant expression vector such as a chimeric virus or a colloidal dispersion system. Preferred for therapeutic delivery of GDF/BMP antagonist polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the GDF/BMP antagonist. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF/BMP antagonist polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and di stearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

EXEMPLIFICATION

The invention now being generally described, it will be more readily understood by reference to the following examples, which are included merely for purposes of illustration of certain embodiments of the present invention, and are not intended to limit the invention.

Example 1: ActRIIa-Fc Fusion Proteins

A soluble ActRIIA fusion protein was constructed that has the extracellular domain of human ActRIIa fused to a human or mouse Fc domain with a minimal linker in between. The constructs are referred to as ActRIIA-hFc and ActRIIA-mFc, respectively.

ActRIIA-hFc is shown below as purified from CHO cell lines (SEQ ID NO: 32):

```
ILGRSETQECLFFNANWEKDRTNQTGVEPCYGDKDKRRHCFATWKNISG

SIEIVKQGCWLDDINCYDRTDCVEKKDSPEVYFCCCEGNMCNEKFSYFP

EMEVTQPTSNPVTPKPPTGGGTHTCPPCPAPELLGGPSVFLFPPKPKDT

LMISRTPEVTCVVVDVSHEDPEVKFNWYVDGVEVHNAKTKPREEQYNST

YRVVSVLTVLHQDWLNGKEYKCKVSNKALPVPIEKTISKAKGQPREPQV
```

-continued

YTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

K

The ActRIIA-hFc and ActRIIA-mFc proteins were expressed in CHO cell lines. Three different leader sequences were considered:

(i) Honey bee mellitin (HBML):
(SEQ ID NO: 33)
MKFLVNVALVFMVVYISYIYA (ii) Tissue plasminogen activator (TPA):
(SEQ ID NO: 34)
MDAMKRGLCCVLLLCGAVFVSP (iii) Native:
(SEQ ID NO: 35)
MGAAAKLAFAVFLISCSSGA.

The selected form employs the TPA leader and has the following unprocessed amino acid sequence:

(SEQ ID NO: 36)
MDAMKRGLCCVLLLCGAVEVSPGAAILGRSETQECLFFNANWEKDRTNQ

TGVEPCYGDKDKRRHCFATWKNISGSIEIVKQGCWLDDINCYDRTDCVE

KKDSPEVYFCCCEGNMCNEKFSYFPEMEVTQPTSNPVTPKPPTGGGTHT

CPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKV

SNKALPVPIEKTISKAKGQPREPQVYTLPPSREEMTKNQVSLTCLVKGE

YPSDIAVEWESNGQPENNYKTTPPVLDSDGSFFLYSKLTVDKSRWQQGN

VFSCSVMHEALHNHYTQKSLSLSPGK

This polypeptide is encoded by the following nucleic acid sequence:

(SEQ ID NO: 37)
ATGGATGCAATGAAGAGAGGGCTCTGCTGTGTGCTGCTGCTGTGTGGAG

CAGTCTTCGTTTCGCCCGGCGCCGCTATACTTGGTAGATCAGAAACTCA

GGAGTGTCTTTTTTTAATGCTAATTGGGAAAAAGACAGAACCAATCAAA

CTGGTGTTGAACCGTGTTATGGTGACAAAGATAAACGGCGGCATTGTTT

TGCTACCTGGAAGAATATTTCTGGTTCCATTGAATAGTGAAACAAGGTT

GTTGGCTGGATGATATCAACTGCTATGACAGGACTGATTGTGTAGAAAA

AAAAGACAGCCCTGAAGTATATTTCTGTTGCTGTGAGGGCAATATGTGT

AATGAAAAGTTTTCTTATTTTCCGGAGATGGAAGTCACACAGCCCACTT

CAAATCCAGTTACACCTAAGCCACCCACCGGTGGTGGAACTCACACATG

CCCACCGTGCCCAGCACCTGAACTCCTGGGGGACCGTCAGTCTTCCTC

TTCCCCCCAAAACCCAAGGACACCCTCATGATCTCCCGGACCCCTGAGG

TCACATGCGTGGTGGTGGACGTGAGCCACGAAGACCCTGAGGTCAAGTT

CAACTGGTACGTGGACGGCGTGGAGGTGCATAATGCCAAGACAAAGCCG

CGGGAGGAGCAGTACAACAGCACGTACCGTGTGGTCAGCGTCCTCACCG

TCCTGCACCAGGACTGGCTGAATGGCAAGGAGTACAAGTGCAAGGTCTC

-continued

CAACAAAGCCCTCCCAGTCCCCATCGAGAAAACCATCTCCAAAGCCAAA

GGGCAGCCCCGAGAACCACAGGTGTACACCCTGCCCCCATCCCGGGAGG

AGATGACCAAGAACCAGGTCAGCCTGACCTGCCTGGTCAAAGGCTTCTA

TCCCAGCGACATCGCCGTGGAGTGGGAGAGCAATGGGCAGCCGGAGAAC

AACTACAAGACCACGCCTCCCGTGCTGGACTCCGACGGCTCCTTCTTCC

TCTATAGCAAGCTCACCGTGGACAAGAGCAGGTGGCAGCAGGGGAACGT

CTTCTCATGCTCCGTGATGCATGAGGCTCTGCACAACCACTACACGCAG

AAGAGCCTCTCCCTGTCTCCGGGTAAATGAGAATTC

Figure 5:
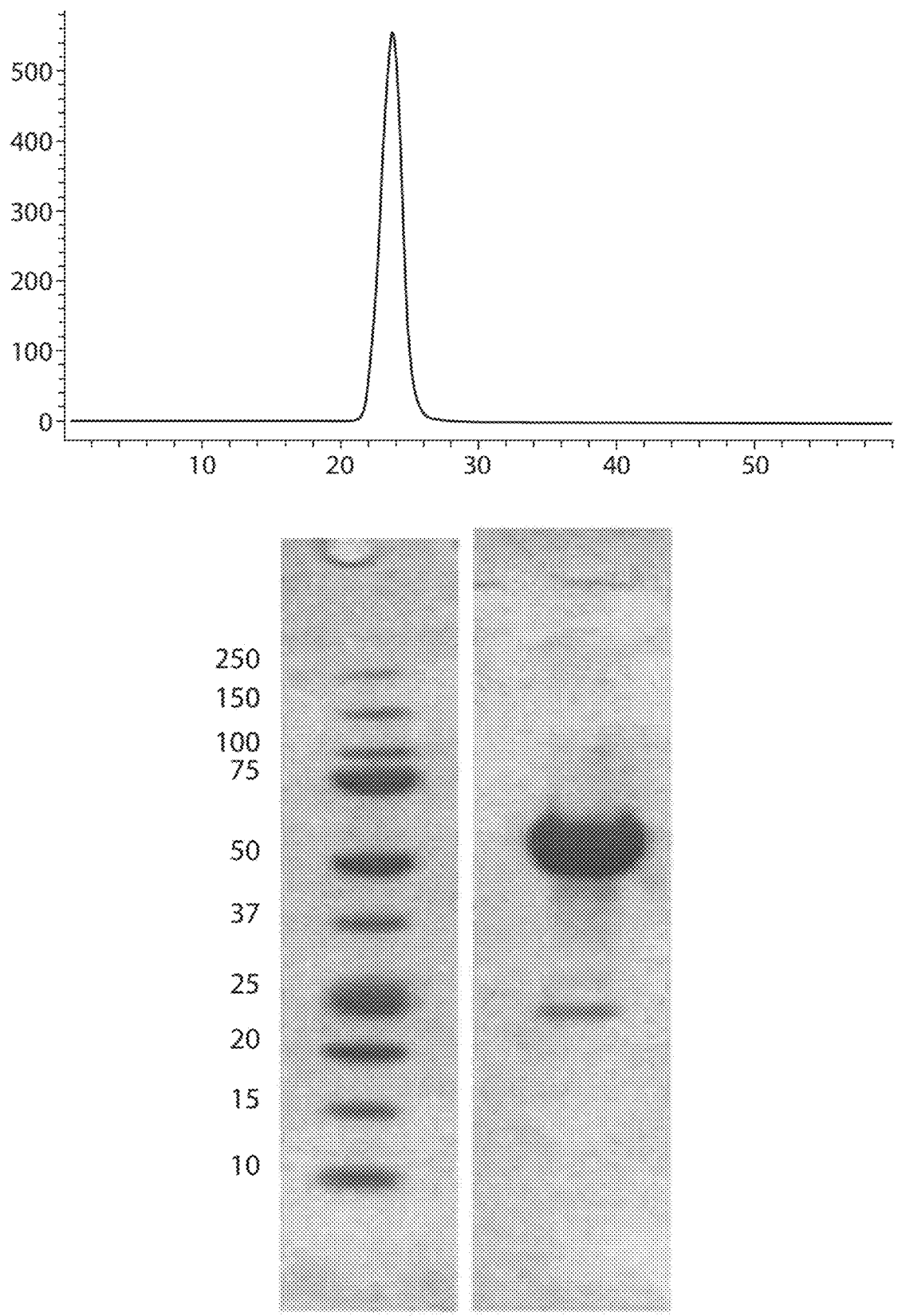
FIG. 5 shows the purification of ActRIIA-hFc expressed in CHO cells. The protein purifies as a single, well-defined peak as visualized by sizing column (top panel) and Coomassie stained SDS-PAGE (bottom panel) (left lane: molecular weight standards; right lane: ActRIIA-hFc).

Both ActRIIA-hFc and ActRIIA-mFc were remarkably amenable to recombinant expression. As shown in FIG. 5, the protein was purified as a single, well-defined peak of protein. N-terminal sequencing revealed a single sequence of -ILGRSETQE (SEQ ID NO: 38). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIA-hFc protein was purified to a purity of >98% as determined by size exclusion chromatography and >95% as determined by SDS PAGE.

ActRIIA-hFc and ActRIIA-mFc showed a high affinity for ligands. GDF11 or activin A were immobilized on a Biacore™ CM5 chip using standard amine-coupling procedure. ActRIIA-hFc and ActRIIA-mFc proteins were loaded onto the system, and binding was measured. ActRIIA-hFc bound to activin with a dissociation constant ($K_D$) of $5 \times 10^{-12}$ and bound to GDF11 with a $K_D$ of $9.96 \times 10^{-9}$. See FIG. 6. Using a similar binding assay, ActRIIA-hFc was determined to have high to moderate affinity for other TGF-beta superfamily ligands including, for example, activin B, GDF8, BMP6, and BMP10. ActRIIA-mFc behaved similarly.

The ActRIIA-hFc was very stable in pharmacokinetic studies. Rats were dosed with 1 mg/kg, 3 mg/kg, or 10 mg/kg of ActRIIA-hFc protein, and plasma levels of the protein were measured at 24, 48, 72, 144 and 168 hours. In a separate study, rats were dosed at 1 mg/kg, 10 mg/kg, or 30 mg/kg. In rats, ActRIIA-hFc had an 11-14 day serum half-life, and circulating levels of the drug were quite high after two weeks (11m/ml, 110m/ml, or 304m/ml for initial administrations of 1 mg/kg, 10 mg/kg, or 30 mg/kg, respectively.) In cynomolgus monkeys, the plasma half-life was substantially greater than 14 days, and circulating levels of the drug were 25 µg/ml, 304m/ml, or 1440m/ml for initial administrations of 1 mg/kg, 10 mg/kg, or 30 mg/kg, respectively.

Example 2: Characterization of an ActRIIA-hFc Protein

ActRIIA-hFc fusion protein was expressed in stably transfected CHO-DUKX B11 cells from a pAID4 vector (SV40 ori/enhancer, CMV promoter), using a tissue plasminogen leader sequence of SEQ ID NO: 34. The protein, purified as described above in Example 1, had a sequence of SEQ ID NO: 32. The Fc portion is a human $IgG_1$ Fc sequence, as shown in SEQ ID NO: 32. Protein analysis reveals that the ActRIIA-hFc fusion protein is formed as a homodimer with disulfide bonding.

The CHO-cell-expressed material has a higher affinity for activin B ligand than that reported for an ActRIIa-hFc fusion protein expressed in human 293 cells [see, del Re et al. (2004) J Biol Chem. 279(50:53126-53135]. Additionally, the use of the TPA leader sequence provided greater production than other leader sequences and, unlike ActRIIA-Fc expressed with a native leader, provided a highly pure N-terminal sequence. Use of the native leader sequence resulted in two major species of ActRIIA-Fc, each having a different N-terminal sequence.

Example 3: Alternative ActRIIA-Fc Proteins

A variety of ActRIIA variants that may be used according to the methods described herein are described in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIA. The sequence for such a construct is presented below (Fc portion underlined) (SEQ ID NO: 39):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

TGGGTHTCPPCPAPELLGGPSVFLEPPKPKDTLMISRTPEVTCVVVDVSH

EDPEVKFNWYVDGVEVHNAKTKPREEQYNSTYRVVSVLTVLHQDWLNGKE

YKCKVSNKALPVPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

Example 4: Generation of ActRIIB-Fc Fusion Proteins

Applicants constructed a soluble ActRIIB fusion protein that has the extracellular domain of human ActRIIB fused to a human or mouse Fc domain with a minimal linker in between. The constructs are referred to as ActRIIB-hFc and ActRIIB-mFc, respectively.

ActRIIB-hFc is shown below as purified from CHO cell lines (SEQ ID NO: 40):

GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPTGGGTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPVPIEKTISKAKGQPREPQVYTLPPS

REEMTKNQVSLTCLVKGFYPSDIAVEWESNGQPENNYKTTPPVLDSDGSFV

FLYSKLTVDKSRWQQGNVFSCSVMHEALHNHYTQKSLSLSPGK

The ActRIIB-hFc and ActRIIB-mFc proteins were expressed in CHO cell lines. Three different leader sequences were considered: (i) Honey bee mellitin (HBML), ii) Tissue plasminogen activator (TPA), and (iii) Native: MGAAAKLAFAVFLISCSSGA (SEQ ID NO: 41).

The selected form employs the TPA leader and has the following unprocessed amino acid sequence (SEQ ID NO: 42):

MDAMKRGLCCVLLLCGAVFVSPGASGRGEAETRECIYYNANWELERTNQS

GLERCEGEQDKRLHCYASWRNSSGTIELVKKGCWLDDFNCYDRQECVATE

ENPQVYFCCCEGNFCNERFTHLPEAGGPEVTYEPPPTAPTGGGTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

VPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

This polypeptide is encoded by the following nucleic acid sequence (SEQ ID NO: 43):

A TGGATGCAAT GAAGAGAGGG CTCTGCTGTG TGCTGCTGCT

GTGTGGAGCA GTCTTCGTTT CGCCCGGCGC CTCTGGGCGT

GGGGAGGCTG AGACACGGGA GTGCATCTAC TACAACGCCA

ACTGGGAGCT GGAGCGCACC AACCAGAGCG GCCTGGAGCG

CTGCGAAGGC GAGCAGGACA AGCGGCTGCA CTGCTACGCC

TCCTGGCGCA ACAGCTCTGG CACCATCGAG CTCGTGAAGA

AGGGCTGCTG GCTAGATGAC TTCAACTGCT ACGATAGGCA

GGAGTGTGTG GCCACTGAGG AGAACCCCCA GGTGTACTTC

TGCTGCTGTG AAGGCAACTT CTGCAACGAG CGCTTCACTC

ATTTGCCAGA GGCTGGGGGC CCGGAAGTCA CGTACGAGCC

ACCCCCGACA GCCCCCACCG GTGGTGGAAC TCACACATGC

CCACCGTGCC CAGCACCTGA ACTCCTGGGG GGACCGTCAG

TCTTCCTCTT CCCCCCAAAA CCCAAGGACA CCCTCATGAT

CTCCCGGACC CCTGAGGTCA CATGCGTGGT GGTGGACGTG

AGCCACGAAG ACCCTGAGGT CAAGTTCAAC TGGTACGTGG

ACGGCGTGGA GGTGCATAAT GCCAAGACAA AGCCGCGGGA

GGAGCAGTAC AACAGCACGT ACCGTGTGGT CAGCGTCCTC

ACCGTCCTGC ACCAGGACTG GCTGAATGGC AAGGAGTACA

AGTGCAAGGT CTCCAACAAA GCCCTCCCAG TCCCCATCGA

GAAAACCATC TCCAAAGCCA AAGGGCAGCC CCGAGAACCA

CAGGTGTACA CCCTGCCCCC ATCCCGGGAG GAGATGACCA

AGAACCAGGT CAGCCTGACC TGCCTGGTCA AAGGCTTCTA

TCCCAGCGAC ATCGCCGTGG AGTGGGAGAG CAATGGGCAG

CCGGAGAACA ACTACAAGAC CACGCCTCCC GTGCTGGACT

CCGACGGCTC CTTCTTCCTC TATAGCAAGC TCACCGTGGA

CAAGAGCAGG TGGCAGCAGG GGAACGTCTT CTCATGCTCC

GTGATGCATG AGGCTCTGCA CAACCACTAC ACGCAGAAGA

GCCTCTCCCT GTCTCCGGGT AAATGA

N-terminal sequencing of the CHO-cell-produced material revealed a major sequence of -GRGEAE (SEQ ID NO: 44). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

ActRIIB-Fc fusion proteins were also expressed in HEK293 cells and COS cells. Although material from all cell lines and reasonable culture conditions provided protein with muscle-building activity in vivo, variability in potency was observed perhaps relating to cell line selection and/or culture conditions.

Applicants generated a series of mutations in the extracellular domain of ActRIIB and produced these mutant proteins as soluble fusion proteins between extracellular ActRIIB and an Fc domain. The background ActRIIB-Fc fusion has the sequence of SEQ ID NO: 40.

Various mutations, including N- and C-terminal truncations, were introduced into the background ActRIIB-Fc protein. Based on the data presented herein, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG$_1$. Upon transformation into *E. coli* DH5 alpha, colonies were picked and DNAs were isolated. For murine constructs (mFc), a murine IgG$_2$a was substituted for the human IgG$_1$. Sequences of all mutants were verified.

All of the mutants were produced in HEK293T cells by transient transfection. In summary, in a 500 ml spinner, HEK293T cells were set up at 6×10$^5$ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, a protein A column, and eluted with low pH (3.0) glycine buffer. After neutralization, these were dialyzed against PBS.

Mutants were also produced in CHO cells by similar methodology. Mutants were tested in binding assays and/or bioassays described in WO 2008/097541 and WO 2006/012627 incorporated by reference herein. In some instances, assays were performed with conditioned medium rather than purified proteins. Additional variations of ActRIIB are described in U.S. Pat. No. 7,842,663.

Applicant generated an ActRIIB(25-131)-hFc fusion protein, which comprises the human ActRIIB extracellular domain with N-terminal and C-terminal truncations (residues 25-131 of the native protein SEQ ID NO: 1) fused N-terminally with a TPA leader sequence substituted for the native ActRIIB leader and C-terminally with a human Fc domain via a minimal linker (three glycine residues) (FIG. 7). A nucleotide sequence encoding this fusion protein is shown in FIG. 8. Applicants modified the codons and found a variant nucleic acid encoding the ActRIIB(25-131)-hFc protein that provided substantial improvement in the expression levels of initial transformants (FIG. 9).

The mature protein has an amino acid sequence as follows (N-terminus confirmed by N-terminal sequencing)(SEQ ID NO: 45):

```
ETRECIYYNA NWELERTNQS GLERCEGEQD KRLHCYASWR

NSSGTIELVK KGCWLDDFNC YDRQECVATE ENPQVYFCCC

EGNFCNERFT HLPEAGGPEV TYEPPPTGGG THTCPPCPAP

ELLGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSREEMTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

The expressed molecule was purified using a series of column chromatography steps, including for example, three or more of the following, in any order: Protein A chromatography, Q sepharose chromatography, phenylsepharose chromatography, size exclusion chromatography and cation exchange chromatography. The purification could be completed with viral filtration and buffer exchange.

Affinities of several ligands for ActRIIB(25-131)-hFc and its full-length counterpart ActRIIB(20-134)-hFc were evaluated in vitro with a Biacore™ instrument, and the results are summarized in the table below. Kd values were obtained by steady-state affinity fit due to very rapid association and dissociation of the complex, which prevented accurate determination of k$_{on}$ and k$_{off}$. ActRIIB(25-131)-hFc bound, for example, activin A, activin B, and GDF11 with high affinity. Ligand Affinities of ActRIIB-hFc Forms:

| Fusion Construct | Activin A (e−11) | Activin B (e−11) | GDF11 (e−11) |
|---|---|---|---|
| ActRIIB(20-134)-hFc | 1.6 | 1.2 | 3.6 |
| ActRIIB(25-131)-hFc | 1.8 | 1.2 | 3.1 |

Example 5: Generation of a GDF Trap

A GDF trap was constructed as follows. A polypeptide having a modified extracellular domain of ActRIIB (amino acids 20-134 of SEQ ID NO: 1 with an L79D substitution) with greatly reduced activin A binding relative to GDF11 and/or myostatin (as a consequence of a leucine-to-aspartate substitution at position 79 in SEQ ID NO:1) was fused to a human or mouse Fc domain with a minimal linker in between. The constructs are referred to as ActRIIB(L79D 20-134)-hFc and ActRIIB(L79D 20-134)-mFc, respectively. Alternative forms with a glutamate rather than an aspartate at position 79 performed similarly (L79E). Alternative forms with an alanine rather than a valine at position 226 with respect to SEQ ID NO: 64, below were also generated and performed equivalently in all respects tested. The aspartate at position 79 (relative to SEQ ID NO: 1) is indicated with double underlining below. The valine at position 226 relative to SEQ ID NO: 64 is also indicated by double underlining below.

The GDF trap ActRIIB(L79D 20-134)-hFc is shown below as purified from CHO cell lines (SEQ ID NO: 46).

GRGEAETRECIYYNANWELERTNQSGLERCEGEQDKRLHCYASWRNSSGT

IELVKKGCW<u>D</u>DDENCYDRQECVATEENPQVYFCCCEGNECNERFTHLPEA

GGPEVTYEPPPTAPT<u>GGGTHTCPPCPAPELLGGPSVFLEPPKPKDTLMIS

RTPEVTCVVVDVSHEDPEVKFNWYVDGVEVHNAKTKPREEQYNSTYRVVS

VLTVLHQDWLNGKEYKCKVSNKALP<u>V</u>PIEKTISKAKGQPREPQVYTLPPS

REEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

The ActRIIB-derived portion of the GDF trap has an amino acid sequence set forth below (SEQ ID NO: 47), and that portion could be used as a monomer or as a non-Fc fusion protein as a monomer, dimer, or greater-order complex.

(SEQ ID NO: 47)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEVTYEPPPTAPT

The GDF trap protein was expressed in CHO cell lines. Three different leader sequences were considered:
(i) Honey bee melittin (HBML), (ii) Tissue plasminogen activator (TPA), and (iii) Native.
The selected form employs the TPA leader and has the following unprocessed amino acid sequence:

(SEQ ID NO: 48)
<u>MDAMKRGLCCVLLLCGAVFVSPGAS</u>GRGEAETRECIYYNANWELERTNQS

GLERCEGEQDKRLHCYASWRNSSGTIELVKKGCWDDDFNCYDRQECVATE

ENPQVYFCCCEGNFCNERFTHLPEAGGPEVTYEPPPTAPT<u>GGGTHTCPPC

PAPELLGGPSVFLEPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

This polypeptide is encoded by the following nucleic acid sequence (SEQ ID NO: 49):

```
A TGGATGCAAT GAAGAGAGGG CTCTGCTGTG TGCTGCTGCT

GTGTGGAGCA GTCTTCGTTT CGCCCGGCGC CTCTGGGCGT

GGGGAGGCTG AGACACGGGA GTGCATCTAC TACAACGCCA

ACTGGGAGCT GGAGCGCACC AACCAGAGCG GCCTGGAGCG

CTGCGAAGGC GAGCAGGACA AGCGGCTGCA CTGCTACGCC

TCCTGGCGCA ACAGCTCTGG CACCATCGAG CTCGTGAAGA

AGGGCTGCTG GGACGATGAC TTCAACTGCT ACGATAGGCA

GGAGTGTGTG GCCACTGAGG AGAACCCCCA GGTGTACTTC

TGCTGCTGTG AAGGCAACTT CTGCAACGAG CGCTTCACTC

ATTTGCCAGA GGCTGGGGGC CCGGAAGTCA CGTACGAGCC

ACCCCCGACA GCCCCCACCG GTGGTGGAAC TCACACATGC

CCACCGTGCC CAGCACCTGA ACTCCTGGGG GGACCGTCAG

TCTTCCTCTT CCCCCCAAAA CCCAAGGACA CCCTCATGAT

CTCCCGGACC CCTGAGGTCA CATGCGTGGT GGTGGACGTG

AGCCACGAAG ACCCTGAGGT CAAGTTCAAC TGGTACGTGG

ACGGCGTGGA GGTGCATAAT GCCAAGACAA AGCCGCGGGA

GGAGCAGTAC AACAGCACGT ACCGTGTGGT CAGCGTCCTC

ACCGTCCTGC ACCAGGACTG GCTGAATGGC AAGGAGTACA

AGTGCAAGGT CTCCAACAAA GCCCTCCCAG TCCCCATCGA

GAAAACCATC TCCAAAGCCA AAGGGCAGCC CCGAGAACCA

CAGGTGTACA CCCTGCCCCC ATCCCGGGAG GAGATGACCA

AGAACCAGGT CAGCCTGACC TGCCTGGTCA AAGGCTTCTA

TCCCAGCGAC ATCGCCGTGG AGTGGGAGAG CAATGGGCAG

CCGGAGAACA ACTACAAGAC CACGCCTCCC GTGCTGGACT

CCGACGGCTC CTTCTTCCTC TATAGCAAGC TCACCGTGGA

CAAGAGCAGG TGGCAGCAGG GGAACGTCTT CTCATGCTCC

GTGATGCATG AGGCTCTGCA CAACCACTAC ACGCAGAAGA

GCCTCTCCCT GTCTCCGGGT AAATGA
```

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. In an example of a purification scheme, the cell culture medium is passed over a protein A column, washed in 150 mM Tris/NaCl (pH 8.0), then washed in 50 mM Tris/NaCl (pH 8.0) and eluted with 0.1 M glycine, pH 3.0. The low pH eluate is kept at room temperature for 30 minutes as a viral clearance step. The eluate is then neutralized and passed over a Q-sepharose ion-exchange column and washed in 50 mM Tris pH 8.0, 50 mM NaCl, and eluted in 50 mM Tris pH 8.0, with an NaCl concentration between 150 mM and 300 mM. The eluate is then changed into 50 mM Tris pH 8.0, 1.1 M ammonium sulfate and passed over a phenyl sepharose column, washed, and eluted in 50 mM Tris pH 8.0 with ammonium sulfate between 150 and 300 mM. The eluate is dialyzed and filtered for use.

Additional GDF traps (ActRIIB-Fc fusion proteins modified so as to reduce the ratio of activin A binding relative to myostatin or GDF11 binding) are described in WO 2008/097541 and WO 2006/012627, incorporated by reference herein.

Example 6: Bioassay for GDF11- and Activin-Mediated Signaling

An A-204 reporter gene assay was used to evaluate the effects of ActRIIB-Fc proteins and GDF traps on signaling by GDF-11 and activin A. Cell line: human rhabdomyosarcoma (derived from muscle). Reporter vector: pGL3 (CAGA)12 (described in Dennler et al, 1998, EMBO 17: 3091-3100). The CAGA12 motif is present in TGF-beta responsive genes (e.g., PAI-1 gene), so this vector is of general use for factors signaling through SMAD2 and 3.

Day 1: Split A-204 cells into 48-well plate.

Day 2: A-204 cells transfected with 10 ug pGL3(CAGA) 12 or pGL3(CAGA)12(10 ug)+pRLCMV (1 µg) and Fugene.

Day 3: Add factors (diluted into medium+0.1% BSA). Inhibitors need to be preincubated with factors for 1 hr before adding to cells. Six hrs later, cells were rinsed with PBS and lysed.

This is followed by a luciferase assay. In the absence of any inhibitors, activin A showed 10-fold stimulation of reporter gene expression and an ED50 ~2 ng/ml. GDF-11: 16 fold stimulation, ED50: ~1.5 ng/ml.

ActRIIB(20-134) is a potent inhibitor of, for example, activin A, GDF-8, and GDF-11 activity in this assay. As described below, ActRIIB variants were also tested in this assay.

Example 7: ActRIIB-Fc Variants, Cell-Based Activity

Activity of ActRIIB-Fc proteins and GDF traps was tested in a cell-based assay as described above. Results are summarized in the table below. Some variants were tested in different C-terminal truncation constructs. As discussed above, truncations of five or fifteen amino acids caused reduction in activity. The GDF traps (L79D and L79E variants) showed substantial loss of activin A inhibition while retaining almost wild-type inhibition of GDF11. Soluble ActRIIB-Fc binding to GDF11 and Activin A:

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64 | 20-134 | +++ (approx. $10^{-8}$ M $K_I$) | +++ (approx. $10^{-8}$ M $K_I$) |
| A64 | 20-134 | + (approx. $10^{-6}$ M $K_I$) | + (approx. $10^{-6}$ M $K_I$) |
| R64 | 20-129 | +++ | +++ |
| R64 K74A | 20-134 | ++++ | ++++ |
| R64 A24N | 20-134 | +++ | +++ |
| R64 A24N | 20-119 | ++ | ++ |
| R64 A24N K74A | 20-119 | + | + |
| R64 L79P | 20-134 | + | + |
| R64 L79P K74A | 20-134 | + | + |
| R64 L79D | 20-134 | +++ | + |
| R64 L79E | 20-134 | +++ | + |
| R64K | 20-134 | +++ | +++ |
| R64K | 20-129 | +++ | +++ |
| R64 P129S P130A | 20-134 | +++ | +++ |
| R64N | 20-134 | + | + |

+ Poor activity (roughly $1 \times 10^{-6}$ $K_I$)
++ Moderate activity (roughly $1 \times 10^{-7}$ $K_I$)
+++ Good (wild-type) activity (roughly $1 \times 10^{-8}$ $K_I$)
++++ Greater than wild-type activity The A24N variant has activity in the cell-based assay (above) and that is equivalent to the wild-type molecule. The A24N variant, and any of the other variants tested above, may be combined with the GDF trap molecules, such as the L79D or L79E variants.

Example 8: GDF11 and Activin A Binding

Binding of certain ActRIIB-Fc proteins and GDF traps to ligands was tested in a Biacore assay.

The ActRIIB-Fc variants or wild-type protein were captured onto the system using an anti-hFc antibody. Ligands were injected and flowed over the captured receptor proteins. Results are summarized in the tables below. Ligand-binding specificity IIB variants.

| Protein | Kon (1/Ms) | Koff (1/s) | KD (M) |
|---|---|---|---|
| | | GDF11 | |
| ActRIIB(20-134)-hFc | 1.34e-6 | 1.13e-4 | 8.42e-11 |
| ActRIIB(A24N 20-134)-hFc | 1.21e-6 | 6.35e-5 | 5.19e-11 |
| ActRIIB(L79D 20-134)-hFc | 6.7e-5 | 4.39e-4 | 6.55e-10 |
| ActRIIB(L79E 20-134)-hFc | 3.8e-5 | 2.74e-4 | 7.16e-10 |
| ActRIIB(R64K 20-134)-hFc | 6.77e-5 | 2.41e-5 | 3.56e-11 |
| | | GDF8 | |
| ActRIIB(20-134)-hFc | 3.69e-5 | 3.45e-5 | 9.35e-11 |
| ActRIIB(A24N 20-134)-hFc | | | |
| ActRIIB(L79D 20-134)-hFc | 3.85e-5 | 8.3e-4 | 2.15e-9 |
| ActRIIB(L79E 20-134)-hFc | 3.74e-5 | 9e-4 | 2.41e-9 |
| ActRIIB(R64K 20-134)-hFc | 2.25e-5 | 4.71e-5 | 2.1e-10 |
| ActRIIB(R64K 20-129)-hFc | 9.74e-4 | 2.09e-4 | 2.15e-9 |
| ActRIIB(P129S, P130R 20-134)-hFc | 1.08e-5 | 1.8e-4 | 1.67e-9 |
| ActRIIB(K74A 20-134)-hFc | 2.8e-5 | 2.03e-5 | 7.18e-11 |
| | | Activin A | |
| ActRIIB(20-134)-hFc | 5.94e6 | 1.59e-4 | 2.68e-11 |
| ActRIIB(A24N 20-134)-hFc | 3.34e6 | 3.46e-4 | 1.04e-10 |
| ActRIIB(L79D 20-134)-hFc | | | Low binding |
| ActRIIB(L79E 20-134)-hFc | | | Low binding |
| ActRIIB(R64K 20-134)-hFc | 6.82e6 | 3.25e-4 | 4.76e-11 |
| ActRIIB(R64K 20-129)-hFc | 7.46e6 | 6.28e-4 | 8.41e-11 |
| ActRIIB(P129S, P130R 20-134)-hFc | 5.02e6 | 4.17e-4 | 8.31e-11 |

These data obtained in a cell-free assay confirm the cell-based assay data, demonstrating that the A24N variant retains ligand-binding activity that is similar to that of the ActRIIB(20-134)-hFc molecule and that the L79D or L79E molecule retains myostatin and GDF11 binding but shows markedly decreased (non-quantifiable) binding to activin A.

Other variants have been generated and tested, as reported in WO2006/012627 (incorporated herein by reference in its entirety). See, e.g., pp. 59-60, using ligands coupled to the device and flowing receptor over the coupled ligands. Notably, K74Y, K74F, K74I (and presumably other hydrophobic substitutions at K74, such as K74L), and D80I, cause a decrease in the ratio of activin A (ActA) binding to GDF11 binding, relative to the wild-type K74 molecule. A table of data with respect to these variants is reproduced below:

Soluble ActRIIB-Fc variants binding to GDF11 and Activin A (Biacore™ assay)

| ActRIIB | ActA | GDF11 |
|---|---|---|
| WT (64A) | KD = 1.8e-7M (+) | KD = 2.6e-7M (+) |
| WT (64R) | na | KD = 8.6e-8M (+++) |
| +15tail | KD ~2.6e-8M (+++) | KD = 1.9e-8M (++++) |
| E37A | * | * |
| R40A | – | – |
| D54A | – | * |
| K55A | ++ | * |
| R56A | * | * |
| K74A | KD = 4.35e-9M +++++ | KD = 5.3e-9M +++++ |
| K74Y | * | -- |
| K74F | * | -- |
| K74I | * | -- |

| ActRIIB | ActA | GDF11 |
|---------|------|-------|
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | -- |
| F82A | ++ | - |

\* No observed binding
-- <⅓ WT binding
- ~½ WT binding
+ WT
++ <2x increased binding
+++ ~5x increased binding
++++ ~10x increased binding
+++++ ~40x increased binding

Example 9: Generation of a GDF Trap with Truncated ActRIIB Extracellular Domain A GDF trap referred to as ActRIIB(L79D 20-134)-hFc was generated by N-terminal fusion of TPA leader to the ActRIIB extracellular domain (residues 20-134 in SEQ ID NO: 1) containing a leucine-to-aspartate substitution (at residue 79 in SEQ ID NO: 1) and C-terminal fusion of human Fc domain with minimal linker (three glycine residues) (FIG. 10; SEQ ID NO: 74). A nucleotide sequence corresponding to this fusion protein is shown in FIG. 11 (SEQ ID NO: 75, sense strand; and SEQ ID NO: 76, antisense strand).

A GDF trap with truncated ActRIIB extracellular domain, referred to as ActRIIB(L79D 25-131)-hFc, was generated by N-terminal fusion of TPA leader to truncated extracellular domain (residues 25-131 in SEQ ID NO:1) containing a leucine-to-aspartate substitution (at residue 79 in SEQ ID NO:1) and C-terminal fusion of human Fc domain with minimal linker (three glycine residues) (FIG. 12, SEQ ID NO: 77). The sequence of the cell purified form of ActRIIB(L79D 25-131)-hFc is presented in FIG. 13 (SEQ ID NO: 78). One nucleotide sequence encoding this fusion protein is shown in FIG. 15 (SEQ ID NO: 80) along with its complementary sequence (SEQ ID NO: 81), and an alternative nucleotide sequence encoding exactly the same fusion protein is shown in FIG. 16 (SEQ ID NO: 82) and its complementary sequence (SEQ ID NO: 83).

Example 10: Selective Ligand Binding by GDF Trap with Double-Truncated ActRIIB Extracellular Domain The affinity of GDF traps and other ActRIIB-hFc proteins for several ligands was evaluated in vitro with a Biacore™ instrument. Results are summarized in the table below. Kd values were obtained by steady-state affinity fit due to the very rapid association and dissociation of the complex, which prevented accurate determination of $k_{on}$ and $k_{off}$.

Ligand Selectivity of ActRIIB-hFc Variants:

| Fusion Construct | Activin A (Kd e−11) | Activin B (Kd e−11) | GDF11 (Kd e−11) |
|---|---|---|---|
| ActRIIB(L79 20-134)-hFc | 1.6 | 1.2 | 3.6 |
| ActRIIB(L79D 20-134)-hFc | 1350.0 | 78.8 | 12.3 |
| ActRIIB(L79 25-131)-hFc | 1.8 | 1.2 | 3.1 |
| ActRIIB(L79D 25-131)-hFc | 2290.0 | 62.1 | 7.4 |

The GDF trap with a truncated extracellular domain, ActRIIB(L79D 25-131)-hFc, equaled or surpassed the ligand selectivity displayed by the longer variant, ActRIIB(L79D 20-134)-hFc, with pronounced loss of activin A binding, partial loss of activin B binding, and nearly full retention of GDF11 binding compared to ActRIIB-hFc counterparts lacking the L79D substitution. Note that truncation alone (without L79D substitution) did not alter selectivity among the ligands displayed here [compare ActRIIB(L79 25-131)-hFc with ActRIIB(L79 20-134)-hFc]. ActRIIB(L79D 25-131)-hFc also retains strong to intermediate binding to the Smad 2/3 signaling ligand GDF8 and the Smad 1/5/8 ligands BMP6 and BMP10.

Example 11: GDF Trap Derived from ActRIIB5

Others have reported an alternate, soluble form of ActRIIB (designated ActRIIB5), in which exon 4, including the ActRIIB transmembrane domain, has been replaced by a different C-terminal sequence (see, e.g., WO 2007/053775).

The sequence of native human ActRIIB5 without its leader is as follows:

```
                                       (SEQ ID NO: 50)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEGPWASTTIPSGGPEATAAAGDQGSGALWLCLEGPAHE
```

An leucine-to-aspartate substitution, or other acidic substitutions, may be performed at native position 79 (underlined) as described to construct the variant ActRIIB5(L79D), which has the following sequence:

```
                                       (SEQ ID NO: 51)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHE
```

This variant may be connected to human Fc (double underline) with a TGGG linker (SEQ ID NO: 23) (single underline) to generate a human ActRIIB5(L79D)-hFc fusion protein with the following sequence:

```
                                       (SEQ ID NO: 52)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHETGGGTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI
```

-continued

AVEWESNGQPENNYKTTPPVLDSDGSFFLYSKLTVDKSRWQQGNVFSCSV

MHEALHNHYTQKSLSLSPGK.

This construct may be expressed in CHO cells.

Example 12: Generation of an ALK4:ActRIIB Heterodimer

An ALK4-Fc:ActRIIB-Fc heteromeric complex was constructed comprising the extracellular domains of human ActRIIB and human ALK4, which are each separately fused to an Fc domain with a linker positioned between the extracellular domain and the Fc domain. The individual constructs are referred to as ActRIIB-Fc fusion polypeptide and ALK4-Fc fusion polypeptide, respectively, and the sequences for each are provided below.

A methodology for promoting formation of ALK4-Fc:ActRIIB-Fc heteromeric complexes, as opposed to ActRIIB-Fc or ALK4-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB-Fc and ALK4-Fc polypeptide sequences of SEQ ID NOs: 108 and 110 and SEQ ID Nos: 111 and 113, respectively, one Fc domain is altered to introduce cationic amino acids at the interaction face, while the other Fc domain is altered to introduce anionic amino acids at the interaction face. ActRIIB-Fc fusion polypeptide and ALK4-Fc fusion polypeptide each employ the tissue plasminogen activator (TPA) leader.

The ActRIIB-Fc polypeptide sequence (SEQ ID NO: 108) is shown below:

```
                                        (SEQ ID NO: 108)
  1 MDAMKRGLCC VLLLCGAVFV SPGASGRGEA ETRECIYYNA
    NWELERTNQS

51 GLERCEGEQD KRLHCYASWR NSSGTIELVK KGCWLDDFNC
    YDRQECVATE

101 ENPQVYFCCC EGNFCNERFT HLPEAGGPEV TYEPPPTAPT
    GGGTHTCPPC

151 PAPELLGGPS VFLFPPKPKD TLMISRTPEV TCVVVDVSHE
    DPEVKFNWYV

201 DGVEVHNAKT KPREEQYNST YRVVSVLTVL HQDWLNGKEY
    KCKVSNKALP

251 APIEKTISKA KGQPREPQVY TLPPSRKEMT KNQVSLTCLV
    KGFYPSDIAV

301 EWESNGQPEN NYKTTPPVLK SDGSFFLYSK LTVDKSRWQQ
    GNVFSCSVMH

351 EALHNHYTQK SLSLSPGK
```

The leader (signal) sequence and linker are underlined. To promote formation of ALK4-Fc:ActRIIB-Fc heterodimer rather than either of the possible homodimeric complexes, two amino acid substitutions (replacing acidic amino acids with lysine) can be introduced into the Fc domain of the ActRIIB fusion protein as indicated by double underline above. The amino acid sequence of SEQ ID NO: 108 may optionally be provided with lysine (K) removed from the C-terminus.

This ActRIIB-Fc fusion protein is encoded by the following nucleic acid sequence (SEQ ID NO: 109):

```
                                         (SEQ ID NO: 109)
   1 ATGGATGCAA TGAAGAGAGG GCTCTGCTGT GTGCTGCTGC
     TGTGTGGAGC

51 AGTCTTCGTT TCGCCCGGCG CCTCTGGGCG TGGGGAGGCT
     GAGACACGGG

101 AGTGCATCTA CTACAACGCC AACTGGGAGC TGGAGCGCAC
     CAACCAGAGC

151 GGCCTGGAGC GCTGCGAAGG CGAGCAGGAC AAGCGGCTGC
     ACTGCTACGC

201 CTCCTGGCGC AACAGCTCTG GCACCATCGA GCTCGTGAAG
     AAGGGCTGCT

251 GGCTAGATGA CTTCAACTGC TACGATAGGC AGGAGTGTGT
     GGCCACTGAG

301 GAGAACCCCC AGGTGTACTT CTGCTGCTGT GAAGGCAACT
     TCTGCAACGA

351 GCGCTTCACT CATTTGCCAG AGGCTGGGGG CCCGGAAGTC
     ACGTACGAGC

401 CACCCCCGAC AGCCCCCACC GGTGGTGGAA CTCACACATG
     CCCACCGTGC

451 CCAGCACCTG AACTCCTGGG GGGACCGTCA GTCTTCCTCT
     TCCCCCCAAA

501 ACCCAAGGAC ACCCTCATGA TCTCCCGGAC CCCTGAGGTC
     ACATGCGTGG

551 TGGTGGACGT GAGCCACGAA GACCCTGAGG TCAAGTTCAA
     CTGGTACGTG

601 GACGGCGTGG AGGTGCATAA TGCCAAGACA AAGCCGCGGG
     AGGAGCAGTA

651 CAACAGCACG TACCGTGTGG TCAGCGTCCT CACCGTCCTG
     CACCAGGACT

701 GGCTGAATGG CAAGGAGTAC AAGTGCAAGG TCTCCAACAA
     AGCCCTCCCA

751 GCCCCCATCG AGAAAACCAT CTCCAAAGCC AAAGGGCAGC
     CCCGAGAACC

801 ACAGGTGTAC ACCCTGCCCC CATCCCGGAA GGAGATGACC
     AAGAACCAGG

851 TCAGCCTGAC CTGCCTGGTC AAAGGCTTCT ATCCCAGCGA
     CATCGCCGTG

901 GAGTGGGAGA GCAATGGGCA GCCGGAGAAC AACTACAAGA
     CCACGCCTCC

951 CGTGCTGAAG TCCGACGGCT CCTTCTTCCT CTATAGCAAG
     CTCACCGTGG

1001 ACAAGAGCAG GTGGCAGCAG GGGAACGTCT TCTCATGCTC
     CGTGATGCAT

1051 GAGGCTCTGC ACAACCACTA CACGCAGAAG AGCCTCTCCC
     TGTCTCCGGG

1101 TAA
```

A mature ActRIIB-Fc fusion polypeptide (SEQ ID NO: 110) is as follows, and may optionally be provided with lysine (K) removed from the C-terminus.

```
                                         (SEQ ID NO: 110)
  1 GRGEAETREC IYYNANWELE RTNQSGLERC EGEQDKRLHC
    YASWRNSSGT

51 IELVKKGCWL DDFNCYDRQE CVATEENPQV YFCCCEGNFC
    NERFTHLPEA
```

```
101 GGPEVTYEPP PTAPTGGGTH TCPPCPAPEL LGGPSVFLFP
    PKPKDTLMIS

151 RTPEVTCVVV DVSHEDPEVK FNWYVDGVEV HNAKTKPREE
    QYNSTYRVVS

201 VLTVLHQDWL NGKEYKCKVS NKALPAPIEK TISKAKGQPR
    EPQVYTLPPS

251 RKEMTKNQVS LTCLVKGFYP SDIAVEWESN GQPENNYKTT
    PPVLKSDGSF

301 FLYSKLTVDK SRWQQGNVFS CSVMHEALHN HYTQKSLSLS
    PGK
```

A complementary form of ALK4-Fc fusion polypeptide (SEQ ID NO: 111) is as follows:

```
                                           (SEQ ID NO: 111)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The leader sequence and linker are underlined. To guide heterodimer formation with the ActRIIB-Fc fusion polypeptide of SEQ ID NOs: 108 and 110 above, two amino acid substitutions (replacing lysines with aspartic acids) can be introduced into the Fc domain of the ALK4-Fc fusion polypeptide as indicated by double underline above. The amino acid sequence of SEQ ID NO: 111 may optionally be provided with lysine (K) added at the C-terminus.

This ALK4-Fc fusion protein is encoded by the following nucleic acid (SEQ ID NO: 112):

```
                                           (SEQ ID NO: 112)
  1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTACACCCTG CCCCCATCCC GGGAGGAGAT

801 GACCAAGAAC CAGGTCAGCC TGACCTGCCT GGTCAAAGGC TTCTATCCCA

851 GCGACATCGC CGTGGAGTGG GAGAGCAATG GGCAGCCGGA GAACAACTAC
```

```
-continued
 901 GACACCACGC CTCCCGTGCT GGACTCCGAC GGCTCCTTCT TCCTCTATAG

951 CGACCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGT
```

A mature ALK4-Fc fusion protein sequence (SEQ ID NO: 113) is as follows and may optionally be provided with lysine (K) added at the C-terminus.

```
                                                    (SEQ ID NO: 113)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

The ActRIIB-Fc and ALK4-Fc proteins of SEQ ID NO: 110 and SEQ ID NO: 113, respectively, may be co-expressed and purified from a CHO cell line, to give rise to a heteromeric complex comprising ALK4-Fc:ActRIIB-Fc.

In another approach to promote the formation of heteromultimer complexes using asymmetric Fc fusion proteins the Fc domains are altered to introduce complementary hydrophobic interactions and an additional intermolecular disulfide bond as illustrated in the ActRIIB-Fc and ALK4-Fc polypeptide sequences of SEQ ID NOs: 114 and 115 and SEQ ID Nos: 116 and 117, respectively. The ActRIIB-Fc fusion polypeptide and ALK4-Fc fusion polypeptide each employ the tissue plasminogen activator (TPA) leader.

The ActRIIB-Fc polypeptide sequence (SEQ ID NO: 114) is shown below:

```
                                                    (SEQ ID NO: 114)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT KNQVSLWCLV KGFYPSDIAV

301 EWESNGQPEN NYKTTPPVLD SDGSFFLYSK LTVDKSRWQQ GNVFSCSVMH

351 EALHNHYTQK SLSLSPGK
```

The leader (signal) sequence and linker are underlined. To promote formation of the ALK4-Fc:ActRIIB-Fc heterodimer rather than either of the possible homodimeric complexes, two amino acid substitutions (replacing a serine with a cysteine and a threonine with a tryptophan) can be introduced into the Fc domain of the fusion protein as indicated by double underline above. The amino acid sequence of SEQ ID NO: 114 may optionally be provided with lysine (K) removed from the C-terminus.

A mature ActRIIB-Fc fusion polypeptide is as follows:

```
                                                    (SEQ ID NO: 115)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS
```

```
151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTKNQVS LWCLVKGFYP SDIAVEWESN GQPENNYKTT PPVLDSDGSF

301 FLYSKLTVDK SRWQQGNVFS CSVMHEALHN HYTQKSLSLS PGK
```

A complementary form of ALK4-Fc fusion polypeptide (SEQ ID NO: 116) is as follows and may optionally be provided with lysine (K) removed from the C-terminus.

```
                                                (SEQ ID NO: 116)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and the linker are underlined. To guide heterodimer formation with the ActRIIB-Fc fusion polypeptide of SEQ ID NOs: 114 and 115 above, four amino acid substitutions can be introduced into the Fc domain of the ALK4 fusion polypeptide as indicated by double underline above. The amino acid sequence of SEQ ID NO: 116 may optionally be provided with lysine (K) removed from the C-terminus.

A mature ALK4-Fc fusion protein sequence is as follows and may optionally be provided with lysine (K) removed from the C-terminus.

```
                                                (SEQ ID NO: 117)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

ActRIIB-Fc and ALK4-Fc proteins of SEQ ID NO: 115 and SEQ ID NO: 117 respectively, may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another approach to promote the formation of heteromultimer complexes using asymmetric Fc fusion proteins, the Fc domains are altered to introduce complementary hydrophobic interactions, an additional intermolecular disulfide bond, and electrostatic differences between the two Fc domains for facilitating purification based on net molecular charge, as illustrated in the ActRIIB-Fc and ALK4-Fc polypeptide sequences of SEQ ID NOs: 118-121 and 122-125, respectively. The ActRIIB-Fc fusion polypeptide and ALK4-Fc fusion polypeptide each employ the tissue plasminogen activator (TPA) leader).

The ActRIIB-Fc polypeptide sequence (SEQ ID NO: 118) is shown below:

```
                                                    (SEQ ID NO: 118)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT ENQVSLWCLV KGFYPSDIAV

301 EWESNGQPEN NYKTTPPVLD SDGSFFLYSK LTVDKSRWQQ GNVFSCSVMH

351 EALHNHYTQD SLSLSPG
```

The leader sequence and linker are underlined. To promote formation of the ALK4-Fc:ActRIIB-Fc heterodimer rather than either of the possible homodimeric complexes, two amino acid substitutions (replacing a serine with a cysteine and a threonine with a tryptophan) can be introduced into the Fc domain of the fusion protein as indicated by double underline above. To facilitate purification of the ALK4-Fc:ActRIIB-Fc heterodimer, two amino acid substitutions (replacing lysines with acidic amino acids) can also be introduced into the Fc domain of the fusion protein as indicated by double underline above. The amino acid sequence of SEQ ID NO: 118 may optionally be provided with a lysine added at the C-terminus.

This ActRIIB-Fc fusion protein is encoded by the following nucleic acid (SEQ ID NO: 119):

```
                                                    (SEQ ID NO: 119)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCGAGAACC

801 ACAGGTGTAC ACCCTGCCCC CATGCCGGGA GGAGATGACC GAGAACCAGG

851 TCAGCCTGTG GTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGGAC TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGGAC AGCCTCTCCC TGTCTCCGGG

1101 T
```

The mature ActRIIB-Fc fusion polypeptide is as follows (SEQ ID NO: 120) and may optionally be provided with a lysine added to the C-terminus.

```
                                                            (SEQ ID NO: 120)
     1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTENQVS LWCLVKGFYP SDIAVEWESN GQPENNYKTT PPVLDSDGSF

301 FLYSKLTVDK SRWQQGNVFS CSVMHEALHN HYTQDSLSLS PG
```

This ActRIIB-Fc fusion polypeptide is encoded by the following nucleic acid (SEQ ID NO: 121):

```
                                                            (SEQ ID NO: 121)
     1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAGCGCT TCACTCATTT GCCAGAGGCT

301 GGGGGCCCGG AAGTCACGTA CGAGCCACCC CCGACAGCCC CCACCGGTGG

351 TGGAACTCAC ACATGCCCAC CGTGCCCAGC ACCTGAACTC CTGGGGGGAC

401 CGTCAGTCTT CCTCTTCCCC CCAAAACCCA AGGACACCCT CATGATCTCC

451 CGGACCCCTG AGGTCACATG CGTGGTGGTG GACGTGAGCC ACGAAGACCC

501 TGAGGTCAAG TTCAACTGGT ACGTGGACGG CGTGGAGGTG CATAATGCCA

551 AGACAAAGCC GCGGGAGGAG CAGTACAACA GCACGTACCG TGTGGTCAGC

601 GTCCTCACCG TCCTGCACCA GGACTGGCTG AATGGCAAGG AGTACAAGTG

651 CAAGGTCTCC AACAAAGCCC TCCCAGCCCC CATCGAGAAA ACCATCTCCA

701 AAGCCAAAGG GCAGCCCCGA GAACCACAGG TGTACACCCT GCCCCCATGC

751 CGGGAGGAGA TGACCGAGAA CCAGGTCAGC CTGTGGTGCC TGGTCAAAGG

801 CTTCTATCCC AGCGACATCG CCGTGGAGTG GGAGAGCAAT GGGCAGCCGG

851 AGAACAACTA CAAGACCACG CCTCCCGTGC TGGACTCCGA CGGCTCCTTC

901 TTCCTCTATA GCAAGCTCAC CGTGGACAAG AGCAGGTGGC AGCAGGGGAA

951 CGTCTTCTCA TGCTCCGTGA TGCATGAGGC TCTGCACAAC CACTACACGC

1001 AGGACAGCCT CTCCCTGTCT CCGGGT
```

The complementary form of ALK4-Fc fusion polypeptide (SEQ ID NO: 122) is as follows and may optionally be provided with lysine removed from the C-terminus.

```
                                                            (SEQ ID NO: 122)
     1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF
```

```
151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESRGQPENNY

301 KTTPPVLDSR GSFFLVSKLT VDKSRWQQGN VFSCSVMHEA LHNHYTQKSL

351 SLSPGK
```

The leader sequence and the linker are underlined. To guide heterodimer formation with the ActRIIB-Fc fusion polypeptide of SEQ ID NOs: 118 and 120 above, four amino acid substitutions (replacing a tyrosine with a cysteine, a threonine with a serine, a leucine with an alanine, and a tyrosine with a valine) can be introduced into the Fc domain of the ALK4 fusion polypeptide as indicated by double underline above. To facilitate purification of the ALK4-Fc:ActRIIB-Fc heterodimer, two amino acid substitutions (replacing an asparagine with an arginine and an aspartate with an arginine) can also be introduced into the Fc domain of the ALK4-Fc fusion polypeptide as indicated by double underline above. The amino acid sequence of SEQ ID NO: 122 may optionally be provided with lysine removed from the C-terminus.

This ALK4-Fc fusion polypeptide is encoded by the following nucleic acid (SEQ ID NO: 123):

```
                                          (SEQ ID NO: 123)
   1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTGCACCCTG CCCCCATCCC GGGAGGAGAT

801 GACCAAGAAC CAGGTCAGCC TGTCCTGCGC CGTCAAAGGC TTCTATCCCA

851 GCGACATCGC CGTGGAGTGG GAGAGCCGCG GGCAGCCGGA GAACAACTAC

901 AAGACCACGC CTCCCGTGCT GGACTCCCGC GGCTCCTTCT TCCTCGTGAG

951 CAAGCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGTAAA
```

The mature ALK4-Fc fusion polypeptide sequence is as follows (SEQ ID NO: 124) and may optionally be provided with lysine removed from the C-terminus.

```
                                          (SEQ ID NO: 124)
   1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG
```

```
101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESRG QPENNYKTTP PVLDSRGSFF LVSKLTVDKS

301 RWQQGNVFSC SVMHEALHNH YTQKSLSLSP GK
```

This ALK4-Fc fusion polypeptide is encoded by the following nucleic acid (SEQ ID NO: 125):

```
                                            (SEQ ID NO: 125)
  1 TCCGGGCCCC GGGGGGTCCA GGCTCTGCTG TGTGCGTGCA CCAGCTGCCT

51 CCAGGCCAAC TACACGTGTG AGACAGATGG GGCCTGCATG GTTTCCATTT

101 TCAATCTGGA TGGGATGGAG CACCATGTGC GCACCTGCAT CCCCAAAGTG

151 GAGCTGGTCC CTGCCGGGAA GCCCTTCTAC TGCCTGAGCT CGGAGGACCT

201 GCGCAACACC CACTGCTGCT ACACTGACTA CTGCAACAGG ATCGACTTGA

251 GGGTGCCCAG TGGTCACCTC AAGGAGCCTG AGCACCCGTC CATGTGGGGC

301 CCGGTGGAGA CCGGTGGTGG AACTCACACA TGCCCACCGT GCCCAGCACC

351 TGAACTCCTG GGGGACCGT CAGTCTTCCT CTTCCCCCCA AAACCCAAGG

401 ACACCCTCAT GATCTCCCGG ACCCCTGAGG TCACATGCGT GGTGGTGGAC

451 GTGAGCCACG AAGACCCTGA GGTCAAGTTC AACTGGTACG TGGACGGCGT

501 GGAGGTGCAT AATGCCAAGA CAAAGCCGCG GGAGGAGCAG TACAACAGCA

551 CGTACCGTGT GGTCAGCGTC CTCACCGTCC TGCACCAGGA CTGGCTGAAT

601 GGCAAGGAGT ACAAGTGCAA GGTCTCCAAC AAAGCCCTCC CAGCCCCCAT

651 CGAGAAAACC ATCTCCAAAG CCAAAGGGCA GCCCCGAGAA CCACAGGTGT

701 GCACCCTGCC CCCATCCCGG GAGGAGATGA CCAAGAACCA GGTCAGCCTG

751 TCCTGCGCCG TCAAAGGCTT CTATCCCAGC GACATCGCCG TGGAGTGGGA

801 GAGCCGCGGG CAGCCGGAGA ACAACTACAA GACCACGCCT CCCGTGCTGG

851 ACTCCCGCGG CTCCTTCTTC CTCGTGAGCA AGCTCACCGT GGACAAGAGC

901 AGGTGGCAGC AGGGGAACGT CTTCTCATGC TCCGTGATGC ATGAGGCTCT

951 GCACAACCAC TACACGCAGA AGAGCCTCTC CCTGTCTCCG GGTAAA
```

ActRIIB-Fc and ALK4-Fc proteins of SEQ ID NO: 120 and SEQ ID NO: 124, respectively, may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography, cation exchange chromatography, epitope-based affinity chromatography (e.g., with an antibody or functionally equivalent ligand directed against an epitope on ALK4 or ActRIIB), and multimodal chromatography (e.g., with resin containing both electrostatic and hydrophobic ligands). The purification could be completed with viral filtration and buffer exchange.

Example 13. Ligand Binding Profile of ALK4-Fc:ActRIIB-Fc Heterodimer Compared to ActRIIB-Fc Homodimer and ALK4-Fc Homodimer A Biacore™-based binding assay was used to compare ligand binding selectivity of the ALK4-Fc:ActRIIB-Fc heterodimeric complex described above with that of ActRIIB-Fc and ALK4-Fc homodimer complexes. The ALK4-Fc:ActRIIB-Fc heterodimer, ActRIIB-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold font.

Ligand binding profile of ALK4-Fc:ActRIIB-Fc heterodimer compared to ActRIIB-Fc homodimer and ALK4-Fc homodimer

| Ligand | ActRIIB-Fc homodimer | | | ALK4-FC homodimer | | | ALK4-Fc:ActRIIB-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $2.3 \times 10^{-4}$ | 19 | $5.8 \times 10^5$ | $1.2 \times 10^{-2}$ | 20000 | $1.3 \times 10^7$ | $1.5 \times 10^{-4}$ | 12 |
| Activin B | $5.1 \times 10^6$ | $1.0 \times 10^{-4}$ | 20 | No binding | | | $7.1 \times 10^6$ | $4.0 \times 10^{-5}$ | 6 |
| BMP6 | $3.2 \times 10^7$ | $6.8 \times 10^{-3}$ | 190 | — | | | $2.0 \times 10^6$ | $5.5 \times 10^{-3}$ | 2700 |
| BMP9 | $1.4 \times 10^7$ | $1.1 \times 10^{-3}$ | 77 | — | | | Transient* | | 3400 |
| BMP10 | $2.3 \times 10^7$ | $2.6 \times 10^{-4}$ | 11 | — | | | $5.6 \times 10^7$ | $4.1 \times 10^{-3}$ | 74 |
| GDF3 | $1.4 \times 10^6$ | $2.2 \times 10^{-3}$ | 1500 | — | | | $3.4 \times 10^6$ | $1.7 \times 10^{-2}$ | 4900 |
| GDF8 | $8.3 \times 10^5$ | $2.3 \times 10^{-4}$ | 280 | $1.3 \times 10^5$ | $1.9 \times 10^{-3}$ | 15000† | $3.9 \times 10^5$ | $2.1 \times 10^{-4}$ | 550 |
| GDF11 | $5.0 \times 10^7$ | $1.1 \times 10^{-4}$ | 2 | $5.0 \times 10^6$ | $4.8 \times 10^{-3}$ | 270† | $3.8 \times 10^7$ | $1.1 \times 10^{-4}$ | 3 |

Figure 19:
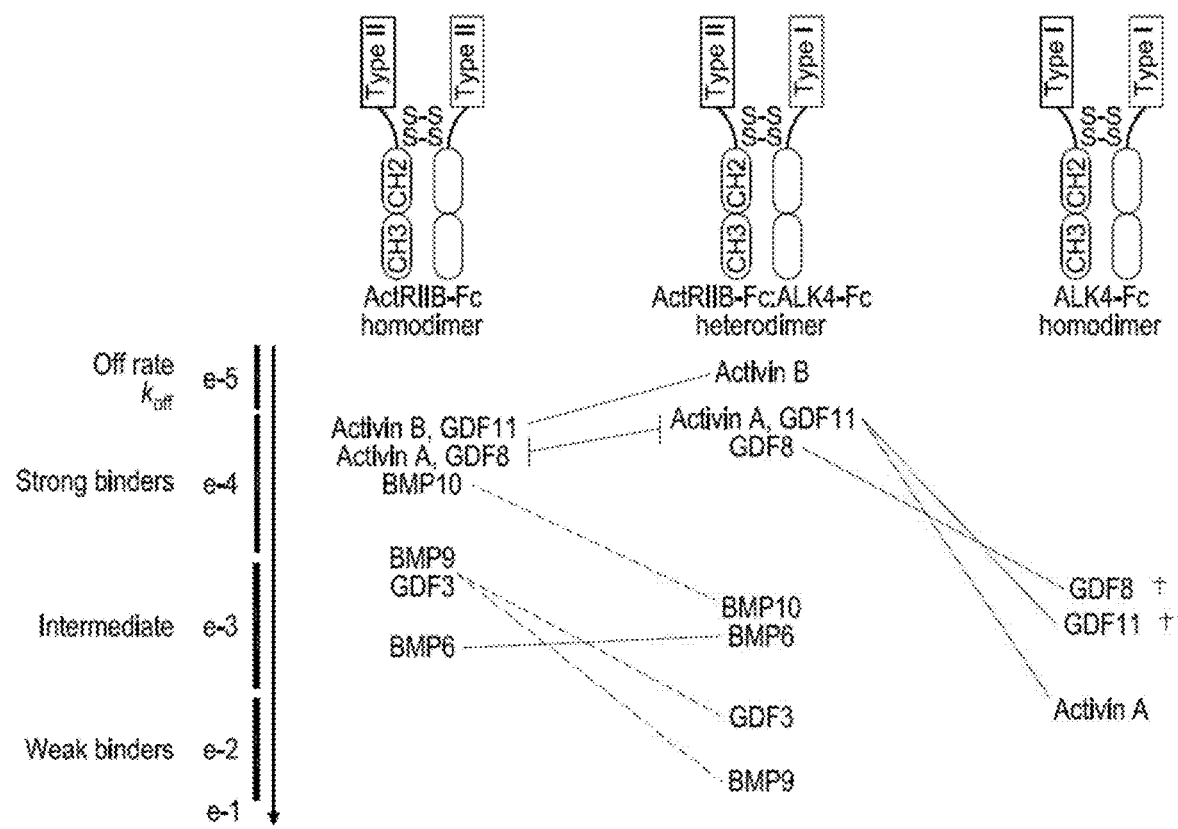
FIG. 19 shows comparative ligand binding data for an ALK4-Fc:ActRIIB-Fc heterodimeric protein complex compared to ActRIIB-Fc homodimer and ALK4-Fc homodimer. For each protein complex, ligands are ranked by $k_{off}$, a kinetic constant that correlates well with ligand signaling inhibition, and listed in descending order of binding affinity (ligands bound most tightly are listed at the top). At left, yellow, red, green, and blue lines indicate magnitude of the off-rate constant. Solid black lines indicate ligands whose binding to heterodimer is enhanced or unchanged compared with homodimer, whereas dashed red lines indicate substantially reduced binding compared with homodimer. As shown, the ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. Like ActRIIB-Fc homodimer, the heterodimer retains intermediate-level binding to BMP6.
Figure 20:
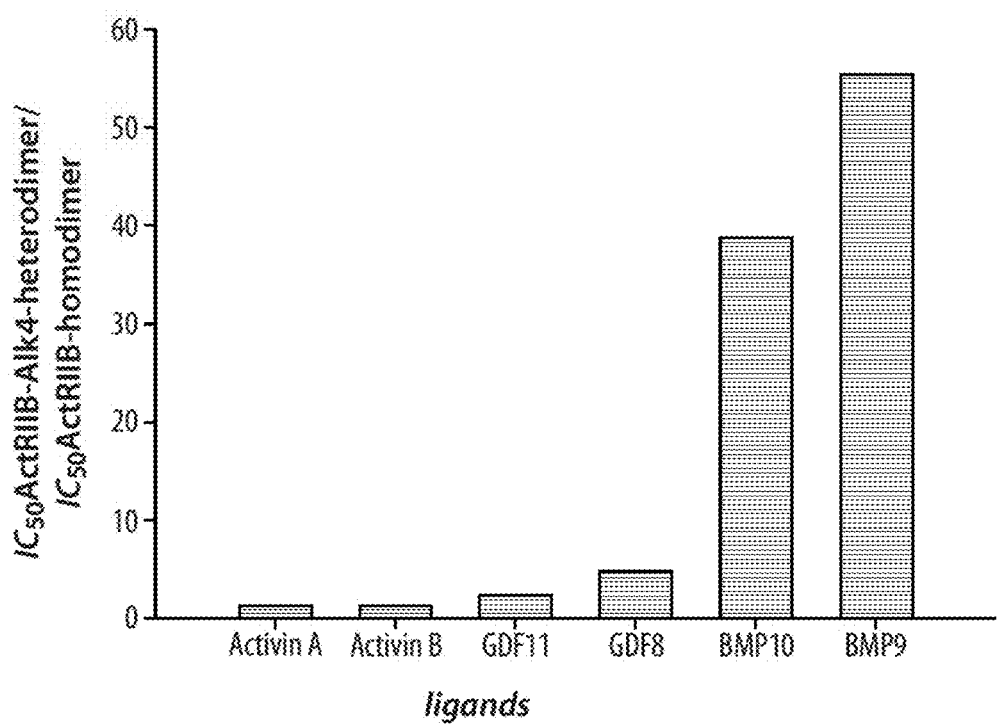
FIG. 20 shows comparative ALK4-Fc:ActRIIB-Fc heterodimer/ActRIIB-Fc:ActRIIB-Fc homodimer $IC_{50}$ data as determined by an A-204 Reporter Gene Assay as described herein. ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. These data demonstrate that ALK4:ActRIIB heterodimers are more selective antagonists of activin A, activin B, GDF8, and GDF11 compared to corresponding ActRIIB. ActRIIB homodimers.

*Indeterminate due to transient nature of interaction
†Very low signal
— Not tested These comparative binding data demonstrate that ALK4-Fc:ActRIIB-Fc heterodimer has an altered binding profile/selectivity relative to either ActRIIB-Fc or ALK4-Fc homodimers. ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. In particular, BMP9 displays low or no observable affinity for ALK4-Fc:ActRIIB-Fc heterodimer, whereas this ligand binds strongly to ActRIIB-Fc homodimer. Like the ActRIIB-Fc homodimer, the heterodimer retains intermediate-level binding to BMP6. See FIG. 19.

In addition, an A-204 Reporter Gene Assay was used to evaluate the effects of ALK4-Fc:ActRIIB-Fc heterodimer and ActRIIB-Fc:ActRIIB-Fc homodimer on signaling by activin A, activin B, GDF11, GDF8, BMP10, and BMP9. Cell line: Human Rhabdomyosarcoma (derived from muscle). Reporter vector: pGL3(CAGA)12 (as described in Dennler et al, 1998, EMBO 17: 3091-3100). The CAGA12 motif is present in TGFβ responsive genes (PAI-1 gene), so this vector is of general use for factors signaling through Smad2 and 3. An exemplary A-204 Reporter Gene Assay is outlined below.

Day 1: Split A-204 cells into 48-well plate.
Day 2: A-204 cells transfected with 10 ug pGL3(CAGA) 12 or pGL3(CAGA)12(10 ug)+pRLCMV (1 ug) and Fugene.
Day 3: Add factors (diluted into medium+0.1% BSA). Inhibitors need to be pre-incubated with Factors for about one hr before adding to cells. About six hrs later, cells are rinsed with PBS and then lysed.

Following the above steps, a Luciferase assay was performed.

Both the ALK4-Fc:ActRIIB-Fc heterodimer and ActRIIB-Fc:ActRIIB-Fc homodimer were determined to be potent inhibitors of activin A, activin B, GDF11, and GDF8 in this assay. In particular, as can be seen in the comparative homodimer/heterodimer $IC_{50}$ data illustrated in FIG. 19, ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. This data is consistent with the above-discussed binding data in which it was observed that both the ALK4-Fc:ActRIIB-Fc heterodimer and ActRIIB-Fc:ActRIIB-Fc homodimer display strong binding to activin A, activin B, GDF8, and GDF11, but BMP10 and BMP9 have significantly reduced affinity for the ALK4-Fc:ActRIIB-Fc heterodimer compared to the ActRIIB-Fc:ActRIIB-Fc homodimer.

Together, these data therefore demonstrate that ALK4-Fc:ActRIIB-Fc heterodimer is a more selective antagonist of activin A, activin B, GDF8, and GDF11 compared to ActRIIB-Fc homodimer. Accordingly, an ALK4-Fc:ActRIIB-Fc heterodimer will be more useful than an ActRIIB-Fc homodimer in certain applications where such selective antagonism is advantageous. Examples include therapeutic applications where it is desirable to retain antagonism of one or more of activin A, activin B, activin AC, GDF8, and GDF11 but minimize antagonism of one or more of BMP9, BMP10, GDF3, and BMP6.

Example 14: Effects of an ActRII Polypeptide and ALK4:ActRIIB Heterodimer on Pulmonary Hypertension in a Monocrotaline Rat Model The effects of an ActRIIA-mFc fusion protein (ActRIIA-mFc homodimer as described in Example 1), an ALK4-Fc:ActRIIB-Fc heterodimer (as described in Examples 12 and 13), and sildenafil (a phosphodiesterase-5 inhibitor approved for the treatment of PAH) were examined in a rat model of pulmonary arterial hypertension (PAH). In this model, Sprague Dawley rats received a subcutaneous injection of monocrotaline (MCT) to induce PAH 24 hours prior to start of therapy.

Rats were separated into different treatment groups (10 mice per group): 1) treatment with MCT (60 mg/kg administered i.p. as a single dose at day 1 of study) and Tris buffered saline (i.p. as 1 ml/kg, every three days) (vehicle treatment group), 2) treatment with an ActRIIA-mFc polypeptide (10 mg/kg administered i.p. every three days) and MCT (60 mg/kg administered i.p. as a single dose at day 1 of study), 3) treatment with an ALK4-Fc:ActRIIB-Fc heterodimer (10 mg/kg administered i.p. every three days) and MCT (60 mg/kg administered i.p. as a single dose at day 1 of study), 4) treatment with sildenafil (30 mg/kg administered orally twice daily) and MCT (60 mg/kg administered i.p. as a single dose at day 1 of study), and 5) control rats (Tris buffered saline administered i.p. as 1 ml/kg, every three days). Rats were treated for 28 days. Body weights were recorded prior to first dose on Day 1 and then weekly throughout the study.

On day 28, rats were anesthetized by an intraperitoneal injection of ketamine/xylazine (80/10 mg/kg). An incision was made in the neck, and a jugular vein was isolated and ligated anteriorly. A fluid-filled pressure catheter was introduced into the right jugular vein to measure pulmonary artery pressure (PAP). Another incision was made in the inguinal region, and femoral artery was isolated and ligated anteriorly. A Millar pressure catheter was introduced into a femoral artery to measure systolic arterial pressure, diastolic pressure, and heart rate. Mean arterial pressure and right PAP were monitored using the Notocord HEM (Croissy sur Seine, France) v3.5 data capture system for approximately 5-10 minutes until stable measurements were obtained. During the measurements, rats were maintained at approximately 37° C. on a heating pad and body temperature was monitored throughout the procedure with a rectal temperature probe. At the conclusion of the procedure, rats were euthanized, and the hearts and lungs were removed. The entire heart was weighed. Next, the atria were removed and the left ventricle with septum (LV+S) was separated from the right ventricle (RV). The ventricles were weighed separately. Hypertrophy was assessed, in part, by calculating RV/LV+S. The lungs were also weighed.

Compared to control animals, monocrotaline treated rats (vehicle treatment group) were observed to have decreased body weight, elevated PAP, right heart hypertrophy, and increased lung weight, indicating establishment of PAH. Sildenafil treated rats did not have any improvement in body weight compared to monocrotaline treated rats. However, sildenafil treatment did reduce elevated PAP by 30%, decrease right heart hypertrophy by 18.5%, and decrease lung weight by 10% compared to monocrotaline treated rats. Surprisingly, both ALK4-Fc:ActRIIB-Fc and ActRIIA-mFc were found have significantly greater effects in treating PAH in this model compared to sildenafil. For example, ALK4-Fc:ActRIIB-Fc treatment resulted in improvement in body weight (+5.1%), reduced elevated PAP by 44.6%, decreased right heart hypertrophy by 39.6%, and decreased lung weight by 19.0%. While ActRIIA-mFc treatment did not show improvement in body weight, it had significant effects in treating other complications of PAH. For example, ActRIIA-Fc treatment resulted in a reduction of elevated PAP by 68%, decreased right heart hypertrophy by 47.1%, and decreased lung weight by 18.4%.

Similar trends were observed on vessel muscularity based on histopathologic scoring. After staining tissue samples to detect αSMA/elastin, 100 pulmonary arterioles, between 10 μm and 50 μm in size, per animal were categorized as non-muscularized, partially muscularized, or completely muscularized. Pulmonary arterioles from vehicle treated rats were determined to be 62.3% completely muscularized, 36.4% partially muscularized, and 1.4% non-muscularized. Sildenafil treatment had only a modest effect on decreasing vessel muscularity (e.g., pulmonary arterioles being 57.9% completely muscularized, 41.6% partially muscularized, and 0.9% non-muscularized). In contrast, ActRIIA-mFc treatment resulted in significant decreases in vessel muscularity compared to sildenafil treated animals (e.g., pulmonary arterioles being 25.8% completely muscularized, 66.9% partially muscularized, and 7.3% non-muscularized compared to vehicle treated animals). Histopathological scoring of smooth muscle hypertrophy of pulmonary arterioles were also recorded as follows: 0 (normal), 1 (minimal), 2 (mild), 3 (moderate), or 4 (marked). Vehicle treated rats had an average smooth muscle hypertrophy of moderate to marked (3.8 score). Again, sildenafil treatment was observed to have a modest effect on hypertrophy with an average score of 3 (moderate). While ActRIIA-mFc treated animals were observed to have significant reduction in smooth muscle hypertrophy (average score of 1.6) compared to both vehicle and sildenafil treated animals. Overall, ActRIIA-mFc treatment significantly reduced vessel muscularity and hypertrophy in this PAH model.

Together, these data demonstrate that both ActRIIA-mFc and ALK4-Fc:ActRIIB-Fc are effective in ameliorate various complications of PAH in this monocrotaline-induced model. In particular, both ActRIIA-mFc and ALK4-Fc:ActRIIB-Fc had a greater effect in reducing artery pressure, right heart hypertrophy, and vascular muscularization than was observed for sildenafil, which is an approved drug for the treatment of PAH. Furthermore, the data indicate that other GDF/BMP antagonists, particularly ones having activities similar to ActRIIA-mFc and ALK4-Fc:ActRIIB-Fc, may be useful in the treatment of PAH, particularly in preventing or reducing the severity various complications of PAH.

Example 15: Effects of an ActRII Polypeptide and ALK4:ActRIIB Heterodimer on Pulmonary Hypertension in the Sugen Hypoxia Rat Model The effects of an ActRIIA-mFc fusion protein (ActRIIA-mFc homodimer as described in Example 1 and sildenafil (a phosphodiesterase-5 inhibitor approved for the treatment of PAH) were further examined the Sugen Hypoxia model of PAH. In this model, rats receive daily doses of semaxanib and are placed in a low oxygen environment (approximately 13% oxygen) to induce PAH 24 hours prior to start of therapy.

Rats were separated into different treatment groups (10 mice per group): 1) treatment with semaxanib (200 mg/kg administered s.c. as a single dose daily)/hypoxia and Tris buffered saline (administered i.p. as 1 ml/kg, every three days) (vehicle treatment group), 2) treatment with an ActRIIA-mFc polypeptide (10 mg/kg administered i.p. every three days) and semaxanib (200 mg/kg administered s.c. as a single dose daily)/hypoxia, 3) treatment with sildenafil (30 mg/kg administered orally twice daily) and semaxanib (200 mg/kg administered s.c. as a single dose daily)/hypoxia, and 4) control rats (Tris buffered saline administered i.p. as 1 ml/kg, every three days). Rats were treated for 28 days. Body weights were recorded prior to first dose on Day 1 and then weekly throughout the study.

On day 28, rats were anesthetized by an intraperitoneal injection of ketamine/xylazine (80/10 mg/kg). An incision was made in the neck, and a jugular vein was isolated and ligated anteriorly. A fluid-filled pressure catheter was introduced into the right jugular vein to measure pulmonary artery pressure (PAP). Another incision was made in the inguinal region, and femoral artery was isolated and ligated anteriorly. A Millar pressure catheter was introduced into a femoral artery to measure systolic arterial pressure, diastolic pressure, and heart rate. Mean arterial pressure and right PAP were monitored using the Notocord HEM (Croissy sur Seine, Frnace) v3.5 data capture system for approximately 5-10 minutes until stable measurements were obtained. During the measurements, rats were maintained at approximately 37° C. on a heating pad and body temperature was monitored throughout the procedure with a rectal temperature probe. At the conclusion of the procedure, rats were euthanized, and the hearts and lungs were removed. The entire heart was weighed. Next, the atria were removed and the left ventricle with septum (LV+S) was separated from the right ventricle (RV). The ventricles were weighed separately. Hypertrophy was assessed, in part, by calculating RV/LV+S. The lungs were also weighed.

Compared to control animals, semaxanib/hypoxia treated rats (vehicle treatment group) were observed to have decreased body weight, elevated PAP, right heart hypertrophy, and increased lung weight, indicating establishment of PAH. Sildenafil treatment reduced mean pulmonary arterial pressure by 22.4% and decreased right heart hypertrophy by 10% compared to vehicle treated animals. Again, ActRIIA-mFc treatment was found have significantly greater effects in treating PAH in this model compared to sildenafil. For example, ActRIIA-mFc treatment resulted in a reduction of mean pulmonary arterial pressure by 51.3% and decreased right heart hypertrophy by 53.5% compared to vehicle treated animals.

Similar trends were observed on vessel muscularity based on histopathologic scoring. After staining tissue samples to detect αSMA/elastin, 100 pulmonary arterioles, between 10 μm and 50 μm in size, per animal were categorized as non-muscularized, partially muscularized, or completely muscularized. Pulmonary arterioles from vehicle treated rats were determined to be 72.5% completely muscularized, 27.4% partially muscularized, and 0.1% non-muscularized. Sildenafil treatment had only a modest effect on decreasing vessel muscularity (e.g., pulmonary arterioles being 67.4% completely muscularized, 31.6% partially muscularized, and 1.0% non-muscularized) compared to vehicle treated animals. In contrast, ActRIIA-mFc treatment resulted in significant decreases in vessel muscularity compared to sildenafil treated animals (e.g., pulmonary arterioles being 29.3% completely muscularized, 69.3% partially muscularized, and 1.4% non-muscularized compared to vehicle treated animals). Histopathological scoring of smooth muscle hypertrophy of pulmonary arterioles were also recorded as follows: 0 (normal), 1 (minimal), 2 (mild), 3 (moderate), or 4 (marked). Vehicle treated rats had an average smooth muscle hypertrophy of moderate to marked (3.6 score). Again, sildenafil treatment was observed to have a modest effect on hypertrophy with an average score of 3 (moderate). While ActRIIA-mFc treated animals were observed to have significant reduction in smooth muscle hypertrophy (average score of 1.4) compared to sildenafil treated animals. Overall, ActRIIA-mFc treatment significantly reduced vessel muscularity and hypertrophy in this PAH model.

Together, these data demonstrate that ActRIIA-mFc is effective in ameliorate various complications of PAH in the Sugen Hypoxia model. In particular, ActRIIA-mFc had a greater effect in reducing artery pressure, right heart hypertrophy, and vessel muscularization than was observed for sildenafil, which is an approved drug for the treatment of PAH. Furthermore, the data indicate that other GDF/BMP antagonists, particularly ones having activities similar to ActRIIA-mFc may be useful in the treatment of PAH, particularly in preventing or reducing the severity various complications of PAH.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method of treating pulmonary arterial hypertension, comprising administering to a patient in need thereof a fusion protein comprising:
   a) an ActRIIA polypeptide comprising the amino acid sequence of SEQ ID NO: 10;
   b) an Fc domain of an IgG1 immunoglobulin; and
   c) a linker domain,
wherein the linker domain is positioned between the ActRIIA polypeptide and the Fc domain of the IgG1 immunoglobulin.

2. The method of claim 1, wherein proliferation of smooth muscle and endothelial cells in the pulmonary artery is inhibited.

3. The method of claim 1, wherein the method increases the exercise capacity of the patient.

4. The method of claim 3, wherein the method increases the patient's 6-minute walk distance (6MWD).

5. The method of claim 4, wherein the patient's 6MWD is increased by at least 10 meters.

6. The method of claim 4, wherein the patient's 6MWD is increased by at least 50 meters.

7. The method of claim 1, wherein the method reduces the patient's Borg dyspnea index (BDI).

8. The method of claim 7, wherein the method reduces the patient's BDI by at least 0.5 index points.

9. The method of claim 7, wherein the method reduces the patient's BDI by at least 5 index points.

10. The method of claim 1, wherein the method reduces pulmonary vascular resistance in the patient.

11. The method of claim 1, wherein the method increases pulmonary capillary wedge pressure.

12. The method of claim 1, wherein the method increases left ventricular end-diastolic pressure.

13. The method of claim 1, wherein the method decreases pulmonary arterial pressure in the patient.

14. The method of claim 13, wherein the method decreases pulmonary arterial pressure in the patient by at least 10%.

15. The method of claim 1, wherein the method decreases ventricle hypertrophy in the patient.

16. The method of claim 15, wherein the method decreases ventricle hypertrophy in the patient by at least 10%.

17. The method of claim 2, wherein the method decreases smooth muscle hypertrophy in the patient.

18. The method of claim 17, wherein the method decreases smooth muscle hypertrophy in the patient by at least 10%.

19. The method of claim 1, wherein the method decreases pulmonary arteriole muscularity in the patient.

20. The method of claim 19, wherein the method decreases pulmonary arteriole muscularity in the patient by at least 10%.

21. The method of claim 1, wherein the method decreases pulmonary vascular resistance in the patient.

22. The method of claim 21, wherein the method decreases pulmonary vascular resistance in the patient by at least 10%.

23. The method of claim 1, wherein the patient has a hemoglobin level from greater than 8 and less than 15 g/dl.

24. The method of claim 1, wherein the method delays clinical worsening of pulmonary arterial hypertension.

25. The method of claim 1, wherein the method reduces the risk of hospitalization for one or more complications associated with pulmonary arterial hypertension.

26. A method of treating pulmonary arterial hypertension, comprising administering to a patient in need thereof a fusion protein comprising:
   a) an ActRIIA polypeptide comprising the amino acid sequence of SEQ ID NO: 10;
   b) an Fc domain of an IgG1 immunoglobulin; and
   c) a linker domain,
wherein the linker domain is positioned between the ActRIIA polypeptide and the Fc domain of the IgG1 immunoglobulin, and wherein the method increases exercise capacity of the patient.

27. The method of claim 1, wherein the linker domain comprises an amino acid sequence of SEQ ID NO: 23.

28. The method of claim 26, wherein the linker domain comprises an amino acid sequence of SEQ ID NO: 23.

29. The method of claim 1, wherein the Fc domain comprises an amino acid sequence that is at least 95% identical to SEQ ID NO: 14.

30. The method of claim 26, wherein the Fc domain comprises an amino acid sequence that is at least 95% identical to SEQ ID NO: 14.

31. The method of claim 1, wherein the Fc domain comprises an amino acid sequence that is at least 99% identical to SEQ ID NO: 14.

32. The method of claim 26, wherein the Fc domain comprises an amino acid sequence that is at least 99% identical to SEQ ID NO: 14.

33. The method of claim 1, wherein the Fc domain comprises an amino acid sequence of SEQ ID NO: 14.

34. The method of claim 26, wherein the Fc domain comprises an amino acid sequence of SEQ ID NO: 14.

35. A method of treating pulmonary arterial hypertension in a human patient in need thereof, comprising administering to the human patient an effective amount of a fusion protein comprising:
   a) an ActRIIA polypeptide domain comprising the amino acid sequence of SEQ ID NO: 10;

b) an Fc domain of an IgG1 immunoglobulin; and c) a linker domain comprising the amino acid sequence of SEQ ID NO: 23;

wherein the linker domain is positioned between the ActRIIA polypeptide domain and the Fc domain.

36. The method of claim 35, wherein the Fc domain comprises an amino acid sequence that is at least 95% identical to SEQ ID NO: 14.

37. The method of claim 35, wherein the Fc domain comprises an amino acid sequence that is at least 96% identical to SEQ ID NO: 14.

38. The method of claim 35, wherein the Fc domain comprises an amino acid sequence that is at least 97% identical to SEQ ID NO: 14.

39. The method of claim 35, wherein the Fc domain comprises an amino acid sequence that is at least 98% identical to SEQ ID NO: 14.

40. The method of claim 35, wherein the Fc domain comprises an amino acid sequence that is at least 99% identical to SEQ ID NO: 14.

41. The method of claim 35, wherein the Fc domain comprises the amino acid sequence of SEQ ID NO: 14.

42. The method of claim 35, wherein the fusion protein comprises an amino acid sequence that is at least 95% identical to SEQ ID NO: 32.

43. The method of claim 35, wherein the fusion protein comprises an amino acid sequence that is at least 96% identical to SEQ ID NO: 32.

44. The method of claim 35, wherein the fusion protein comprises an amino acid sequence that is at least 97% identical to SEQ ID NO: 32.

45. The method of claim 35, wherein the fusion protein comprises an amino acid sequence that is at least 98% identical to SEQ ID NO: 32.

46. The method of claim 35, wherein the fusion protein comprises an amino acid sequence that is at least 99% identical to SEQ ID NO: 32.

47. The method of claim 35, wherein the fusion protein comprises the amino acid sequence of SEQ ID NO: 32.

48. The method of claim 35, wherein the fusion protein is a homodimer.

49. The method of claim 46, wherein the fusion protein is a homodimer.

50. The method of claim 35, wherein the human patient has Functional Class II or Class III pulmonary hypertension in accordance with the World Health Organization's functional classification system for pulmonary hypertension.

51. The method of claim 49, wherein the human patient has Functional Class II pulmonary hypertension in accordance with the World Health Organization's functional classification system for pulmonary hypertension.

52. The method of claim 50, wherein the human patient has Functional Class III pulmonary hypertension in accordance with the World Health Organization's functional classification system for pulmonary hypertension.

53. The method of claim 35, wherein the human patient has one or more subtypes of pulmonary arterial hypertension selected from the group consisting of: idiopathic pulmonary arterial hypertension, heritable pulmonary arterial hypertension, drug- and/or toxin-induced pulmonary hypertension, pulmonary hypertension associated with connective tissue disease, and pulmonary hypertension associated with congenital systemic-to-pulmonary shunts at least 1 year following shunt repair.

54. The method of claim 53, wherein the human patient has idiopathic pulmonary arterial hypertension.

55. The method of claim 35, wherein the treatment increases an exercise capacity of the human patient.

56. The method of claim 38, wherein the method promotes the regression from Functional Class II or Class III to Functional Class I or Class II pulmonary hypertension in accordance with the World Health Organization's functional classification system for pulmonary hypertension.

57. The method of claim 35, wherein the method delays clinical worsening of pulmonary arterial hypertension.

58. The method of claim 35, wherein the treatment reduces pulmonary vascular resistance of the human patient.

59. The method of claim 35, wherein the treatment reduces pulmonary arterial pressure of the human patient.

60. The method of claim 35, wherein the fusion protein is administered subcutaneously.

61. The method of claim 35, wherein the fusion protein is administered as a pharmaceutical composition comprising the fusion protein and one or more physiologically acceptable carriers or excipients.

* * * * *

SEQUENCE LISTING

```
Sequence total quantity: 138
SEQ ID NO: 1            moltype = AA   length = 512
FEATURE                 Location/Qualifiers
source                  1..512
                        mol_type = protein
                        organism = Homo sapiens
SEQUENCE: 1
MTAPWVALAL LWGSLCAGSG RGEAETRECI YYNANWELER TNQSGLERCE GEQDKRLHCY    60
ASWRNSSGTI ELVKKGCWLD DFNCYDRQEC VATEENPQVY FCCCEGNFCN ERFTHLPEAG   120
GPEVTYEPPP TAPTLLTVLA YSLLPIGGLS LIVLLAFWMY RHRKPPYGHV DIHEDPGPPP   180
PSPLVGLKPL QLLEIKARGR FGCVWKAQLM NDFVAVKIFP LQDKQSWQSE REIFSTPGMK   240
HENLLQFIAA EKRGSNLEVE LWLITAFHDK GSLTDYLKGN IITWNELCHV AETMSRGLSY   300
LHEDVPWCRG EGHKPSIAHR DFKSKNVLLK SDLTAVLADF GLAVRFEPGK PPGDTHGQVG   360
TRRYMAPEVL EGAINFQRDA FLRIDMYAMG LVLWELVSRC KAADGPVDEY MLPFEEEIGQ   420
HPSLEELQEV VVHKKMRPTI KDHWLKHPGL AQLCVTIEEC WDHDAEARLS AGCVEERVSL   480
IRRSVNGTTS DCLVSLVTSV TNVDLPPKES SI                                 512

SEQ ID NO: 2            moltype = AA   length = 115
FEATURE                 Location/Qualifiers
source                  1..115
                        mol_type = protein
                        organism = Homo sapiens
SEQUENCE: 2
GRGEAETREC IYYNANWELE RTNQSGLERC EGEQDKRLHC YASWRNSSGT IELVKKGCWL    60
DDFNCYDRQE CVATEENPQV YFCCCEGNFC NERFTHLPEA GGPEVTYEPP PTAPT        115

SEQ ID NO: 3            moltype = AA   length = 100
FEATURE                 Location/Qualifiers
source                  1..100
                        mol_type = protein
                        organism = Homo sapiens
SEQUENCE: 3
GRGEAETREC IYYNANWELE RTNQSGLERC EGEQDKRLHC YASWRNSSGT IELVKKGCWL    60
```

```
DDFNCYDRQE  CVATEENPQV  YFCCCEGNFC  NERFTHLPEA                 100

SEQ ID NO: 4            moltype = AA  length = 512
FEATURE                 Location/Qualifiers
source                  1..512
                        mol_type = protein
                        organism = Homo sapiens
SEQUENCE: 4
MTAPWVALAL  LWGSLCAGSG  RGEAETRECI  YYNANWELER  TNQSGLERCE  GEQDKRLHCY   60
ASWANSSGTI  ELVKKGCWLD  DFNCYDRQEC  VATEENPQVY  FCCCEGNFCN  ERFTHLPEAG  120
GPEVTYEPPP  TAPTLLTVLA  YSLLPIGGLS  LIVLLAFWMY  RHRKPPYGHV  DIHEDPGPPP  180
PSPLVGLKPL  QLLEIKARGR  FGCVWKAQLM  NDFVAVKIFP  LQDKQSWQSE  REIFSTPGMK  240
HENLLQFIAA  EKRGSNLEVE  LWLITAFHDK  GSLTDYLKGN  IITWNELCHV  AETMSRGLSY  300
LHEDVPWCRG  EGHKPSIAHR  DFKSKNVLLK  SDLTAVLADF  GLAVRFEPGK  PPGDTHGQVG  360
TRRYMAPEVL  EGAINFQRDA  FLRIDMYAMG  LVLWELVSRC  KAADGPVDEY  MLPFEEEIGQ  420
HPSLEELQEV  VVHKKMRPTI  KDHWLKHPGL  AQLCVTIEEC  WDHDAEARLS  AGCVEERVSL  480
IRRSVNGTTS  DCLVSLVTSV  TNVDLPPKES  SI                                  512

SEQ ID NO: 5            moltype = AA  length = 115
FEATURE                 Location/Qualifiers
source                  1..115
                        mol_type = protein
                        organism = Homo sapiens
SEQUENCE: 5
GRGEAETREC  IYYNANWELE  RTNQSGLERC  EGEQDKRLHC  YASWANSSGT  IELVKKGCWL   60
DDFNCYDRQE  CVATEENPQV  YFCCCEGNFC  NERFTHLPEA  GGPEVTYEPP  PTAPT       115

SEQ ID NO: 6            moltype = AA  length = 100
FEATURE                 Location/Qualifiers
source                  1..100
                        mol_type = protein
                        organism = Homo sapiens
SEQUENCE: 6
GRGEAETREC  IYYNANWELE  RTNQSGLERC  EGEQDKRLHC  YASWANSSGT  IELVKKGCWL   60
DDFNCYDRQE  CVATEENPQV  YFCCCEGNFC  NERFTHLPEA                          100

SEQ ID NO: 7            moltype = DNA  length = 1536
FEATURE                 Location/Qualifiers
source                  1..1536
                        mol_type = other DNA
                        organism = Homo sapiens
SEQUENCE: 7
atgacggcgc  cctgggtggc  cctcgccctc  tctggggat   cgctgtgcgc  cggctctggg    60
cgtggggagg  ctgagacacg  ggagtgcatc  tactacaacg  ccaactggga  gctggagcgc   120
accaaccaga  gcggcctgga  gcgctgcgaa  ggcgagcagg  acaagcggct  gcactgctac   180
gcctcctggc  gcaacagctc  tggcaccatc  gagctcgtga  agaagggctg  ctggctagat   240
gacttcaact  gctacgatag  gcaggagtgt  gtggccatcg  aggaaaaccc  ccaggtgtac   300
ttctgctgct  gtgaaggcaa  cttctgcaac  gaacgcttca  ctcatttgcc  agaggctggg   360
ggcccggaag  tcacgtacga  gccaccccccg acgccccca   cctgctcac   ggtgctggcc   420
tactcactgc  tgcccatcgg  gggcctttcc  ctcatcgtcc  tgctggcctt  ttggatgtac   480
cggcatcgca  agcccccta   cggtcatgtg  gacatccatg  aggaccctgg  gcctccacca   540
ccatcccctc  tggtgggcct  gaagccactg  cagctgctgg  agatcaaggc  tcggggcgc    600
tttggctgtg  tctggaaggc  ccagctcatg  aatgactttg  tagctgtcaa  gatcttccca   660
ctccaggaca  gcagtcgtg   gcagagtgaa  cgggagatct  tcagcacacc  tggcatgaag   720
cacgagaacc  tgctacagtt  cattgctgcc  gagaagcgaa  gctccaacct  cgaagtagag   780
ctgtggctca  tcacggcctt  ccatgacaag  ggctccctca  cggattacct  caagggggaac  840
atcatcacat  ggaacgaact  gtgtcatgta  cagagacga   tgtcacgagg  cctctctac    900
ctgcatgagg  atgtgccctg  gtgccgtggc  gagggccaca  agccgtctat  tgcccacagg   960
gactttaaaa  gtaagaatgt  attgctgaag  agcgacctca  cagccgtgct  ggctgacttt  1020
ggcttggctg  ttcgatttga  gccagggaaa  cctccagggg  acacccacgg  acaggtaggc  1080
acgagacggt  acatggctcc  tgaggtgctc  gagggagcca  tcaacttcca  gagagatgcc  1140
ttcctgcgca  ttgacatgta  tgccatgggg  ttggtgctgt  gggagcttgt  gtctcgctgc  1200
aaggctgcag  acggacccgt  ggatgagtac  atgctgccct  tgaggaagaa  gattggccag  1260
caccccttcgt tggaggagct  gcaggaggtg  gtggtgcaca  agaagatgag  gcccaccatt  1320
aaagatcact  ggttgaaaca  cccggggcct  gcccagcttt  gtgtgaccat  cgaggagtgc  1380
tgggaccatg  atgcagaggc  tcgcttgtcc  gcgggctgtg  tggaggagcg  ggtgtccctg  1440
attcggaggt  cggtcaacgg  cactacctcg  gactgtctcg  tttccctggt  gacctctgtc  1500
accaatgtgg  acctgccccc  taaagagtca  agcatc                              1536

SEQ ID NO: 8            moltype = DNA  length = 345
FEATURE                 Location/Qualifiers
source                  1..345
                        mol_type = other DNA
                        organism = Homo sapiens
SEQUENCE: 8
gggcgtgggg  aggctgagac  acggagtgc   atctactaca  acgccaactg  ggagctggag    60
cgcaccaacc  agagcggcct  ggagcgctgc  gaaggcgagc  aggacaagcg  gctgcactgc   120
tacgcctcct  ggcgcaacag  ctctggcacc  atcgagctcg  tgaagaaggg  ctgctggcta   180
gatgacttca  actgctacga  taggcaggag  tgtgtggcca  tcgaggagaa  ccccaggtg    240
```

```
tacttctgct gctgtgaagg caacttctgc aacgaacgct tcactcattt gccagaggct    300
gggggcccgg aagtcacgta cgagccaccc ccgacagccc ccacc                    345

SEQ ID NO: 9           moltype = AA  length = 513
FEATURE                Location/Qualifiers
source                 1..513
                       mol_type = protein
                       organism = Homo sapiens
SEQUENCE: 9
MGAAAKLAFA VFLISCSSGA ILGRSETQEC LFFNANWEKD RTNQTGVEPC YGDKDKRRHC     60
FATWKNISGS IEIVKQGCWL DDINCYDRTD CVEKKDSPEV YFCCCEGNMC NEKFSYFPEM    120
EVTQPTSNPV TPKPPYYNIL LYSLVPLMLI AGIVICAFWV YRHHKMAYPP VLVPTQDPGP    180
PPPSPLLGLK PLQLLEVKAR GRFGCVWKAQ LLNEYVAVKI FPIQDKQSWQ NEYEVYSLPG    240
MKHENILQFI GAEKRGTSVD VDLWLITAFH EKGSLSDFLK ANVVSWNELC HIAETMARGL    300
AYLHEDIPGL KDGHKPAISH RDIKSKNVLL KNNLTACIAD FGLALKFEAG KSAGDTHGQV    360
GTRRYMAPEV LEGAINFQRD AFLRIDMYAM GLVLWELASR CTAADGPVDE YMLPFEEEIG    420
QHPSLEDMQE VVVHKKKRPV LRDYWQKHAG MAMLCETIEE CWDHDAEARL SAGCVGERIT    480
QMQRLTNIIT TEDIVTVVTM VTNVDFPPKE SSL                                 513

SEQ ID NO: 10          moltype = AA  length = 115
FEATURE                Location/Qualifiers
source                 1..115
                       mol_type = protein
                       organism = Homo sapiens
SEQUENCE: 10
ILGRSETQEC LFFNANWEKD RTNQTGVEPC YGDKDKRRHC FATWKNISGS IEIVKQGCWL     60
DDINCYDRTD CVEKKDSPEV YFCCCEGNMC NEKFSYFPEM EVTQPTSNPV TPKPP         115

SEQ ID NO: 11          moltype = AA  length = 100
FEATURE                Location/Qualifiers
source                 1..100
                       mol_type = protein
                       organism = Homo sapiens
SEQUENCE: 11
ILGRSETQEC LFFNANWEKD RTNQTGVEPC YGDKDKRRHC FATWKNISGS IEIVKQGCWL     60
DDINCYDRTD CVEKKDSPEV YFCCCEGNMC NEKFSYFPEM                          100

SEQ ID NO: 12          moltype = DNA  length = 1539
FEATURE                Location/Qualifiers
source                 1..1539
                       mol_type = other DNA
                       organism = Homo sapiens
SEQUENCE: 12
atgggagctg ctgcaaagtt ggcgtttgcc gtcttcctta tctcctgttc ttcaggtgct     60
atacttggta gatcagaaac tcaggagtgt cttttcttta atgctaattg ggaaaaagac    120
agaaccaatc aaactggtgt tgaaccgtgt tatggtgaca agataaacg gcggcattgt     180
tttgctacct ggaagaatat ttctggttcc attgaaatag tgaaacaagg ttgttggctg    240
gatgatatca actgctatga caggactgat tgtgtagaaa aaaagacag ccctgaagta    300
tattttgtt gctgtgaggg caatatgtgt aatgaaaagt ttctctattt tccggagatg    360
gaagtcacac agcccacttc aaatccagtt acacctaagc cacccatta caacatcctg    420
ctctattcct tggtgccact tatgttaatt gcggggatg tcatttgtgc attttgggtg    480
tacaggcatc acaagatggc ctaccctcct gtacttgttc caactcaaga cccaggacca    540
ccccaccttt ctccattact aggtttgaaa ccactgcagt tattagaagt gaaagcaagg    600
ggaagatttg gttgtgtctg gaaagcccag ttgcttaacg aatatgtggc tgtcaaaata    660
tttccaatac aggacaaaca gtcatgcaa atgaatacg aagtctacag tttgcctgga    720
atgaagcatg agaacatatt acagttcatt ggtgcagaaa acgaggcac cagtgttgat    780
gtggatcttt ggctgatcac agcatttcat gaaaagggtt cactatcaga cttcttaag    840
gctaatgtgt tctcttggaa tgaactgtgt catattgcag aaaccatggc tagaggattg    900
gcatatttac atgaggatat acctggccta aaagatggcc acaaacctgc catatcctac    960
agggacatca aaagtaaaaa tgtgctgttg aaaaacaacc tgacagcttg cattgctgac   1020
tttgggttgg ccttaaaatt tgaggctggc aagtctgcag gcgataccca tggacaggtt   1080
ggtacccgga ggtacatggc tccagaggta ttagagggtg ctataaactt ccaaagggat   1140
gcattttga ggatagatat gtatgccatg ggattagtcc tatgggaact ggcttctcgc   1200
tgtactgctg cagatggacc tgtagataa tacatgcc catttgagga ggaaattggc   1260
cagcatccat ctcttgaaga catgcaggaa gttgttgtgc ataaaaaaaa gaggcctgtt   1320
ttaagagatt attggcagaa acatgctgga atgcaatgc tctgtgaaac cattgaagaa   1380
tgtgggatc acgacgcaga agccaggtta tcagctggat gtgtaggtga agaattacc    1440
cagatgcaga gactaacaaa tattattacc acagaggaca ttgtaacagt ggtcacaatg   1500
gtgacaaatg ttgactttcc tcccaaagaa tctagtcta                           1539

SEQ ID NO: 13          moltype = DNA  length = 345
FEATURE                Location/Qualifiers
source                 1..345
                       mol_type = other DNA
                       organism = Homo sapiens
SEQUENCE: 13
atacttggta gatcagaaac tcaggagtgt cttttcttta atgctaattg ggaaaaagac     60
agaaccaatc aaactggtgt tgaaccgtgt tatggtgaca agataaacg gcggcattgt    120
tttgctacct ggaagaatat ttctggttcc attgaaatag tgaaacaagg ttgttggctg    180
```

```
gatgatatca actgctatga caggactgat tgtgtagaaa aaaaagacag ccctgaagta    240
tattttgtt gctgtgaggg caatatgtgt aatgaaaagt tttcttattt tccggagatg    300
gaagtcacac agcccacttc aaatccagtt acacctaagc caccc                  345

SEQ ID NO: 14              moltype = AA   length = 225
FEATURE                    Location/Qualifiers
source                     1..225
                           mol_type = protein
                           organism = Homo sapiens
SEQUENCE: 14
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLTCLVKGF YPSDIAVEWE SNGQPENNYK TTPPVLDSDG   180
SFFLYSKLTV DKSRWQQGNV FSCSVMHEAL HNHYTQKSLS LSPGK                   225

SEQ ID NO: 15              moltype = AA   length = 223
FEATURE                    Location/Qualifiers
source                     1..223
                           mol_type = protein
                           organism = Homo sapiens
SEQUENCE: 15
VECPPCPAPP VAGPSVFLFP PKPKDTLMIS RTPEVTCVVV DVSHEDPEVQ FNWYVDGVEV    60
HNAKTKPREE QFNSTFRVVS VLTVVHQDWL NGKEYKCKVS NKGLPAPIEK TISKTKGQPR   120
EPQVYTLPPS REEMTKNQVS LTCLVKGFYP SDIAVEWESN GQPENNYKTT PPMLDSDGSF   180
FLYSKLTVDK SRWQQGNVFS CSVMHEALHN HYTQKSLSLS PGK                     223

SEQ ID NO: 16              moltype = AA   length = 232
FEATURE                    Location/Qualifiers
source                     1..232
                           mol_type = protein
                           organism = Homo sapiens
SEQUENCE: 16
EPKSCDTPPP CPRCPAPELL GGPSVFLFPP KPKDTLMISR TPEVTCVVVD VSHEDPEVQF    60
KWYVDGVEVH NAKTKPREEQ YNSTFRVVSV LTVVHQDWLN GKEYKCKVSN KALPAPIEKT   120
ISKTKGQPRE PQVYTLPPSR EEMTKNQVSL TCLVKGFYPS DIAVEWESSG QPENNYNTTP   180
PMLDSDGSFF LYSKLTVDKS RWQQGNIFSC SVMHEALHNR FTQKSLSLSP GK           232

SEQ ID NO: 17              moltype = AA   length = 279
FEATURE                    Location/Qualifiers
source                     1..279
                           mol_type = protein
                           organism = Homo sapiens
SEQUENCE: 17
ELKTPLGDTT HTCPRCPEPK SCDTPPPCPR CPEPKSCDTP PPCPRCPEPK SCDTPPPCPR    60
CPAPELLGGP SVFLFPPKPK DTLMISRTPE VTCVVVDVSH EDPEVQFKWY VDGVEVHNAK   120
TKPREEQYNS TFRVVSVLTV LHQDWLNGKE YKCKVSNKAL PAPIEKTISK TKGQPREPQV   180
YTLPPSREEM TKNQVSLTCL VKGFYPSDIA VEWESSGQPE NNYNTTPPML DSDGSFFLYS   240
KLTVDKSRWQ QGNIFSCSVM HEALHNRFTQ KSLSLSPGK                          279

SEQ ID NO: 18              moltype = AA   length = 229
FEATURE                    Location/Qualifiers
source                     1..229
                           mol_type = protein
                           organism = Homo sapiens
SEQUENCE: 18
ESKYGPPCPS CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK                229

SEQ ID NO: 19              moltype =      length =
SEQUENCE: 19
000

SEQ ID NO: 20              moltype = AA   length = 4
FEATURE                    Location/Qualifiers
REGION                     1..4
                           note = Description of Artificial Sequence: Synthetic peptide
source                     1..4
                           mol_type = protein
                           organism = synthetic construct
SEQUENCE: 20
GGGG                                                                  4

SEQ ID NO: 21              moltype = AA   length = 5
FEATURE                    Location/Qualifiers
REGION                     1..5
                           note = Description of Artificial Sequence: Synthetic peptide
source                     1..5
```

```
                        mol_type = protein
                        organism = synthetic construct
SEQUENCE: 21
TGGGG                                                                         5

SEQ ID NO: 22           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 22
SGGGG                                                                         5

SEQ ID NO: 23           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 23
TGGG                                                                          4

SEQ ID NO: 24           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 24
SGGG                                                                          4

SEQ ID NO: 25           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 25
GGGGS                                                                         5

SEQ ID NO: 26           moltype = AA  length = 344
FEATURE                 Location/Qualifiers
source                  1..344
                        mol_type = protein
                        organism = Homo sapiens
SEQUENCE: 26
MVRARHQPGG LCLLLLLLCQ FMEDRSAQAG NCWLRQAKNG RCQVLYKTEL SKEECCSTGR             60
LSTSWTEEDV NDNTLFKWMI FNGGAPNCIP CKETCENVDC GPGKKCRMNK KNKPRCVCAP            120
DCSNITWKGP VCGLDGKTYR NECALLKARC KEQPELEVQY QGRCKKTCRD VFCPGSSTCV            180
VDQTNNAYCV TCNRICPEPA SSEQYLCGND GVTYSSACHL RKATCLLGRS IGLAYEGKCI            240
KAKSCEDIQC TGGKKCLWDF KVGRGRCSLC DELCPDSKSD EPVCASDNAT YASECAMKEA            300
ACSSGVLLEV KHSGSCNSIS EDTEEEEEDE DQDYSFPISS ILEW                             344

SEQ ID NO: 27           moltype = AA  length = 317
FEATURE                 Location/Qualifiers
source                  1..317
                        mol_type = protein
                        organism = Homo sapiens
SEQUENCE: 27
MVRARHQPGG LCLLLLLLCQ FMEDRSAQAG NCWLRQAKNG RCQVLYKTEL SKEECCSTGR             60
LSTSWTEEDV NDNTLFKWMI FNGGAPNCIP CKETCENVDC GPGKKCRMNK KNKPRCVCAP            120
DCSNITWKGP VCGLDGKTYR NECALLKARC KEQPELEVQY QGRCKKTCRD VFCPGSSTCV            180
VDQTNNAYCV TCNRICPEPA SSEQYLCGND GVTYSSACHL RKATCLLGRS IGLAYEGKCI            240
KAKSCEDIQC TGGKKCLWDF KVGRGRCSLC DELCPDSKSD EPVCASDNAT YASECAMKEA            300
ACSSGVLLEV KHSGSCN                                                          317

SEQ ID NO: 28           moltype = AA  length = 63
FEATURE                 Location/Qualifiers
source                  1..63
                        mol_type = protein
                        organism = Homo sapiens
SEQUENCE: 28
GNCWLRQAKN GRCQVLYKTE LSKEECCSTG RLSTSWTEED VNDNTLFKWM IFNGGAPNCI             60
PCK                                                                          63
```

```
SEQ ID NO: 29          moltype = AA  length = 25
FEATURE                Location/Qualifiers
source                 1..25
                       mol_type = protein
                       organism = Homo sapiens
SEQUENCE: 29
ETCENVDCGP GKKCRMNKKN KPRCV                                        25

SEQ ID NO: 30          moltype = AA  length = 26
FEATURE                Location/Qualifiers
source                 1..26
                       mol_type = protein
                       organism = Homo sapiens
SEQUENCE: 30
KTCRDVFCPG SSTCVVDQTN NAYCVT                                       26

SEQ ID NO: 31          moltype = AA  length = 263
FEATURE                Location/Qualifiers
source                 1..263
                       mol_type = protein
                       organism = Homo sapiens
SEQUENCE: 31
MRPGAPGPLW PLPWGALAWA VGFVSSMGSG NPAPGGVCWL QQGQEATCSL VLQTDVTRAE   60
CCASGNIDTA WSNLTHPGNK INLLGFLGLV HCLPCKDSCD GVECGPGKAC RMLGGRPRCE   120
CAPDCSGLPA RLQVCGSDGA TYRDECELRA ARCRGHPDLS VMYRGRCRKS CEHVVCPRPQ   180
SCVVDQTGSA HCVVCRAAPC PVPSSPGQEL CGNNNVTYIS SCHMRQATCF LGRSIGVRHA   240
GSCAGTPEEP PGGESAEEEE NFV                                          263

SEQ ID NO: 32          moltype = AA  length = 344
FEATURE                Location/Qualifiers
REGION                 1..344
                       note = Description of Artificial Sequence: Synthetic
                        polypeptide
source                 1..344
                       mol_type = protein
                       organism = synthetic construct
SEQUENCE: 32
ILGRSETQEC LFFNANWEKD RTNQTGVEPC YGDKDKRRHC FATWKNISGS IEIVKQGCWL   60
DDINCYDRTD CVEKKDSPEV YFCCCEGNMC NEKFSYFPEM EVTQPTSNPV TPKPPTGGGT   120
HTCPPCPAPE LLGGPSVFLF PPKPKDTLMI SRTPEVTCVV VDVSHEDPEV KFNWYVDGVE   180
VHNAKTKPRE EQYNSTYRVV SVLTVLHQDW LNGKEYKCKV SNKALPVPIE KTISKAKGQP   240
REPQVYTLPP SREEMTKNQV SLTCLVKGFY PSDIAVEWES NGQPENNYKT TPPVLDSDGS   300
FFLYSKLTVD KSRWQQGNVF SCSVMHEALH NHYTQKSLSL SPGK                   344

SEQ ID NO: 33          moltype = AA  length = 21
FEATURE                Location/Qualifiers
source                 1..21
                       mol_type = protein
                       organism = Apis mellifera
SEQUENCE: 33
MKFLVNVALV FMVVYISYIY A                                            21

SEQ ID NO: 34          moltype = AA  length = 22
FEATURE                Location/Qualifiers
REGION                 1..22
                       note = Description of Unknown: Tissue plasminogen activator
                        (TPA) sequence
source                 1..22
                       mol_type = protein
                       organism = unidentified
SEQUENCE: 34
MDAMKRGLCC VLLLCGAVFV SP                                           22

SEQ ID NO: 35          moltype = AA  length = 20
FEATURE                Location/Qualifiers
REGION                 1..20
                       note = Description of Unknown: Native leader sequence
source                 1..20
                       mol_type = protein
                       organism = unidentified
SEQUENCE: 35
MGAAAKLAFA VFLISCSSGA                                              20

SEQ ID NO: 36          moltype = AA  length = 369
FEATURE                Location/Qualifiers
REGION                 1..369
                       note = Description of Artificial Sequence: Synthetic
                        polypeptide
```

```
source                      1..369
                            mol_type = protein
                            organism = synthetic construct
SEQUENCE: 36
MDAMKRGLCC VLLLCGAVFV SPGAAILGRS ETQECLFFNA NWEKDRTNQT GVEPCYGDKD      60
KRRHCFATWK NISGSIEIVK QGCWLDDINC YDRTDCVEKK DSPEVYFCCC EGNMCNEKFS     120
YFPPEMEVTQP TSNPVTPKPP TGGGTHTCPP CPAPELLGGP SVFLFPPKPK DTLMISRTPE    180
VTCVVVDVSH EDPEVKFNWY VDGVEVHNAK TKPREEQYNS TYRVVSVLTV LHQDWLNGKE     240
YKCKVSNKAL PVPIEKTISK AKGQPREPQV YTLPPSREEM TKNQVSLTCL VKGFYPSDIA     300
VEWESNGQPE NNYKTTPPVL DSDGSFFLYS KLTVDKSRWQ QGNVFSCSVM HEALHNHYTQ     360
KSLSLSPGK                                                            369

SEQ ID NO: 37               moltype = DNA  length = 1114
FEATURE                     Location/Qualifiers
misc_feature                1..1114
                            note = Description of Artificial Sequence: Synthetic
                             polynucleotide
source                      1..1114
                            mol_type = other DNA
                            organism = synthetic construct
SEQUENCE: 37
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta     120
attgggaaaa agacagaacc aatcaaactg gtgttgaacc gttatatggt gacaaagata     180
aacggcggca ttgttttgct acctggaaga atatttctgg ttccattgaa tagtgaaaca     240
aggttgttgg ctggatgata tcaactgcta tgacaggact gattgtgtag aaaaaaaaga     300
cagccctgaa gtatatttct gttgctgtga gggcaatatg tgtaatgaaa agttttctta     360
tttccggag atggaagtca cacagcccac ttcaaatcca gttacaccta agccaccac      420
cggtggtgga actcacacat gcccaccgtg cccagcacct gaactcctgg ggggaccgtc     480
agtcttcctc ttccccccaa aacccaagga caccctcatg atctcccgga ccctgaggt     540
cacatgcgtg gtggtggacg tgagccacga gaccctgag gtcaagttca actggtacgt      600
ggacggcgtg gaggtgcata atgccaagac aaagccgcgg gaggagcagt acaacagcac     660
gtaccgtgtg gtcagcgtcc tcaccgtcct gcaccaggac tggctgaatg caaggagta     720
caagtgcaag gtctccaaca aagccctccc agtcccatc gagaaaaccatctccaaagc     780
caaagggcag ccccgagaac cacaggtgta caccctgccc ccatcccggg aggagatgac     840
caagaaccag gtcagcctga cctgcctggt caaaggcttc tatcccagcg acatcgccgt     900
ggagtgggag agcaatgggc agccggagaa caactacaag accacgcctc ccgtgctgga    960
ctccgacggc tccttcttcc tctatagcaa gctcaccgtg gacaagagca ggtggcagca    1020
ggggaacgtc ttctcatgct ccgtgatgca tgaggctctg cacaaccact acacgcagaa    1080
gagcctctcc ctgtctccgg gtaaatgaga attc                                1114

SEQ ID NO: 38               moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 38
ILGRSETQE                                                              9

SEQ ID NO: 39               moltype = AA  length = 329
FEATURE                     Location/Qualifiers
REGION                      1..329
                            note = Description of Artificial Sequence: Synthetic
                             polypeptide
source                      1..329
                            mol_type = protein
                            organism = synthetic construct
SEQUENCE: 39
ILGRSETQEC LFFNANWEKD RTNQTGVEPC YGDKDKRRHC FATWKNISGS IEIVKQGCWL      60
DDINCYDRTD CVEKKDSPEV YFCCCEGNMC NEKFSYFPEM TGGGTHTCPP CPAPELLGGP     120
SVFLFPPKPK DTLMISRTPE VTCVVVDVSH EDPEVKFNWY VDGVEVHNAK TKPREEQYNS     180
TYRVVSVLTV LHQDWLNGKE YKCKVSNKAL PVPIEKTISK AKGQPREPQV YTLPPSREEM     240
TKNQVSLTCL VKGFYPSDIA VEWESNGQPE NNYKTTPPVL DSDGSFFLYS KLTVDKSRWQ     300
QGNVFSCSVM HEALHNHYTQ KSLSLSPGK                                      329

SEQ ID NO: 40               moltype = AA  length = 343
FEATURE                     Location/Qualifiers
REGION                      1..343
                            note = Description of Artificial Sequence: Synthetic
                             polypeptide
source                      1..343
                            mol_type = protein
                            organism = synthetic construct
SEQUENCE: 40
GRGEAETREC IYYNANWELE RTNQSGLERC EGEQDKRLHC YASWRNSSGT IELVKKGCWL      60
DDFNCYDRQE CVATEENPQV YFCCCEGNFC NERFTHLPEA GGPEVTYEPP PTAPTGGGTH     120
TCPPCPAPEL LGGPSVFLFP PKPKDTLMIS RTPEVTCVVV DSHEDPEVK FNWYVDGVEV     180
```

-continued

```
HNAKTKPREE QYNSTYRVVS VLTVLHQDWL NGKEYKCKVS NKALPVPIEK TISKAKGQPR  240
EPQVYTLPPS REEMTKNQVS LTCLVKGFYP SDIAVEWESN GQPENNYKTT PPVLDSDGSF  300
FLYSKLTVDK SRWQQGNVFS CSVMHEALHN HYTQKSLSLS PGK                   343

SEQ ID NO: 41            moltype = AA  length = 20
FEATURE                  Location/Qualifiers
REGION                   1..20
                         note = Description of Unknown: Native leader sequence
source                   1..20
                         mol_type = protein
                         organism = unidentified
SEQUENCE: 41
MGAAAKLAFA VFLISCSSGA                                              20

SEQ ID NO: 42            moltype = AA  length = 368
FEATURE                  Location/Qualifiers
REGION                   1..368
                         note = Description of Artificial Sequence: Synthetic
                         polypeptide
source                   1..368
                         mol_type = protein
                         organism = synthetic construct
SEQUENCE: 42
MDAMKRGLCC VLLLCGAVFV SPGASGRGEA ETRECIYYNA NWELERTNQS GLERCEGEQD   60
KRLHCYASWR NSSGTIELVK KGCWLDDFNC YDRQECVATE ENPQVYFCCC EGNFCNERFT  120
HLPEAGGPEV TYEPPPTAPT GGGTHTCPPC PAPELLGGPS VFLFPPKPKD TLMISRTPEV  180
TCVVVDVSHE DPEVKFNWYV DGVEVHNAKT KPREEQYNST YRVVSVLTVL HQDWLNGKEY  240
KCKVSNKALP VPIEKTISKA KGQPREPQVY TLPPSREEMT KNQVSLTCLV KGFYPSDIAV  300
EWESNGQPEN NYKTTPPVLD SDGSFFLYSK LTVDKSRWQQ GNVFSCSVMH EALHNHYTQK  360
SLSLSPGK                                                          368

SEQ ID NO: 43            moltype = DNA  length = 1107
FEATURE                  Location/Qualifiers
misc_feature             1..1107
                         note = Description of Artificial Sequence: Synthetic
                         polynucleotide
source                   1..1107
                         mol_type = other DNA
                         organism = synthetic construct
SEQUENCE: 43
atggatgcaa tgaagagagg gctctgctgt gtgctgctgc tgtgtggagc agtcttcgtt   60
tcgcccggcg cctctgggcg tggggaggct gagacacggg agtgcatcta ctacaacgcc  120
aactgggagc tggagcgcac caaccagagc ggcctggaag cgagcaggac                180
aagcggctgc actgctacgc ctcctggcgc aacagtctg gcaccatcga gctcgtgaag   240
aagggctgct ggctagatga cttcaactgc tacgataggc aggagtgtgt ggccactgag  300
gagaaccccc aggtgtactt ctgctgctgt gaaggcaact tctgcaacga gcgcttcact  360
catttgccag aggctggggg cccggaagtc acgtacgagc cacccccgac agcccccacc  420
ggtggtggaa ctcacacatg cccaccgtgc ccagcacctg aactcctggg gggaccgtca  480
gtcttcctct tccccccaaa acccaaggac accctcatga tctcccggac ccctgaggtc  540
acatgcgtgg tggtggacgt gagccacgaa gaccctgagg tcaagttcaa ctggtacgtg  600
gacggcgtgg aggtgcataa tgccaagaca aagccgcggg aggagcagta caacagcacg  660
taccgtgtgg tcagcgtcct caccgtcctg caccaggact ggctgaatgg caaggagtac  720
aagtgcaagg tctccaacaa agccctccca gtccccatcg agaaaaccat ctccaaagcc  780
aaagggcagc cccgagaacc acaggtgtac accctgcccc catcccggga ggagatgacc  840
aagaaccagg tcagcctgac ctgcctggtc aaaggcttct atcccagcga catcgccgtg  900
gagtgggaga gcaatgggca gccggagaac aactacaaga ccacgcctcc cgtgctggac  960
tccgacggct ccttcttcct ctatagcaag ctcaccgtgg acaagagcag gtggcagcag 1020
gggaacgtct tctcatgctc cgtgatgcat gaggctctgc acaaccacta cacgcagaag 1080
agcctctccc tgtctccggg taaatga                                    1107

SEQ ID NO: 44            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 44
GRGEAE                                                              6

SEQ ID NO: 45            moltype = AA  length = 335
FEATURE                  Location/Qualifiers
REGION                   1..335
                         note = Description of Artificial Sequence: Synthetic
                         polypeptide
source                   1..335
                         mol_type = protein
                         organism = synthetic construct
SEQUENCE: 45
```

```
ETRECIYYNA  NWELERTNQS  GLERCEGEQD  KRLHCYASWR  NSSGTIELVK  KGCWLDDFNC   60
YDRQECVATE  ENPQVYFCCC  EGNFCNERFT  HLPEAGGPEV  TYEPPPTGGG  THTCPPCPAP  120
ELLGGPSVFL  FPPKPKDTLM  ISRTPEVTCV  VVDVSHEDPE  VKFNWYVDGV  EVHNAKTKPR  180
EEQYNSTYRV  VSVLTVLHQD  WLNGKEYKCK  VSNKALPAPI  EKTISKAKGQ  PREPQVYTLP  240
PSREEMTKNQ  VSLTCLVKGF  YPSDIAVEWE  SNGQPENNYK  TTPPVLDSDG  SFFLYSKLTV  300
DKSRWQQGNV  FSCSVMHEAL  HNHYTQKSLS  LSPGK                               335

SEQ ID NO: 46           moltype = AA   length = 343
FEATURE                 Location/Qualifiers
REGION                  1..343
                        note = Description of Artificial Sequence: Synthetic
                        polypeptide
source                  1..343
                        mol_type = protein
                        organism = synthetic construct
SEQUENCE: 46
GRGEAETREC  IYYNANWELE  RTNQSGLERC  EGEQDKRLHC  YASWRNSSGT  IELVKKGCWD   60
DDFNCYDRQE  CVATEENPQV  YFCCCEGNFC  NERFTHLPEA  GGPEVTYEPP  PTAPTGGGTH  120
TCPPCPAPEL  LGGPSVFLFP  PKPKDTLMIS  RTPEVTCVVV  DVSHEDPEVK  FNWYVDGVEV  180
HNAKTKPREE  QYNSTYRVVS  VLTVLHQDWL  NGKEYKCKVS  NKALPVPIEK  TISKAKGQPR  240
EPQVYTLPPS  REEMTKNQVS  LTCLVKGFYP  SDIAVEWESN  GQPENNYKTT  PPVLDSDGSF  300
FLYSKLTVDK  SRWQQGNVFS  CSVMHEALHN  HYTQKSLSLS  PGK                     343

SEQ ID NO: 47           moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 47
GRGEAETREC  IYYNANWELE  RTNQSGLERC  EGEQDKRLHC  YASWRNSSGT  IELVKKGCWD   60
DDFNCYDRQE  CVATEENPQV  YFCCCEGNFC  NERFTHLPEA  GGPEVTYEPP  PTAPT       115

SEQ ID NO: 48           moltype = AA   length = 368
FEATURE                 Location/Qualifiers
REGION                  1..368
                        note = Description of Artificial Sequence: Synthetic
                        polypeptide
source                  1..368
                        mol_type = protein
                        organism = synthetic construct
SEQUENCE: 48
MDAMKRGLCC  VLLLCGAVFV  SPGASGRGEA  ETRECIYYNA  NWELERTNQS  GLERCEGEQD   60
KRLHCYASWR  NSSGTIELVK  KGCWDDDFNC  YDRQECVATE  ENPQVYFCCC  EGNFCNERFT  120
HLPEAGGPEV  TYEPPPTAPT  GGGTHTCPPC  PAPELLGGPS  VFLFPPKPKD  TLMISRTPEV  180
TCVVVDVSHE  DPEVKFNWYV  DGVEVHNAKT  KPREEQYNST  YRVVSVLTVL  HQDWLNGKEY  240
KCKVSNKALP  APIEKTISKA  KGQPREPQVY  TLPPSREEMT  KNQVSLTCLV  KGFYPSDIAV  300
EWESNGQPEN  NYKTTPPVLD  SDGSFFLYSK  LTVDKSRWQQ  GNVFSCSVMH  EALHNHYTQK  360
SLSLSPGK                                                                368

SEQ ID NO: 49           moltype = DNA   length = 1107
FEATURE                 Location/Qualifiers
misc_feature            1..1107
                        note = Description of Artificial Sequence: Synthetic
                        polynucleotide
source                  1..1107
                        mol_type = other DNA
                        organism = synthetic construct
SEQUENCE: 49
atggatgcaa tgaagagagg gctctgctgt gtgctgctgc tgtgtggagc agtcttcgtt   60
tcgcccggcg cctctgggcg tggggaggct gagacacggg agtgcatcta ctacaacgcc  120
aactgggagc tggagcgcac caaccagagc ggcctggaac gcgagcaggac  180
aagcggctgc actgctacgc ctcctggcgc aacagtctg gcaccatcga gctcgtgaag  240
aagggctgct gggacgatga cttcaactgc tacgataggc aggagtgtgt ggccactgag  300
gagaaccccc aggtgtactt ctgctgctgt gaaggcaact tctgcaacga gcgcttcact  360
catttgccag aggctggggg cccggaagtc acgtacgagc cacccccgac agcccccacc  420
ggtggtggaa ctcacacatg cccaccgtgc ccagcacctg aactcctggg gggaccgtca  480
gtcttcctct tccccccaaa acccaaggac accctcatga tctcccggac ccctgaggtc  540
acatgcgtgg tggtggacgt gagccacgaa gaccctgagg tcaagttcaa ctggtacgtg  600
gacggcgtgg aggtgcataa tgccaagaca aagccgcggg aggagcagta caacagcacg  660
taccgtgtgg tcagcgtcct caccgtcctg caccaggact ggctgaatgg caaggagtac  720
aagtgcaagg tctccaacaa agccctccca gtccccatcg agaaaaccat ctccaaagcc  780
aaagggcagc ccgagaacc acaggtgtac accctgcccc catcccggga ggagatgacc  840
aagaaccagg tcagcctgac ctgcctggtc aaaggcttct atcccagcga catcgccgtg  900
gagtgggaga gcaatgggca gccggagaac aactacaaga ccacgcctcc cgtgctggac  960
tccgacggct ccttcttcct ctatagcaag ctcaccgtgg acaagagcag gtggcagcag 1020
gggaacgtct tctcatgctc cgtgatgcat gaggctctgc acaaccacta cacgcagaag 1080
```

-continued

```
agcctctccc tgtctccggg taaatga                                              1107

SEQ ID NO: 50              moltype = AA  length = 141
FEATURE                    Location/Qualifiers
source                     1..141
                           mol_type = protein
                           organism = Homo sapiens
SEQUENCE: 50
GRGEAETREC IYYNANWELE RTNQSGLERC EGEQDKRLHC YASWRNSSGT IELVKKGCWL           60
DDFNCYDRQE CVATEENPQV YFCCCEGNFC NERFTHLPEA GGPEGPWAST TIPSGGPEAT          120
AAAGDQGSGA LWLCLEGPAH E                                                    141

SEQ ID NO: 51              moltype = AA  length = 141
FEATURE                    Location/Qualifiers
REGION                     1..141
                           note = Description of Artificial Sequence: Synthetic
                            polypeptide
source                     1..141
                           mol_type = protein
                           organism = synthetic construct
SEQUENCE: 51
GRGEAETREC IYYNANWELE RTNQSGLERC EGEQDKRLHC YASWRNSSGT IELVKKGCWD           60
DDFNCYDRQE CVATEENPQV YFCCCEGNFC NERFTHLPEA GGPEGPWAST TIPSGGPEAT          120
AAAGDQGSGA LWLCLEGPAH E                                                    141

SEQ ID NO: 52              moltype = AA  length = 370
FEATURE                    Location/Qualifiers
REGION                     1..370
                           note = Description of Artificial Sequence: Synthetic
                            polypeptide
source                     1..370
                           mol_type = protein
                           organism = synthetic construct
SEQUENCE: 52
GRGEAETREC IYYNANWELE RTNQSGLERC EGEQDKRLHC YASWRNSSGT IELVKKGCWD           60
DDFNCYDRQE CVATEENPQV YFCCCEGNFC NERFTHLPEA GGPEGPWAST TIPSGGPEAT          120
AAAGDQGSGA LWLCLEGPAH ETGGGTHTCP PCPAPELLGG PSVFLFPPKP KDTLMISRTP          180
EVTCVVVDVS HEDPEVKFNW YVDGVEVHNA KTKPREEQYN STYRVVSVLT VLHQDWLNGK          240
EYKCKVSNKA LPAPIEKTIS KAKGQPREPQ VYTLPPSREE MTKNQVSLTC LVKGFYPSDI          300
AVEWESNGQP ENNYKTTPPV LDSDGSFFLY SKLTVDKSRW QQGNVFSCSV MHEALHNHYT          360
QKSLSLSPGK                                                                 370

SEQ ID NO: 53              moltype = AA  length = 150
FEATURE                    Location/Qualifiers
source                     1..150
                           mol_type = protein
                           organism = Rattus sp.
SEQUENCE: 53
MTAPWAALAL LWGSLCAGSG RGEAETRECI YYNANWELER TNQSGLERCE GEQDKRLHCY           60
ASWPNSSGTI ELVKKGCWLD DFNCYDRQEC VATEENPQVY FCCCEGNFCN ERFTHLPEPG          120
GPEVTYEPPP TAPTLLTVLA YSLLPIGGLS                                           150

SEQ ID NO: 54              moltype = AA  length = 150
FEATURE                    Location/Qualifiers
source                     1..150
                           mol_type = protein
                           organism = Sus scrofa
SEQUENCE: 54
MTAPWAALAL LWGSLCVGSG RGEAETRECI YYNANWELER TNQSGLERCE GEQDKRLHCY           60
ASWRNSSGTI ELVKKGCWLD DFNCYDRQEC VATEENPQVY FCCCEGNFCN ERFTHLPEAG          120
GPEVTYEPPP TAPTLLTVLA YSLLPIGGLS                                           150

SEQ ID NO: 55              moltype = AA  length = 150
FEATURE                    Location/Qualifiers
source                     1..150
                           mol_type = protein
                           organism = Mus musculus
SEQUENCE: 55
MTAPWAALAL LWGSLCAGSG RGEAETRECI YYNANWELER TNQSGLERCE GEQDKRLHCY           60
ASWRNSSGTI ELVKKGCWLD DFNCYDRQEC VATEENPQVY FCCCEGNFCN ERFTHLPEPG          120
GPEVTYEPPP TAPTLLTVLA YSLLPIGGLS                                           150

SEQ ID NO: 56              moltype = AA  length = 150
FEATURE                    Location/Qualifiers
source                     1..150
                           mol_type = protein
                           organism = Homo sapiens
SEQUENCE: 56
MTAPWVALAL LWGSLCAGSG RGEAETRECI YYNANWELER TNQSGLERCE GEQDKRLHCY           60
```

```
ASWRNSSGTI ELVKKGCWLD DFNCYDRQEC VATEENPQVY FCCCEGNFCN ERFTHLPEAG    120
GPEVTYEPPP TAPTLLTVLA YSLLPIGGLS                                    150

SEQ ID NO: 57           moltype = AA  length = 150
FEATURE                 Location/Qualifiers
source                  1..150
                        mol_type = protein
                        organism = Bos taurus
SEQUENCE: 57
MTAPWAALAL LWGSLCAGSG RGEAETRECI YYNANWELER TNQSGLERCE GERDKRLHCY    60
ASWRNSSGTI ELVKKGCWLD DFNCYDRQEC VATEENPQVY FCCCEGNFCN ERFTHLPEAG   120
GPEVTYEPPP TAPTLLTVLA YSLLPVGGLS                                    150

SEQ ID NO: 58           moltype = AA  length = 150
FEATURE                 Location/Qualifiers
source                  1..150
                        mol_type = protein
                        organism = Xenopus sp.
SEQUENCE: 58
MGASVALTFL LLLATFRAGS GHDEVETREC IYYNANWELE KTNQSGVERL VEGKKDKRLH    60
CYASWRNNSG FIELVKKGCW LDDFNCYDRQ ECIAKEENPQ VFFCCCEGNY CNKKFTHLPE   120
VETFDPKPQP SASVLNILIY SLLPIVGLSM                                    150

SEQ ID NO: 59           moltype = AA  length = 150
FEATURE                 Location/Qualifiers
source                  1..150
                        mol_type = protein
                        organism = Homo sapiens
SEQUENCE: 59
MGAAAKLAFA VFLISCSSGA ILGRSETQEC LFFNANWEKD RTNQTGVEPC YGDKDKRRHC    60
FATWKNISGS IEIVKQGCWL DDINCYDRTD CVEKKDSPEV YFCCCEGNMC NEKFSYFPEM   120
EVTQPTSNPV TPKPPYYNIL LYSLVPLMLI                                    150

SEQ ID NO: 60           moltype = AA  length = 154
FEATURE                 Location/Qualifiers
REGION                  1..154
                        note = Description of Artificial Sequence: Synthetic
                         consensus sequence
MOD_RES                 8
                        note = Thr, Ala or absent
MOD_RES                 121
                        note = Pro, Ala, Val or Met
source                  1..154
                        mol_type = protein
                        organism = synthetic construct
SEQUENCE: 60
MTAPWAAXLA LLWGSLCAGS GRGEAETREC IYYNANWELE RTNQSGLERL CEGEQDKRLH    60
CYASWRNSSG TIELVKKGCW LDDFNCYDRQ ECVATEENPQ VYFCCCEGNF CNERFTHLPE   120
XGGPEVTYEP KPPTAPTLLT VLAYSLLPIG GLSM                               154

SEQ ID NO: 61           moltype = AA  length = 115
FEATURE                 Location/Qualifiers
source                  1..115
                        mol_type = protein
                        organism = Homo sapiens
SEQUENCE: 61
ILGRSETQEC LFFNANWEKD RTNQTGVEPC YGDKDKRRHC FATWKNISGS IEIVKQGCWL    60
DDINCYDRTD CVEKKDSPEV YFCCCEGNMC NEKFSYFPEM EVTQPTSNPV TPKPP        115

SEQ ID NO: 62           moltype = AA  length = 115
FEATURE                 Location/Qualifiers
source                  1..115
                        mol_type = protein
                        organism = Ovis aries
SEQUENCE: 62
ILGRSETQEC IFYNANWERD RTNRTGVESC YGDKDKRRHC FATWKNISGS IDIVKQGCWL    60
DDINCYDRTD CIEKKDSPEV YFCCCEGNMC NERFSYFPEM EVTQPTSNPV TPKPP        115

SEQ ID NO: 63           moltype = AA  length = 115
FEATURE                 Location/Qualifiers
source                  1..115
                        mol_type = protein
                        organism = Condylura cristata
SEQUENCE: 63
ILGRSETQEC LFFNANWERD RTNQTGVEPC YGDKDKRRHC FATWKNISGS IEIVKQGCWL    60
DDINCYDRTD CIEKKDSPEV YFCCCEGNMC NEKFSYFPEM EVTQPTSNPV TPKAP        115

SEQ ID NO: 64           moltype = AA  length = 115
FEATURE                 Location/Qualifiers
```

```
source                  1..115
                        mol_type = protein
                        organism = Mus musculus
SEQUENCE: 64
ILGRSETQEC LFFNANWERD RTNQTGVEPC YGDKDKRRHC FATWKNISGS IEIVKQGCWL    60
DDINCYDRTD CIEKKDSPEV YFCCCEGNMC NEKFSYFPEM EVTQPTSNPV TPKPP        115

SEQ ID NO: 65           moltype = AA  length = 115
FEATURE                 Location/Qualifiers
source                  1..115
                        mol_type = protein
                        organism = Gallus gallus
SEQUENCE: 65
ILGRSETQEC IYYNANWEKD KTNRSGIEPC YGDKDKRRHC FATWKNISGS IEIVKQGCWL    60
DDINCYDRND CIEKKDSPEV FFCCCEGNMC NERFFYFPEM EVTQPTSNPV TPKPP        115

SEQ ID NO: 66           moltype = AA  length = 115
FEATURE                 Location/Qualifiers
source                  1..115
                        mol_type = protein
                        organism = Bos taurus
SEQUENCE: 66
ILGRSETQEC IFYNANWERD RTNRTGVESC YGDKDKRRHC FATWKNISGS IEIVKQGCWL    60
DDINCYDRTD CIEKKDSPEV YFCCCEGNMC NERFSYFPEM EVTQPTSNPV TPKPP        115

SEQ ID NO: 67           moltype = AA  length = 115
FEATURE                 Location/Qualifiers
source                  1..115
                        mol_type = protein
                        organism = Tyto alba
SEQUENCE: 67
ILGRSETQEC IYYNANWEKD KTNRSGIEPC YGDKDKRRHC FATWKNISGS IEIVKQGCWL    60
DDINCYDRND CIEKKDSPEV FFCCCEGNMC NERFFYFPEM EVTQPTSNPV TPKPP        115

SEQ ID NO: 68           moltype = AA  length = 115
FEATURE                 Location/Qualifiers
source                  1..115
                        mol_type = protein
                        organism = Myotis davidii
SEQUENCE: 68
ILGRSETQEC IFYNANWERD KTNRTGVELC YGDKDKRRHC FATWKNISGS IEIVKQGCWL    60
DDINCYDRTD CIEKKDSPEV YFCCCEGNMC NERFSYFPEM EVTQPTSNPV TPKPP        115

SEQ ID NO: 69           moltype = AA  length = 360
FEATURE                 Location/Qualifiers
REGION                  1..360
                        note = Description of Artificial Sequence: Synthetic
                         polypeptide
source                  1..360
                        mol_type = protein
                        organism = synthetic construct
SEQUENCE: 69
MDAMKRGLCC VLLLCGAVFV SPGAAETREC IYYNANWELE RTNQSGLERC EGEQDKRLHC    60
YASWRNSSGT IELVKKGCWL DDFNCYDRQE CVATEENPQV YFCCCEGNFC NERFTHLPEA   120
GGPEVTYEPP PTGGGTHTCP PCPAPELLGG PSVFLFPPKP KDTLMISRTP EVTCVVVDVS   180
HEDPEVKFNW YVDGVEVHNA KTKPREEQYN STYRVVSVLT VLHQDWLNGK EYKCKVSNKA   240
LPAPIEKTIS KAKGQPREPQ VYTLPPSREE MTKNQVSLTC LVKGFYPSDI AVEWESNGQP   300
ENNYKTTPPV LDSDGSFFLY SKLTVDKSRW QQGNVFSCSV MHEALHNHYT QKSLSLSPGK   360

SEQ ID NO: 70           moltype = DNA  length = 1083
FEATURE                 Location/Qualifiers
misc_feature            1..1083
                        note = Description of Artificial Sequence: Synthetic
                         polynucleotide
source                  1..1083
                        mol_type = other DNA
                        organism = synthetic construct
CDS                     73..396
SEQUENCE: 70
atggatgcaa tgaagagagg gctctgctgt gtgctgctgc tgtgtggagc agtcttcgtt    60
tcgcccggcg ccgctgagac acgggagtgc atctactaca acgccaactg ggagctggag   120
cgcaccaacc agagcggcct ggagcgctgc gaaggcgagc aggacaagcg gctgcactgc   180
tacgcctcct ggcgcaacag ctctggcacc atcgagctcg tgaagaaggg ctgctggcta   240
gatgacttca actgctacga taggcaggag tgtgtggcca ctgaggagaa cccccaggtg   300
tacttctgct gctgtgaagg caacttctgc aacgagcgct tcactcattt gccagaggct   360
ggggccccgg aagtcacgta cgagccaccc ccgacaggtg gtggaactca cacatgccca   420
ccgtgcccag cacctgaact cctgggggga cgtcagtct  tcctcttccc cccaaaaccc   480
aaggacaccc tcatgatctc ccggacccct gaggtcacat gcgtggtggt ggacgtgagc   540
cacgaagacc ctgaggtcaa gttcaactgg tacgtggacg gcgtggaggt gcataatgcc   600
```

```
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag ggcagccccg agaaccacag    780
gtgtacaccc tgcccccatc ccgggaggag atgaccaaga accaggtcag cctgacctgc    840
ctggtcaaag gcttctatcc cagcgacatc gccgtggag tgggagcaa tgggcagccg      900
gagaacaact acaagaccac gcctcccgtg ctggactccg acggctcctt cttcctctat    960
agcaagctca ccgtggacaa gagcaggtgg cagcagggga acgtcttctc atgctccgtg   1020
atgcatgagg ctctgcacaa ccactacacg cagaagagcc tctccctgtc cccgggtaaa   1080
tga                                                                 1083

SEQ ID NO: 71          moltype = DNA   length = 1083
FEATURE                Location/Qualifiers
misc_feature           1..1083
                       note = Description of Artificial Sequence: Synthetic
                       polynucleotide
source                 1..1083
                       mol_type = other DNA
                       organism = synthetic construct
SEQUENCE: 71
tcatttaccc ggggacaggg agaggctctt ctgcgtgtag tggttgtgca gagcctcatg     60
catcacggag catgagaaga cgttcccctg ctgccacctg ctcttgtcca cggtgagctt    120
gctatagagg aagaaggagc cgtcggagtc cagcacggga ggcggtgtct tgtagttgtt    180
ctccggctgc ccattgctct cccactccac ggcgatgtcg ctgggataga agcctttgac    240
caggcaggtc aggctgacct ggttcttggt catctcctcc cggatgggg gcagggtgta    300
cacctgtggt tctcggggct gccctttggc tttggagatg gttttctcga tggggctgg   360
gagggctttg ttggagacct tgcacttgta ctccttgaca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcaggggtc cggagatca tgagggtgtc     600
cttgggttttt ggggggaaga ggaagactga cggtccccc aggagttcag gtgctgggca    660
cggtgggcat gtgtgagttc caccaccgt cgggggtggc tcgtacgtga cttccgggcc    720
cccagcctct ggcaaatgag tgaagcgctc gttcagaag ttgccttcac agcagcagaa    780
gtacacctgg gggttctcct cagtggccac acactcctgc ctatcgtagc agttgaagtc    840
atctagccag cagcccttct tcacgagctc gatggtgcca gagctgttgc gccaggaggc    900
gtagcagtga agccgcttgt cctgctcgcc ttcgcagcgc tccaggccgc tctggttggt    960
gcgctccagc tcccagttgg cgttgtagta gatgcactcc cgtgtctcag cggcgccggg   1020
cgaaacgaag actgctccac acagcagcag cacacagcag agccctctct tcattgcatc   1080
cat                                                                 1083

SEQ ID NO: 72          moltype = DNA   length = 1083
FEATURE                Location/Qualifiers
misc_feature           1..1083
                       note = Description of Artificial Sequence: Synthetic
                       polynucleotide
source                 1..1083
                       mol_type = other DNA
                       organism = synthetic construct
CDS                    73..396
SEQUENCE: 72
atggatgcaa tgaagagagg gctctgctgt gtgctgctgc tgtgtggagc agtcttcgtt     60
tcgcccggcg ccgccgaaac ccgcgaatgt atttattaca atgctaattg ggaactgaa    120
cggacgaacc aatccgggct cgaacggtgt gaggggaac aggataaacg cctccattgc    180
tatgcgtcgt ggaggaactc ctccgggacg attgaactgg tcaagaaagg gtgctggctg    240
gacgatttca attgttatga ccgccaggaa tgtgtcgcga ccgaagagaa tccgcaggtc    300
tatttctgtt gttgcgaggg gaatttctgt aatgaacggt ttacccacct ccccgaagcc    360
ggcgggcccg aggtgaccta tgaacccccg cccaccggtg gtgaactca cacatgccca    420
ccgtgcccag cacctgaact cctggggga cgtcagtct tcctcttccc cccaaaaccc    480
aaggacaccc tcatgatctc ccggacccct gaggtcacat gcgtggtggt ggacgtgagc    540
cacgaagacc ctgaggtcaa gttcaactgg tacgtggacg gcgtggaggt gcataatgac    600
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag ggcagccccg agaaccacag    780
gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga acgtcttctc atgctccgtg   1020
atgcatgagg ctctgcacaa ccactacacg cagaagagcc tctccctgtc cccgggtaaa   1080
tga                                                                 1083

SEQ ID NO: 73          moltype = DNA   length = 1083
FEATURE                Location/Qualifiers
misc_feature           1..1083
                       note = Description of Artificial Sequence: Synthetic
                       polynucleotide
source                 1..1083
                       mol_type = other DNA
                       organism = synthetic construct
SEQUENCE: 73
tcatttaccc ggggacaggg agaggctctt ctgcgtgtag tggttgtgca gagcctcatg     60
```

```
catcacggag catgagaaga cgttccsctg ctgccacctg ctcttgtcca cggtgagctt    120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcc cgggatgggg gcagggtgta    300
cacctgtggt tctcgggct gcccctttggc tttggagagt gttttctcga tggggggctgg   360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcaggggtc cggagatca tgagggtgtc     600
cttgggtttt gggggaaga ggaagactga cggtccccc aggagttcag gtgctgggca     660
cggtgggcat gtgtgagttc caccaccggt gggcgggggt tcataggtca cctcgggccc    720
gccggcttcg gggaggtggg taaaccgttc attacagaaa ttcccctcgc aacaacagaa    780
atagacctgc ggattctctt cggtcgcgac acattcctgg cggtcataac aattgaaatc    840
gtccagccag cacccttct tgaccagtca aatcgtcccg gaggagttcc tccacgacgc     900
atagcaatgg aggcgtttat cctgttcccc ctcacaccgt tcgagcccgg attggttcgt    960
ccgttcgagt tcccaattag cattgtaata aatacattcg cgggtttcgg cggcgccggg   1020
cgaaacgaag actgctccac acagcagcag cacacagcag agccctctct tcattgcatc   1080
cat                                                                   1083

SEQ ID NO: 74          moltype = AA  length = 368
FEATURE                Location/Qualifiers
REGION                 1..368
                       note = Description of Artificial Sequence: Synthetic
                       polypeptide
source                 1..368
                       mol_type = protein
                       organism = synthetic construct
SEQUENCE: 74
MDAMKRGLCC VLLLCGAVFV SPGASGRGEA ETRECIYYNA NWELERTNQS GLERCEGEQD     60
KRLHCYASWR NSSGTIELVK KGCWDDDFNC YDRQECVATE ENPQVYFCCC EGNFCNERFT    120
HLPEAGGPEV TYEPPPTAPT GGGTHTCPPC PAPELLGGPS VFLFPPKPKD TLMISRTPEV    180
TCVVVDVSHE DPEVKFNWYV DGVEVHNAKT KPREEQYNST YRVVSVLTVL HQDWLNGKEY    240
KCKVSNKALP APIEKTISKA KGQPREPQVY TLPPSREEMT KNQVSLTCLV KGFYPSDIAV    300
EWESNGQPEN NYKTTPPVLD SDGSFFLYSK LTVDKSRWQQ GNVFSCSVMH EALHNHYTQK    360
SLSLSPGK                                                             368

SEQ ID NO: 75          moltype = DNA  length = 1107
FEATURE                Location/Qualifiers
misc_feature           1..1107
                       note = Description of Artificial Sequence: Synthetic
                       polynucleotide
source                 1..1107
                       mol_type = other DNA
                       organism = synthetic construct
SEQUENCE: 75
atggatgcaa tgaagagagg gctctgctgt gtgctgctgc tgtgtggagc agtcttcgtt     60
tcgcccggcg cctctgggcg tggggaggct gagacacggg agtgcatcta ctacaacgcc    120
aactgggagc tggagcgcac caaccagagc ggcctggagc gctgcgaagg cgagcaggac    180
aagcggctgc actgctacgc ctcctggcgc aacagctctg gcaccatcga gctcgtgaag    240
aagggctgct gggatgatga cttcaactgc tacgataggc aggagtgtgt ggccactgag    300
gagaacccc aggtgtactt ctgctgctgt gaaggcaact tctgcaacga gcgcttcact    360
catttgccag aggctggggg cccggaagtc acgtacgagc cacccccgac agcccccacc    420
ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtccccggg taaatga                                        1107

SEQ ID NO: 76          moltype = DNA  length = 1107
FEATURE                Location/Qualifiers
misc_feature           1..1107
                       note = Description of Artificial Sequence: Synthetic
                       polynucleotide
source                 1..1107
                       mol_type = other DNA
                       organism = synthetic construct
SEQUENCE: 76
tcatttaccc ggggacaggg agaggctctt ctgcgtgtag tggttgtgca gagcctcatg     60
catcacggag catgagaaga cgttcccctg ctgccacctg ctcttgtcca cggtgagctt    120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcc cgggatgggg gcagggtgta    300
```

```
cacctgtggt tctcgggget gcccttggc tttggagatg gttttctcga tgggggetgg    360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcagggtc cgggagatca tgagggtgtc    600
cttgggtttt ggggggaaga ggaagactga cggtccccc aggagttcag gtgctgggca    660
cggtgggcat gtgtgagttc caccaccggt ggggctgtc gggggtggct cgtacgtgac    720
ttccgggccc ccagcctctg gcaaatgagt gaagcgctcg ttgcagaagt tgccttcaca    780
gcagcagaag tacacctggg ggttctcctc agtggccaca cactcctgcc tatcgtagca    840
gttgaagtca tcatcccagc agcccttctt cacgagctcg atggtgccag agctgttgcg    900
ccaggaggcg tagcagtgca gccgcttgtc ctgctcgcct tcgcagcgct ccaggccgct    960
ctggttggtg cgctccagct cccagttggc gttgtagtag atgcactccc gtgtctcagc    1020
ctccccacgc ccagaggcgc cgggcgaaac gaagactgct ccacacagca gcagcacaca    1080
gcagagccct ctcttcattg catccat                                         1107

SEQ ID NO: 77          moltype = AA  length = 360
FEATURE                Location/Qualifiers
REGION                 1..360
                       note = Description of Artificial Sequence: Synthetic
                       polypeptide
source                 1..360
                       mol_type = protein
                       organism = synthetic construct
SEQUENCE: 77
MDAMKRGLCC VLLLCGAVFV SPGAAETREC IYYNANWELE RTNQSGLERC EGEQDKRLHC   60
YASWRNSSGT IELVKKGCWD DDFNCYDRQE CVATEENPQV YFCCCEGNFC NERFTHLPEA   120
GGPEVTYEPP PTGGGTHTCP PCPAPELLGG PSVFLFPPKP KDTLMISRTP EVTCVVVDVS   180
HEDPEVKFNW YVDGVEVHNA KTKPREEQYN STYRVVSVLT VLHQDWLNGK EYKCKVSNKA   240
LPAPIEKTIS KAKGQPREPQ VYTLPPSREE MTKNQVSLTC LVKGFYPSDI AVEWESNGQP   300
ENNYKTTPPV LDSDGSFFLY SKLTVDKSRW QQGNVFSCSV MHEALHNHYT QKSLSLSPGK   360

SEQ ID NO: 78          moltype = AA  length = 335
FEATURE                Location/Qualifiers
REGION                 1..335
                       note = Description of Artificial Sequence: Synthetic
                       polypeptide
source                 1..335
                       mol_type = protein
                       organism = synthetic construct
SEQUENCE: 78
ETRECIYYNA NWELERTNQS GLERCEGEQD KRLHCYASWR NSSGTIELVK KGCWDDDFNC   60
YDRQECVATE ENPQVYFCCC EGNFCNERFT HLPEAGGPEV TYEPPPTGGG THTCPPCPAP   120
ELLGGPSVFL FPPKPKDTLM ISRTPEVTCV VVDVSHEDPE VKFNWYVDGV EVHNAKTKPR   180
EEQYNSTYRV VSVLTVLHQD WLNGKEYKCK VSNKALPAPI EKTISKAKGQ PREPQVYTLP   240
PSREEMTKNQ VSLTCLVKGF YPSDIAVEWE SNGQPENNYK TTPPVLDSDG SFFLYSKLTV   300
DKSRWQQGNV FSCSVMHEAL HNHYTQKSLS LSPGK                               335

SEQ ID NO: 79          moltype = AA  length = 107
FEATURE                Location/Qualifiers
REGION                 1..107
                       note = Description of Artificial Sequence: Synthetic
                       polypeptide
source                 1..107
                       mol_type = protein
                       organism = synthetic construct
SEQUENCE: 79
ETRECIYYNA NWELERTNQS GLERCEGEQD KRLHCYASWR NSSGTIELVK KGCWDDDFNC   60
YDRQECVATE ENPQVYFCCC EGNFCNERFT HLPEAGGPEV TYEPPPT                  107

SEQ ID NO: 80          moltype = DNA  length = 1083
FEATURE                Location/Qualifiers
misc_feature           1..1083
                       note = Description of Artificial Sequence: Synthetic
                       polynucleotide
source                 1..1083
                       mol_type = other DNA
                       organism = synthetic construct
CDS                    76..396
SEQUENCE: 80
atgqatgcaa tgaagagagg gctctgctgt gtgctgctgc tgtgtggagc agtcttcgtt    60
tcgcccggcg ccgctgagac acgggagtgc atctactaca acgccaactg ggagctggag    120
cgcaccaacc agagcggcct ggagcgctgc gaaggcgagc aggacaagcg gctgcactgc    180
tacgcctcct ggcgcaacag ctctggcacc atcgagctcg tgaagaaggg ctgctgggac    240
gatgacttca actgctacga taggcaggag tgtgtggcca ctgaggagaa ccccaggtg    300
tacttctgct gctgtgaagg caacttctgc aacgagcgct tcactcattt gccagaggct    360
gggggccccg aagtcacgta cgagccaccc ccgacaggtg gtggaactca cacatgccca    420
ccgtgcccag cacctgaact cctggggga ccgtcagtct tcctcttccc cccaaaaccc    480
aaggacaccc tcatgatctc ccggaccct gaggtcacat gcgtggtggt ggacgtgagc    540
cacgaagacc ctgaggtcaa gttcaactgg tacgtggacg gcgtggaggt gcataatgcc    600
```

```
aagacaaagc cgcgggagga gcagtacaac agcacgtacc gtgtggtcag cgtcctcacc   660
gtcctgcacc aggactggct gaatggcaag gagtacaagt gcaaggtctc caacaaagcc   720
ctcccagccc ccatcgagaa aaccatctcc aaagccaaag gcagccccg agaaccacag    780
gtgtacaccc tgcccccatc ccgggaggag atgaccaaga accaggtcag cctgacctgc   840
ctggtcaaag gcttctatcc cagcgacatc gccgtggagt gggagagcaa tgggcagccg   900
gagaacaact acaagaccac gcctcccgtg ctggactccg acggctcctt cttcctctat   960
agcaagctca ccgtggacaa gagcaggtgg cagcagggga cgtcttctc atgctccgtg    1020
atgcatgagg ctctgcacaa ccactacacg cagaagagcc tctccctgtc cccgggtaaa   1080
tga                                                                1083

SEQ ID NO: 81           moltype = DNA  length = 1083
FEATURE                 Location/Qualifiers
misc_feature            1..1083
                        note = Description of Artificial Sequence: Synthetic
                         polynucleotide
source                  1..1083
                        mol_type = other DNA
                        organism = synthetic construct
SEQUENCE: 81
tcatttaccc ggggacaggg agaggctctt ctgcgtgtag tggttgtgca gagcctcatg    60
catcacggag catgagaaga cgttcccctg ctgccacctg ctcttgtcca cggtgagctt   120
gctatagagg aagaaggagc cgtcggagtc cagcacgggg ggcgtggtct tgtagttgtt   180
ctccggctgc ccattgctct cccactccac ggcgatgtcg ctgggataga agcctttgac   240
caggcaggtc aggctgacct ggttcttggt catctcctcc cgggatgggg gcagggtgta   300
cacctgtggt tctcggggct gcccttggc tttggagatg gttttctcga tggggctgg    360
gagggctttg ttggagacct tgcacttgta ctccttgaca ttcagccagt cctggtgcag   420
gacggtgagg acgctgacca cacggtacgt gctgttgtac tgctcctccc gcggctttgt   480
cttggcatta tgcacctcca cgccgtccac gtaccagttg aacttgacct cagggtcttc   540
gtggctcacg tccaccacca cgcatgtgac ctcaggggtc cggagatca tgagggtgtc    600
cttgggtttt gggggggaaga ggaagactga cggtcccccc aggagttcag gtgctgggca   660
cggtgggcat gtgtgagttc caccaccgt cggggggtggc tcgtacgtga cttccgggcc   720
cccagcctct ggcaaatgag tgaagcgctc gttcagaag ttgccttcac agcagcagaa    780
gtacacctgg gggttctcct cagtggccac acactcctgc ctatcgtagc agttgaagtc   840
atcgtcccag cagcccttct tcacgagctc gatggtgcca gagctgttgc gccaggaggc   900
gtagcagtgt agccgcttgt cctgctcgcc ttcgcagcgc tccaggccgc tctggttggt   960
gcgctccagc tcccagttgg cgttgtagta gatgcactcc cgtgtctcag cggcgccggg   1020
cgaaacgaag actgctccac acagcagcag cacacagcag agccctctct tcattgcatc   1080
cat                                                                1083

SEQ ID NO: 82           moltype = DNA  length = 1083
FEATURE                 Location/Qualifiers
misc_feature            1..1083
                        note = Description of Artificial Sequence: Synthetic
                         polynucleotide
source                  1..1083
                        mol_type = other DNA
                        organism = synthetic construct
CDS                     76..396
SEQUENCE: 82
atggatgcaa tgaagagagg gctctgctgt gtgctgctgc tgtgtggagc agtcttcgtt    60
tcgccccggcg ccgccgaaac ccgcgaatgt atttattaca atgctaattg ggaactgcaa   120
cggacgaacc aatccgggct cgaacggtgt gaggggggaac aggataaacg cctccattgc   180
tatgcgtcgt ggaggaactc ctccgggacg attgaactgg tcaagaaagg gtgctgggac   240
gacgatttca attgttatga ccgccaggaa tgtgtcgcga ccgaagagaa tccgcaggtc   300
tatttctgtt gttgcgaggg gaatttctgt aatgaaccgt ttacccacct ccccgaagcc   360
ggcgggcccg aggtgaccta tgaaccccg cccaccggtg gtggaactca cacatgccca   420
ccgtgcccag cacctgaact cctggggggga ccgtcagtct tcctcttccc cccaaaaccc   480
aaggacaccc tcatgatctc ccggacccct gaggtcacat gcgtggtggt ggacgtgagc   540
cacgaagacc ctgaggtcaa gttcaactgg tacgtggacg gcgtggaggt gcataatgac   600
aagacaaagc cgcgggagga gcagtacaac agcacgtacc gtgtggtcag cgtcctcacc   660
gtcctgcacc aggactggct gaatggcaag gagtacaagt gcaaggtctc caacaaagcc   720
ctcccagccc ccatcgagaa aaccatctcc aaagccaaag gcagccccg agaaccacag    780
gtgtacaccc tgcccccatc ccgggaggag atgaccaaga accaggtcag cctgacctgc   840
ctggtcaaag gcttctatcc cagcgacatc gccgtggagt gggagagcaa tgggcagccg   900
gagaacaact acaagaccac gcctcccgtg ctggactccg acggctcctt cttcctctat   960
agcaagctca ccgtggacaa gagcaggtgg cagcagggga cgtcttctc atgctccgtg    1020
atgcatgagg ctctgcacaa ccactacacg cagaagagcc tctccctgtc cccgggtaaa   1080
tga                                                                1083

SEQ ID NO: 83           moltype = DNA  length = 1083
FEATURE                 Location/Qualifiers
misc_feature            1..1083
                        note = Description of Artificial Sequence: Synthetic
                         polynucleotide
source                  1..1083
                        mol_type = other DNA
                        organism = synthetic construct
SEQUENCE: 83
tcatttaccc ggggacaggg agaggctctt ctgcgtgtag tggttgtgca gagcctcatg    60
```

```
catcacggag catgagaaga cgttcccctg ctgccacctg ctcttgtcca cggtgagctt    120
gctatagagg aagaaggagc cgtcggagtc cagcacggga ggcgtggtct tgtagttgtt    180
ctccggctgc ccattgctct cccactccac ggcgatgtcg ctgggataga agcctttgac    240
caggcaggtc aggctgacct ggttcttggt catctcctcc cgggatgggg gcagggtgta    300
cacctgtggt tctcggggct gccctttggc ttttggagatg gttttctcga tggggctgg    360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcaggggtc cggagatca tgagggtgtc    600
cttgggtttt gggggaaga ggaagactga cggtcccccc aggagttcag gtgctgggca    660
cggtgggcat gtgtgagttc caccaccggt gggcggggt tcataggtca cctcgggccc    720
gccggcttcg gggaggtggg taaaccgttc attacagaaa ttcccctcgc aacaacagaa    780
atagacctgc ggattctctt cggtcgcgac acattcctgg cggtcataac aattgaaatc    840
gtcgtcccag caccctttct tgaccagttc aatcgtcccg gaggagttcc tccacgacgc    900
atagcaatgg aggcgtttat cctgttcccc ctcacaccgt tcgagcccgg attggttcgt    960
ccgttcgagt tcccaattag cattgtaata aatacattcg cgggtttcgg cggcgccggg   1020
cgaaacgaag actgctccac acagcagcag cacacagcag agccctctct tcattgcatc   1080
cat                                                                  1083

SEQ ID NO: 84          moltype = DNA  length = 321
FEATURE                Location/Qualifiers
misc_feature           1..321
                       note = Description of Artificial Sequence: Synthetic
                       polynucleotide
source                 1..321
                       mol_type = other DNA
                       organism = synthetic construct
SEQUENCE: 84
gaaacccgcg aatgtattta ttacaatgct aattgggaac tcgaacggac gaaccaatcc     60
gggctcgaac ggtgtgaggg ggaacaggat aaacgcctcc attgctatgc gtcgtggagg    120
aactcctccg ggacgattga actggtcaag aaagggtgct gggacgacga tttcaattgt    180
tatgaccgcc aggaatgtgt cgcgaccgaa gagaatccgc aggtctattt ctgttgttgc    240
gaggggaatt tctgtaatga acggtttacc cactcccccg aagccggcgg gcccgaggtg    300
acctatgaac ccccgcccac c                                              321

SEQ ID NO: 85          moltype =     length =
SEQUENCE: 85
000

SEQ ID NO: 86          moltype =     length =
SEQUENCE: 86
000

SEQ ID NO: 87          moltype =     length =
SEQUENCE: 87
000

SEQ ID NO: 88          moltype =     length =
SEQUENCE: 88
000

SEQ ID NO: 89          moltype =     length =
SEQUENCE: 89
000

SEQ ID NO: 90          moltype =     length =
SEQUENCE: 90
000

SEQ ID NO: 91          moltype =     length =
SEQUENCE: 91
000

SEQ ID NO: 92          moltype =     length =
SEQUENCE: 92
000

SEQ ID NO: 93          moltype =     length =
SEQUENCE: 93
000

SEQ ID NO: 94          moltype =     length =
SEQUENCE: 94
000

SEQ ID NO: 95          moltype =     length =
SEQUENCE: 95
000
```

```
SEQ ID NO: 96          moltype =    length =
SEQUENCE: 96
000

SEQ ID NO: 97          moltype =    length =
SEQUENCE: 97
000

SEQ ID NO: 98          moltype =    length =
SEQUENCE: 98
000

SEQ ID NO: 99          moltype =    length =
SEQUENCE: 99
000

SEQ ID NO: 100         moltype = AA   length = 505
FEATURE                Location/Qualifiers
source                 1..505
                       mol_type = protein
                       organism = Homo sapiens
SEQUENCE: 100
MAESAGASSF FPLVVLLLAG SGGSGPRGVQ ALLCACTSCL QANYTCETDG ACMVSIFNLD    60
GMEHHVRTCI PKVELVPAGK PFYCLSSEDL RNTHCCYTDY CNRIDLRVPS GHLKEPEHPS   120
MWGPVELVGI IAGPVFLLFL IIIIVFLVIN YHQRVYHNRQ RLDMEDPSCE MCLSKDKTLQ   180
DLVYDLSTSG SGSGLPLFVQ RTVARTIVLQ EIIGKGRFGE VWRGRWRGGD VAVKIFSSRE   240
ERSWFREAEI YQTVMLRHEN ILGFIAADNK DNGTWTQLWL VSDYHEHGSL FDYLNRYTVT   300
IEGMIKLALS AASGLAHLHM EIVGTQGKPG IAHRDLKSKN ILVKKNGMCA IADLGLAVRH   360
DAVTDTIDIA PNQRVGTKRY MAPEVLDETI NMKHFDSFKC ADIYALGLVY WEIARRCNSG   420
GVHEEYQLPY YDLVPSDPSI EEMRKVVCDQ KLRPNIPNWW QSYEALRVMG KMMRECWYAN   480
GAARLTALRI KKTLSQLSVQ EDVKI                                        505

SEQ ID NO: 101         moltype = AA   length = 103
FEATURE                Location/Qualifiers
source                 1..103
                       mol_type = protein
                       organism = Homo sapiens
SEQUENCE: 101
SGPRGVQALL CACTSCLQAN YTCETDGACM VSIFNLDGME HHVRTCIPKV ELVPAGKPFY    60
CLSSEDLRNT HCCYTDYCNR IDLRVPSGHL KEPEHPSMWG PVE                    103

SEQ ID NO: 102         moltype = DNA   length = 1515
FEATURE                Location/Qualifiers
source                 1..1515
                       mol_type = other DNA
                       organism = Homo sapiens
SEQUENCE: 102
atggcggagt cggccggagc ctcctccttc ttccccttg ttgtcctcct gctcgccggc      60
agcggcgggt ccgggccccg ggggtccag gctctgctgt gtgcgtgcac cagctgcctc    120
caggccaact acacgtgtga gacagatggg gcctgcatgg tttccatttt caatctggat   180
gggatggagc accatgtgcg cacctgcatc cccaaagtg agctggtccc tgccgggaag    240
cccttctact gcctgagctc ggaggacctg cgcaacaccc actgctgcta cactgactac    300
tgcaacagga tcgacttgag ggtgcccagt ggtcacctca aggagcctga gcacccgtcc    360
atgtgggggcc cggtggagct ggtaggcatc atcgccggcc cggtgttcct cctgttcctc    420
atcatcatca ttgttttcct tgtcattaac tatcatcagc gtgtctatca caaccgccaa    480
agactggaca tggaagatcc ctcatgtgag atgtgtctct ccaaagacaa gacgctccag    540
gatcttgtct acgatctctc cacctcaggg tctggctcag ggttacccct ctttgtccag    600
cgcacagtgg cccgaaccat cgttttacaa gagattattg gcaagggtcg gtttggggaa    660
gtatggcggg gccgctggag gggtggtgat gtggctgtga aaatattctc ttctcgtgaa    720
gaacggtctt ggttcaggga agcagagata taccagacga tcatgctgcg ccatgaaaac    780
atccttggat ttattgctgc tgacaataaa gataatggca cctggacaca gctgtggctt    840
gtttctgact atcatgagca cgggtccctg tttgattatc tgaaccggta cacagtgaca    900
attgagggga tgattaagct ggccttgtct gctgctagtg gctggcaca cctgcacatg    960
gagatcgtgg gcacccaagg aagcctggaa attgctcatc gagacttaaa gtcaaagaac   1020
attctggtga gaaaaatgg catgtgtgcc atagcagacc tgggcctggc tgtccgtcat   1080
gatgcagtca ctgacaccat tgacattgcc ccgaatcaga gggtggggac aaacgatac   1140
atggccctg aagtacttga tgaaaccatt aatatgaaac actttgactc ctttaaatgt   1200
gctgatattt atgccctcgg gcttgtatat tgggagattg ctcgaagatg caattctgga   1260
ggagtccatg aagaatatca gctgccatat tacgacttag tgccctctga cccttccatt   1320
gaggaaatgc gaaaggttgt atgtgatcag aagctgcgtc ccaacatccc caactggtgg   1380
cagagttatg aggcactgcg ggtgatgggg aagatgatgc gagagtgttg gtatgccaac   1440
ggcgcagccc gcctgacggc cctgcgcatc aagaagaccc tctcccagct cagcgtgcag   1500
gaagacgtga agatc                                                    1515

SEQ ID NO: 103         moltype = DNA   length = 309
FEATURE                Location/Qualifiers
source                 1..309
                       mol_type = other DNA
                       organism = Homo sapiens
```

```
SEQUENCE: 103
tccgggcccc gggggtcca ggctctgctg tgtgcgtgca ccagctgcct ccaggccaac    60
tacacgtgtg agacagatgg ggcctgcatg gtttccattt tcaatctgga tgggatggag   120
caccatgtgc gcacctgcat ccccaaagtg gagctggtcc ctgccgggaa gcccttctac   180
tgcctgagct cggaggacct gcgcaacacc cactgctgct acactgacta ctgcaacagg   240
atcgacttga gggtgcccag tggtcacctc aaggagcctg agcacccgtc catgtggggc   300
ccggtggag                                                           309

SEQ ID NO: 104          moltype = AA  length = 453
FEATURE                 Location/Qualifiers
source                  1..453
                        mol_type = protein
                        organism = Homo sapiens
SEQUENCE: 104
MVSIFNLDGM EHHVRTCIPK VELVPAGKPF YCLSSEDLRN THCCYTDYCN RIDLRVPSGH    60
LKEPEHPSMW GPVELVGIIA GPVFLLFLII IIVFLVINYH QRVYHNRQRL DMEDPSCEMC   120
LSKDKTLQDL VYDLSTSGSG SGLPLFVQRT VARTIVLQEI IGKGRFGEVW RGRWRGGDVA   180
VKIFSSREER SWFREAEIYQ TVMLRHENIL GFIAADNKDN GTWTQLWLVS DYHEHGSLFD   240
YLNRYTVTIE GMIKLALSAA SGLAHLHMEI VGTQGKPGIA HRDLKSKNIL VKKNGMCAIA   300
DLGLAVRHDA VTDTIDIAPN QRVGTKRYMA PEVLDETINM KHFDSFKCAD IYALGLVYWE   360
IARRCNSGGV HEEYQLPYYD LVPSDPSIEE MRKVVCDQKL RPNIPNWWQS YEALRVMGKM   420
MRECWYANGA ARLTALRIKK TLSQLSVQED VKI                                453

SEQ ID NO: 105          moltype = AA  length = 74
FEATURE                 Location/Qualifiers
source                  1..74
                        mol_type = protein
                        organism = Homo sapiens
SEQUENCE: 105
MVSIFNLDGM EHHVRTCIPK VELVPAGKPF YCLSSEDLRN THCCYTDYCN RIDLRVPSGH    60
LKEPEHPSMW GPVE                                                      74

SEQ ID NO: 106          moltype = DNA  length = 1362
FEATURE                 Location/Qualifiers
source                  1..1362
                        mol_type = other DNA
                        organism = Homo sapiens
SEQUENCE: 106
atggtttcca ttttcaatct ggatgggatg gagcaccatg tgcgcacctg catccccaaa    60
gtggagctgg tccctgccgg gaagcccttc tactgcctga gctcggagga cctgcgcaac   120
acccactgct gctacactga ctactgcaac aggatcgact tgagggtgcc cagtggtcac   180
ctcaaggagc ctgagcaccc gtccatgtgg ggccgtgg agctggtagg catcatcgcc   240
ggcccggtgt tcctcctgtt cctcatcatc atcattgttt tccttgtcat taactatcat   300
cagcgtgtct atcacaaccg ccagagactg gacatgaag atccctcatg tgagatgtgt   360
ctctccaaag acaagacgct ccaggatctt gtctacgatc tctccacctc agggtctggc   420
tcagggttac ccctctttgt ccagcgcaca gtggcccgaa ccatcgtttt acaagagatt   480
attggcaagg gtcggtttgg ggaagtatgg cggggccgct ggaggggtgg tgatgtggct   540
gtgaaaatat tctcttctcg tgaagaacgg tcttggttca gggaagcaga gatataccag   600
acggtcatgc tgcgccatga aacatccttg gatttattg ctgctgacaa taaagataat   660
ggcacctgga cacagctgtg gcttgtttct gactatcatg agcacgggtc cctgtttgat   720
tatctgaacc ggtacacagt gacaattgag gggatgatta agctggcctt gtctgctgct   780
agtgggctgg cacacctgca catggagatc gtgggcaccc aagggaagcc tggaattgct   840
catcgagact taaagtcaaa gaacattctg tgaagaaaa atggcatgtg tgccatagca   900
gacctgggcc tggctgtccg tcatgatgca gtcactgaca ccattgacat tgccccgaat   960
cagagggtgg ggaccaaacg atacatggcc cctgaagtac ttgatgaaac cattaatatg  1020
aaacactttg actccttaa atgtgctgat atttatgccc tcgggcttgt atattgggag  1080
attgctcgaa gatgcaattc tggaggagtc catgaagaat atcagctgcc atattacgac  1140
ttagtgccct ctgacccttc cattgaggaa atgcgaaagg ttgtatgtga tcagaagctg  1200
cgtcccaaca tccccaactg gtggcagagt tatgaggcac tgcgggtgat ggggaagatg  1260
atgcgagagt gttggtatgc caacggcgca gcccgcctga cggccctgcg catcaagaag  1320
accctctccc agctcagcgt gcaggaagac gtgaagatct aa                     1362

SEQ ID NO: 107          moltype = DNA  length = 230
FEATURE                 Location/Qualifiers
source                  1..230
                        mol_type = other DNA
                        organism = Homo sapiens
SEQUENCE: 107
atggtttcca ttttcaatct ggatgggatg gagcaccatg tgcgcacctg catccccaaa    60
gtggagctgg tccctgccgg gaagcccttc tactgcctga gctcggagga cctgcgcaac   120
acccactgct gctacactga ctactgcaac aggatcgact tgagggtgcc cagtggtcac   180
ctcaaggagc ctgagcaccc gtccatgtgg ggccgtgg agctggtagg                230

SEQ ID NO: 108          moltype = AA  length = 368
FEATURE                 Location/Qualifiers
REGION                  1..368
                        note = Description of Artificial Sequence: Synthetic
                        polypeptide
source                  1..368
```

```
                              mol_type = protein
                              organism = synthetic construct
SEQUENCE: 108
MDAMKRGLCC  VLLLCGAVFV  SPGASGRGEA  ETRECIYYNA  NWELERTNQS  GLERCEGEQD   60
KRLHCYASWR  NSSGTIELVK  KGCWLDDFNC  YDRQECVATE  ENPQVYFCCC  EGNFCNERFT  120
HLPEAGGPEV  TYEPPPTAPT  GGGTHTCPPC  PAPELLGGPS  VFLFPPKPKD  TLMISRTPEV  180
TCVVVDVSHE  DPEVKFNWYV  DGVEVHNAKT  KPREEQYNST  YRVVSVLTVL  HQDWLNGKEY  240
KCKVSNKALP  APIEKTISKA  KGQPREPQVY  TLPPSRKEMT  KNQVSLTCLV  KGFYPSDIAV  300
EWESNGQPEN  NYKTTPPVLK  SDGSFFLYSK  LTVDKSRWQQ  GNVFSCSVMH  EALHNHYTQK  360
SLSLSPGK                                                                368

SEQ ID NO: 109           moltype = DNA  length = 1104
FEATURE                  Location/Qualifiers
misc_feature             1..1104
                         note = Description of Artificial Sequence: Synthetic
                           polynucleotide
source                   1..1104
                         mol_type = other DNA
                         organism = synthetic construct
SEQUENCE: 109
atggatgcaa tgaagagagg gctctgctgt gtgctgctgc tgtgtggagc agtcttcgtt   60
tcgccgggcg cctctgggcg tggggaggct gagacacgag agtgcatcta ctacaacgcc  120
aactgggagc tggagcgcac caaccagagc ggcctggagc gctgcgaagg cgagcaggac  180
aagcggctgc actgctacgc ctcctggcgc aacagctctg gcaccatcga gctcgtgaag  240
aagggctgct ggctagatga cttcaactgc tacgataggc aggagtgtgt ggccactgag  300
gagaaccccc aggtgtactt ctgctgctgt gaaggcaact tctgcaacga gcgcttcact  360
catttgccag aggctggggg cccggaagtc acgtacgagc cccccccgac agcccccacc  420
ggtggtggaa ctcacacatg cccaccgtgc ccagcacctg aactcctggg gggaccgtca  480
gtcttcctct tccccccaaa acccaaggac accctcatga tctcccggac ccctgaggtc  540
acatgcgtgg tggtggacgt gagccacgaa gaccctgagg tcaagttcaa ctggtacgtg  600
gacggcgtgg aggtgcataa tgccaagaca aagccgcggg aggagcagta caacagcacg  660
taccgtgtgg tcagcgtcct caccgtcctg caccaggact ggctgaatgg caaggagtac  720
aagtgcaagg tctccaacaa agccctccca gcccccatcg agaaaaccat ctccaaagcc  780
aaagggcagc cccgagaacc acaggtgtac accctgcccc catcccggga ggagatgacc  840
aagaaccagg tcagcctgac ctgcctggtc aaaggcttct atcccagcga catcgccgtg  900
gagtgggaga gcaatgggca gccggagaac aactacaaga ccacgcctcc cgtgctgaag 960
tccgacggct ccttcttcct ctatagcaag ctcaccgtgg acaagagcag gtggcagcag 1020
gggaacgtct tctcatgctc cgtgatgcat gaggctctgc acaaccacta cacgcagaag 1080
agcctctccc tgtctccggg taaa                                        1104

SEQ ID NO: 110           moltype = AA  length = 343
FEATURE                  Location/Qualifiers
REGION                   1..343
                         note = Description of Artificial Sequence: Synthetic
                           polypeptide
source                   1..343
                         mol_type = protein
                         organism = synthetic construct
SEQUENCE: 110
GRGEAETREC  IYYNANWELE  RTNQSGLERC  EGEQDKRLHC  YASWRNSSGT  IELVKKGCWL   60
DDFNCYDRQE  CVATEENPQV  YFCCCEGNFC  NERFTHLPEA  GGPEVTYEPP  PTAPTGGGTH  120
TCPPCPAPEL  LGGPSVFLFP  PKPKDTLMIS  RTPEVTCVVV  DVSHEDPEVK  FNWYVDGVEV  180
HNAKTKPREE  QYNSTYRVVS  VLTVLHQDWL  NGKEYKCKVS  NKALPAPIEK  TISKAKGQPR  240
EPQVYTLPPS  RKEMTKNQVS  LTCLVKGFYP  SDIAVEWESN  GQPENNYKTT  PPVLKSDGSF  300
FLYSKLTVDK  SRWQQGNVFS  CSVMHEALHN  HYTQKSLSLS  PGK                    343

SEQ ID NO: 111           moltype = AA  length = 355
FEATURE                  Location/Qualifiers
REGION                   1..355
                         note = Description of Artificial Sequence: Synthetic
                           polypeptide
source                   1..355
                         mol_type = protein
                         organism = synthetic construct
SEQUENCE: 111
MDAMKRGLCC  VLLLCGAVFV  SPGASGPRGV  QALLCACTSC  LQANYTCETD  GACMVSIFNL   60
DGMEHHVRTC  IPKVELVPAG  KPFYCLSSED  LRNTHCCYTD  YCNRIDLRVP  SGHLKEPEHP  120
SMWGPVETGG  GTHTCPPCPA  PELLGGPSVF  LFPPKPKDTL  MISRTPEVTC  VVVDVSHEDP  180
EVKFNWYVDG  VEVHNAKTKP  REEQYNSTYR  VVSVLTVLHQ  DWLNGKEYKC  VSNKALPAP   240
IEKTISKAKG  QPREPQVYTL  PPSREEMTKN  QVSLTCLVKG  FYPSDIAVEW  ESNGQPENNY  300
DTTPPVLDSD  GSFFLYSDLT  VDKSRWQQGN  VFSCSVMHEA  LHNHYTQKSL  SLSPG       355

SEQ ID NO: 112           moltype = DNA  length = 1065
FEATURE                  Location/Qualifiers
misc_feature             1..1065
                         note = Description of Artificial Sequence: Synthetic
                           polynucleotide
source                   1..1065
                         mol_type = other DNA
```

-continued

```
                        organism = synthetic construct
SEQUENCE: 112
atggatgcaa tgaagagagg gctctgctgt gtgctgctgc tgtgtggagc agtcttcgtt   60
tcgcccggcg cctccgggcc ccgggggtc caggctctgc tgtgtgcgtg caccagctgc   120
ctccaggcca actacacgtg tgagacagat ggggcctgca tggtttccat tttcaatctg   180
gatgggatgg agcaccatgt gcgcacctgc atccccaaag tggagctggt ccctgccggg   240
aagcccttct actgcctgag ctcggaggac ctgcgcaaca cccactgctg ctacactgac   300
tactgcaaca ggatcgactt gagggtgccc agtggtcacc tcaaggagcc tgagcacccg   360
tccatgtggg gccggtgga gaccggtggt ggaactcaca catgcccacc gtgcccagca   420
cctgaactcc tggggggacc gtcagtcttc ctcttccccc caaaacccaa ggacaccctc   480
atgatctccc ggaccctga ggtcacatgc gtggtggtgg acgtgagcca cgaagaccct   540
gaggtcaagt tcaactggta cgtggacggc gtggaggtgc ataatgccaa gacaaagccg   600
cgggaggagc agtacaacag cacgtaccgt gtggtcagcg tcctcaccgt cctgcaccag   660
gactggctga atggcaagga gtacaagtgc aaggtctcca acaaagccct cccagcccc   720
atcgagaaaa ccatctccaa agccaaaggg cagccccgag aaccacaggt gtacaccctg   780
cccccatccc gggaggagat gaccaagaac caggtcagcc tgacctgcct ggtcaaaggc   840
ttctatccca gcgacatcgc cgtggagtgg gagagcaatg gcagccgga gaacaactac   900
gacaccacgc ctcccgttct ggactccgac ggctccttct tcctctatag cgacctcacc   960
gtggacaaga gcaggtggca caggggaac gtcttctcat gctccgtgat gcatgaggct  1020
ctgcacaacc actacacgca gaagagcctc tccctgtctc cgggt              1065

SEQ ID NO: 113          moltype = AA   length = 331
FEATURE                 Location/Qualifiers
REGION                  1..331
                        note = Description of Artificial Sequence: Synthetic
                         polypeptide
source                  1..331
                        mol_type = protein
                        organism = synthetic construct
SEQUENCE: 113
SGPRGVQALL CACTSCLQAN YTCETDGACM VSIFNLDGME HHVRTCIPKV ELVPAGKPFY   60
CLSSEDLRNT HCCYTDYCNR IDLRVPSGHL KEPEHPSMWG PVETGGGTHT CPPCPAPELL  120
GGPSVFLFPP KPKDTLMISR TPEVTCVVVD VSHEDPEVKF NWYVDGVEVH NAKTKPREEQ  180
YNSTYRVVSV LTVLHQDWLN GKEYKCKVSN KALPAPIEKT ISKAKGQPRE PQVYTLPPSR  240
EEMTKNQVSL TCLVKGFYPS DIAVEWESNG QPENNYDTTP PVLDSDGSFF LYSDLTVDKS  300
RWQQGNVFSC SVMHEALHNH YTQKSLSLSP G                                331

SEQ ID NO: 114          moltype = AA   length = 368
FEATURE                 Location/Qualifiers
REGION                  1..368
                        note = Description of Artificial Sequence: Synthetic
                         polypeptide
source                  1..368
                        mol_type = protein
                        organism = synthetic construct
SEQUENCE: 114
MDAMKRGLCC VLLLCGAVFV SPGASGRGEA ETRECIYYNA NWELERTNQS GLERCEGEQD   60
KRLHCYASWR NSSGTIELVK KGCWLDDFNC YDRQECVATE ENPQVYFCCC EGNFCNERFT  120
HLPEAGGPEV TYEPPPTAPT GGGTHTCPPC PAPELLGGPS VFLFPPKPKD TLMISRTPEV  180
TCVVVDVSHE DPEVKFNWYV DGVEVHNAKT KPREEQYNST YRVVSVLTVL HQDWLNGKEY  240
KCKVSNKALP APIEKTISKA KGQPREPQVY TLPPCREEMT KNQVSLWCLV KGFYPSDIAV  300
EWESNGQPEN NYKTTPPVLD SDGSFFLYSK LTVDKSRWQQ GNVFSCSVMH EALHNHYTQK  360
SLSLSPGK                                                          368

SEQ ID NO: 115          moltype = AA   length = 343
FEATURE                 Location/Qualifiers
REGION                  1..343
                        note = Description of Artificial Sequence: Synthetic
                         polypeptide
source                  1..343
                        mol_type = protein
                        organism = synthetic construct
SEQUENCE: 115
GRGEAETREC IYYNANWELE RTNQSGLERC EGEQDKRLHC YASWRNSSGT IELVKKGCWL   60
DDFNCYDRQE CVATEENPQV YFCCCEGNFC NERFTHLPEA GGPEVTYEPP PTAPTGGGTH  120
TCPPCPAPEL LGGPSVFLFP PKPKDTLMIS RTPEVTCVVV DVSHEDPEVK FNWYVDGVEV  180
HNAKTKPREE QYNSTYRVVS VLTVLHQDWL NGKEYKCKVS NKALPAPIEK TISKAKGQPR  240
EPQVYTLPPC REEMTKNQVS LWCLVKGFYP SDIAVEWESN GQPENNYKTT PPVLDSDGSF  300
FLYSKLTVDK SRWQQGNVFS CSVMHEALHN HYTQKSLSLS PGK                   343

SEQ ID NO: 116          moltype = AA   length = 356
FEATURE                 Location/Qualifiers
REGION                  1..356
                        note = Description of Artificial Sequence: Synthetic
                         polypeptide
source                  1..356
                        mol_type = protein
                        organism = synthetic construct
SEQUENCE: 116
```

```
MDAMKRGLCC VLLLCGAVFV SPGASGPRGV QALLCACTSC LQANYTCETD GACMVSIFNL    60
DGMEHHVRTC IPKVELVPAG KPFYCLSSED LRNTHCCYTD YCNRIDLRVP SGHLKEPEHP   120
SMWGPVETGG GTHTCPPCPA PELLGGPSVF LFPPKPKDTL MISRTPEVTC VVVDVSHEDP   180
EVKFNWYVDG VEVHNAKTKP REEQYNSTYR VVSVLTVLHQ DWLNGKEYKC KVSNKALPAP   240
IEKTISKAKG QPREPQVCTL PPSREEMTKN QVSLSCAVKG FYPSDIAVEW ESNGQPENNY   300
KTTPPVLDSD GSFFLVSKLT VDKSRWQQGN VFSCSVMHEA LHNHYTQKSL SLSPGK       356

SEQ ID NO: 117          moltype = AA   length = 332
FEATURE                 Location/Qualifiers
REGION                  1..332
                        note = Description of Artificial Sequence: Synthetic
                         polypeptide
source                  1..332
                        mol_type = protein
                        organism = synthetic construct
SEQUENCE: 117
SGPRGVQALL CACTSCLQAN YTCETDGACM VSIFNLDGME HHVRTCIPKV ELVPAGKPFY    60
CLSSEDLRNT HCCYTDYCNR IDLRVPSGHL KEPEHPSMWG PVETGGGTHT CPPCPAPELL   120
GGPSVFLFPP KPKDTLMISR TPEVTCVVVD VSHEDPEVKF NWYVDGVEVH NAKTKPREEQ   180
YNSTYRVVSV LTVLHQDWLN GKEYKCKVSN KALPAPIEKT ISKAKGQPRE PQVCTLPPSR   240
EEMTKNQVSL SCAVKGFYPS DIAVEWESNG QPENNYKTTP PVLDSDGSFF LVSKLTVDKS   300
RWQQGNVFSC SVMHEALHNH YTQKSLSLSP GK                                 332

SEQ ID NO: 118          moltype = AA   length = 367
FEATURE                 Location/Qualifiers
REGION                  1..367
                        note = Description of Artificial Sequence: Synthetic
                         polypeptide
source                  1..367
                        mol_type = protein
                        organism = synthetic construct
SEQUENCE: 118
MDAMKRGLCC VLLLCGAVFV SPGASGRGEA ETRECIYYNA NWELERTNQS GLERCEGEQD    60
KRLHCYASWR NSSGTIELVK KGCWLDDFNC YDRQECVATE ENPQVYFCCC EGNFCNERFT   120
HLPEAGGPEV TYEPPPTAPT GGGTHTCPPC PAPELLGGPS VFLFPPKPKD TLMISRTPEV   180
TCVVVDVSHE DPEVKFNWYV DGVEVHNAKT KPREEQYNST YRVVSVLTVL HQDWLNGKEY   240
KCKVSNKALP APIEKTISKA KGQPREPQVY TLPPCREEMT ENQVSLWCLV KGFYPSDIAV   300
EWESNGQPEN NYKTTPPVLD SDGSFFLYSK LTVDKSRWQQ GNVFSCSVMH EALHNHYTQD   360
SLSLSPG                                                             367

SEQ ID NO: 119          moltype = DNA   length = 1101
FEATURE                 Location/Qualifiers
misc_feature            1..1101
                        note = Description of Artificial Sequence: Synthetic
                         polynucleotide
source                  1..1101
                        mol_type = other DNA
                        organism = synthetic construct
SEQUENCE: 119
atggatgcaa tgaagagagg gctctgctgt gtgctgctgc tgtgtggagc agtcttcgtt    60
tcgccggcg cctctgggcg tggggaggct gagacacgag agtgcatcta ctacaacgcc   120
aactgggagc tggagcgcac caaccagagc ggcctggagc gctgcgaagg cgagcaggac   180
aagcggctgc actgctacgc ctccggcgc aacagctctg gcaccatcga gctcgtgaag   240
aagggctgct ggctagatga cttcaactgc tacgataggc aggagtgtgt ggccactgag   300
gagaaccccc aggtgtactt ctgctgctgt gaaggcaact tctgcaacga gcgcttcact   360
catttgccag aggctggggg cccggaagtc acgtacgagc cacccccgac agccccacc    420
ggtggtggaa ctcacacatg cccaccgtgc ccagcacctg aactcctggg gggaccgtca   480
gtcttcctct tccccccaaa acccaaggac accctcatga tctcccggac ccctgaggtc   540
acatgcgtgg tggtggacgt gagccacgaa gaccctgagg tcaagttcaa ctggtacgtg   600
gacggcgtgg aggtgcataa tgccaagaca aagccgcggg aggagcagta caacagcacg   660
taccgtgtgg tcagcgtcct caccgtcctg caccaggact ggctgaatgg caaggagtac   720
aagtgcaagg tctccaacaa agccctccca gcccccatcg agaaaccat ctccaaagcc    780
aaagggcagc ccgagaacc acaggtgtac accctgcccc catgccggga ggagatgacc   840
gagaaccagg tcagcctgtg tgtcctggtc aaaggcttct atcccagcga catcgccgtg   900
gagtgggaga gcaatgggca gccggagaac aactacaaga ccacgcctcc cgtgctggac   960
tccgacggct ccttcttcct ctatagcaag ctcaccgtgg acaagagcag gtggcagcag  1020
gggaacgtct tctcatgctc cgtgatgcat gaggctctgc acaaccacta cacgcaggac  1080
agcctctccc tgtctccggg t                                            1101

SEQ ID NO: 120          moltype = AA   length = 342
FEATURE                 Location/Qualifiers
REGION                  1..342
                        note = Description of Artificial Sequence: Synthetic
                         polypeptide
source                  1..342
                        mol_type = protein
                        organism = synthetic construct
SEQUENCE: 120
GRGEAETREC IYYNANWELE RTNQSGLERC EGEQDKRLHC YASWRNSSGT IELVKKGCWL    60
```

```
DDFNCYDRQE CVATEENPQV YFCCCEGNFC NERFTHLPEA GGPEVTYEPP PTAPTGGGTH  120
TCPPCPAPEL LGGPSVFLFP PKPKDTLMIS RTPEVTCVVV DVSHEDPEVK FNWYVDGVEV  180
HNAKTKPREE QYNSTYRVVS VLTVLHQDWL NGKEYKCKVS NKALPAPIEK TISKAKGQPR  240
EPQVYTLPPC REEMTENQVS LWCLVKGFYP SDIAVEWESN GQPENNYKTT PPVLDSDGSF  300
FLYSKLTVDK SRWQQGNVFS CSVMHEALHN HYTQDSLSLS PG                     342

SEQ ID NO: 121          moltype = DNA  length = 1026
FEATURE                 Location/Qualifiers
misc_feature            1..1026
                        note = Description of Artificial Sequence: Synthetic
                         polynucleotide
source                  1..1026
                        mol_type = other DNA
                        organism = synthetic construct
SEQUENCE: 121
gggcgtgggg aggctgagac acgggagtgc atctactaca acgccaactg ggagctggag  60
cgcaccaacc agagcggcct ggagcgctgc gaaggcgagc aggacaagcg gctgcactgc  120
tacgcctcct ggcgcaacag ctctggcacc atcgagctcg tgaagaaggg ctgctggcta  180
gatgacttca actgctacga taggcaggag tgtgtggcca ctgaggagaa cccccaggtg  240
tacttctgct gctgtgaagg caacttctgc aacgagcgct tcactcattt gccagaggct  300
gggggcccga agtcacgta cgagccaccc ccgacagccc caccggtgg tggaactcac  360
acatgccacc cgtgcccagc acctgaactc ctggggggacc cgtcagtctt cctcttcccc  420
ccaaaaccca aggacaccct catgatctcc cggacccctg aggtcacatg cgtggtggtg  480
gacgtgagcc acgaagaccc tgaggtcaag ttcaactggt acgtggacgg cgtggaggtg  540
cataatgcca agacaaagcc gcgggaggag cagtacaaca gcacgtaccg tgtggtcagc  600
gtcctcaccg tcctgcacca ggactggctg aatggcaagg agtacaagtg caaggtctcc  660
aacaaagccc tcccagcccc catcgagaaa accatctcca aagccaaagg gcagccccga  720
gaaccacagg tgtacaccct gcccccatgc cgggaggaga tgaccgagaa ccaggtcagc  780
ctgtggtgcc tggtcaaagg cttctatccc agcgacatcg ccgtggagtg ggagagcaat  840
gggcagccgg agaacaacta caagaccacg cctcccgtgc tggactccga cggctccttc  900
ttcctctata gcaagctcac cgtggacaag agcaggtggc agcaggggaa cgtcttctca  960
tgctccgtga tgcatgaggc tctgcacaac cactacacgc aggacagcct ctccctgtct  1020
ccgggt                                                              1026

SEQ ID NO: 122          moltype = AA  length = 356
FEATURE                 Location/Qualifiers
REGION                  1..356
                        note = Description of Artificial Sequence: Synthetic
                         polypeptide
source                  1..356
                        mol_type = protein
                        organism = synthetic construct
SEQUENCE: 122
MDAMKRGLCC VLLLCGAVFV SPGASGPRGV QALLCACTSC LQANYTCETD GACMVSIFNL  60
DGMEHHVRTC IPKVELVPAG KPFYCLSSED LRNTHCCYTD YCNRIDLRVP SGHLKEPEHP  120
SMWGPVETGG GTHTCPPCPA PELLGGPSVF LFPPKPKDTL MISRTPEVTC VVVDVSHEDP  180
EVKFNWYVDG VEVHNAKTKP REEQYNSTYR VVSVLTVLHQ DWLNGKEYKC KVSNKALPAP  240
IEKTISKAKG QPREPQVCTL PPSREEMTKN QVSLSCAVKG FYPSDIAVEW ESRGQPENNY  300
KTTPPVLDSR GSFFLVSKLT VDKSRWQQGN VFSCSVMHEA LHNHYTQKSL SLSPGK      356

SEQ ID NO: 123          moltype = DNA  length = 1068
FEATURE                 Location/Qualifiers
misc_feature            1..1068
                        note = Description of Artificial Sequence: Synthetic
                         polynucleotide
source                  1..1068
                        mol_type = other DNA
                        organism = synthetic construct
SEQUENCE: 123
atggatgcaa tgaagagagg gctctgctgt gtgctgctgc tgtgtggagc agtcttcgtt  60
tcgcccggcg cctccgggcc ccgggggggtc caggctctgc tgtgtgcgtg caccagctgc  120
ctccaggcca actacgtg tgagacagat ggggcctgca tggtttccat tttcaatctg  180
gatgggatgg agcaccatgt gcgcacctgc atccccaaag tggagctggt ccctgccggg  240
aagccccttct actgcctgag ctcggaggac ctgcgcaaca cactgtg ctacactgac  300
tactgcaaca ggatcgactt gagggtgccc agtggtcacc tcaaggagcc tgagcaccg  360
tccatgtggg gcccggtgga gaccggtggt ggaactcaca catgccacc gtgcccagca  420
cctgaactcc tggggggacc gtcagtcttc ctcttcccc caaaacccaa ggacaccctc  480
atgatctccc ggacccctga ggtcacatgc gtggtggtgg acgtgagcca cgaagaccct  540
gaggtcaagt tcaactggta cgtggacggc gtggaggtgc ataatgccaa gacaaagcct  600
cgggaggagc agtacaacag cacgtaccgt gtggtcagcg tcctcaccgt cctgcaccag  660
gactggctga atggcaagga gtacaagtgc aaggtctcca acaaagccct cccagccccc  720
atcgagaaaa ccatctccaa agccaaaggg cagccccgag aaccacaggt gtacaccctg  780
cccccatccc gggaggagat gaccaagaac caggtcagcc tgtcctgcgc cgtcaaaggc  840
ttctatccca gcgacatcgc cgtggagtgg gagagcaatg ggcagccgga gaacaactac  900
aagaccacgc ctcccgtgct ggactcccgc ggctccttct tcctcgtgag caagctcacc  960
gtggacaaga gcaggtggca gcaggggaac gtcttctcat gctccgtgat gcatgaggct  1020
ctgcacaacc actacacgca gaagagcctc tccctgtctc cgggtaaa             1068

SEQ ID NO: 124          moltype = AA  length = 332
```

| FEATURE | Location/Qualifiers |
|---|---|
| REGION | 1..332 |
| | note = Description of Artificial Sequence: Synthetic polypeptide |
| source | 1..332 |
| | mol_type = protein |
| | organism = synthetic construct |

SEQUENCE: 124
```
SGPRGVQALL CACTSCLQAN YTCETDGACM VSIFNLDGME HHVRTCIPKV ELVPAGKPFY   60
CLSSEDLRNT HCCYTDYCNR IDLRVPSGHL KEPEHPSMWG PVETGGGTHT CPPCPAPELL  120
GGPSVFLFPP KPKDTLMISR TPEVTCVVVD VSHEDPEVKF NWYVDGVEVH NAKTKPREEQ  180
YNSTYRVVSV LTVLHQDWLN GKEYKCKVSN KALPAPIEKT ISKAKGQPRE PQVCTLPPSR  240
EEMTKNQVSL SCAVKGFYPS DIAVEWESRG QPENNYKTTP PVLDSRGSFF LVSKLTVDKS  300
RWQQGNVFSC SVMHEALHNH YTQKSLSLSP GK                                332
```

| SEQ ID NO: 125 | moltype = DNA length = 996 |
|---|---|
| FEATURE | Location/Qualifiers |
| misc_feature | 1..996 |
| | note = Description of Artificial Sequence: Synthetic polynucleotide |
| source | 1..996 |
| | mol_type = other DNA |
| | organism = synthetic construct |

SEQUENCE: 125
```
tccgggcccc gggggtcca ggctctgctg tgtgcgtgca ccagctgcct ccaggccaac    60
tacacgtgtg agacagatgg ggcctgcatg gtttccattt tcaatctgga tgggatggag  120
caccatgtgc gcacctgcat ccccaaagtg gagctggtcc ctgccgggaa gcccttctac  180
tgcctgagct cggaggacct gcgcaacacc cactgctgct acactgacta ctgcaacagg  240
atcgacttga gggtgcccag tggtcacctc aaggagcctg agcacccgtc catgtggggc  300
ccggtgggaga ccggtggtgg aactcacaca tgcccaccgt gcccagcacc tgaactcctg  360
gggggaccgt cagtcttcct cttccccca aaacccaagg acaccctcat gatctcccgg   420
acccctgagg tcacatgcgt ggtggtggac gtgagccacg aagaccctga ggtcaagttc  480
aactggtacg tggacggcgt ggaggtgcat aatgccaaga caaagccgcg ggaggagcag  540
tacaacagca cgtaccgtgt ggtcagcgtc ctcaccgtcc tgcaccagga ctggctgaat  600
ggcaaggagt acaagtgcaa ggtctccaac aaagccctcc cagccccat cgagaaaacc   660
atctccaaag ccaaagggca gccccgagaa ccacaggtgt gcaccctgcc cccatcccgg  720
gaggagatga ccaagaacca ggtcagcctg tcctgcgccg tcaaaggctt ctatcccagc  780
gacatcgccg tggagtggga gagccgcggg cagccggaga acaactacaa gaccacgcct  840
cccgtgctgg actcccgcgg ctccttcttc ctcgtgatga gctcaccgt ggacaagagc   900
aggtggcagc aggggaacgt cttctcatgc tccgtgatgc atgaggctct gcacaaccac  960
tacacgcaga gagcctctc cctgtctccg ggtaaa                             996
```

| SEQ ID NO: 126 | moltype = AA length = 103 |
|---|---|
| FEATURE | Location/Qualifiers |
| source | 1..103 |
| | mol_type = protein |
| | organism = Homo sapiens |

SEQUENCE: 126
```
SGPRGVQALL CACTSCLQAN YTCETDGACM VSIFNLDGME HHVRTCIPKV ELVPAGKPFY   60
CLSSEDLRNT HCCYTDYCNR IDLRVPSGHL KEPEHPSMWG PVE                    103
```

| SEQ ID NO: 127 | moltype = AA length = 103 |
|---|---|
| FEATURE | Location/Qualifiers |
| source | 1..103 |
| | mol_type = protein |
| | organism = Condylura cristata |

SEQUENCE: 127
```
SGPRGIQALL CACTSCLQAN LTCETDGACM VSIFNLDGLE HHVRTCIPKV ELVPAGKPFY   60
CLSSEDLRNT HCCYTDFCNK IDLRVPSGHV KEPERPSVWG PVE                    103
```

| SEQ ID NO: 128 | moltype = AA length = 103 |
|---|---|
| FEATURE | Location/Qualifiers |
| source | 1..103 |
| | mol_type = protein |
| | organism = Erinaceus europaeus |

SEQUENCE: 128
```
SGPRGIQALL CACTSCLQTN YTCETDGACM VSIFNLDGME HHVRTCIPKV ELVPAGKPFY   60
CLSSEDLRNT HCCYTDFCNR IDLRVPSGHP KESEQASMWG PVE                    103
```

| SEQ ID NO: 129 | moltype = AA length = 102 |
|---|---|
| FEATURE | Location/Qualifiers |
| source | 1..102 |
| | mol_type = protein |
| | organism = Gallus gallus |

SEQUENCE: 129
```
APGGARALTC LCSDCKQANS TCETDGACMV SVFNLDGVKH HVRTCIPEAK LIPAGKPFYC   60
LSSEDLRNTH CCYSDFCNKI DLMVPSGHLK DNEPPSSWGP VE                     102
```

SEQ ID NO: 130          moltype = AA length = 103

```
FEATURE                 Location/Qualifiers
source                  1..103
                        mol_type = protein
                        organism = Mus musculus
SEQUENCE: 130
SGPRGIQALL CACTSCLQTN YTCETDGACM VSIFNLDGVE HHVRTCIPKV ELVPAGKPFY    60
CLSSEDLRNT HCCYIDFCNK IDLRVPSGHL KEPAHPSMWG PVE                    103

SEQ ID NO: 131          moltype = AA   length = 103
FEATURE                 Location/Qualifiers
source                  1..103
                        mol_type = protein
                        organism = Sus scrofa
SEQUENCE: 131
SGPRGIQALL CACTSCLQAN YTCETDGACM VSIFNLDGME HHVRTCIPKV ELVPAGKPFY    60
CLSSEDLRNT HCCYTDFCNK IDLRVPSGHL KEPEHPSMWG PVE                    103

SEQ ID NO: 132          moltype = AA   length = 103
FEATURE                 Location/Qualifiers
source                  1..103
                        mol_type = protein
                        organism = Rattus norvegicus
SEQUENCE: 132
SGPRGIQALL CACTSCLQTN YTCETDGACM VSIFNLDGME HHVRTCIPKV ELVPAGKPFY    60
CLSSEDLRNT HCCYIDFCNK IDLRVPSGHL KEPEHPSMWG PVE                    103

SEQ ID NO: 133          moltype = AA   length = 225
FEATURE                 Location/Qualifiers
source                  1..225
                        mol_type = protein
                        organism = Homo sapiens
SEQUENCE: 133
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLTCLVKGF YPSDIAVEWE SNGQPENNYK TTPPVLDSDG   180
SFFLYSKLTV DKSRWQQGNV FSCSVMHEAL HNHYTQKSLS LSPGK                  225

SEQ ID NO: 134          moltype = AA   length = 229
FEATURE                 Location/Qualifiers
source                  1..229
                        mol_type = protein
                        organism = Homo sapiens
SEQUENCE: 134
ESKYGPPCPS CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 135          moltype = AA   length = 223
FEATURE                 Location/Qualifiers
source                  1..223
                        mol_type = protein
                        organism = Homo sapiens
SEQUENCE: 135
VECPPCPAPP VAGPSVFLFP PKPKDTLMIS RTPEVTCVVV DVSHEDPEVQ FNWYVDGVEV    60
HNAKTKPREE QFNSTFRVVS VLTVVHQDWL NGKEYKCKVS NKGLPAPIEK TISKTKGQPR   120
EPQVYTLPPS REEMTKNQVS LTCLVKGFYP SDIAVEWESN GQPENNYKTT PPMLDSDGSF   180
FLYSKLTVDK SRWQQGNVFS CSVMHEALHN HYTQKSLSLS PGK                    223

SEQ ID NO: 136          moltype = AA   length = 232
FEATURE                 Location/Qualifiers
source                  1..232
                        mol_type = protein
                        organism = Homo sapiens
SEQUENCE: 136
EPKSCDTPPP CPRCPAPELL GGPSVFLFPP KPKDTLMISR TPEVTCVVVD VSHEDPEVQF    60
KWYVDGVEVH NAKTKPREEQ YNSTFRVVSV LTVLHQDWLN GKEYKCKVSN KALPAPIEKT   120
ISKTKGQPRE PQVYTLPPSR EEMTKNQVSL TCLVKGFYPS DIAVEWESSG QPENNYNTTP   180
PMLDSDGSFF LYSKLTVDKS RWQQGNIFSC SVMHEALHNR FTQKSLSLSP GK          232

SEQ ID NO: 137          moltype = AA   length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 137
```

```
HHHHHH                                                                   6

SEQ ID NO: 138         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 138
AETRECIYYN ANWELERTNQ SGLERCEGEQ DKRLHCYASW RNSSGTIELV KKGCWLDDFN   60
CYDRQECVAT EENPQVYFCC CEGNFCNERF THLPEAGGPE VTYEPPPT               108
```